US009169486B2

(12) United States Patent
Burk et al.

(10) Patent No.: US 9,169,486 B2
(45) Date of Patent: Oct. 27, 2015

(54) MICROORGANISMS FOR PRODUCING BUTADIENE AND METHODS RELATED THERETO

(75) Inventors: Mark J. Burk, San Diego, CA (US); Anthony P. Burgard, Bellefonte, PA (US); Robin E. Osterhout, San Diego, CA (US); Jun Sun, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 13/527,440

(22) Filed: Jun. 19, 2012

(65) Prior Publication Data

US 2013/0011891 A1    Jan. 10, 2013

Related U.S. Application Data

(60) Provisional application No. 61/500,130, filed on Jun. 22, 2011, provisional application No. 61/502,264, filed on Jun. 28, 2011.

(51) Int. Cl.
| | |
|---|---|
| *C12N 1/20* | (2006.01) |
| *C12P 5/02* | (2006.01) |
| *C12N 15/52* | (2006.01) |
| *C12P 7/04* | (2006.01) |
| *C12P 7/16* | (2006.01) |

(52) U.S. Cl.
CPC .............. *C12N 15/52* (2013.01); *C12P 5/026* (2013.01); *C12P 7/04* (2013.01); *C12P 7/16* (2013.01)

(58) Field of Classification Search
CPC ............... C12P 5/02; C12P 5/00; C12P 1/04; C12P 7/16; C12N 9/88; C12N 1/20; C12N 9/0006; C12N 15/52; C12N 15/74; C12N 9/001; C12N 15/8243; C12R 1/01; C07C 29/60; C07C 11/167; C07C 31/12; C12Q 1/04
See application file for complete search history.

(56) References Cited

U.S. PATENT DOCUMENTS

| | | | |
|---|---|---|---|
| 5,413,922 A | 5/1995 | Matsuyama et al. | |
| 5,830,716 A | 11/1998 | Kojima et al. | |
| 5,849,970 A | 12/1998 | Fall et al. | |
| 5,958,745 A | 9/1999 | Gruys et al. | |
| 6,117,658 A | 9/2000 | Dennis et al. | |
| 6,455,284 B1 | 9/2002 | Gokarn et al. | |
| 7,127,379 B2 | 10/2006 | Palsson et al. | |
| 7,223,567 B2 | 5/2007 | Ka-Yiu et al. | |
| 7,244,610 B2 | 7/2007 | San et al. | |
| 7,256,016 B2 | 8/2007 | San et al. | |
| 7,262,046 B2 | 8/2007 | Ka-Yiu et al. | |
| 7,309,597 B2 | 12/2007 | Liao et al. | |
| 7,947,483 B2 | 5/2011 | Burgard et al. | |
| 2002/0012939 A1 | 1/2002 | Palsson | |
| 2002/0168654 A1 | 11/2002 | Maranas et al. | |
| 2003/0059792 A1 | 3/2003 | Palsson et al. | |
| 2003/0087381 A1 | 5/2003 | Gokarn | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2004/0152159 A1 | 8/2004 | Causey et al. | |
| 2005/0042736 A1 | 2/2005 | San et al. | |
| 2005/0079482 A1 | 4/2005 | Maranas et al. | |
| 2006/0046288 A1 | 3/2006 | Ka-Yiu et al. | |
| 2006/0073577 A1 | 4/2006 | Ka-Yiu et al. | |
| 2007/0184539 A1 | 8/2007 | San et al. | |
| 2009/0047718 A1 | 2/2009 | Blaschek et al. | |
| 2009/0047719 A1 | 2/2009 | Burgard et al. | |
| 2009/0191593 A1 | 7/2009 | Burk et al. | |
| 2010/0003716 A1 | 1/2010 | Cervin et al. | |
| 2010/0184171 A1 | 7/2010 | Jantama et al. | |
| 2010/0304453 A1 | 12/2010 | Trawick et al. | |
| 2010/0330635 A1 | 12/2010 | Burgard et al. | |
| 2011/0008861 A1 | 1/2011 | Berry et al. | |
| 2011/0300597 A1* | 12/2011 | Burk et al. ................... 435/167 |
| 2012/0225466 A1 | 9/2012 | Burk et al. | |
| 2013/0011891 A1 | 1/2013 | Burk et al. | |

FOREIGN PATENT DOCUMENTS

| | | |
|---|---|---|
| WO | WO 02/055995 | 7/2002 |
| WO | WO 02/061115 | 8/2002 |
| WO | WO 03/106998 | 12/2003 |
| WO | WO 2004/018621 | 3/2004 |
| WO | WO 2005/047498 | 5/2005 |
| WO | WO 2006/031424 | 3/2006 |
| WO | WO 2006/034156 | 3/2006 |
| WO | WO 2007/141208 | 12/2007 |
| WO | WO 2008/080124 | 7/2008 |
| WO | WO 2008/115840 | 9/2008 |
| WO | WO 2008/131286 | 10/2008 |

(Continued)

OTHER PUBLICATIONS

Adams et al., "Oxidoreductase-Type Enzymes and Redox Proteins Involved in Fermentative Metabolisms of Hyperthermophilic Archaea," Archaea. Adv. Protein Chem. 48:101-180 (1996).

Andersson et al., "Effect of different carbon sources on the production of succinic acid using metabolically engineered *Escherichia coli*," Biotechnol. Prog. 23(2):381-388 (2007).

Aoshima and Igarashi, "A novel oxalosuccinate-forming enzyme involved in the reductive carboxylation of 2-oxoglutarate in *Hydrogenobacter thermophilus* TK-6," Mol. Microbiol. 62:748-759 (2006).

Aoshima and Igarashi, "Nondecarboxylating and Decarboxylating Isocitrate Dehydrogenases: Oxalosuccinate Reductase as an Ancestral Form of Isocitrate Dehydrogenase," J. Bacteriol. 190:2050-2055 (2008).

Aoshima et al., "A novel biotin protein required for reductive carboxylation of 2-oxoglutarate by isocitrate dehydrogenase in *Hydrogenobacter thermophilus* TK-6," Mol. Microbiol. 51:791-798 (2004).

(Continued)

*Primary Examiner* — Iqbal H Chowdhury
(74) *Attorney, Agent, or Firm* — Jones Day

(57) ABSTRACT

The invention provides non-naturally occurring microbial organisms having a butadiene or crotyl alcohol pathway. The invention additionally provides methods of using such organisms to produce butadiene or crotyl alcohol.

16 Claims, 24 Drawing Sheets

(56) References Cited

FOREIGN PATENT DOCUMENTS

| WO | WO 2009/076676 | 6/2009 |
|---|---|---|
| WO | WO 2009/094485 | 7/2009 |
| WO | WO 2009/111513 | 9/2009 |
| WO | WO 2010/031077 | 3/2010 |
| WO | WO 2010/031079 | 3/2010 |
| WO | WO 2011/052718 | 5/2011 |

OTHER PUBLICATIONS

Aoshima et al., "A novel enzyme, citryl-CoA lyase, catalysing the second step of the citrate cleavage reaction in *Hydrogenobacter thermophilus* TK-6," Mol. Microbiol. 52:763-770 (2004).

Aoshima et al., "A novel enzyme, citryl-CoA synthetase, catalysing the first step of the citrate cleavage reaction in *Hydrogenobacter thermophilus* TK-6," Mol. Micrbiol. 52:751-761 (2004).

Aoshima, M., "Novel enzyme reactions related to the tricarboxylic acid cycle: phylogenetic/functional implications and biotechnological applications," Appl. Microbiol. Biotechnol. 75:249-255 (2007).

Arikawa et al., "Soluble fumarate reductase isoenzymes from *Saccharomyces cerevisiae* are required for anaerobic growth," FEMS Microbiol. Lett. 165:111-116 (1998).

Arps et al., "Genetics of Serine Pathway Enzymes in *Methylobacterium extorquens* AM1: Phosphoenolpyruvate Carboxylase and Malyl Coenzyme A Lyase," J. Bacteriol. 175:3776-3783 (1993).

Bekal et al., "Purification of *Leuconostoc mesenteroides* Citrate Lyase and Cloning and Characterization of the citCDEFG Gene Cluster," J. Bacteriol. 180:647-654 (1998).

Bernhard et al., "Functional and structural role of the cytochrome b subunit of the membrane-bound hydrogenase complex of *Alcaligenes eutrophus* H16," Eur. J. Biochem. 248, 179-186 (1997).

Bisswanger, "Substrate Specificity of the Pyruvate Dehydrogenase Complex from *Escherichia Coli*," H., J. Biol. Chem. 256:815-82 (1981).

Blaschkowski et al., "Routes of Flavodoxin and Ferredoxin Reduction in *Escherichia coli*," Eur. J. Biochem. 123:563-569 (1982).

Bock et al., "Purification and Characterization of Two Extremely Thermostable Enzymes, Phosphate Acetyltransferase and Acetate Kinase, from the Hyperthermophilic Eubacterium Thermotoga maritime," J. Bacteriol. 181:1861-1867 (1999).

Bott and Dimroth, "Lkebsiella pneumonia genes for citrate lyase and citrate lyase ligase: localization, sequencing, and expression," Mol. Microbiol. 14:347-356 (1994).

Bott, "Anaerobic citrate metabolism and its regulation in enterobacteria," Arch. Microbiol. 167: 78-88 (1997).

Bremer, J., "Pyruvate Dehydrogenase, Substrate Specificity and Product Inhibition," Eur. J. Biochem. 8:535-540 (1969).

Bridger et al., "The subunits of succinyl-coenzyme. A synthetase—function and assembly," In Krebs' Citric Acid Cycle- Half a Century and Still Turning, Biochem. Soc. Symp. 54:103-111 (1987).

Brown et al., "The Enzymatic Interconversion of Acetate and Acetyl-coenzyme A in *Escherichia coli*," J. Gen. Microbiol. 102:327-336 (1977).

Burgdorf, "The Soluble NAD-Reducing [NiFe]-Hydrogenase from *Ralstonia eutropha* H16 Consists of Six Subunits and Can Be Specifically Activated by NADPH," J. Bact. 187(9) 3122-3132(2005).

Cary et al., "Cloning and expression of *Clostridium acetobutylicum* phosphotransbutyrylase and butyrate kinase genes in *Escherichia coli*," J. Bacteriol. 170(10):4613-4618 (1988).

Clark, "Molybdenum cofactor negative mutants of *Escherichia coli* use citrate anaerobically," FEMS Microbiol. Lett. 55:245-249 (1990).

Colonna et al., "Synthesis and radiocarbon evidence of terephthalate polyesters completely prepared from renewable resources," Green Chemistry, 13:2543-2548 (2011).

Coppi, "The hydrogenases of *Geobacter sulfurreducens*: a comparative genomic perspective," Microbiology 151, 1239-1254 (2005).

Cox et al., "Development of a metabolic network design and optimization framework incorporating implementation constraints: A succinate production case study," Metab. Eng. 8(1):46-57 (2006).

Cracknell, et al., "A kinetic and thermodynamic understanding of O2 tolerance in [NiFe]- ydrogenases," Proc Nat Acad Sci, 106(49) 20681-20686 (2009).

Cunningham et al., "Transcriptional regulation of the aconitase genes (acnA and acnB) of *Escherichia coli*," Microbiology 143 (Pt 12):3795-3805 (1997).

Currie et al., "Authentication and dating of biomass components of industrial materials; links to sustainable technology," Nuclear Instruments and Methods in Physics Research B, 172:281-287 (2000).

Devos et al., "Practical limits of function prediction," Proteins 41:98-107 (2000).

Dobbek et al., "Crystal Structure of a Carbon Monoxide Dehydrogenase Reveals a [Ni-4Fe-5S] Cluster," Science 293:1281-1285 (2001).

Dorner and Boll, J, "Properties of 2-Oxoglutarate:Ferredoxin Oxidoreductase from *Thauera aromatica* and Its Role in Enzymatic Reduction of the Aromatic Ring," Bacteriol. 184 (14), 3975-83 (2002).

Drake and Daniel, "Physiology of the thermophilic acetogen *Moorella thermoacetica*," Res. Microbiol. 155:869-883 (2004).

Drake, "Acetogenesis, Acetogenic Bacteria, and the Acetyl-CoA 'Wood/Ljungdahl 'Pathway: Past and Current Perspectives," pp. 3-60 Chapman and Hall, New York, (1994).

Drake, H. L., "Demonstration of Hydrogenase in Extracts of the Homoacetate-Fermenting Bacterium Clostridium thermoaceticum," J. Bacteriol. 150:702-709 (1982).

Duncombe and Frerman, "Molecular and catalytic properties of the acetoacetyl-Coenzyme A thiolase of *Escherichia coli*," Arch. Biochem. Biophys. 176(1):159-170 (1976).

Edwards and Palsson, "Metabolic flux balance analysis and the in silico analysis of *Escherichia coli* K-12 gene deletions," BMC Bioinform. 1:1 (2000).

Edwards and Palsson, "The *Escherichia coli* MG1655 in silico Metabolic Genotype: Its Definition, Characteristics, and Capabilities," Proc. Natl. Acad. Sci. U.S.A. 97(10):5528-5533 (2000).

Edwards et al., "Metabolic modelling of microbes: the flux-balance approach," Environ. Microbiol. 4(3):133-140 (2002).

Edwards et al., "In Silico Predictions of *Escherichia coli* metabolic capabilities are Consistent with Experimental Data," Nat. Biotechnol. 19(2):125-130 (2001).

Eikmanns et al., "The phosphoenolpyruvate carboxylae gene of *Corynebacterium glutamicum*: Molecular cloning, nucleotide sequence, and expression," Mol. Gen. Genet. 218:330-339 (1989).

Eisen et al., "The complete genome sequence of Chlorobium tepidum TLS, a photosynthetic, anaerobic, green-sulfur bacterium," PNAS 99(14): 9509-14 (2002).

Ekiel et al., "Acetate and CO2 Assimilation by *Methanothrix concilii*," J. Bacteriol. 162:905-908 (1985).

Enomoto et al., "Cloning and Sequencing of the Gene Encoding the Soluble Fumarate Reductase from *Saccharomyces cerevisiae*," DNA Res. 3:263-267 (1996).

Evans et al., "A new ferredoxin-dependent carbon reduction cycle in a photosynthetic bacterium," Proc. Natl. Acad. Sci. U.S.A. 55:928-934 (1966).

Feist et al., "The growing scope of applications of genome-scale metabolic reconstructions using *Escherichia coli*," Nat. Biotechnol. 26(6):659-667 (2008).

Fong and Palsson, "Metabolic gene-deletion strains of *Escherichia coli* evolve to computationally predicted growth phenotypes," Nat. Genet. 36(10):1056-1058 (2004).

Fong et al., "Description and Interpretation of Adaptive Evolution of *Escherichia coli* K-12 MG1655 by Using a Genome-Scale in Silico Metabolic Model," J. Bacteriol. 185(21):6400-6408 (2003).

Fong et al., "In Silico design and adaptive evolution of *escherichia coli* for production of lactic acid," Biotechnol. Bioeng. 91(5):643-648 (2005).

Fox and Roseman, "Isolation and Characterization of Homogeneous Acetate Kinase from *Salmonella typhimurium* and *Escherichia coli*," J. Biol. Chem. 261:13487-13497 (1986).

(56) References Cited

OTHER PUBLICATIONS

Fox et al., "Characterization of the Region Encoding the CO-Induced Hydrogenase of *Rhodospirillum rubrum*," J Bacteriol. 178:6200-6208 (1996).

Fuhrer, et al., "Computational prediction and experimental verification of the gene encoding the NAD+/NADP+-dependent succinate semialdehyde dehydrogenase in *Escherichia coli*," J. Bacteriol. 189:8073-8078 (2007).

Fujinaga and Meyer, "Cloning and Expression in *Escherichia Coli* of The Gene Encoding the [2Fe-2S] Ferredoxin from Clostridium Pasteurianum," Biochemical and Biophysical Research Communications, 192(3):1115-1122 (1993).

Fukuda and Wakagi, "Substrate recognition by 2-oxoacid:ferredoxin oxidoreductase from *Sulfolobus sp* strain 7," Biochim. Biophys. Acta 1597:74-80 (2002).

Fukuda et al., "Role of a highly conserved YPITP motif in 2-oxoacid:ferredoxin Oxidoreductase," Eur. J. Biochem. 268:5639-5646 (2001).

Furdui and Ragsdale, "The Role of Pyruvate Ferredoxin Oxidoreductase in Pyruvate Synthesis during Autotrophic Growth by the Wood-Ljungdahl Pathway," J. Biol. Chem. 275:28494-28499 (2000)).

Gangloff et al., "Molecular Cloning of the Yeast Mitochondrial Aconitase Gene (AC01) and Evidence of a Synergistic Regulation of Expression by Glucose plus Glutamate," Mol. Cell. Biol. 10:3551-3561 (1990).

Germer, "Overexpression, Isolation, and Spectroscopic Characterization of the Bidirectional [NiFe] Hydrogenase from *Synechocystis sp*. PCC 6803," J. Biol. Chem. 284(52), 36462-36472 (2009).

Gibson and McAlister-Henn, "Physical and Genetic Interactions of Cytosolic Malate Dehydrogenase with Other Gluconeogenic Enzymes," J. Biol. Chem. 278:25628-25636 (2003)).

Goldberg et al., "Improved Conversion of Fumarate to Succinate by *Escherichia coli* Strains Amplified for Fumarate Reductase," Appl. Environ. Microbiol. 45:1838-1847 (1983).

Gong et al., "Specificity Determinants for the Pyruvate Dehydrogenase Component Reaction Mapped with Mutated and Prosthetic Group Modified Lipoyl Domains," J. Biol. Chem. 275:13645-13653 (2000).

Gonzalez and Robb, "Genetic analysis of Carboxydothermus hydrogenoformans carbon monoxide dehydrogenase genes cooF and cooS," FEMS Microbiol Lett. 191:243-247 (2000).

Guest et al., "The Fumarase Genes of *Escherichia coli*: Location of the fumB Gene and Discovery of a New Gene," J. Gen. Microbiol. 131:2971-2984 (1985).

Gulick et al., "The 1.75 Å Crystal Structure of Acetyl-CoA Synthetase Bound to Adenosine-5-propylphosphate and Coenzyme A," Biochemistry 42:2866-2873 (2003).

Hartmanis, M.G., "Butyrate Kinase from *Clostridium acetobutylicum*," J. Biol. Chem. 262:617-621 (1987).

Haselbeck and McAlister-Henn, "Isolation, Nucleotide Sequence, and Disruption of the *Saccharomyces cerevisiae* Gene Encoding Mitochondrial NADP(H)-specific Isocitrate Dehydrogenase," J. Biol. Chem. 266:2339-2345 (1991).

Henriksson et al., "Structures of Mycobacterium tuberculosis1-Deoxy-D-xylulose-5-phosphate Reductoisomerase Provide New Insights into Catalysis," J Biol.Chem. 282:19905-19916 (2007).

Herrmann et al., "Energy Conservation via Electron-Transferring Flavoprotein in Anaerobic Bacteria," J. Bacteriol. 190:784-791 (2008).

Hesslinger et al., "Novel keto acid formate-lyase and propionate kinase enzymes are components of an anaerobic pathway in *Escherichia coli* that degrades L-threonine to propionate," Mol. Microbiol 27:477-492 (1998).

Holms, "The central metabolic pathways in *Escherichia coli*: relationship between flux and control at a branch point, efficiency of conversion to biomass. and excretion of acetate," Curr. Top Cell. Regul. 28:69-105 (1986).

Hong and Lee, "Enhanced Production of Succinic Acid by Metabolically Engineered *Escherichia coli* with Amplified Activities of Malic Enzyme and Fumarase," Biotechnol. Bioprocess. Eng. 9:4:252-255 (2004).

Hong et al., "Importance of redox balance on the production of succinic acid by metabolically engineered *Escherichia coli*," Appl. Microbiol. Biotechnol. 58:286-290 (2002).

Horswill and Escalante-Semerena, "In Vitro Conversion of Propionate to Pyruvate by *Salmonella enterica* Enzymes: 2-Methylcitrate Dehydratase (PrpD) and Aconitase Enzymes Catalyze the Conversion of 2-Methylcitrate to 2-Methylisocitrate," Biochemistry 40:4703-4713 (2001).

Hugler et al., "Autotrophic CO2 fixation via the reductive tricarboxylic acid cycle in different lineages within the phylum Aquificae: evidence for two ways of citrate cleavage," Environ. Microbiol. 9:81-92 (2007).

Hugler et al., "Evidence for Autotrophic CO2 Fixation via the Reductive Tricarboxylic Acid Cycle by Members of the Subdivision of *Proteobacteria*," J. Bacteriol. 187:3020-3027 (2005).

Hynes and Murray, "ATP-Citrate Lyase Is Required for Production of Cytosolic Acetyl Coenzyme A and Development in *Aspergillus nidulans*," Eukaryotic Cell, July: 1039-1048, (2010).

Ibarra et al., "*Escherichia coli* K-12 undergoes adaptive evolution to achieve in silico predicted optimal growth," Nature 420(6912):186-189 (2002).

Ingram-Smith and Smith, "AMP-forming acetyl-CoA synthetases in *Archaea* show unexpected diversity in substrate utilization," *Archaea* 2:95-107 (2007).

Ingram-Smith et al., "Characterization of the Acetate Binding Pocket in the *Methanosarcina thermophila* Acetate Kinase," J. Bacteriol. 187:2386-2394 (2005).

Iverson et al., "Structure of the *Escherichia coli* Fumarate Reductase Respiratory Complex," Science 284:1961-1966 (1999).

Iwakura et al., "Studies on Regulatory Functions of Malic Enzymes," J. Biochem. 85(5):1355-65 (1979).

Jacobi et al., "The hyp operon gene product are required for the maturation of catalytically active hydrogenase isoenzymes in *Escherichia coli*," Arch.Microbiol 158:444-451 (1992).

Jantama et al., "Eliminating Side Products and Increasing succinate Yields in Engineered Strains of *Escherichia coli* C," Biotechnol. Bioeng. 101(5) 881-893 (2008).

Jogl and Tong, "Crystal Structure of Yeast Acetyl-Coenzyme A Synthetase in Complex with AMP," Biochemistry 43:1425-1431 (2004).

Jojima et al., "Production of isopropanol by metabolically engineered *Escherichia coli*," Appl Microbiol Biotechnol 77:1219-1224 (2008).

Kai et al., "Phosphoenolpyruvate carboxylase: three-dimensional structure and molecular mechanisms,"Arch. Biochem. Biophys. 414:170-179 (2003).

Kanao et al., "Characterization of isocitrate dehydrogenase from the green sulfur bacterium *Chlorobium* limicola,"Eur. J. Biochem. 269:1926-1931 (2002).

Kanao et al., "Kinetic and biochemical analyses on the reaction mechanism of a bacterial ATP-citrate lyase," Eur. J. Biochem. 269:3409-3416 (2002).

Karlen et al., "Absolute determination of the activity of two C14 dating standards," Arkiv Geofysik, 4:465-471 (1968).

Kellum and Drake, "Effects of Cultivation Gas Phase on Hydrogenase of the Acetogen Clostridium thermoaceticum," J. Bacteriol. 160:466-469 (1984).

Kim and Tabita, "Both Subunits of ATP-Citrate Lyase from Chlorobium tepidum Contribute to Catalytic Activity," J. Bacteriol. 188:6544-6552 (2006).

Kim et al., "Construction of an *Escherichia coli* K-12 Mutant for Homoethanologenic Fermentation of Glucose or Xylose without Foreign Genes," Appl. Environ. Microbiol. 73:1766-1771 (2007).

Kim et al., "Dihydrolipoamide Dehydrogenase Mutation Alters the NADH Sensitivity of Pyruvate Dehydrogenase Complex of *Escherichia coli* K-12," J. Bacteriol. 190:3851-3858 (2008).

Kim et al., "Effect of Overexpression of *Actinobacillus succinogenes* Phosphoenolpyruvate Carboxykinase on Succinate Production in *Escherichia coli*," Appl. Environ. Microbiol. 70:1238-1241 (2004).

(56) References Cited

OTHER PUBLICATIONS

Kizer et al., "Application of Functional Genomics to Pathway Optimization for Increased Isoprenoid Production," *Appl. Environ. Microbiol.* 74(10):3229-3241 (2008).

Knappe and Sawers, "A radical-chemical route to acetyl-CoA: the anaerobically induced pyruvate formate-lyase system of *Escherichia coli*," FEMS.Microbiol Rev. 6:383-398 (1990).

Kobayashi et al., "Physicochemical, Catalytic, and Immunochemical Properties of Fumarases Crystallized Separately from Mitochondrial and Cytosolic Fraction of Rat Liver," J. Biochem. 89:1923-1931 (1981).

Koland and Gennis, "Proximity of Reactive Cysteine Residue and Flavin in *Escherichia coli* Pyruvate Oxidase As Estimated by Fluorescence Energy Transfer," Biochemistry 21:4438-4442 (1982).

Kretz et al., "Gene Site Saturation Mutagenesis: A Comprehensive Mutagenesis Approach," Methods Enzymol. 388:3-11 (2004).

Kumari et al., "Cloning, Characterization, and Functional Expression of acs, the Gene Which Encodes Acetyl Coenzyme A Synthetase in *Escherichia coli*," J. Bacteriol. 177:2878-2886 (1995).

Kwon et al., "Influence of Gluconeogenic Phosphoenolpyruvate Carboxykinase (PCK) Expression on Succinic Acid Fermentation in *Escherichia coli* Under High Bicarbonate Condition," J. Microbiol. Biotechnol. 16:1448-1452 (2006).

Laivenieks et al., "Cloning, Sequencing, and Overexpression of the *Anaerobiospirillum succiniciproducens* Phosphoenolpyruvate Carboxykinase (pckA) Gene," Appl. Environ. Microbiol. 63:2273-2280 (1997).

Lee et al., "Fermentative production of chemicals that can be used for polymer synthesis," *Macromol. Biosci.* 4:157-164 (2004).

Lee et al., "Genome-based metabolic engineering of Mannheimia succiniciproducens for succinic acid productiion," *Appl. Environ. Microbiol.* 72(3):1939-1948 (2006).

Lee et al., "Cloning and Characterization of Mannheimia succiniciproducens MBEL55E Phosphoenolpyruvate Carboxykinase (pckA) Gene," Biotechnol. Bioprocess Eng. 7:95-99 (2002).

Lee et al., "Metabolic engineering of *Escherichia coli* for enhanced production of succinic acid, based on genome comparison and in silico gene knockout simulation," Appl Environ Microbiol. 71(12):7880-7887 (2005).

Leutwein and Heider, "Succinyl-CoA:(R)-Benzylsuccinate CoA-Transferase: an Enzyme of the Anaerobic Toluene Catabolic Pathway in Denitrifying Bacteria," J. Bact. 183(14) 4288-4295 (2001).

Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol. Prog.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, "Metabolic Network Design and Engineering in *Escherichia coli*" Ph.D. Thesis, Rice University, Dept. of Bioengineering (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).

Louis et al., "Restricted Distribution of the Butyrate Kinase Pathway among Butyrate-Producing Bacteria from the Human Colon," J. Bacteriol. 186:2099-2106 (2004).

Lukey et al., How *E. coli* is equipped to oxidize hydrogen under different redox conditions, J Biol Chem published online Nov. 16, 2009).

Maeda et al., "*Escherichia coli* hydrogenase 3 is a reversible enzyme possessing hydrogen uptake and synthesis activities," Appl Microbiol Biotechnol 76(5):1035-42 (2007).

Mahadevan and Schilling, "The effects of alternate optimal solutions in constraint-based genome-scale metabolic models," Metab. Eng. 5(4):264-276 (2003).

Mahadevan et al., "Application of metabolic modeling to drive bioprocess development for the production of value-added chemicals," Biotechnol. Bioprocess Eng. 10(5):408-417 (2005).

Mann, "An International Reference Material for Radiocarbon Dating," Radiocarbon, 25(2):519-527 (1983).

Marolewski et al., "Cloning and Characterization of a New Purine Biosyntetic Enzyme: A Non-Folate Glycinamide Ribonucleotide Transformylase from *E. coli*," Biochemistry 33:2531-2537 (1994).

McAlister-Heim and Thompson, "Isolation and Expression of the Gene Encoding Yeast Mitochondrial Malate Dehydrogenase," J. Bacteriol. 169:5157-5166 (1987).

Meijer et al., "Gene deletion of cytosolic ATP: citrate lyase leads to altered organic acid production in *Aspergillus niger*," J. Ind. Microbiol. Biotechnol. 36:1275-1280 (2009).

Melchiorsen et al., "The level of pyruvate-formate lyase controls the shift from homolactic to mixed-acid product formation in *Lactococcus lactis*," Appl Microbiol Biotechnol 58:338-344 (2002).

Menon and Ragsdale, "Mechanism of the Clostridium thermoaceticum Pyruvate:Ferredoxin Oxidoreductase: Evidence for the Common Catalytic Intermediacy of the Hydroxyethylthiamine Pyropyrosphate Radical," Biochemistry 36:8484-8494 (1997).

Mileni et al., "Heterologous production in Wolinella succinogenes and characterization of the quinol: fumarate reductase enzymes from *Helicovacter pylori* and *Campylobacter jejuni*," Biochem J, 395:191-201 (2006).

Miles and Guest, "Molecular genetic aspects of the citric acid cycle of *Escherichia coli*," Biochem. Soc. Symp. 54:45-65 (1987).

Millard et al., "Enhanced production of succinic acid by overexpression of phosphoenolpyruvate carboxylase in *Escherichia coli*," Appl. Environ. Microbiol. 62(5):1808-1810 (1996).

Minard and McAlister-Henn, "Isolation, Nucleotide Sequence Analysis, and Disruption of the MDH2 Gene from *Saccharomyces cerevisiae*: Evidence for Three Isozymes of Yeast Malate Dehydrogenase," Mol. Cell. Biol. 11:370-380 (1991).

Mizobata et al., "Purification and Characterization of a Thermostable Class II Fumarase from *Thermus thermophilus*," Arch. Biochem. Biophys. 355:49-55 (1998).

Mukhopadhyay and Purwantini, "Pyruvate carboxylase from *Mycobacterium smegmatis*: stabilization, rapid purification, molecular and biochemical characterization and regulation of the cellular level," Biochim Biophys. Acta 1475:191-206 (2000).

Muratsubaki et al., "One of the Fumarate Reductase Isoenzymes from *Saccharomyces cerevisiae* Is Encoded by the OSM1 Gene," Arch. Biochem. Biophys. 352:175-181 (1998).

Nakano et al., "Characterization of Anaerobic Fermentative Growth of *Bacillus subtilis*: Identification of Fermentation End Products and Genes Required for Growth," J. Bacteriol. 179:6749-6755 (1997).

Nilekani and SivaRaman, "Purification and Properties of Citrate Lyase from *Escherichia coli*," Biochemistry 22:4657-4663 (1983).

Nimmo, H.G., "Kinetic mechanism of *Escherichia coli* isocitrate dehydrogenase and its inhibition by glyoxylate and oxaloacetate," Biochem. J. 234:317-232 (1986).

Nishizawa et al., "Gene expression and characterization of two 2-oxoacid:ferredoxin oxidoreductases from *Aeropyrum pernix* K1," FEBS Lett. 579:2319-2322 (2005).

Nowrousian et al., "The fungal acl1 and acl2 genes encode two polypeptides with homology to the N- and C-terminal parts of the animal ATP citrate lyase polypeptide," Curr. Genet. 37:189-93 (2000).

O'Brien and Gennis, "Studies of the Thiamin Pyrophosphate Binding Siotef *Escherichia coli* Pyruvate Oxidase," J. Biol. Chem. 255:3302-3307 (1980).

O'Brien et al., "Regulation by Lipids of Cofactor Binding to a Peripheral Membrane Enzyme: Binding of Thiamin Pyrophosphate to Pyruvate Oxidase," Biochemistry 16:3105-3109 (1977).

Okino et al., "An efficient succinic acid production process in a metabolically engineered *Corynebacterium glutamicum* strain," Appl. Microbiol. Biotechnol. 81(3):459-464 (2008).

Parkin et al., "Rapid and Efficient Electrocatalytic CO2/CO Interconversions by *Carboxydothermus hydrogenoformans* CO Dehydrogenase I on an Electrode," J Am.Chem.Soc. 129:10328-10329 (2007).

(56) References Cited

OTHER PUBLICATIONS

Patil et al., "Use of genome-scale microbial models for metabolic engineering," Curr. Opin. Biotechnol. 15(1):64-69 (2004).

Pharkya et al., "OptiStrain: A computational Framework for redesign of microbial production systems," Genome Res. 14(11):2367-2376 (2004).

Pieulle et al., "Isolation and Analysis of the Gene Encoding the Pyruvate-Ferredoxin Oxidoreductase of *Desulfovibrio africanus*, Production of the Recombinant Enzyme in *Escherichia coli*, and Effect of Carboxy-Terminal Deletions on Its Stability," J. Bacteriol. 179:5684-5692 (1997).

Postma et al., "Phosphoenolpyruvate Carbohydrate Phosphotransferase Systems of Bacteria," Microbiol Rev. 57(3):543-594 (1993).

Price et al., "Genome-scale microbial in silico models: the constraints-based approach," Trends Biotechnol. 21(4):162-196 (2003).

Price et al., "Genome-scale models of microbial cells: evaluating the consequences of constraints," Nat. Rev. Microbiol. 2(11):886-897 (2004).

Priefert and Steinbuchel, "Identification and Molecular Characterization of the Acetyl Coenzyme A Synthetase Gene (aceE) of *Alcaligenes eutrophus*," J. Bacteriol. 174:6590-6599 (1992).

Radhakrishnan et al., "Applications of metabolic modeling to drive bioprocess development for the production of value-aded chemicals," Biotechnol. Bioprocess. Eng. 10:408-417 (2005).

Rado and Hoch, "Phophotransacetylase from *Bacillus Subtilis*: Purification and Physiological Studies," Biochim. Biophys. Acta 321:114-125 (1973).

Ragsdale, "Enzymology of the Wood—Ljungdahl Pathway of Acetogenesis," Annals of the New York Academy of Sciences 1125: 129-136 (2008).

Ragsdale, S.W., "Pyruvate Ferredoxin Oxidoreductase and Its Radical Intermediate," Chem. Rev. 103:2333-2346 (2003).

Rakhely, "Cyanobacterial-Type, Heteropentameric, NAD-Reducing NiFe Hydrogenase in the Purple Sulfur Photosynthetic *Bacterium Thiocapsa roseopersicina*," Appl. Environ. Microbiol. 70(2) 722-728 (2004).

Rangarajan et al., "Structure of [NiFe] Hydrogenase Maturation Protein HypE from *Escherichia coli* and Its Interaction with HypF," J. Bacteriol. 190:1447-1458 (2008).

Reed et al., "An expanded genome-scale model of *Escherichia coli* K-12 (iJR904 GSM/GPR)," Genome Biol. 4(9):R54 (2003).

Regev-Rudzki et al., "Yeast Aconitase in Two Locations and Two Metabolic Pathways: Seeing Small Amounts Is Believing," Mol. Biol. Cell. 16:4163-4171 (2005).

Sanchez et al., "Efficient succinic acid production from glucose through overexpression of pyruvate carboxylase in an *Escherichia coli* alcohol dehydrogenase and lactate dehydrogenase mutant," Biotechnol. Prog. 21(2):358-365 (2005).

Sanchez et al., "Novel pathway engineering design of the anaerobic central metabolic pathway in *Escherichia coli* to increase succinate yield and productivity," Metab. Eng. 7(3): 229-239 (2005).

Sanchez et al., "Batch culture characterization and metabolic flux analysis of succinate-producing *Escherichia coli* strains," Metab Eng. 8(3):209-226 (2006).

Sass et al., "Folding of Fumarase during Mitochondrial Import Determines its Dual Targeting in Yeast," J. Biol. Chem. 278:45109-45116 (2003).

Sawers and Boxer, "Purification and properties of membrane-bound hydrogenase isoenzyme 1 from anaerobically grown *Escherichia coli* K12," Eur.J Biochem. 156:265-275 (1986).

Sawers et al., "Characterization and Physiological Roles of Membrane-Bound Hydrogenase Isoenzymes from *Salmonella typhimurium*," J Bacteriol. 168:398-404 (1986).

Sawers et al., "Differnetial Expression of Hydrogenase Isoenzymes in *Escherichia coli* K-12: Evidence for a Third Isoenzyme," J Bacteriol. 164:1324-1331 (1985).

Sawers, G., "The hydrogenases and formate dehydrogenases of *Escherichia coli*," Antonie Van Leeuwenhoek 66:57-88 (1994).

Schilling et al., "Combining Pathway Analysis with Flux Balance Analysis for the Comprehensive Study of Metabolic Systems," Biotechnol. Bioeng. 71(4):286-306 (2000/2001).

Schilling et al., "Theory for the Systematic Definition of Metabolic Pathways and Their Use in Interpreting Metabolic Function from a Pathway-Oriented Perspective," J. Theor. Biol. 203(3):229-248 (2000).

Schilling et al., "Toward Metabolic Phenomics: Analysis of Genomic Data Using Flux Balances," Biotechnol. Prog. 15(3):288-295 (1999).

Schink and Schlegel, "The Membrane-Bound Hydrogenase of *Alcaligenes Eutrophus*," Biochim Biophys. Acta, 567, 315-324 (1979).

Schneider and Schlegel, "Purification and Properties of Soluble Hydrogenase from *Alcaligenes Eutrphus* H16," Biochim. Biophys. Acta 452, 66-80 (1976).

Schneider et al., "Biosynthesis of the Prosthetic Group of Citrate Lyase," Biochemistry 39:9438-9450 (2000).

Seedorf et al., "The genome of *Clostridium kluyveri*, a strict anaerobe with unique metabolic features," Proc. Natl. Acad. Sci. U.S.A. 105:2128-2133 (2008).

Segre et al., "Analysis of optimality in natural and perturbed metabolic networks," Proc. Natl. Acad. Sci. U.S.A. 99:15112-15117 (2002).

Seravalli et al., "Evidence That NiNi Acetyl-CoA Synthase Is Active and That the CuNi Enzyme Is Not," Biochemistry 43:3944-3955 (2004).

Shimoyama et al., "MmcBC in *Pelotomaculum thermopropionicum* represents a novel group of prokaryotic fumarases," FEMS Microbiol. Lett. 270:207-213 (2007).

Siebers et al., "Reconstruction of the Central Carbohydrate Metabolism of *Thermoproteus tenax* by Use of Genomic and Biochemical Data," J. Bacteriol. 186:2179-2194 (2004).

Smith et al., "Fumarate metabolism and the microaerophily of *Campylobacter* species," Int. J. Biochem. Cell. Biol. 31:961-975 (1999).

St Maurice et al., "Flavodoxin:Quinone Reductase (FqrB): a Redox Partner of Pyruvate:Ferredoxin Oxidoreductase That Reversibly Couples Pyruvate Oxidation to NADPH Production in *Helicobacter pylori* and *Campylobacter jejuni*," J. Bacteriol. 189:4764-4773 (2007).

Stadtman, E., "Phosphotransacetylase from *Clostridium kluyveri*," Methods Enzymol. 1:596-599 (1955).

Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," Microbiology 151:3793-3801 (2005).

Starai et al., "Residue Leu-641 of Acetyl-CoA Synthetase is Critical for the Acetylation of Residue Lys-609 by the Protein Acetyltransferase Enzyme of *Salmonella enteric*," J. Biol. Chem. 280:26200-26205 (2005).

Steffan and McAlister-Henn, "Isolation and Characterization of the Yeast Gene Encoding the MDH3 Isozyme of Malate Dehydrogenase," J. Biol. Chem. 267:24708-24715 (1992).

Stols and Donnelly, "Production of Succinic Acid through Overexpression of NAD1-Dependent Malic Enzyme in an *Escherichia coli* Mutant," Appl. Environ. Microbiol. 63(7) 2695-2701 (1997).

Stols et al., "Expression of Ascaris suum Malic Enzyme in a Mutant *Escherichia coli* Allows Production of Succinic Acid from Glucose," Appl. Biochem. Biotechnol. 63-65(1), 153-158 (1997).

Suzuki, T., "Phosphotransacetylase of *Escherichia Coli* B, Activation by Pyruvate and Inhibition by NADH and Certain Nucleotides," Biochim Biophys. Acta 191:559-569 (969).

Svetlitchnyi et al., "Two Membrane-Associated NiFeS-Carbon Monoxide Dehydrogenases from the Anaerobic Carbon-Monoxide-Utilizing *Eubacterium Carboxydothermus hydrogenoformans*," J Bacteriol. 183:5134-5144 (2001).

Takahashi-Abbe et al., "Biochemical and functional properties of a pyruvate formate-lyase (PFL)-activating system in *Streptococcus mutans*," Oral.Microbiol Immunol. 18:293-297 (2003).

Takeo, "Existence and Properties of Two Malic Enzymes in *Escherichia coli*," J. Biochem. 66:379-387 (1969).

(56) References Cited

OTHER PUBLICATIONS

Tsao et al., "Production of multifunctional organic acids from renewable resources," Adv. Biochem. Eng. Biotechnol. 65:243-280 (1999).
Tseng et al., "Oxygen- and Growth Rate-Dependent Regulation of *Escherichia coli* Fumarase (FumA, FumB, and FumC) Activity," J. Bacteriol. 183:461-467 (2001).
Valdes-Hevia et al., "Isolation and characterization of the gene encoding phosphoenolpyruvate carboxykinase from *Saccharomyces cerevisiae*," FEBS Lett. 258:313-316 (1989).
Varma et al., "Biochemical Production Capabilities of *Escherichia coli*," Biotechnol. Bioeng. 42:59-73 (1993).
Vazquez et al., "Phosphotransbutyrylase Expression in *Bacillus megaterium*," Curr. Microbiol. 42:345-349 (2001).
Vemuri et al. "Succinate production in dual-phase *Escherichia coli* fermentations depends on the time of transition from aerobic to anaerobic conditions," J. Ind. Microbiol. Biotechnol. 28:325-332 (2002).
Vey et al., "Structural basis for glycyl radical formation by pyruvate formate-lyase activating enzyme," Proc.Natl. Acad. Sci. U.S.A. 105:16137-16141 (2008).
Walker et al., "Yeast Pyruvate Carboxylase: Identification of Two Genes Encoding Isoenzymes," Biochem. Biophys. Res. Commun. 176:1210-1217 (1991).
Walter et al., "Sequence and arrangement of two genes of the butyrate-synthesis pathway of *Clostridium acetobutylicum* ATCC 824," Gene 134:107-111 (1993).
Wang et al., "Genome-scale in silico aided metabolic analysis and flux comparisons of *Escherichia coli* to improve succinate production," Appl. Microbiol. Biotechnol. 73(4):887-894 (2006).
Weidner et al., "Molecular Characterization of the Genes Encoding Pyruvate Formate-Lyase and Its Activating Enzyme of Clostridium pasteurianum," J Bacteriol. 178:2440-2444 (1996).
Wiesenborn et al., "Phosphotransbutyrylase from *Clostridium acetobutylicum* ATCC 824 and Its Role in Acidogenesis," App. Environ. Microbiol. 55:317-322 (1989).
Winzer et al., "Acetate kinase from Clostridium acetobutylicum: a highly specific enzyme that is actively transcribed during acidogenesis and solventogenesis," Microbioloy 143 (Pt 10):3279-3286 (1997).
Wood et al., "A challenge for 21st century molecular biology and biochemistry: what are the causes of obligate autotrophy and methanotrophy?," FEMS Microbiol. Rev. 28:335-352 (2004).
Woods et al., "Two biochemically distinct classes of fumarase in *Escherichia coli*," Biochim Biophys. Acta 954:14-26 (1988).
Wu et al., "Life in Hot Carbon Monoxide: The Complete Genome Sequence of *Carboxydothermus hydrogenoformans* Z-2901," PLoS Genet. 1:e65 (2005).
Yamamoto et al., "Carboxylation reaction catalyzed by 2-oxoglutarate:ferredoxin oxidoreductases from *Hydrogenobacter thermophilus*," Extremophiles 14:79-85 (2010).
Yamamoto et al., "Characterization of two different 2-oxoglutarate:ferredoxin oxidoredutasees from *Hydrogenobacter thermophilus* TK-6," Biochem Biophys Res Commun, 312:1297-1302 (2003).
Yun et al., "The Genes for Anabolic 2-Oxoglutarate: Ferredoxin Oxidoreductase from *Hydrogenobacter thermophilus* TK-6," Biochem. Biophys. Res. Commun. 282:589-594 (2001).
Zhou et al., "Engineering a native homoethanol pathway in *Escherichia coli* B for ethanol production," Biotechnol. Lett. 30:335-342 (2008).
Aberhart and Hsu, "Stereospecific hydrogen loss in the conversion of [2H7] isobutyrate to β-hydroxyisobutyrate in *Pseudomonas putida*. The stereochemistry of β-hydroxyisobutyrate dehydrogenase," J. Chem. Soc. [Perkin1] 6:1404-1406 (1979).
Ajjawi et al., "Thiamin pyrophosphokinase is required for thiamin cofactor activation in *Arabidopsis*," Plant Mol. Biol. 65(1-2):151-162 (2007). (Epub Jul. 5, 2007).
Alber et al., "Malonyl-Coenzyme A reductase in the modified 3-hydroxypropionate cycle for autotrophic carbon fixation in archaeal *Metallosphaera* and *Sulfolobus* spp.," J. Bacteriol. 188(24):8551-8559 (2006).

Alber et al., "Study of an alternate glyoxylate cycle for acetate assimilation by *Rhodobacter sphaeroides*," Mol. Microbiol. 61(2):297-309 (2006).
Altincicek et al., "LytB protein catalyzes the terminal step of the 2-C-methyl-D-erythritol-4-phosphate pathway of isoprenoid biosynthesis," FEBS Lett. 532(3):437-440 (2002).
Anderson et al., "Isopentenyl diphosphate:dimethylallyl diphosphate isomerase. An improved purification of the enzyme and isolation of the gene from *Saccharomyces cerevisiae*," J. Biol. Chem. 264(32):19169-19175 (1989).
Atsumi et al., "Metabolic engineering of *Escherichia coli* for 1-butanol production," Metab. Eng. 10(6):305-311.
Atsumi et al., "Non-fermentative pathways for synthesis of branched-chain higher alcohols as biofuels," Nature 451(7174):86-89 (2008).
Basson et al., "*Saccharomyces cerevisiae* contains two functional genes encoding 3-hydroxy-3-methylglutaryl-coenzyme A reductase," Proc. Natl. Acad. Sci. U.S.A. 83(15):5563-5567 (1986).
Beatrix et al., "The biotin-dependent sodium ion pump glutaconyl-CoA decarboxylase from *Fusobactevium nucleatum* (subsp. nucleatum). Comparison with the glutaconyl-CoA decarboxylases from gram-positive bacteria," Arch. Microbiol. 154(4):362-369 (1990).
Berg et al., "A 3-Hydroxypropionate/4-Hydroxybutyrate Autotrophic Carbon Dioxide Assimilation Pathway in *Archaea*," Science 318(5857) 1782-1786 (2007).
Bergquist and Gibbs, "Degenerate oligonucleotide gene shuffling," Meth. Mol. Biol. 352:191-204 (2007).
Bergquist et al., "Degenerate oligonucleotide gene shuffling (DOGS) and random drift mutagenesis (RNDM): Two complementary techniques for enzyme evolution," Biomol. Eng. 22:63-72 (2005).
Binstock and Schulz, "Fatty acid oxidation complex from *Escherichia coli*," Methods Enzymol. 71(Pt C):403-411 (1981).
Blazquez et al., "Identification and analysis of a glutaryl-CoA dehydrogenase-encoding gene and its cognate transcriptional regulator from *Azoarcus sp.* CIB," Environ. Microbiol. 10(2):474-482 (2008).
Bochar et al., "3-hydroxy-3-methylglutaryl coenzyme A reductase of *Sulfolobus solfataricus*: DNA sequence, phylogeny, expression in *Escherichia coli* of the hmgA gene, and purification and kinetic characterization of the gene product," J. Bacteriol. 179(11):3632-3638 (1997).
Boiangiu et al., "Sodium Ion Pumps and Hydrogen Production in Glutamate Fermenting Anaerobic Bacteria," J. Mol. Microbiol. Biotechnol. 10:105-119 (2005).
Bonner and Bloch, "Purification and properties of fatty acyl thioesterase I from *Escherichia coli*," J. Biol. Chem. 247(10):3123-3133 (1972).
Botella-Pavia et al., "Regulation of carotenoid biosynthesis in plants: evidence for a key role of hydroxymethylbutenyl diphosphate reductase in controlling the supply of plastidial isoprenoid precursors," Plant J. 40(2):188-199 (2004).
Bower et al., "Cloning, sequencing, and characterization of the *Bacillus subtilis* biotin biosynthetic operon," J. Bacteriol. 178(14):4122-4130 (1996).
Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," J. Bacteriol. 178(11):3015-3024 (1996).
Bräsen and Schönheit, "Unusual ADP-forming acetyl-Coenzyme A synthetases from the mesophilic halophilic euryarchaeon *Haloarcula marismortui* and from the hyperthermophilic crenarchaeon *Pyrobaculum aerophilum*," Arch. Microbiol. 182(4):277-287 (2004).
Braune et al., "The sodium ion translocating glutaconyl-CoA decarboxylase from *Acidaminococcus fermentans*: cloning and function on the genes forming a second operon," Mol. Microbiol. 31(2):473-487 (1999).
Bravo et al., "Reliable, sensitive, rapid and quantitative enzyme-based assay for gamma-hydroxybutyric acid (GHB)," J. Forensic Sci. 49:379-387 (2004).

(56) References Cited

OTHER PUBLICATIONS

Breitkreuz et al., "A novel γ-hydroxybutyrate dehydrogenase: Identification and expression of an *Arabidopsis* cDNA and potential role under oxygen deficiency," *J. Biol. Chem.* 278:41552-41556 (2003).
Buck et al., "Primary structure of the succinyl-CoA synthetase of *Escherichia coli*," *Biochemistry* 24(22):6245-6252 (1985).
Buckel et al., "Glutaconate CoA-Transferase from *Acidaminococcus fermentans*," *Eur. J. Biochem.* 118:315-321 (1981).
Buckel, "Sodium ion-translocating decarboxylases," *Biochimica. Biophysica. Acta* 1505:15-27 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Buu et al., "Functional characterization and localization of acetyl-CoA hydrolase, Ach1p, in *Saccharomyces erevisiae*," *J. Biol. Chem.* 278:17203-17209 (2003).
Byres et al., "Crystal structures of *Trypanosoma brucei* and *Staphylococcus aureus* mevalonate diphosphate decarboxylase inform on the determinants of specificity and reactivity," *J. Mol. Biol.* 371(2):540-553 (2007).(Epub Jun. 4, 2007).
Cahyanto et al., "Regulation of aspartokinase, asparate semialdehyde dehydrogenase, dihydrodipicolinate synthease and dihydropdipicolinate reductase in *Lactobacillus plantarum*," *Microbiology* 152 (Pt 1): 105-112 (2006).
Cane et al., "Molecular cloning, expression and characterization of the first three genes in the mevalonate-independent isoprenoid pathway in *Streptomyces coelicolor*," *Bioorg. Med. Chem.* 9(6):1467-1477 (2001).
Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).
Charrier et al., "A novel class of CoA-transferase involved in short-chain fatty acid metabolism in butyrate-producing human colonic bacteria," *Microbiology* 152:179-185 (2006).
Chowdhury et al., "3-Hydroxyisobutyrate dehydrogenase from *Pseudomonas putida* E23: purification and characterization," *Biosci. Biotechnol. Biochem.* 60(12):2043-2047 (1996).
Chowdhury et al., "Cloning and overexpression of the 3-hydroxyisobutyrate dehydrogenase gene from *pseudomonas putida* E23," *Biosci. Biotechnol. Biochem.* 67(2):438-441 (2003).
Coco et al., "DNA shuffling method for generating highly recombined genes and evolved enzymes," *Nat. Biotechnol.* 19:354-359 (2001).
Colby and Chen, "Purification and properties of 3-hydroxybutyryl-Coenzyme A dehydrogenase from *Clostridium beijerinckii* ("*Clostridium butylicum*") NRRL B593," *Appl. Environ. Microbiol.* 58:3297-3302.
Corthesy-Theulaz et al., "Cloning and Characterization of *Helicobacter* pylori Succinyl CoA:Acetoacetate CoA-transferase, a Novel Prokaryotic Member of the CoA-transferase Family," *J. Biol. Chem.* 272(41):25659-25667 (1997).
Crans et al., "Glycerol Kinase: Substrate Specificity," *J. Am. Chem. Soc.* 107:7008-7018 (2010).
de Ruyck et al., "Structural role for Tyr-104 in *Escherichia coli* isopentenyl-diphosphate isomerase: site-directed mutagenesis, enzymology, and protein crystallography," *J. Biol. Chem.* 281(26):17864-17869 (2006). (Epub Apr. 15, 2006).
Deana, "Substrate specificity of a dicarboxyl-CoA: dicarboxylic acid Coenzyme A transferase from rat liver mitochondria," *Biochem. Int.* 26(4):767-773 (1992).
Desai et al., "A metabolic bypass of the triosephosphate isomerase reaction," *Biochemistry* 47(31):7983-7985 (2008). (Epub Jul. 12, 2008).

Di Gennaro, "Styrene lower catabolic pathway in *Pseudomonas fluorescens* ST: identification and characterization of genes for phenylacetic acid degradation," *Arch. Microbiol.* 188(2):117-125 (2007).
Doten et al., "Cloning and Genetic Organization of the pca Gene cluster from *Acinetobacter calcoaceticus*," *J. Bacteriol.* 169(7):3168-3174 (1987).
Doun et al., "*Enterococcus faecalis* phosphomevalonate kinase," *Protein Sci.* 14(5):1134-1139 (2005). (Epub Mar. 31, 2005).
Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).
Dwyer et al., "Proton Abstraction reaction, Steady-State kinetics, and Oxidation-Reduction Potential of Human Glutaryl-CoA Dehydrogenase," *Biochemistry* 39:11488-11499 (2000).
Fernandes et al., "Kinetic characterization of *Synechocystis sp.* PCC6803 1-deoxy-D-xylulose 5-phosphate reductoisomerase mutants," *Biochim Biophys. Acta* 1764(2):223-229 (2006). (Epub Sep. 23, 2005).
Fernandes et al., "Mutation in the flexible loop of 1-deoxy-D-xylulose 5-phosphate reductoisomerase broadens substrate utilization," *Arch. Biochem. Biophys.* 444(2):159-164 (2005). (Epub Oct. 27, 2005).
Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).
Ford et al., "Molecular properties of the lyst1+ gene and the regulation of α-aminoadipate reductase in *Schizosaccharomyces pombe*," *Curr. Genet.* 28:131-137 (1995).
Freidrich et al., "The complete stereochemistry of the enzymatic dehydration of 4-hydroxybutyryl Coenzyme A to crotonyl Coenzyme A," *Angew. Chem. Int. Ed.* 47:3254-3257 (2008).
Fu et al., "Crystal structures of human glutaryl-CoA dehydrogenase with and without an alternate substrate: structural bases of dehydrogenation and decarboxylation reactions," *Biochemistry* 43(30):9674-9684 (2004).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 32:e145 (2004).
Gabrielsen et al., "Hexameric assembly of the bifunctional methylerythritol 2,4-cyclodiphosphate synthase and protein-protein associations in the deoxy-xylulose-dependent pathway of isoprenoid precursor biosynthesis," *J. Biol. Chem.* 279(50):52753-52761 (2004). (Epub Oct. 2, 2004).
Gibbs et al., "Degenerate oligonucleotide gene shuffling (DOGS): a method for enhancing the frequence of recombination with family shuffling," *Gene* 271:13-20 (2001).
Grawert et al., "IspH protein of *Escherichia coli*: studies on iron-sulfur cluster implementation and catalysis," *J. Am. Chem. Soc.* 126(40):12847-12855 (2004).
Guo and Bhattacharjee, "Posttranslational activation, site-directed mutation and phylogenetic analyses of the lysine biosynthesis enzymes a-aminoadipate reductase Lyslp (AAR) and the phosphopantetheinyl transferase Lys7p (PPTase) from *Schizosaccharomyces pombe*," *Yeast* 21:1279-1288 (2004).
Guo and Bhattacharjee, "Site-directed mutational analysis of the novel catalytic domains of a-aminoadipate reductase (Lys2p) from *candida albicans*," *Mol. Gen. Gemonics* 269:271-279 (2003).
Hajny et al., "Erythritol Production by a Yeastlike *Fungus*," *Appl. Microbiol.* 12:240-246 (1964).
Haller et al., "Discovering new enzymes and metabolic pathways: conversion of succinate to propionate by *Escherichia coli*," *Biochem.* 39(16):4622-4629 (2000).
Hanai et al., "Engineered synthetic pathway for isopropanol production in *Escherichia coli*," *Appl. Environ. Microbiol.* 73(24):7814-7818 (2007).

(56) References Cited

OTHER PUBLICATIONS

Harrison and Harwood, "The pimFABCDE operon from *Rhodopseudomonas palustris* mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood et al., "Identification of the pcaRKF Gene cluster from *Pseudomonas putida*: Involvement in Chemotaxis, Biodegradation, and Transport of 4-Hydroxybenzoate," *J. Bacteriol.* 176(21):6479-6488 (1994).

Hasegawa et al., "Transcriptional regulation of ketone body-utilizing enzyme, acetoacetyl-CoA synthetase, by C/EBPa during adipocyte differentiatiion," *Biochimica. Biophysica. Acta* 1779:414-419 (2008).

Hawes et al., "Mammalian 3-hydroxyisobutyrate dehydrogenase," *Methods Enzymol.* 324:218-228 (2000).

Hayashi et al., "Purification and properties of glycerol kinase from *Escherichia coli*," *J. Biol. Chem.* 242(5):1030-1035 (1967).

Hayes et al., "Combining computational and experimental screening for rapid optimization of protein properties," *Proc. Natl. Acad. Sci. U.S.A.* 99(25):15926-15931 (2002).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).

Hibbert et al., "Directed evolution of biocatalytic processes," *Biomol. Eng.* 22:11-19 (2005).

Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).

Hillmer and Gottschalk, "Particulate Nature of Enzymes Involved in the Fermentation of Ethanol and Acetate by *Clostridium Kluyveri*," *FEBS Lett.* 21(3):351-354 (1972).

Hillmer and Gottschalk, "Solubilization and partial characterization of particulate dehydrogenases from *Clostridium kluyveri*," *Biochim. Biophys. Acta*. 334:12-23 (1974).

Hiser et al., "ERG10 from *Saccharomyces cerevisiae* encodes acetoacetyl-CoA thiolase," *J. Biol. Chem.* 269:31383-31389 (1994).

Hoffmeister et al., "Mitochondrial trans-2-enoyl-CoA reductase of wax ester fermentation from *Euglena gracilis* defines a new family of enzymes involved in lipid synthesis," *J. Biol. Chem.* 280(6):4329-4338 (2005).

Hove-Jenson et al., "Phosphoribosylpyrophosphate synthetase of *Escherichia coli*. Properties of the purified enzyme and primary structure of the prs gene," *J. Biol. Chem.* 261(15):6765-6771 (1986).

Hugler et al., "Malonyl-Coenzyme A Reductase from *Chloroflexus aurantiacus*, a Key Enzyme of the 3-Hydroxypropionate Cycle for Autotrophic CO2 Fixation," *J. Bacteriol.* 184(9):2404-2410 (2002).

Huisman and Lalonde, "Enzyme evolution for chemical process applications," In R.N. Patel (ed.), *Biocatalysis in the pharmaceutical and biotechnology industries*, CRC Press, p. 717-742 (2007).

Huo and Viola, "Functional group characterization of homoserine kinase from *Escherichia coli*," *Arch. Biochem. Biophys.* 330(2):373-379 (1996).

Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2003).

Itoh et al., "Continuous production of chiral 1,3-butanediol using immobilized biocatalysts in a packed bed reactor: promising biocatalysis method with an asymmetric hydrogen-transfer bioreduction," *Appl. Microbiol. Biotechnol.* 75(6):1249-1256 (2007). (Epub Apr. 19, 2007).

Jacques et al., "Characterization of yeast homoserine dehydrogenase, an antifungal target: the invariant histidine 309 is important for enzyme integrity," *Biochem. Biophys. Acta* 1544:28-41 (2001).

James and Viola, "Production and characterization of bifunctional enzymes. Domain swapping to produce new bifunctional enzymes in the aspartate pathway," *Biochemistry* 41(11) 3720-3725 (2002).

Jeon et al., "Heterologous expression of the alcohol dehydrogenase (adhI) gene from *Geobacillius thermoglucosidasius* strain M10EXG," *J. Biotechnol.* 135:127-133 (2008).

Jones and Woods, "Acetone-butanol fermentation revisited," *Microbiol. Rev.* 50(4):484-524 (1986).

Julsing et al., "Functional analysis of genes involved in the biosynthesis of isoprene in *Bacillus subtitis*," *Appl. Microbiol. Biotechnol.* 75(6):1377-1384 (2007).

Kajiwara et al., "Expression of an exogenous isopentenyl diphosphate isomerase gene enhances isoprenoid biosynthesis in *Escherichia coli*," *Biochem J.* 324 ( Pt 2):421-426 (1997).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).

Kazahaya et al, "Aerobic Dissimilation of Glucose by Heterolactic Bacteria III. Aldehyde dehydrogenase and alcohol dehydrogenase of luconostoc mesenteroides" *J. Gen. Appl. Microbiol.* 18(1):43-55 (1972).

Kemp et al., "Crystallization and preliminary X-ray diffraction studies of recombinant *Escherichia coli* 4-diphosphocytidyl-2-C-methyl-D-erythritol synthetase," *Acta Crystallogr. D Biol. Crystallogr.* 57(Pt 8):1189-1191 (2001). (Epub Jul. 23, 2001).

Kemp et al., "Structure of a tetragonal crystal form of *Escherichia coli* 2-C-methyl-D-erythritol 4-phosphate cytidylyltransferase," *Acta Crystallogr. D Biol. Crystallogr.* 59(Pt 3):607-610 (2003). (Epub Feb. 21, 2003).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Kinoshita, "Purification of two alcohol dehydrogenases from *Zymomonas mobilis* and their properties," *Appl. Microbiol. Biotechnol.* 22:249-254 (1985).

Kishida et al., "Structure and catalytic mechanism of 2-C-methyl-D-erythritol 2,4-cyclodiphosphate (MECDP) synthase, an enzyme in the non-mevalonate pathway of isoprenoid synthesis," *Acta Crystallogr. D Biol. Crystallogr.* 59(Pt 1):23-31 (2003). (Epub Dec. 19, 2002).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

Koh et al., "Scale-up of erythritol production by an osmophilic mutant of Candida magnoliae," *Biotechnol. Lett.* 25(24):2103-2105 (2003).

Kollas et al., "Functional characterization of GcpE, an essential enzyme of the non-mevalonate pathway of isoprenoid biosynthesis," *FEBS Lett.* 532(3):432-436 (2002).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

(56) References Cited

OTHER PUBLICATIONS

Korolev et al., "Autotracing of *Escherichia coli* acetate CoA-transferase a-subunit structure using 3.4 Å MAD and 1.9 Å native data," *Acta. Crystallogr. D. Biol. Crystallogr.* 58(Pt 12):2116-2121 (2002).
Kosaka et al., "Characterization of the sol operon in butanol-hyperproducing Clostridium *saccharoperbutylacetonicum* strain N1-4 and its degeneration mechanism," *Biosci. Biotechnol. Biochem.* 71:58-68 (2007).
Kosjek et al., "Purification and characterization of a chemotolerant alcohol dehydrogenase applicable to coupled redox reactions," *Biotechnol. Bioeng.* 86(1):55-62 (2004).
Kowalchuk et al., "Contrasting patterns of evolutionary divergence within the *Acinetobacter calcoaceticus* pca operon," *Gene* 146:23-30 (1994).
Kreimeyer et al., "Identification of the Last Unknown Genes in the Fermentation Pathway of Lysine," *J. Biol. Chem.* 282(10):7191-7197 (2007).
Kuznetsova et al., "Enzyme genomics: Application of general enzymatic screens to discover new enzymes," *FEMS Microbiol. Rev.* 29(2):263-279 (2005).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).
Lamed and Zeikus, "Novel NADP-linked alcohol-aldehyde/ketone oxidoreductase in thermophilic ethanologenic bacteria," *Biochem. J.* 195:183-190 (1981).
Laupitz et al., "Biochemical characterization of *Bacillus subtilis* type II isopentenyl diphosphate isomerase, and phylogenetic distribution of isoprenoid biosynthesis pathways," *Eur. J. Biochem.* 271(13):2658-2669 (2004).
Learned et al., "3-Hydroxy-3-methylglutaryl-coenzyme A reductase from *Arabidopsis thaliana* is structurally distinct from the yeast and animal enzymes," *Proc. Natl. Acad. Sci. U. S. A.* 86(8):2779-2783 (1989).
Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).
Lee et al., "A new approach to directed gene evolution by recombined extension on truncated templates (RETT)," *J. Molec. Catalysis* 26:119-129 (2003).
Lee et al., "Fumarate-mediated inhibition of erythrose reductase, a key enzyme for erythritol production by *Torula corallina*," *Appl. Environ. Microbiol.* 68(9):4534-4538 (2002).
Lee et al., "Purification and characterization of a novel erythrose reductase from Candida magnoliae," *Appl. Environ. Microbiol.* 69(7):3710-3718 (2003).
Lee et al., "Purification and properties of a NADPH-dependent erythrose reductase from the newly isolated *Torula corallina*," *Biotechnol. Prog.* 19(2):495-500 (2003).
Lehmann et al., "Structure of 2C-methyl-D-erythrol-2,4-cyclodiphosphate synthase from *Haemophilus influenzae*: activation by conformational transition," *Proteins* 49(1):135-138 (2002).
Lillo et al., "Functional expression and characterization of EryA, the erythritol kinase of *Brucella abortus*, and enzymatic synthesis of L-erythritol-4-phosphate," *Bioorg. Med. Chem. Lett.* 13(4):737-739 (2003).
Lin et al., "Fed-batch culture of a metabolically engineered *Escherichia coli* strain designed for high-level succinate production and yield under aerobic conditions," *Biotechnol. Bioeng.* 90:775-779 (2005).
Lindberg et al., "Engineering a platform for photosynthetic isoprene production in cyanobacteria, using *Synechocystis* as the model organism," *Metab. Eng.* 12(1):70-79 (2010). (Epub Oct. 13, 2009).
Lokanath et al., "Crystal structure of novel NADP-dependent 3-hydroxyisobutyrate dehydrogenase from *Thermus thermophilus* HB8," *J. Mol. Biol.* 352(4):905-917 (2005).

Low et al., "Mimicking somatic hypermutation: Affinity maturation of antibodies displayed on baceriophage using a bacterial mutator strain," *J. Mol. Biol.* 260(3):359-368 (1996).
Lutz et al., "Creating multiple-crossover DNA libraries independent of sequence identity," *Proc. Natl. Acad. Sci. U.S.A.* 98:11248-11253 (2001).
Lutz et al., "Rapid generation of incremental truncation libraries for protein enginering using α-phosphothioate nucleotides," *Nucleic Acids Res.* 29:E16 (2001).
Mac Sweeney et al., "The crystal structure of *E.coli* 1-deoxy-D-xylulose-5-phosphate reductoisomerase in a ternary complex with the antimalarial compound fosmidomycin and NADPH reveals a tight-binding closed enzyme conformation," *J. Mol. Biol.* 345(1):115-127 (2005).
Mack and Buckel, "Conversion of glutaconate CoA-transferase from *Acidaminococcus* fermentans into an acyl-CoA hydrolase by site-directed mutagenesis," *FEBS Lett.* 405(2):209-212 (1997).
Mack et al., "Location of the two genes encoding glutaconate Coenzyme A-transferase at the beginning of the hydroxyglutarate operon in *Acidaminococcus* fermentans," *Eur. J. Biochem.* 226:41-51 (1994).
Manning and Pollitt, "Tracer studies of the interconversion of R- and S-methylmalonic semialdehydes in man," *Biochem. J.* 231(2):481-484 (1985).
Marks et al., "Molecular cloning and characterization of (R)-3-hydroxybutyrate dehydrogenase from human heart," *J. Biol. Chem.* 267(22):15459-15463 (1992).
Martin et al., "Engineering a mevalonate pathway in *Escherichia coli* for production of terpenoids," *Nat. Biotechnol.* 21:796-802 (2003).
Martinez-Blanco, et al, "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).
Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).
McElwain et al., International Journal of Systematic Bacteriology, 38:417-423 (1988).
Metz et al., "Purification of a jojoba embryo fatty acyl-Coenzyme A reductase and expression of its cDNA in high erucic acid rapeseed," *Plant Phys.* 122:635-644 (2000).
Miallau et al., "Biosynthesis of isoprenoids: crystal structure of 4-diphosphocytidyl-2C-methyl-D-erythritol kinase," *Proc. Natl. Acad. Sci. U. S. A.* 100(16):9173-9178 (2003). (Epub Jul. 23, 2003).
Miller et al., "First isolation of an isoprene synthase gene from poplar and successful expression of the gene in *Escherichia coli*," *Planta* 213(3):483-487 (2001).
Moon et al., "Biotechnological production of erythritol and its applications," *Appl. Microbiol. Biotechnol.* 86(4):1017-1025 (2010). (Epub Feb. 26, 2010).
Morris and Jinks-Robertson, "Nucleotide sequence of the LYS2 gene of *Saccharomyces cerevisiae*: homology to *Bacillus brevis* tyrocidine synthetase 1," *Gene* 98:141-145 (1991).
Mouttaki et al., "Cyclohexane Carboxylate and Benzoate Formation from Crotonate in *Syntrophus aciditrophicus*," *Appl. Environl. Microbiol.* 73(3):930-938 (2007).
Müh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).
Müh et al., "Mössbauer study of 4-hydroxybutyryl-CoA dehydratase probing the role of an iron-sulfur cluster in an overall non-redox reaction," *Eur. J. Biochem.* 248:380-384 (1997).
Muller et al., "Nucleotide exchange and excisiion technology (NExT) DNA shuffling; a robust method for DNA fragmentation and directed evolution," *Nucleic Acids Res.* 33:e117 (2005).
Musfeldt and Schönheit, "Novel type of ADP-forming acetyl Coenzyme A synthetase in *hyperthermophilic archaea*: heterologous expression and characterization of isoenzymes from the sulfate reducer *Archaeoglobus fulgidus* and the methanogen *Methanococcus jannaschii*," *J. Bacteriol.* 184(3):636-644 (2002).

(56) References Cited

OTHER PUBLICATIONS

Naggert et al., "Cloning, sequencing, and characterization of *Escherichia coli* thioesterase II," *J. Biol. Chem.* 266(17):11044-11050 (1991).
Nelson et al., "Evidence for lateral gene transfer between *Archaea* and bacteria from genome sequence of *Thermotoga maritima*, " *Nature* 399(6734):323-329 (1999).
Ness et al., "Synthetic shuffling expands functional protein diversity by allowing amino acids to recombine independently," *Nat. Biotechnol.* 20:1251-1255 (2002).
Nogales et al., "Characterization of the last step of the aerobic phenylacetic acid degradation pathway," *Microbiology* 153(Pt 2):357-365 (2007).
Oh et al., "Increased erythritol production in fed-batch cultures of *Torula* sp. By controlling glucose concentration," *J. Ind. Microbiol. Biotechnol.* 26(4):248-252 (2001).
Ohgami et al., "Expression of acetoacetyl-CoA synthetase, a novel cytosolic ketone body-utilizing enzyme, in human brain," *Biochem. Pharmacol.* 65:989-994 (2003).
Okada et al, "Cyanobacterial non-mevalonate pathway: (E)-4-hydroxy-3-methylbut-2-enyl diphosphate synthase interacts with ferredoxin in *Thermosynechococcus elongatus* BP-1," *J. Biol. Chem.* 280(21):20672-20679 (2005). (Epub Mar. 25, 2005).
Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).
Ostermeier et al., "A Combinatorial approach to hybrid enzymes independent of DNA homology," *Nat. Biotechnol.* 17:1205-1209 (1999).
Ostermeier et al., "Combinatorial protein engineering by incremental truncation," *Proc. Natl. Acad. Sci. U.S.A.* 96:3562-3567 (1999).
Often and Quax, "Directed evolution:selecting today's biocatalysts," *Biomol. Eng.* 22:1-9 (2005).
Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Peoples and Sinskey, "Fine structural analysis of the *Zoogloea ramigera* phbA-phbB locus encoding β-ketothiolase and acetoacetyl-CoA reductase: nucleotide sequence of phbB," *Mol. Microbiol.* 3:349-357 (1989).
Peretz and Burstein, "Amino acid sequence of alcohol dehydrogenase from the thermophilic bacterium *Thermoanaerobium brockii*," *Biochemistry* 28(16):6549-6555 (1989).
Perez et al., "*Escherichia coli* YqhD exhibits aldehyde reductase activity and protects from the harmful effect of lipid peroxidation-derived aldehydes," *J. Biol. Chem.* 283(12):7346-7353 (2008).
Pilloff et al., "The kinetic mechanism of phosphomevalonate kinase," *J. Biol. Chem.* 278(7):4510-4515 (2003). (Epub Nov. 6, 2002).
Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).
Pritchard et al., "A general model of error-prone PCR," *J. Theor. Biol.* 234:497-509 (2005).
Rajpal et al., "A general method for greatly improving the affinity of antibodies by using combinatorial libraries," *Proc. Natl. Acad. Sci. U.S.A.* 102:8466-8471 (2005).

Rathinasabapathi, "Propionate, a source of β-alanine, is an inhibitor of β-alanine methylation in Limonium latifoilium Plunbaginaces," *J. Plant Physiol.* 159:671-674 (2002).
Reetz and Carballeira, "Iterative saturation mutagenesis (ISM) for rapid directed evolution of functional enzymes," *Nat. Protoc.* 2:891-903 (2007).
Reetz et al., "Directed Evolution of an Enantioselective Enzyme through Combinatorial Multiple-Cassette Mutagenesis," *Angew. Chem. Int. Ed. Engl.* 40:3589-3591 (2001).
Reetz et al., "Iterative saturation mutagenesis on the basis of B factors as a strategy for incresing protein thermostability," *Angew. Chem. Int. Ed.* 45:7745-7751 (2006).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).
Richard et al., "Structure and mechanism of 2-C-methyl-D-erythritol 2,4-cyclodiphosphate synthase. An enzyme in the mevalonate-independent isoprenoid biosynthetic pathway," *J. Biol. Chem.* 277(10):8667-8672 (2002) (Epub Jan. 10, 2002).
Richard et al., "Structure of 4-diphosphocytidyl-2-C-methylerythritol synthetase involved in mevalonate-independent isoprenoid biosynthesis," *Nat. Struct. Biol.* 8(7):641-648 (2001).
Riviere et al., "Acetyl:succinate CoA-transferase in procyclic *Trypanosoma brucei*. Gene identification and role in carbohydrate metabolism." *J. Biol. Chem.* 279:45337-45346 (2004).
Roberts et al, "The Role of Enoyl-CoA Hydratase in the Metabolism of Isoleucine by *Pseudomonas putida*," *Arch. Microbiol.* 117:99-108 (1978).
Robinson et al., "Studies on Rat Brain Acyl-Coenzyme A Hydrolase (Short Chain)," *Biochem. Biophys. Res. Commun.* 71(4):959-965 (1976).
Rodriguez-Concepción et al., "Genetic evidence of branching in the isoprenoid pathway for the production of isopentenyl diphosphate and dimethylallyl diphosphate in *Escherichia coli*," *FEBS Lett.* 473(3):328-332 (2000).
Sasaki et al., "Gene expression and characterization of isoprene synthase from *Populus alba*," *FEBS Lett.* 579(11):2514-2518 (2005).
Sawada et al., "Key role for transketolase activity in erythritol production by *Trichosporonoides megachiliensis* SN-G42," *J. Biosci. Bioeng.* Nov. 2009;108(5):385-390 (2009). (Epub Jul. 29, 2009).
Scherf and Buckel, "Purification and properties of an iron-sulfur and FAD-containing 4-hydroxybutyryl-CoA dehadratase/vinylacetyl-CoA $\Delta^3$- $\Delta^2$-isomerase from *Clostridium aminobutricum*," *Eur. J. Biochem.* 215:421-429 (1993).
Scherf et al, "Succinate-ethanol fermentation in *clostridium kluyveri*: purification and characterisation of 4-hydroxybutyryl-CoA dehydratase/vinylacetyl-CoA $\Delta^3$- $\Delta^2$-isomerase," *Arch. Microbiol.* 161(3):239-245 (1994).
Schweiger and Buckel, "On the dehydration of (R)-lactate in the fermentation of alanine to propionat by *Clostridium propionicum*" *FEBS Lett.* 171:79-84 (1984).
Seemann et al., "Isoprenoid biosynthesis in chloroplasts via the methylerythritol phosphate pathway: the (E)-4-hydroxy-3-methylbut-2-enyl diphosphate synthase (GcpE) from *Arabidopsis thaliana* is a [4Fe-4S] protein," *J. Biol. Inorg. Chem.* 10(2):131-137 (2005). (Epub Jan. 14, 2005).
Selifonova et al., "Rapid evolution of novel traits in microorganisms," *Appl. Environ. Microbiol.* 67:3645-3649 (2001).
Selmer et al., "Propionate CoA-transferase from *Clostridium propionicum*. Cloning of gene identification of glutamate 324 at the active site," *Eur. J. Biochem.* 269:372-380 (2002).
Sen et al., "Developments in directed evolution for improving enzyme functins," *Appl. Biochem. Biotechnol.* 143:212-223 (2007).

(56) References Cited

OTHER PUBLICATIONS

Sgraja et al., "Characterization of *Aquifex aeolicus* 4-diphosphocytidyl-2C-methyl-d-erythritol kinase—ligand recognition in a template for antimicrobial drug discovery," *FEBS J.* 275(11):2779-2794 (2008). (Epub Apr. 16, 2008).
Shao et al., "Random-priming in vitro recombination: an effective tool for directed evolution," *Nucleic Acids. Res.* 26:681-683 (1998).
Sharkey et al., "Evolution of the isoprene biosynthetic pathway in kudzu," *Plant Physiol.* 137(21:700-712(2005). (Epub Jan. 14, 2005).
Shi et al., "Biosynthesis of isoprenoids: characterization of a functionally active recombinant 2-C-methyl-D-erythritol 4-phosphate cytidyltransferase (IspD) from *Mycobacterium tuberculosis* H37Rv," *J. Biochem. Mol. Biol.* 40(6):911-920 (2007).
Shimomura et al., "3-hydroxyisobutyryl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).
Sibilli et al., "Two regions of the bifunctional protein aspartokinase I-homoserine dehydrogenase I are connected by a short hinge," *J. Biol. Chem.* 256 (20):10228-10230 (1981).
Sieber et al., "Libraries of hybrid proteins from distantly related sequences," *Nat. Biotechnol.* 19:456-460 (2001).
Slater et al., "Multiple β-ketothiolases mediate poly(β-hydroxyalkanoate) copolymer synthesis in *Ralstonia eutropha*," *J. Bacteriol.* 180(8):1979-1987 (1998).
Söhling and Gottschalk, "Molecular analysis of the anaerobic succinate degradation pathway in *Clostridium kluyveri*," *J. Bacteriol.* 178:871-880 (1996).
Söhling and Gottschalk, "Purification and characterization of a Coenzyme-A-dependent succinate-semialdehyde dehydrogenase from *Clostridium kluyveri*," *Eur. J. Biochem.* 212:121-127 (1993).
Song et al., "Structure, function, and mechanism of the phenylacetate pathway hot dog-fold thioesterase PaaI" *J. Biol. Chem.* 281(16):11028-11038 (2006).
Sperry et al., "Erythritol catabolism by *Brucella abortus*," *J. Bacteriol.* 121(2):619-630 (1975).
Stadtman, "The enzyme synthesis of β-alanyl Coenzyme A," *J. Plant Chem. Soc.* 77:5765-5766 (1955).
Starnes et al., "Threonine-sensitive aspartokinase-homoserine dehydrogenase complex, amino acid composition, molecular weight, and subunit composition of the complex," *Biochemistry* 11:677-687 (1973).
Steinbacher et al., "Structure of 2C-methyl-d-erythritol-2,4-cyclodiphosphate synthase involved in mevalonate-independent biosynthesis of isoprenoids," *J. Mol. Biol.* 316(1):79-88 (2002).
Steinbüchel and Schlegel, "NAD-linked L(+)-lactate dehydrogenase from the strict aerobe *alcaligenes eutrophus*. 2. Kinetic properties and inhibition by oxaloacetate," *Eur. J. Biochem.* 130(2):329-334 (1983).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stols et al., "New vectors for co-expression of proteins: Structure of *Bacillus subtilis* ScoAB obtained by High-throughput protocols," *Protein Expr. Purif.* 53:396-403 (2007).
Strauss and Fuchs, "Enzymes of a novel autotrophic CO2 fixation pathway in the phototrophic bacterium *Chloroflexus aurantiacus*, the 3-hydroxypropionate cycle," *Eur. J. Biochem.* 215:633-643 (1993).
Suda et al., "Purification and properties of α-ketoadipate reductase, a newly discovered enzyme from human placenta," *Arch. Biochem. Biophys.* 176(2):610-620 (1976).
Suda et al., "Subcellular localization and tissue distribution of α-ketoadipate reduction and oxidation in the rat," *Biochem. Biophys. Res. Commun.* 77(2):586-591 (1977).
Sulzenbacher et al., "Crystal structure of *E.coli* alcohol dehydrogenase YqhD: evidence of a covalently modified NADP Coenzyme," *J. Mol. Biol.* 342(2):489-502 (2004).
Suzuki et al., "GriC and GriD Constitute a carboxylic acid reductase involved in grixazone biosynthesis in *streptomyces griseus*," *J. Antibiot.* 60(6):380-387 (2007).
Takahashi and Yamada, "Metabolic pathways for cytoxic and end product formation from glutamate- and aspartate-containing peptides by *Porphyromonas gingivalis*," *J. Bacteriol.* 182:4704-4710 (2000).
Tani et al., "Thermostable NADP+-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).
Thauer, "Microbiology. A Fifth Pathway of Carbon Fixation," *Science* 318:1732-1733 (2007).
Toth et al., "Molecular cloning and expression of the cDNAs encoding human and yeast mevalonate pyrophosphate decarboxylase," *J. Biol. Chem.* 271(14):7895-7898 (1996).
Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).
Tsay and Robinson, "Cloning and characterization of ERG8, an essential gene of *Saccharomyces cerevisiae* that encodes phosphomevalonate kinase," *Mol. Cell Biol.* 11(2):620-631 (1991).
Vamecq et al., "The microsomal dicarboxylyl-CoA synthetase," *Biochem. J.* 230(3):683-693 (1985).
van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).
van Grinsven et al., "Acetate:succinate CoA-transferase in the hydrogenosomes of *Trichomonas vaginalis*: identification and characterization," *J. Biol. Chem.* 283:1411-1418 (2008).
Vanderwinkel et al., "Growth of *Escherichia coli* on fatty acids: requirement for Coenzyme A transferase activity," *Biochem. Biophys. Res. Commun.* 33(6):902-908 (1968).
Veiga-da-Cunha et al., "Pathway and regulation of erythritol formation in Leuconostoc oenos," *J. Bacteriol.* 175(13):3941-3948 (1993).
Venkitasubramanian et al. in *Biocatalysis in the Pharmaceutical and Biotechnology Industires*, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).
Volkov et al., "Random chimeragenesis by heteroduplex recombination," *Methods Enzymol.* 328:456-463.
Volkov et al., "Recombination and chimeragenesis by in vitro heteroduplex formation and in vivo repair," *Nucleic Acids Res.* 27:e18 (1999).
Wada et al., "Crystal structure of 4-(cytidine 5'-diphospho)-2-C-methyl-D-erythritol kinase, an enzyme in the non-mevalonate pathway of isoprenoid synthesis," *J. Biol. Chem.* 278(32):30022-30027 (2003). (Epub May 27, 2003).
Wakil et al., "Studies on the fatty acid oxidizing system of animal tissues. VI. β-Hydroxyacyl Coenzyme A dehydrogenase," *J. Biol. Chem.* 207(2):631-638 (1954).
Walter et al., "Molecular characterization of two *Clostridium acetobutylicum* ATCC 824 butanol dehydrogenase isozyme genes," *J. Bacteriol.* 174(22):7149-7158 (1992).
Wang et al, "Molecular cloning and functional identification of a novel phenylacetyl-CoA ligase gene from *Penicillium chrysogenum*," *Biochem. Biopyhs. Res. Commun.* 360(2):453-458 (2007).
Westin et al., "The identification of a succinyl-CoA thioesterase suggests a novel pathway for succinate production in peroxisomes," *J. Biol. Chem.* 280(46):38125-38132 (2005).
Wilding et al., "Identification, evolution, and essentiality of the mevalonate pathway for isopentenyl diphosphate biosynthesis in gram-positive cocci," *J. Bacteriol.* 182(15):4319-4327 (2000).
Winzer et al., "Differential regulation of two thiolase genes from *Clostridium acetobutylicum* DSM 792," *J. Mol. Microbiol. Biotechnol.* 2(4):531-541 (2000).

(56) References Cited

OTHER PUBLICATIONS

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wolff et al., "Isoprenoid biosynthesis via the methylerythritol phosphate pathway: the (E)-4-hydroxy-3-methylbut-2-enyl diphosphate reductase (LytB/IspH) from *Escherichia coli* is a [4Fe-4S] protein," *FEBS Lett.* 541(1-3):115-120 (2003).

Wong et al., "Sequence saturation mutagenesis (SeSaM): a novel method for directed evolution," *Nucleic Acids. Res.* 32:e26 (2004).

Wong et al., "Sequence saturation mutagenesis with tunable mutation frequencies," *Anal. Biochem.* 341:187-189 (2005).

Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).

Yajima et al., "Structure of 1-deoxy-D-xylulose 5-phosphate reductoisomerase in a quaternary complex with a magnesium ion, NADPH and the antimalarial drug fosmidomycin," *Acta Crystallogr. Sect. F Struct. Biol. Cryst.Commun.* 63(Pt 6):466-470 (2007). (Epub May 31, 2007).

Yamashita et al., "Type 2 isopentenyl diphosphate isomerase from a thermoacidophilic archaeon Sulfolobus shibatae," *Eur. J. Biochem.* 2271(6):1087-1093 (2004).

Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zepeck et al., "Biosynthesis of isoprenoids. purification and properties of IspG protein from *Escherichia coli*," *J. Org. Chem.* 70(23):9168-9174 (2005).

Zhao et al., "Molecular evolution by staggered extension process (StEP) in vitro recombination," *Nat. Biotechnol.* 16:258-261 (1998).

Zhuang, et al., "The YbgC protein encoded by the ybgC gene of the tol-pal gene cluster of *Haemophilus* influenzae catalyzes acyl-Coenzyme A thioester hydrolysis," *FEBS Lett.* 516(1-3):161-163 (2002).

\* cited by examiner

```
ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCTTGCCG
ACGCGGGCAGCTTGGTGATCGTCGAAACGCTCGATGCCGTGCGTGCCCGGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGACATCGGCTTGGTACGTCCCACCGAGATCTTCT
TCGTCCCGCGCGTGTGCGACATGGTCTTCCAGCGCTATCAGAGCGAGCTGGACCGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCGCTGGCCGCGGAGATGAAGACGTTCA
TGGAGTCCGTCCTCGATCTGCCACTGCACGACGGGTACGGGTCGACCGAGGCGGGCCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCGATCTCGCGACAGGC
CAGGCCGATGAGCTGCTCGCCCTGCGCCGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCGGTGGGTGTCGTCGTCAGCCCGGCGAACGAGCTGCGCGATCTGGCGAATTACA
TTGAGGCGGAACGCAACTCGGGCGCGAAGCGTCCCACCTTCACCTCGGTGCACGGCGGCGGTTC
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCGGTTCCTGTGCCTGGAATGGCTGGAGCGGCTGGACAAGACGGGTGGCACGCTGATCTG
```

FIG. 12A

```
CGTCGTGCGCGGTAGTGACGCGGCCGCGGCCCGTAAACGGCTGGACTCGGCGTTCGACAGCGGC
GATCCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCCTACACCCAGCTGTTCGGCCCC
AATGTCGTCGGCACCGCCGAAATCGTCCGGTTGGCGATCACGGCGCGGCGCAAGCCGGTCACCT
ACCTGTCGACCGTCGGAGTGGCCGACCAGGTCGACCCGGCGGAGTATCAGGAGGACAGCGACGT
CCGCGAGATGAGCGCGGTGCGCGTCGTGCGCGAGAGTTACGCCAACGGCTACGGCAACAGCAAG
TGGGCGGGGGAGGTCCTGCTGCGCGAAGCACACGATCTGTGTGGCTTGCCGGTCGCGGTGTTCC
GTTCGGACATGATCCTGGCGCACAGCCGGTACGCGGGTCAGCTCAACGTCCAGGACGTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCGGACTTCACGGCGGCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTTCGAGACGGCCGATCCGCGCGCTGCCGGAAAAGCAAC
GCCAGGCCTCGGTGCTGCCGTTGCTGGACGCCTACCGCAACCCCTGCCCGGCCGGTCCGCGGCGC
GATACTCCCGGCCAAGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTAA
```

FIG. 12A cont.

```
mavdspderlqrriaqlfaedeqvkaarpleavsaavsapgmrlaqiaatvmagyadrpaagqr
afelntddatgrtslrllprfetityrelwqrvgevaaawhhdpenplragdfvallgftsidy
atldladihlgavtvplqasaavsqliailtetsprllastpehldaaveclagttperlvvf
dyhpedddqraafesarrrladagslvivetldavrargrdlpaaplfvpdtdddplalliyts
gstgtpkgamytnrlaatmwqgnsmlqgnsqrvginlnympmshiagrislfgvlarggtayfa
aksdmstlfedigivrpteiffvprvcdmvfqryqseldrrsvagadldtldrevkadlrqnyl
ggrflvavvgsaplaaemktfmesvldlplhdgygsteagasvlldnqiqrppvldyklvdvpe
lgyfrtdrphprgelllkaettipgyykrpevtaeifdedgfyktgdivaelehdrlvyvdrrn
nvlklsqgefvtvahleavfassplirqifiygssersyllavivptddalrgrdtatlksala
esiqriakdanlqpyeiprdflietepftiangllsgiakllrpnlkerygaqleqmytdlatg
qadellalrreaadlpvletvsraakamlgvasadmrpdahftdlggdslsalsfsnllheifg
vevpvgvvvspanelrdlanyieaernsgakrptftsvhgggseiraadltldkfidartlaaa
dsiphapvpaqtvlltgangylgrflclewlerldktggtlicvvrgsdaaaarkrldsafdsg
dpgllehyqqlaartlevlagdigdpnlglddatwqrlaetvdlivhpaalvnhvlpytqlfgp
nvvgtaeivrlaitarrkpvtylstvgvadqvdpaeyqedsdvremsavrvvresyangygnsk
wagevllreahdlcglpvavfrsdmilahsryagqlnvqdvftrlilslvatgiapysfyrtda
dgnrqrahydglpadftaaaitalgiqategfrtydvlnpyddgisldefvdwlvesghpiqri
tdysdwfhrfetairalpekqrqasvlplldayrnpcpavrgailpakefqaavqtakigpeqd
iphlsaplidkyvsdlellqll*
```

FIG. 12B

ATGATTGAAACCATTCTGCCTGCAGGCGTTGAAAGCGCAGAACTGCTGGAATATCCGGAAGATC
TGAAAGCACATCCGGCAGAAGAACATCTGATTGCCAAAAGCGTTGAAAAACGTCGTCGTGATTT
TATTGGTGCACGTCATTGTGCACGTCTGGCACTGGCAGAACTGGGTGAACCTCCGGTTGCAATT
GGTAAAGGTGAACGTGGTGCACCGATTTGGCCTCGTGGTGTTGTTGGTAGCCTGACCCATTGTG
ATGGTTATCGTGCAGCAGCAGTTGCACATAAAATGCGCTTTCGCAGCATTGGTATTGATGCAGA
ACCGCATGCAACCCTGCCGGAAGGTGTTCTGGATAGCGTTAGCCTGCCGCCGGAACGTGAATGG
CTGAAAACCACCGATAGCGCACTGCATCTGGATCGTCTGCTGTTTTGTGCAAAAGAAGCCACCT
ATAAAGCCTGGTGGCCGCTGACAGCACGTTGGCTGGGTTTTGAAGAAGCCCATATTACCTTTGA
AATTGAAGATGGTAGCGCAGATAGCGGTAATGGCACCTTTCATAGCGAACTGCTGGTTCCGGGT
CAGACCAATGATGGTGGTACACCGCTGCTGAGCTTTGATGGTCGTTGGCTGATTGCAGATGGTT
TTATTCTGACCGCAATTGCCTATGCCTAA

FIG. 13A mietilpagvesaelleypedlkahpaeehliaksvekrrrdfigarhcarlalaelgeppvai
gkgergapiwprgvvgslthcdgyraaavahkmrfrsigidaephatlpegvldsvslpperew
lkttdsalhldrllfcakeatykawwpltarwlgfeeahitfeiedgsadsgngtfhsellvpg
qtndggtpllsfdgrwliadgfiltaiaya*

FIG. 13B

```
atgaccagcgatgttcacgacgccacagacggcgtcaccgaaaccgcactcgacgacgagcagtcgacccgccgcat
cgccgagctgtacgccaccgatcccgagttcgccgccgccgcaccgttgcccgccgtggtcgacgcggcgcacaaac
ccgggctgcggctggcagagatcctgcagaccctgttcaccggctacggtgaccgcccggcgctgggataccgcgcc
cgtgaactggccaccgacgagggcgggcgcaccgtgacgcgtctgctgccgcggttcgacaccctcacctacgccca
ggtgtggtcgcgcgtgcaagcggtcgccgcgggccctgcgccacaacttcgcgcagccgatctaccccggcgacgccg
tcgcgacgatcggtttcgcgagtcccgattacctgacgctggatctcgtatgcgcctacctgggcctcgtgagtgtt
ccgctgcagcacaacgcaccggtcagccggctcgccccgatcctggccgaggtcgaaccgcggatcctcaccgtgag
cgccgaatacctcgacctcgcagtcgaatccgtgcgggacgtcaactcggtgtcgcagctcgtggtgttcgaccatc
accccgaggtcgacgaccaccgcgacgcactggcccgcgcgcgtgaacaactcgccggcaagggcatcgccgtcacc
accctggacgcgatcgccgacgagggcgccgggctgccggccgaaccgatctacaccgccgaccatgatcagcgcct
cgcgatgatcctgtacacctcgggttccaccggcgcaccaagggtgcgatgtacaccgaggcgatggtggcgcggc
tgtggaccatgtcgttcatcacgggtgaccccacgccggtcatcaacgtcaacttcatgccgctcaaccacctgggc
gggcgcatccccatttccaccgccgtgcagaacggtggaaccagttacttcgtaccggaatccgacatgtccacgct
gttcgaggatctcgcgctggtgcgcccgaccgaactcggcctggttccgcgcgtcgccgacatgctctaccagcacc
acctcgccaccgtcgaccgcctggtcacgcagggcgccgacgaactgaccgccgagaagcaggccggtgccgaactg
cgtgagcaggtgctcggcggacgcgtgatcaccggattcgtcagcaccgcaccgctggccgcggagatgagggcgtt
cctcgacatcaccctgggcgcacacatcgtcgacggctacgggctcaccgagaccggcgccgtgacacgcgacggtg
tgatcgtgcggccaccggtgatcgactacaagctgatcgacgttcccgaactcggctacttcagcaccgacaagcc
tacccgcgtggcgaactgctggtcaggtcgcaaacgctgactcccgggtactacaagcgccccgaggtcaccgcgag
cgtcttcgaccgggacggctactaccacaccggcgacgtcatggccgagaccgcacccgaccacctggtgtacgtgg
accgtcgcaacaacgtcctcaaactcgcgcagggcgagttcgtggcggtcgccaacctggaggcggtgttctccggc
gcggcgctggtgcgccagatcttcgtgtacggcaacagcgagcgcagtttccttctggccgtggtggtcccgacgcc
ggaggcgctcgagcagtacgatccggccgcgctcaaggccgcgctggccgactcgctgcagcgcaccgcacgcgacg
ccgaactgcaatcctacgaggtgccggccgatttcatcgtcgagaccgagccgttcagcgccgccaacgggctgctg
tcgggtgtcggaaaactgctgcggcccaacctcaaagaccgctacgggcagcgcctggagcagatgtacgccgatat
cgcggccacgcaggccaaccagttgcgcgaactgcggcgcgcggccgccacacaaccggtgatcgacaccctcaccc
aggccgctgccacgatcctcggcaccgggagcgaggtggcatccgacgcccacttcaccgacctgggcggggattcc
ctgtcggcgctgacactttcgaacctgctgagcgatttcttcggtttcgaagttcccgtcggcaccatcgtgaaccc
ggccaccaacctcgcccaactcgcccagcacatcgaggcgcagcgcaccgcgggtgaccgcagggccgagtttcacca
ccgtgcacggcgcggacgccaccgagatccgggcgagtgagctgaccctggacaagttcatcgacgccgaaacgctc
cgggccgcaccgggtctgcccaaggtcaccaccgagccacggacggtgttgctctcgggcgccaacggctggctggg
ccggttcctcacgttgcagtggctggaacgcctggcacctgtcggcggcacccctcatcacgatcgtgcggggccgcg
acgacgccgcggcccgcgcacggctgacccaggcctacgacaccgatcccgagttgtcccgccgcttcgccgagctg
gccgaccgccacctgcgggtggtcgccggtgacatcggcgacccgaatctgggcctcacacccgagatctggcaccg
gctcgccgccgaggtcgacctggtggtgcatccggcagcgctggtcaaccacgtgctccctaccggcagctgttcg
gccccaacgtcgtgggcacggccgaggtgatcaagctggccctcaccgaacggatcaagcccgtcacgtacctgtcc
accgtgtcggtggccatggggatccccgacttcgaggaggacggcgacatccggaccgtgagcccggtgccgcccgct
cgacggcggatacgccaacggctacggcaacagcaagtgggccggcgaggtgctgctgcgggaggcccacgatctgt
gcgggctgcccgtggcgacgttccgctcggacatgatcctggcgcatccgcgctaccgcggtcaggtcaacgtgcca
```

FIG. 14A gacatgttcacgcgactcctgttgagcctcttgatcaccggcgtcgcgccgcggtcgttctacatcggagacggtga
gcgcccgcgggcgcactaccccggcctgacggtcgatttcgtggccgaggcggtcacgacgctcggcgcgcagcagc
gcgagggatacgtgtcctacgacgtgatgaacccgcacgacgacgggatctccctggatgtgttcgtggactggctg
atccgggcgggccatccgatcgaccgggtcgacgactacgacgactgggtgcgtcggttcgagaccgcgttgaccgc
gcttcccgagaagcgccgcgcacagaccgtactgccgctgctgcacgcgttccgcgctccgcaggcaccgttgcgcg
gcgcacccgaacccacggaggtgttccacgccgcggtgcgcaccgcgaaggtggggcccggggagacatcccgcacctc
gacgaggcgctgatcgacaagtacatacgcgatctgcgtgagttcggtctgatctaa

FIG. 14A Cont.

MTSDVHDATDGVTETALDDEQSTRRIAELYATDPEFAAAAPLPAVVDAAHKPGLRLAEILQTLFTGYGDRPALGYRA
RELATDEGGRTVTRLLPRFDTLTYAQVWSRVQAVAAALRHNFAQPIYPGDAVATIGFASPDYLTLDLVCAYLGLVSV
PLQHNAPVSRLAPILAEVEPRILTVSAEYLDLAVESVRDVNSVSQLVVFDHHPEVDDHRDALARAREQLAGKGIAVT
TLDAIADEGAGLPAEPIYTADHDQRLAMILYTSGSTGAPKGAMYTEAMVARLWTMSFITGDPTPVINVNFMPLNHLG
GRIPISTAVQNGGTSYFVPESDMSTLFEDLALVRPTELGLVPRVADMLYQHHLATVDRLVTQGADELTAEKQAGAEL
REQVLGGRVITGFVSTAPLAAEMRAFLDITLGAHIVDGYGLTETGAVTRDGVIVRPPVIDYKLIDVPELGYFSTDKP
YPRGELLVRSQTLTPGYYKRPEVTASVFDRDGYYHTGDVMAETAPDHLVYVDRRNNVLKLAQGEFVAVANLEAVFSG
AALVRQIFVYGNSERSFLLAVVVPTPEALEQYDPAALKAALADSLQRTARDAELQSYEVPADFIVETEPFSAANGLL
SGVGKLLRPNLKDRYGQRLEQMYADIAATQANQLRELRRAAATQPVIDTLTQAAATILGTGSEVASDAHFTDLGGDS
LSALTLSNLLSDFFGFEVPVGTIVNPATNLAQLAQHIEAQRTAGDRRPSFTTVHGADATEIRASELTLDKFIDAETL
RAAPGLPKVTTEPRTVLLSGANGWLGRFLTLQWLERLAPVGGTLITIVRGRDDAAARARLTQAYDTDPELSRRFAEL
ADRHLRVVAGDIGDPNLGLTPEIWHRLAAEVDLVVHPAALVNHVLPYRQLFGPNVVGTAEVIKLALTERIKPVTYLS
TVSVAMGIPDFEEDGDIRTVSPVRPLDGGYANGYGNSKWAGEVLLREAHDLCGLPVATFRSDMILAHPRYRGQVNVP
DMFTRLLLSLLITGVAPRSFYIGDGERPRAHYPGLTVDFVAEAVTTLGAQQREGYVSYDVMNPHDDGISLDVFVDWL
IRAGHPIDRVDDYDDWVRRFETALTALPEKRRAQTVLPLLHAFRAPQAPLRGAPEPTEVFHAAVRTAKVGPGDIPHL
DEALIDKYIRDLREFGLI

FIG. 14B atgtcgactgccacccatgacgaacgactcgaccgtcgcgtccacgaactcatcgccaccgacccgcaattcgccgc
cgcccaacccgacccggcgatcaccgccgccctcgaacagcccgggctgcggctgccgcagatcatccgcaccgtgc
tcgacggctacgccgaccggccggcgctgggacagcgcgtggtggagttcgtcacggacgccaagaccgggcgcacg
tcggcgcagctgctccccgcttcgagaccatcacgtacagcgaagtagcgcagcgtgtttcggcgctgggccgcgc
cctgtccgacgacgcggtgcaccccggcgaccgggtgtgcgtgctgggcttcaacagcgtcgactacgccaccatcg
acatggcgctgggcgccatcggcgccgtctcggtgccgctgcagaccagcgcggcaatcagctcgctgcagccgatc
gtggccgagaccgagcccaccctgatcgcgtccagcgtgaaccagctgtccgacgcggtgcagctgatcaccggcgc
cgagcaggcgcccacccggctggtggtgttcgactaccacccgcaggtcgacgaccagcgcgaggccgtccaggacg
ccgcggcgcggctgtccagcaccggcgtggccgtccagacgctggccgagctgctggagcgcggcaaggacctgccc
gccgtcgcggagccgcccgccgacgaggactcgctggccctgctgatctacacctccgggtccaccggcgcccccaa
gggcgcgatgtacccacagagcaacgtcggcaagatgtggcgccgcggcagcaagaactggttcggcgagagcgccg
cgtcgatcaccctgaacttcatgccgatgagccacgtgatgggccgaagcatcctctacggcacgctgggcaacggc
ggcaccgcctacttcgccgcccgcagcgacctgtccaccctgcttgaggacctcgagctggtgcggccccaccgagct
caacttcgtcccgcgggatctgggagacgctgtacggcgaattccagcgtcaggtcgagcggcggctctccgaggccg
gggacgccggcgaacgtcgcgccgtcgaggccgaggtgctggccgagcagcgccagtacctgctgggcgggcggttc
accttcgcgatgacgggctcggcgcccatctcgccggagctgcgcaactgggtcgagtcgctgctcgaaatgcacct
gatggacggctacggctccaccgaggccggaatggtgttgttcgacggggagattcagcgcccgccggtgatcgact
acaagctggtcgacgtgccggacctgggctacttcagcaccgaccggccgcatccgcgcggcgagctgctgctgcgc
accgagaacatgttccccgggctactacaagcgggccgaaaccaccgcggggcgtcttcgacgaggacggctactaccg
caccggcgacgtgttcgccgagatcgccccggaccggctggtctacgtcgaccgccgcaacaacgtgctcaagctgg
cgcagggcgaattcgtcacgctggccaagctggaggcggtgttcggcaacagcccgctgatccgccagatctacgtc
tacggcaacagcgcccagcccatcctgctggcggtcgtggtgcccaccgaggaggcgctggcctcgggtgaccccga
gacgctcaagcccaagatcgccgactcgctgcagcaggtcgccaaggaggccggcctgcagtcctacgaggtgccgc
gcgacttcatcatcgagaccaccccgttcagcctggaaaacggtctgctgaccgggatccggaagctggcgtggccg
aaactgaagcagcactacggggaacggctggagcagatgtacgccgacctggccgccggacaggccaacgagctggc
cgagctgcgccgcaacggtgcccaggcgccggtgttgcagaccgtgagccgcgccgcgggcgccatgctgggttcgg
ccgcctccgacctgtccccgacgccccacttcaccgatctgggcggagactcgttgtcggcgttgacattcggcaac
ctgctgcgcgagatcttcgacgtcgacgtgccggtaggcgtgatcgtcagcccggccaacgacctggcggccatcgc
gagctacatcgaggccgagcggcagggcagcaagcgccccgacgttcgcctcggtgcacgccgggacgcgaccgtgg
tgcgcgccgccgacctgacgctggacaagttcctcgacgccgagacgctggccgccgcgccgaacctgcccaagccg
gccaccgaggtgcgcaccgtgctgctgaccggcgccaccggcttcctgggccgctacctggccctggaatggctgga
gcggatggacatggtggacggcaaggtcatcgccctggtccgggcccgctccgacgaggaggcacgcgcccggctgg
acaagaccttcgacagcggcgacccgaaactgctcgcgcactaccagcagctggccgccgatcacctggaggtcatc
gccggcgacaagggcgaggccaatctgggccctgggccaagacgtttggcaacgactggccgacacggtcgacgtgat
cgtcgaccccgccgcgctggtcaaccacgtgttgccgtacagcgagctgttcgggcccaacgccctgggcaccgcgg
agctgatccggctggcgctgacgtccaagcagaagccgtacacctacgtgtccaccatcggcgtgggcgaccagatc
gagccgggcaagttcgtcgagaacgccgacatccggcagatgagcgccacccggggcgatcaacgacagctacgccaa
cggctatggcaacagcaagtgggccggcgaggtgctgctgcgcgaggcgcacgacctgtgcgggctgccgtcgcgg
tgttccgctgcgacatgatcctggccgacaccacgtatgccgggcagctcaacctgccggacatgttcacccggctg atgctgagcctggtggccaccgggatcgcgcccggctcgttctacgagctcgacgccgacggcaaccggcagcgggc
gcactacgacggcctgccggtcgagttcatcgccgcggcgatctcgacgctgggttcgagatcaccgacagcgaca
ccggcttccagacctaccacgtgatgaaccccracgatgacggcgtcggtctggacgagtacgtcgattggctggtg
gacgccggctattcgatcgagcggatcgccgactactccgaatggctgcggcggttcgagacctcgctgcgggccct
gccggaccggcagcgccagtactcgctgctgccgctgctgcacaactaccgcacgccggagaagccgatcaacggt
cgatagctccccaccgacgtgttccgggcagcggtgcaggaggcgaaaatcggccccgacaaagacattccgcacgtg
tcgccgccggtcatcgtcaagtacatcaccgacctgcagctgctcgggctgctctaa

FIG. 15A Cont.

MSTATHDERLDRRVHELIATDPQFAAAQPDPAITAALEQPGLRLPQIIRTVLDGYADRPALGQRVVEFVTDAKTGRT
SAQLLPRFETITYSEVAQRVSALGRALSDDAVHPGDRVCVLGFNSVDYATIDMALGAIGAVSVPLQTSAAISSLQPI
VAETEPTLIASSVNQLSDAVQLITGAEQAPTRLVVFDYHPQVDDQREAVQDAAARLSSTGVAVQTLAELLERGKDLP
AVAEPPADEDSLALLIYTSGSTGAPKGAMYPQSNVGKMWRRGSKNWFGESAASITLNFMPMSHVMGRSILYGTLGNG
GTAYFAARSDLSTLLEDLELVRPTELNFVPRIWETLYGEFQRQVERRLSEAGDAGERRAVEAEVLAEQRQYLLGGRF
TFAMTGSAPISPELRNWVESLLEMHLMDGYGSTEAGMVLFDGEIQRPPVIDYKLVDVPDLGYFSTDRPHPRGELLLR
TENMFPGYYKRAETTAGVFDEDGYYRTGDVFAEIAPDRLVYVDRRNNVLKLAQGEFVTLAKLEAVFGNSPLIRQIYV
YGNSAQPYLLAVVVPTEEALASGDPETLKPKIADSLQQVAKEAGLQSYEVPRDFIIETTPFSLENGLLTGIRKLAWP
KLKQHYGERLEQMYADLAAGQANELAELRRNGAQAPVLQTVSRAAGAMLGSAASDLSPDAHFTDLGGDSLSALTFGN
LLREIFDVDVPVGVIVSPANDLAAIASYIEAERQGSKRPTFASVHGRDATVVRAADLTLDKFLDAETLAAAPNLPKP
ATEVRTVLLTGATGFLGRYLALEWLERMDMVDGKVIALVRARSDEEARARLDKTFDSGDPKLLAHYQQLAADHLEVI
AGDKGEANLGLGQDVWQRLADTVDVIVDPAALVNHVLPYSELFGPNALGTAELIRLALTSKQKPYTYVSTIGVGDQI
EPGKFVENADIRQMSATRAINDSYANGYGNSKWAGEVLLREAHDLCGLPVAVFRCDMILADTTYAGQLNLPDMFTRL
MLSLVATGIAPGSFYELDADGNRQRAHYDGLPVEFIAAAISTLGSQITDSDTGFQTYHVMNPYDDGVGLDEYVDWLV
DAGYSIERIADYSEWLRRFETSLRALPDRQRQYSLLPLLHNYRTPEKPINGSIAPTDVFRAAVQEAKIGPDKDIPHV
SPPVIVKYITDLQLLGLL

FIG. 15B atgtcgccaatcacgcgtgaagagcggctcgagcgccgcatccaggacctctacgccaacgacccgcagttcgccgc
cgccaaacccgccacggcgatcaccgcagcaatcgagcggccgggtctaccgctaccccagatcatcgagaccgtca
tgaccggatacgccgatcggccggctctcgctcagcgctcggtcgaattcgtgaccgacgccggcaccggccacacc
acgctgcgactgctcccccacttcgaaaccatcagctacggcgagctttgggaccgcatcagcgcactggccgacgt
gctcagcaccgaacagacggtgaaaccgggcgaccgggtctgcttgttgggcttcaacagcgtcgactacgccacga
tcgacatgactttggcgcggctgggcgcggtggccgtaccactgcagaccagcgcggcgataacccagctgcagccg
atcgtcgccgagacccagcccaccatgatcgcggccagcgtcgacgcactcgctgacgccaccgaattggctctgtc
cggtcagaccgctacccgagtcctggtgttcgaccaccaccggcaggttgacgcacaccgcgcagcggtcgaatccg
cccggggagcgcctggccggctcggcggtcgtcgaaaccctggccgaggccatcgcgcgcggcgacgtgccccgcggt
gcgtccgccggctcggcgcccggcaccgatgtgtccgacgactcgctcgcgctactgatctacacctcgggcagcac
gggtgcgcccaagggcgcgatgtaccccgacgcaacgttgcgaccttctggcgcaagcgcacctggttcgaaggcg
gctacgagccgtcgatcacgctgaacttcatgccaatgagccacgtcatgggccgccaaatcctgtacggcacgctg
tgcaatggcggcaccgcctacttcgtggcgaaaagcgatctctccaccttgttcgaagacctggcgctggtgcggcc
caccgagctgaccttcgtgccgcgcgtgtgggacatggtgttcgacgagtttcagagtgaggtcgaccgccgcctgg
tcgacggcgccgaccgggtcgcgctcgaagcccaggtcaaggccgagatacgcaacgacgtgctcggtggacggtat
accagcgcactgaccggctccgcccctatctccgacgagatgaaggcgtgggtcgaggagctgctcgacatgcatct
ggtcgagggctacggctccaccgaggccgggatgatcctgatcgacggagccattcggcgcccggcggtactcgact
acaagctggtcgatgttcccgacctgggttacttcctgaccgaccggccacatccgcggggcgagttgctggtcaag
accgatagtttgttcccgggctactaccagcgagccgaagtcaccgccgacgtgttcgatgctgacggcttctaccg
gaccggcgacatcatggccgaggtcggccccgaacagttcgtgtacctcgaccgccgcaacaacgtgttgaagctgt
cgcagggcgagttcgtcaccgtctccaaactcgaagcggtgtttggcgacagcccactggtacggcagatctacatc
tacggcaacagcgcccgtgcctacctgttggcggtgatcgtcccccaccccaggaggcgctggacgccgtgcctgtcga
ggagctcaaggcgcggctgggcgactcgctgcaagaggtcgcaaaggccgccggcctgcagtcctacgagatcccgc
gcgacttcatcatcgaaacaacaccatggacgctggagaacggcctgctcaccggcatccgcaagttggccaggccg
cagctgaaaaagcattacggcgagcttctcgagcagatctacacggacctggcacacggccaggccgacgaactgcg
ctcgctgcgccaaagcggtgccgatgcgccggtgctggtgacggtgtgccgtgcggcggccgcgctgtttgggcggca
gcgcctctgacgtccagcccgatgcgcacttcaccgatttgggcggcgactcgctgtcggcgctgtcgttcaccaac
ctgctgcacgagatcttcgacatcgaagtgccggtgggcgtcatcgtcagccccgccaacgacttgcaggccctggc
cgactacgtcgaggcggctcgcaaacccggctcgtcacggccgaccttcgcctcggtccacggcgcctcgaatgggc
aggtcaccgaggtgcatgccggtgacctgtccctggacaaattcatcgatgccgcaaccctggccgaagctccccgg
ctgcccgccgcaaacacccaagtgcgcaccgtgctgctgaccggcgccaccggcttcctcgggcgctacctggcccct
ggaatggctggagcggatggacctggtcgacggcaaactgatctgcctggtccgggccaagtccgacaccgaagcac
gggcgcggctggacaagacgttcgacagcggcgaccccgaactgctggcccactaccgcgcactggccggcgaccac
ctcgaggtgctcgccggtgacaagggcgaagccgacctcggactggaccggcagacctggcaacgcctggccgacac
ggtcgacctgatcgtcgaccccgcggccctggtcaaccacgtactgccatacagccagctgttcgggcccaacgcgc
tgggcaccgccgagctgctgcggctggcgctcacctccaagatcaagcccacagctacacctcgacaatcggtgtc
gccgaccagatcccgccgtcggcgttcaccgaggacgccgacatccgggtcatcagcgccaccccgcgcggtcgacga
cagctacgccaatggctactcgaacagcaagtgggccggcgaggtgctgttgcgcgaggcgcatgacctgtgtggcc
tgccggttgcggtgttccgctgcgacatgatcctggccgacaccacatgggcgggacagctcaatgtgccggacatg
ttcacccggatgatcctgagcctggcggccaccggtatcgcgccgggttcgttctatgagcttgcggccgacggcgc

FIG. 16A ccggcaacgcgcccactatgacggtctgcccgtcgagttcatcgccgaggcgatttcgactttgggtgcgcagagcc
aggatggtttccacacgtatcacgtgatgaaccctacgacgacggcatcggactcgacgagttcgtcgactggctc
aacgagtccggttgccccatccagcgcatcgctgactatggcgactggctgcagcgcttcgaaaccgcactgcgcgc
actgcccgatcggcagcggcacagctcactgctgccgctgttgcacaactatcggcagccggagcggcccgtccgcg
ggtcgatcgccctaccgatcgcttccgggcagcggtgcaagaggccaagatcggccccgacaaagacattccgcac
gtcggcgcgccgatcatcgtgaagtacgtcagcgacctgcgcctactcggcctgctctaa

FIG. 16A cont.

MSPITREERLERRIQDLYANDPQFAAAKPATAITAAIERPGLPLPQIIETVMTGYADRPALAQRSVEFVTDAGTGHT
TLRLLPHFETISYGELWDRISALADVLSTEQTVKPGDRVCLLGFNSVDYATIDMTLARLGAVAVPLQTSAAITQLQP
IVAETQPTMIAASVDALADATELALSGQTATRVLVFDHHRQVDAHRAAVESARERLAGSAVVETLAEAIARGDVPRG
ASAGSAPGTDVSDDSLALLIYTSGSTGAPKGAMYPRRNVATFWRKRTWFEGGYEPSITLNFMPMSHVMGRQILYGTL
CNGGTAYFVAKSDLSTLFEDLALVRPTELTFVPRVWDMVFDEFQSEVDRRLVDGADRVALEAQVKAEIRNDVLGGRY
TSALTGSAPISDEMKAWVEELLDMHLVEGYGSTEAGMILIDGAIRRPAVLDYKLVDVPDLGYFLTDRPHPRGELLVK
TDSLFPGYYQRAEVTADVFDADGFYRTGDIMAEVGPEQFVYLDRRNNVLKLSQGEFVTVSKLEAVFGDSPLVRQIYI
YGNSARAYLLAVIVPTQEALDAVPVEELKARLGDSLQEVAKAAGLQSYEIPRDFIIETTPWTLENGLLTGIRKLARP
QLKKHYGELLEQIYTDLAHGQADELRSLRQSGADAPVLVTVCRAAAALLGGSASDVQPDAHFTDLGGDSLSALSFTN
LLHEIFDIEVPVGVIVSPANDLQALADYVEAARKPGSSRPTFASVHGASNGQVTEVHAGDLSLDKFIDAATLAEAPR
LPAANTQVRTVLLTGATGFLGRYLALEWLERMDLVDGKLICLVRAKSDTEARARLDKTFDSGDPELLAHYRALAGDH
LEVLAGDKGEADLGLDRQTWQRLADTVDLIVDPAALVNHVLPYSQLFGPNALGTAELLRLALTSKIKPYSYTSTIGV
ADQIPPSAFTEDADIRVISATRAVDDSYANGYSNSKWAGEVLLREAHDLCGLPVAVFRCDMILADTTWAGQLNVPDM
FTRMILSLAATGIAPGSFYELAADGARQRAHYDGLPVEFIAEAISTLGAQSQDGFHTYHVMNPYDDGIGLDEFVDWL
NESGCPIQRIADYGDWLQRFETALRALPDRQRHSSLLPLLHNYRQPERPVRGSIAPTDRFRAAVQEAKIGPDKDIPH
VGAPIIVKYVSDLRLLGLL

FIG. 16B atgagcaccgcaacccatgatgaacgtctggatcgtcgtgttcatgaactgattgcaaccgatc
cgcagtttgcagcagcacagccggatcctgcaattaccgcagcactggaacagcctggtctgcg
tctgccgcagattattcgtaccgttctggatggttatgcagatcgtccggcactgggtcagcgt
gttgttgaatttgttaccgatgcaaaaaccggtcgtaccagcgcacagctgctgcctcgttttg
aaaccattacctatagcgaagttgcacagcgtgttagcgcactgggtcgtgcactgagtgatga
tgcagttcatccgggtgatcgtgttttgtgttctgggttttaatagcgttgattatgccaccatt
gatatggcactgggtgcaattggtgcagttagcgttccgctgcagaccagcgcagcaattagca
gcctgcagccgattgttgcagaaaccgaaccgaccctgattgcaagcagcgttaatcagctgtc
agatgcagttcagctgattaccggtgcagaacaggcaccgacccgtctggttgttttttgattat
catccgcaggttgatgatcagcgtgaagcagttcaggatgcagcagcacgtctgagcagcaccg
gtgttgcagttcagaccctggcagaactgctggaacgtggtaaagatctgcctgcagttgcaga
accgcctgcagatgaagatagcctggcactgctgatttataccagcggtagcacaggtgcaccg
aaaggtgcaatgtatccgcagagcaatgttggtaaaatgtggcgtcgtggtagcaaaaattggt
ttggtgaaagcgcagcaagcattaccctgaatttcatgccgatgagccatgttatgggtcgtag
cattctgtatggcacccctgggtaatggtggcaccgcatattttgcagcacgtagcgatctgagc
accctgctggaagatctggaactggttcgtccgaccgaactgaattttgttccgcgtatttggg
aaaccctgtatggtgaatttcagcgtcaggttgaacgtcgtctgagcgaagctggcgatgccgg
tgaacgtcgtgcagttgaagcagaagttctggcagaacagcgtcagtatctgctgggtggtcgt
tttacctttgcaatgaccggtagcgcaccgattagtccggaactgcgtaattgggttgaaagcc
tgctggaaatgcatctgatggatggctatggtagcaccgaagcaggtatggttctgtttgatgg
cgaaattcagcgtccgcctgtgattgattataaactggttgatgttccggatctgggttattt
agcaccgatcgtccgcatccgcgtggtgaactgctgctgcgtaccgaaaatatgtttccgggtt
attataaacgtgcagaaaccaccgcaggcgttttttgatgaagatggttattatcgtaccggtga
tgtgtttgcagaaattgcaccggatcgtctggtttatgttgatcgtcgtaataatgttctgaaa
ctggcacagggtgaatttgtgaccctggccaaactggaagcagttttttggtaatagtccgctga
ttcgtcagatttatgtgtatggtaatagcgcacagccgtatctgctggcagttgttgttccgac
cgaagaggcactggcaagcggtgatccggaaaccctgaaaccgaaaattgcagatagcctgcag
caggttgcaaaagaagcaggtctgcagagctatgaagttccgcgtgattttattattgaaacca
ccccgtttagcctggaaaatggtctgctgaccggtattcgtaaactggcatggccgaaactgaa
acagcattatggtgaacgcctggaacaaatgtatgcagatctggcagcaggtcaggcaaatgaa
ctggccgaactgcgtcgtaatggtgcacaggcaccggttctgcagaccgttagccgtgcagccg
gtgcaatgctgggtagcgcagccagcgatctgagtccggatgcacattttaccgatctgggtgg
tgatagcctgagcgcactgaccctttggtaatctgctgcgtgaaattttttgatgttgatgtgccg
gttggtgttattgttagtccggctaatgatctggcagccattgcaagctatattgaagcagaac
gtcagggtagcaaacgtccgaccttttgcaagcgttcatggtcgtgatgcaaccgttgttcgtgc
agcagatctgaccctggataaatttctggatgcagaaaccctggcagcagcaccgaatctgccg
aaaccggcaaccgaagttcgtaccgtgctgctgacaggtgcaaccggttttctgggtcgttatc
tggcactggaatggctggaacgtatggatatggttgatggtaaagttattgcactggttcgtgc
ccgtagtgatgaagaagcacgcgcacgtctggataaaacctttgatagtggtgatccgaaactg
ctggcacattatcagcagctggctgcagatcatctggaagttattgccggtgataaaggtgaag
caaatctgggtctgggtcaggatgtttggcagcgtctggcagataccgttgatgttattgtgga

FIG. 17A

```
tccggcagcactggttaatcatgttctgccgtatagcgaactgtttggtccgaatgcactgggc
accgcagaactgattcgtctggcactgaccagcaaacagaaaccgtatacctatgttagcacca
ttggtgttggcgatcagattgaaccgggtaaatttgttgaaaatgccgatattcgtcagatgag
cgcaaacccgtgcaattaatgatagctatgcaaatggctacggcaatagcaaatgggcaggcgaa
gttctgctgcgcgaagcacatgatctgtgtggtctgccggttgcagttttcgttgtgatatga
ttctggccgataccacctatgcaggtcagctgaatctgccggatatgtttacccgtctgatgct
gagcctggttgcaaccggtattgcaccgggtagcttttatgaactggatgcagatggtaatcgt
cagcgtgcacattatgatggcctgccggttgaatttattgcagcagccattagcaccctgggtt
cacagattaccgatagcgataccggttttcagacctatcatgttatgaacccgtatgatgatgg
tgttggtctggatgaatatgttgattggctggttgatgccggttatagcattgaacgtattgca
gattatagcgaatggctgcgtcgctttgaaacctcactgcgtgcactgccggatcgtcagcgcc
agtatagcctgctgccgctgctgcacaattatcgtacaccggaaaaaccgattaatggtagcat
tgcaccgaccgatgtttttcgtgcagccgttcaagaagccaaaattggtccggataaagatatt
ccgcatgttagccctccggtgattgttaaatatattaccgatctgcagctgctgggtctgctgt
aa
```

FIG 17A cont.

```
MSTATHDERLDRRVHELIATDPQFAAAQPDPAITAALEQPGLRLPQIIRTVLDGYADRPALGQR
VVEFVTDAKTGRTSAQLLPRFETITYSEVAQRVSALGRALSDDAVHPGDRVCVLGFNSVDYATI
DMALGAIGAVSVPLQTSAAISSLQPIVAETEPTLIASSVNQLSDAVQLITGAEQAPTRLVVFDY
HPQVDDQREAVQDAAARLSSTGVAVQTLAELLERGKDLPAVAEPPADEDSLALLIYTSGSTGAP
KGAMYPQSNVGKMWRRGSKNWFGESAASITLNFMPMSHVMGRSILYGTLGNGGTAYFAARSDLS
TLLEDLELVRPTELNFVPRIWETLYGEFQRQVERRLSEAGDAGERRAVEAEVLAEQRQYLLGGR
FTFAMTGSAPISPELRNWVESLLEMHLMDGYGSTEAGMVLFDGEIQRPPVIDYKLVDVPDLGYF
STDRPHPRGELLLRTENMFPGYYKRAETTAGVFDEDGYYRTGDVFAEIAPDRLVYVDRRNNVLK
LAQGEFVTLAKLEAVFGNSPLIRQIYVYGNSAQPYLLAVVVPTEEALASGDPETLKPKIADSLQ
QVAKEAGLQSYEVPRDFIIETTPFSLENGLLTGIRKLAWPKLKQHYGERLEQMYADLAAGQANE
LAELRRNGAQAPVLQTVSRAAGAMLGSAASDLSPDAHFTDLGGDSLSALTFGNLLREIFDVDVP
VGVIVSPANDLAAIASYIEAERQGSKRPTFASVHGRDATVVRAADLTLDKFLDAETLAAAPNLP
KPATEVRTVLLTGATGFLGRYLALEWLERMDMVDGKVIALVRARSDEEARARLDKTFDSGDPKL
LAHYQQLAADHLEVIAGDKGEANLGLGQDVWQRLADTVDVIVDPAALVNHVLPYSELFGPNALG
TAELIRLALTSKQKPYTYVSTIGVGDQIEPGKFVENADIRQMSATRAINDSYANGYGNSKWAGE
VLLREAHDLCGLPVAVFRCDMILADTTYAGQLNLPDMFTRLMLSLVATGIAPGSFYELDADGNR
QRAHYDGLPVEFIAAAISTLGSQITDSDTGFQTYHVMNPYDDGVGLDEYVDWLVDAGYSIERIA
DYSEWLRRFETSLRALPDRQRQYSLLPLLHNYRTPEKPINGSIAPTDVFRAAVQEAKIGPDKDI
PHVSPPVIVKYITDLQLLGLL
```

FIG. 17B

SEQUENCE LISTING

```
<160> NUMBER OF SEQ ID NOS: 12

<210> SEQ ID NO 1
<211> LENGTH: 3525
<212> TYPE: DNA
<213> ORGANISM: Nocardia iowensis

<400> SEQUENCE: 1
atggcagtgg attcaccgga tgagcggcta cagcgccgca ttgcacagtt gtttgcagaa      60
gatgagcagg tcaaggccgc acgtccgctc gaagcggtga gcgcggcggt gagcgcgccc     120
ggtatgcggc tggcgcagat cgccgccact gttatggcgg gttacgccga ccgcccggcc     180
gccgggcagc gtgcgttcga actgaacacc gacgacgcga cgggccgcac ctcgctgcgg     240
ttacttcccc gattcgagac catcacctat cgcgaactgt ggcagcgagt cggcgaggtt     300
gccgcggcct ggcatcatga tcccgagaac cccttgcgcg caggtgattt cgtcgccctg     360
ctcggcttca ccagcatcga ctacgccacc ctcgacctgg ccgatatcca cctcggcgcg     420
gttaccgtgc cgttgcaggc cagcgcggcg gtgtcccagc tgatcgctat cctcaccgag     480
acttcgccgc ggctgctcgc ctcgaccccg gagcacctcg atgcggcggt cgagtgccta     540
ctcgcgggca ccacaccgga acgactggtg gtcttcgact accaccccga ggacgacgac     600
cagcgtgcgg ccttcgaatc cgcccgccgc cgccttgccg acgcgggcag cttggtgatc     660
gtcgaaacgc tcgatgccgt gcgtgcccgg ggccgcgact accggccgcc gccactgttc     720
gttccgacca ccgacgacga cccgctggcc ctgctgatct acacctccgg cagcaccgga     780
acgccgaagg gcgcgatgta caccaatcgg ttggccgcca cgatgtggca ggggaactcg     840
atgctgcagg ggaactcgca acgggtcggg atcaatctca actacatgcc gatgagccac     900
atcgccggtc gcatatcgct gttcggcgtg ctcgctcgcg gtggcaccgc atacttcgcg     960
gccaagagcg acatgtcgac actgttcgaa gacatcggct tggtacgtcc caccgagatc    1020
ttcttcgtcc cgcgcgtgtg cgacatggtc ttccagcgct atcagagcga gctgaccgg    1080 cgctcggtgg cgggcgccga cctggacacg ctcgatcggg aagtgaaagc cgacctccgg    1140
cagaactacc tcggtgggcg cttcctggtg gcggtcgtcg gcagcgcgcc gctggccgcg    1200
gagatgaaga cgttcatgga gtccgtcctc gatctgccac tgcacgacgg gtacgggtcg    1260
accgaggcgg cgcaagcgt gctgctcgac aaccagatcc agcggccgcc ggtgctcgat    1320
tacaagctcg tcgacgtgcc cgaactgggt tacttccgca ccgaccggcc gcatccgcgc    1380
ggtgagctgt tgttgaaggc ggagaccacg attccgggct actacaagcg gcccgaggtc    1440
accgcggaga tcttcgacga ggacggcttc tacaagaccg gcgatatcgt ggccgagctc    1500
gagcacgatc ggctggtcta tgtcgaccgt cgcaacaatg tgctcaaact gtcgcagggc    1560
gagttcgtga ccgtcgccca tctcgaggcc gtgttcgcca gcagcccgct gatcggcag    1620 atcttcatct acggcagcag cgaacgttcc tatctgctcg cggtgatcgt ccccaccgac    1680
gacgcgctgc gcggccgcga caccgccacc ttgaaatcgg cactggccga atcgattcag    1740
```

```
cgcatcgcca aggacgcgaa cctgcagccc tacgagattc cgcgcgattt cctgatcgag    1800
accgagccgt tcaccatcgc caacggactg ctctccggca tcgcgaagct gctgcgcccc    1860
aatctgaagg aacgctacgg cgctcagctg gagcagatgt acaccgatct cgcgacaggc    1920
caggccgatg agctgctcgc cctgcgccgc gaagccgccg acctgccggt gctcgaaacc    1980
gtcagccggg cagcgaaagc gatgctcggc gtcgcctccg ccgatatgcg tcccgacgcg    2040
cacttcaccg acctgggcgg cgattcccct tccgcgctgt cgttctcgaa cctgctgcac    2100
gagatcttcg ggtcgaggt gccggtgggt gtcgtcgtca gcccggcgaa cgagctgcgc    2160
gatctggcga attacattga gcggaacgca aactcgggcg cgaagcgtcc caccttcacc    2220
tcggtgcacg gcggcggttc cgagatccgc gccgccgatc tgaccctcga caagttcatc    2280
gatgcccgca ccctggccgc cgccgacagc attccgcacg cgccggtgcc agcgcagacg    2340
gtgctgctga ccggcgcgaa cggctacctc ggccggttcc tgtgcctgga atggctggag    2400
cggctggaca agacggggtgg cacgctgatc tgcgtcgtgc gcggtagtga cgcggccgcg    2460
gcccgtaaac ggctggactc ggcgttcgac agcggcgatc ccggcctgct cgagcactac    2520
cagcaactgg ccgcacggac cctggaagtc ctcgccggtg atatcggcga cccgaatctc    2580
ggtctggacg acgcgacttg gcagcggttg gccgaaaccg tcgacctgat cgtccatccc    2640
gccgcgttgg tcaaccacgt ccttccctac acccagctgt tcggcccaa tgtcgtcggc    2700 accgccgaaa tcgtccggtt ggcgatcacg gcgcggcgca agccggtcac ctacctgtcg    2760
accgtcggag tggccgacca ggtcgacccg cggagtatc aggaggacag cgacgtccgc    2820
gagatgagcg cggtgcgcgt cgtgcgcgag agttacgcca acggctacgg caacagcaag    2880 tgggcgggg aggtcctgct cgcgaagca cacgatctgt gtggcttgcc ggtcgcggtg    2940
ttccgttcgg acatgatcct ggcgcacagc cggtacgcg gtcagctcaa cgtccaggac    3000
gtgttcaccc ggctgatcct cagcctggtc gccaccggca tcgcgccgta ctcgttctac    3060
cgaaccgacg cggacggcaa ccggcagcgg gcccactatg acggcttgcc ggcggacttc    3120
acggcggcgg cgatcaccgc gctcggcatc aagccaccg aaggcttccg gacctacgac    3180
gtgctcaatc cgtacgacga tggcatctcc ctcgatgaat cgtcgactg gctcgtcgaa    3240 tccggccacc cgatccagcg catcaccgac tacagcgact ggttccaccg tttcgagacg    3300
gcgatccgcg cgctgccgga aaagcaacgc caggcctcgg tgctgccgtt gctgacgcc    3360 taccgcaacc cctgcccggc ggtccgcggc gcgatactcc cggccaagga gttccaagcg    3420
gcggtgcaaa cagccaaaat cggtccggaa caggacatcc gcatttgtc cgcgccactg    3480 atcgataagt acgtcagcga tctggaactg cttcagctgc tctaa                   3525
```

<210> SEQ ID NO 2  
<211> LENGTH: 1174  
<212> TYPE: PRT  
<213> ORGANISM: Nocardia iowensis

<400> SEQUENCE: 2

```
Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
```

```
                50              55              60
Ala Phe Glu Leu Asn Thr Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                    85                  90                  95

Val Gly Glu Val Ala Ala Ala Trp His His Asp Pro Glu Asn Pro Leu
                100                 105                 110

Arg Ala Gly Asp Phe Val Ala Leu Leu Gly Phe Thr Ser Ile Asp Tyr
                115                 120                 125

Ala Thr Leu Asp Leu Ala Asp Ile His Leu Gly Ala Val Thr Val Pro
                130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
                180                 185                 190

Asp Tyr His Pro Glu Asp Asp Gln Arg Ala Ala Phe Glu Ser Ala
                195                 200                 205

Arg Arg Arg Leu Ala Asp Ala Gly Ser Leu Val Ile Val Glu Thr Leu
210                 215                 220

Asp Ala Val Arg Ala Arg Gly Arg Asp Leu Pro Ala Ala Pro Leu Phe
225                 230                 235                 240

Val Pro Asp Thr Asp Asp Pro Leu Ala Leu Leu Ile Tyr Thr Ser
                    245                 250                 255

Gly Ser Thr Gly Thr Pro Lys Gly Ala Met Tyr Thr Asn Arg Leu Ala
                260                 265                 270

Ala Thr Met Trp Gln Gly Asn Ser Met Leu Gln Gly Asn Ser Gln Arg
                275                 280                 285

Val Gly Ile Asn Leu Asn Tyr Met Pro Met Ser His Ile Ala Gly Arg
                290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
                355                 360                 365

Asp Thr Leu Asp Arg Glu Val Lys Ala Asp Leu Arg Gln Asn Tyr Leu
                370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
                435                 440                 445

Leu Gly Tyr Phe Arg Thr Asp Arg Pro His Pro Arg Gly Glu Leu Leu
                450                 455                 460

Leu Lys Ala Glu Thr Thr Ile Pro Gly Tyr Tyr Lys Arg Pro Glu Val
465                 470                 475                 480
```

```
Thr Ala Glu Ile Phe Asp Glu Asp Gly Phe Tyr Lys Thr Gly Asp Ile
            485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
            515                 520                 525

Glu Ala Val Phe Ala Ser Ser Pro Leu Ile Arg Gln Ile Phe Ile Tyr
            530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
            565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
            595                 600                 605

Gly Leu Leu Ser Gly Ile Ala Lys Leu Leu Arg Pro Asn Leu Lys Glu
            610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
            645                 650                 655

Val Leu Glu Thr Val Ser Arg Ala Ala Lys Ala Met Leu Gly Val Ala
            660                 665                 670

Ser Ala Asp Met Arg Pro Asp His Phe Thr Asp Leu Gly Gly Asp
            675                 680                 685

Ser Leu Ser Ala Leu Ser Phe Ser Asn Leu Leu His Glu Ile Phe Gly
            690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
            725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
            805                 810                 815

Asp Ala Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
            835                 840                 845

Glu Val Leu Ala Gly Asp Ile Gly Asp Pro Asn Leu Gly Leu Asp Asp
            850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
            885                 890                 895
```

```
Asn Val Val Gly Thr Ala Glu Ile Val Arg Leu Ala Ile Thr Ala Arg
                900                 905                 910
Arg Lys Pro Val Thr Tyr Leu Ser Thr Val Gly Val Ala Asp Gln Val
        915                 920                 925
Asp Pro Ala Glu Tyr Gln Glu Asp Ser Asp Val Arg Glu Met Ser Ala
    930                 935                 940
Val Arg Val Val Arg Glu Ser Tyr Ala Asn Gly Tyr Gly Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Ser Asp Met Ile Leu Ala His Ser Arg Tyr
            980                 985                 990
Ala Gly Gln Leu Asn Val Gln Asp Val Phe Thr Arg Leu Ile Leu Ser
        995                 1000                1005
Leu Val Ala Thr Gly Ile Ala Pro Tyr Ser Phe Tyr Arg Thr Asp
    1010                1015                1020
Ala Asp Gly Asn Arg Gln Arg Ala His Tyr Asp Gly Leu Pro Ala
    1025                1030                1035
Asp Phe Thr Ala Ala Ala Ile Thr Ala Leu Gly Ile Gln Ala Thr
    1040                1045                1050
Glu Gly Phe Arg Thr Tyr Asp Val Leu Asn Pro Tyr Asp Asp Gly
    1055                1060                1065
Ile Ser Leu Asp Glu Phe Val Asp Trp Leu Val Glu Ser Gly His
    1070                1075                1080
Pro Ile Gln Arg Ile Thr Asp Tyr Ser Asp Trp Phe His Arg Phe
    1085                1090                1095
Glu Thr Ala Ile Arg Ala Leu Pro Glu Lys Gln Arg Gln Ala Ser
    1100                1105                1110
Val Leu Pro Leu Leu Asp Ala Tyr Arg Asn Pro Cys Pro Ala Val
    1115                1120                1125
Arg Gly Ala Ile Leu Pro Ala Lys Glu Phe Gln Ala Ala Val Gln
    1130                1135                1140
Thr Ala Lys Ile Gly Pro Glu Gln Asp Ile Pro His Leu Ser Ala
    1145                1150                1155
Pro Leu Ile Asp Lys Tyr Val Ser Asp Leu Glu Leu Leu Gln Leu
    1160                1165                1170
Leu

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      codon optimized phosphpantetheine transferase polynucleotide

<400> SEQUENCE: 3
atgattgaaa ccattctgcc tgcaggcgtt gaaagcgcag aactgctgga atatccggaa      60
gatctgaaag cacatccggc agaagaacat ctgattgcca aaagcgttga aaaacgtcgt     120
cgtgatttta ttggtgcacg tcattgtgca cgtctggcac tggcagaact gggtgaacct     180
ccggttgcaa ttggtaaagg tgaacgtggt gcaccgattt ggcctcgtgg tgttgttggt     240
agcctgaccc attgtgatgg ttatcgtgca gcagcagttg cacataaaat gcgctttcgc     300
agcattggta ttgatgcaga accgcatgca accctgccgg aaggtgttct ggatagcgtt     360
```

```
agcctgccgc cggaacgtga atggctgaaa accaccgata gcgcactgca tctggatcgt    420
ctgctgtttt gtgcaaaaga agccacctat aaagcctggt ggccgctgac agcacgttgg    480
ctgggttttg aagaagccca tattaccttt gaaattgaag atggtagcgc agatagcggt    540
aatggcacct tcatagcga actgctggtt ccgggtcaga ccaatgatgg tggtacaccg    600
ctgctgagct ttgatggtcg ttggctgatt gcagatggtt ttattctgac cgcaattgcc    660
tatgcctaa                                                            669
```

```
<210> SEQ ID NO 4
<211> LENGTH: 222
<212> TYPE: PRT
<213> ORGANISM: Artificial Sequence
<220> FEATURE:
<223> OTHER INFORMATION: Description of Artificial Sequence: Synthetic
      codon optimized phosphpantetheine transferase
      polypeptide

<400> SEQUENCE: 4

Met Ile Glu Thr Ile Leu Pro Ala Gly Val Glu Ser Ala Glu Leu Leu
  1               5                  10                  15

Glu Tyr Pro Glu Asp Leu Lys Ala His Pro Ala Glu Glu His Leu Ile
             20                  25                  30

Ala Lys Ser Val Glu Lys Arg Arg Asp Phe Ile Gly Ala Arg His
         35                  40                  45

Cys Ala Arg Leu Ala Leu Ala Glu Leu Gly Glu Pro Val Ala Ile
     50                  55                  60

Gly Lys Gly Glu Arg Gly Ala Pro Ile Trp Pro Arg Gly Val Val Gly
 65                  70                  75                  80

Ser Leu Thr His Cys Asp Gly Tyr Arg Ala Ala Ala Val Ala His Lys
                 85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
        115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 5
<211> LENGTH: 3522
<212> TYPE: DNA
<213> ORGANISM: Mycobacterium smegmatis

<400> SEQUENCE: 5
atgaccagcg atgttcacga cgccacagac ggcgtcaccg aaaccgcact cgacgacgag     60
cagtcgaccc gccgcatcgc cgagctgtac gccaccgatc ccgagttcgc cgccgccgca    120
ccgttgcccg ccgtggtcga cgcggcgcac aaacccgggc tgcggctggc agagatcctg    180
```

```
cagaccctgt tcaccggcta cggtgaccgc ccggcgctgg gataccgcgc ccgtgaactg    240
gccaccgacg agggcgggcg caccgtgacg cgtctgctgc cgcggttcga cacctcacc     300 tacgcccagg tgtggtcgcg cgtgcaagcg gtcgccgcgg ccctgcgcca caacttcgcg    360
cagccgatct accccggcga cgccgtcgcg acgatcggtt tcgcgagtcc cgattacctg    420
acgctggatc tcgtatgcgc ctacctgggc ctcgtgagtg ttccgctgca gcacaacgca    480
ccggtcagcc ggctcgcccc gatcctggcc gaggtcgaac cgcggatcct caccgtgagc    540
gccgaatacc tcgacctcgc agtcgaatcc gtgcgggacg tcaactcggt gtcgcagctc    600
gtggtgttcg accatcaccc cgaggtcgac gaccaccgcg acgcactggc ccgcgcgcgt    660
gaacaactcg ccggcaaggg catcgccgtc accaccctgg acgcgatcgc cgacgagggc    720
gccgggctgc cggccgaacc gatctacacc gccgaccatg atcagcgcct cgcgatgatc    780
ctgtacacct cgggttccac cggcgcaccc aagggtgcga tgtacaccga ggcgatggtg    840
gcgcggctgt ggaccatgtc gttcatcacg ggtgaccca cgccggtcat caacgtcaac     900
ttcatgccgc tcaaccacct gggcgggcgc atccccattt ccaccgccgt gcagaacggt    960
ggaaccagtt acttcgtacc ggaatccgac atgtccacgc tgttcgagga tctcgcgctg    1020
gtgcgcccga ccgaactcgg cctggttccg cgcgtcgccg acatgctcta ccagcaccac    1080
ctcgccaccg tcgaccgcct ggtcacgcag ggcgccgacg aactgaccgc cgagaagcag    1140
gccggtgccg aactgcgtga gcaggtgctc ggcggacgcg tgatcaccgg attcgtcagc    1200
accgcaccgc tggccgcgga gatgagggcg ttcctcgaca tcaccctggg cgcacacatc    1260
gtcgacggct acgggctcac cgagaccggc gccgtgacac gcgacggtgt gatcgtgcgg    1320
ccaccggtga tcgactacaa gctgatcgac gttcccgaac tcggctactt cagcaccgac    1380
aagccctacc cgcgtggcga actgctggtc aggtcgcaaa cgctgactcc cgggtactac    1440
aagcgccccg aggtcaccgc gagcgtcttc gaccgggacg gctactacca caccggcgac    1500
gtcatggccg agaccgcacc cgaccacctg gtgtacgtgg accgtcgcaa caacgtcctc    1560
aaactcgcgc agggcgagtt cgtggcggtc gccaacctgg aggcggtgtt ctccggcgcg    1620
gcgctggtgc gccagatctt cgtgtacggc aacagcgagc gcagtttcct tctgccgtg     1680 gtggtcccga cgccggaggc gctcgagcag tacgatccgg ccgcgctcaa ggccgcgctg    1740
gccgactcgc tgcagcgcac cgcacgcgac gccgaactgc aatcctacga ggtgccggcc    1800
gatttcatcg tcgagaccga gccgttcagc gccgccaacg ggctgctgtc gggtgtcgga    1860
aaactgctgg ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg gagcgaggtg    2040
gcatccgacg cccacttcac cgacctgggc ggggattccc tgtcggcgct gacactttcg    2100
aacctgctga gcgatttctt cggtttcgaa gttcccgtcg gcaccatcgt gaacccggcc    2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cggtctgcc caaggtcacc      2340 accgagccac ggacggtgtt gctctcgggc gccaacggct ggctgggccg gttcctcacg    2400
ttgcagtggc tggaacgcct ggcacctgtc ggcggcaccc tcatcacgat cgtgcggggc    2460
cgcgacgacg ccgcggcccg cgcacggctg acccaggcct acgacaccga tcccgagttg    2520
```

```
tcccgccgct cgccgagct ggccgaccgc cacctgcggg tggtcgccgg tgacatcggc    2580
gacccgaatc tgggcctcac acccgagatc tggcaccggc tcgccgccga ggtcgacctg    2640
gtggtgcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatccccg acttcgagga ggacggcgac    2820
atccggaccg tgagcccggt cgcccgctc gacggcggat acgccaacgg ctacggcaac    2880
agcaagtggg ccggcgaggt gctgctgcgg gaggcccacg atctgtgcgg gctgccgtg    2940 gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg agacggtga gcgcccgcgg gcgcactacc ccggcctgac ggtcgatttc    3120
gtggccgagg cggtcacgac gctcggcgcg cagcagcgcg agggatacgt gtcctacgac    3180
gtgatgaacc cgcacgacga cgggatctcc ctggatgtgt tcgtggactg gctgatccgg    3240
gcgggccatc cgatcgaccg ggtcgacgac tacgacgact gggtgcgtcg gttcgagacc    3300
gcgttgaccg cgcttcccga gaagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggcccggga gacatcccgc acctcgacga ggcgctgatc    3480
gacaagtaca tacgcgatct gcgtgagttc ggtctgatct aa                      3522
```

<210> SEQ ID NO 6
<211> LENGTH: 1173
<212> TYPE: PRT
<213> ORGANISM: Mycobacterium smegmatis

<400> SEQUENCE: 6

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
```

```
                195                 200                 205
Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
                275                 280                 285

Ile Thr Gly Asp Pro Thr Pro Val Ile Asn Val Asn Phe Met Pro Leu
                290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
                340                 345                 350

Ala Asp Met Leu Tyr Gln His His Leu Ala Thr Val Asp Arg Leu Val
                355                 360                 365

Thr Gln Gly Ala Asp Glu Leu Thr Ala Glu Lys Gln Ala Gly Ala Glu
370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
                435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
                500                 505                 510

Val Asp Arg Arg Asn Asn Val Leu Lys Leu Ala Gln Gly Glu Phe Val
                515                 520                 525

Ala Val Ala Asn Leu Glu Ala Val Phe Ser Gly Ala Ala Leu Val Arg
                530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
                580                 585                 590

Leu Gln Ser Tyr Glu Val Pro Ala Asp Phe Ile Val Glu Thr Glu Pro
                595                 600                 605

Phe Ser Ala Ala Asn Gly Leu Leu Ser Gly Val Gly Lys Leu Leu Arg
610                 615                 620
```

```
Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
            645                 650                 655

Ala Ala Thr Gln Pro Val Ile Asp Thr Leu Thr Gln Ala Ala Ala Thr
        660                 665                 670

Ile Leu Gly Thr Gly Ser Glu Val Ala Ser Asp Ala His Phe Thr Asp
    675                 680                 685

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
        995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035
```

Asp Phe Val Ala Glu Ala Val Thr Thr Leu Gly Ala Gln Gln Arg
    1040               1045               1050

Glu Gly Tyr Val Ser Tyr Asp Val Met Asn Pro His Asp Asp Gly
    1055               1060               1065

Ile Ser Leu Asp Val Phe Val Asp Trp Leu Ile Arg Ala Gly His
    1070               1075               1080

Pro Ile Asp Arg Val Asp Asp Tyr Asp Asp Trp Val Arg Arg Phe
    1085               1090               1095

Glu Thr Ala Leu Thr Ala Leu Pro Glu Lys Arg Arg Ala Gln Thr
    1100               1105               1110

Val Leu Pro Leu Leu His Ala Phe Arg Ala Pro Gln Ala Pro Leu
    1115               1120               1125

Arg Gly Ala Pro Glu Pro Thr Glu Val Phe His Ala Ala Val Arg
    1130               1135               1140

Thr Ala Lys Val Gly Pro Gly Asp Ile Pro His Leu Asp Glu Ala
    1145               1150               1155

Leu Ile Asp Lys Tyr Ile Arg Asp Leu Arg Glu Phe Gly Leu Ile
    1160               1165               1170

<210> SEQ ID NO 7
<211> LENGTH: 3522
<212> TYPE: DNA
<213> ORGANISM: Mycobacterium avium

<400> SEQUENCE: 7

```
atgtcgactg ccacccatga cgaacgactc gaccgtcgcg tccacgaact catcgccacc    60
gacccgcaat tcgccgccgc ccaacccgac ccggcgatca ccgccgccct cgaacagccc   120
gggctgcggc tgccgcagat catccgcacc gtgctcgacg gctacgccga ccggccggcg   180
ctgggacagc gcgtggtgga gttcgtcacg gacgccaaga ccgggcgcac gtcggcgcag   240
ctgctccccc gcttcgagac catcacgtac agcgaagtag cgcagcgtgt tcgcgcgctg   300
ggccgcgccc tgtccgacga cgcggtgcac ccggcgacc gggtgtgcgt gctgggcttc   360
aacagcgtcg actacgccac catcgacatg cgctgggcg ccatcggcgc cgtctcggtg   420
ccgctgcaga ccagcgcggc aatcagctcg ctgcagccga tcgtggccga daccgagccc   480
accctgatcg cgtccagcgt gaaccagctg tccgacgcgg tgcagctgat caccggcgcc   540
gagcaggcgc ccaccggct ggtggtgttc gactaccacc gcaggtcga cgaccagcgc   600 gaggccgtcc aggacgccgc ggcgcggctg tccagcaccg gcgtggccgt ccagacgctg   660
gccgagctgc tggagcgcgg caaggacctg cccgccgtcg cggagccgcc cgccgacgag   720
gactcgctgg ccctgctgat ctacacctcc gggtccaccg gcgcccccaa gggcgcgatg   780
tacccacaga gcaacgtcgg caagatgtgg cgccgcggca gcaagaactg gttcggcgag   840
agcgccgcgt cgatcaccct gaacttcatg ccgatgagcc acgtgatggg ccgaagcatc   900
ctctacggca cgctgggcaa cggcggcacc gcctacttcg ccgcccgcag cgacctgtcc   960
accctgcttg aggacctcga gctggtgcgg cccaccgagc tcaacttcgt cccgcggatc   1020
tgggagacgc tgtacggcga attccagcgt caggtcgagc ggcggctctc cgaggccggg   1080
gacgccggcg aacgtcgcgc cgtcgaggcc gaggtgctgg ccgagcagcg ccagtacctg   1140
ctgggcgggc ggttcaccct cgcgatgacg ggctcggcgc ccatctcgcc ggagctgcgc   1200
aactgggtcg agtcgctgct cgaaatgcac ctgatggacg gctacggctc caccgaggcc   1260
ggaatggtgt tgttcgacgg ggagattcag cgcccgccgg tgatcgacta caagctggtc   1320
```

```
gacgtgccgg acctgggcta cttcagcacc gaccggccgc atccgcgcgg cgagctgctg    1380
ctgcgcaccg agaacatgtt cccgggctac tacaagcggg ccgaaaccac cgcgggcgtc    1440
ttcgacgagg acggctacta ccgcaccggc gacgtgttcg ccgagatcgc cccggaccgg    1500
ctggtctacg tcgaccgccg caacaacgtg ctcaagctgg cgcagggcga attcgtcacg    1560
ctggccaagc tggaggcggt gttcggcaac agcccgctga tccgccagat ctacgtctac    1620
ggcaacagcg cccagcccta cctgctggcg gtcgtggtgc ccaccgagga ggcgctggcc    1680
tcgggtgacc ccgagacgct caagcccaag atcgccgact cgctgcagca ggtcgccaag    1740
gaggccggcc tgcagtccta cgaggtgccg cgcgacttca tcatcgagac caccccgttc    1800
agcctggaaa acggtctgct gaccgggatc cggaagctgg cgtggccgaa actgaagcag    1860
cactacgggg aacggctgga gcagatgtac gccgacctgg ccgccggaca ggccaacgag    1920
ctggccgagc tgcgccgcaa cggtgcccag gcgccggtgt tgcagaccgt gagccgcgcc    1980
gcgggcgcca tgctgggttc ggccgcctcc gacctgtccc ccgacgccca cttcaccgat    2040
ctgggcgagg actcgttgtc ggcgttgaca ttcggcaacc tgctgcgcga tcttcgac     2100 gtcgacgtgc cggtaggcgt gatcgtcagc ccggccaacg acctggcggc catcgcgagc    2160
tacatcgagg ccgagcggca gggcagcaag cgcccgacgt tcgcctcggt gcacggccgg    2220
gacgcgaccg tggtgcgcgc cgccgacctg acgctggaca agttcctcga cgccgagacg    2280
ctggccgccg cgccgaacct gcccaagccg gccaccgagg tgcgcaccgt gctgctgacc    2340
ggcgccaccg gcttcctggg ccgctacctg gccctggaat ggctggagcg gatggacatg    2400
gtggacggca aggtcatcgc cctggtccgg gcccgctccg acgaggaggc acgcgcccgg    2460
ctggacaaga ccttcgacag cggcgacccg aaactgctcg cgcactacca gcagctggcc    2520
gccgatcacc tggaggtcat cgccggcgac aagggcgagg ccaatctggg cctgggccaa    2580
gacgtttggc aacgactggc cgacacggtc gacgtgatcg tcgaccccgc cgcgctggtc    2640
aaccacgtgt tgccgtacag cgagctgttc gggcccaacg ccctgggcac cgcggagctg    2700
atccggctgg cgctgacgtc caagcagaag ccgtacacct acgtgtccac catcggcgtg    2760
ggcgaccaga tcgagccggg caagttcgtc gagaacgccg acatccggca gatgagcgcc    2820
acccgggcga tcaacgacag ctacgccaac ggctatggca acagcaagtg ggccggcgag    2880
gtgctgctgc gcgaggcgca cgacctgtgc gggctgcccg tcgcggtgtt ccgctgcgac    2940
atgatcctgg ccgacaccac gtatgccggg cagctcaacc tgccggacat gttcacccgg    3000
ctgatgctga gcctggtggc caccgggatc gcgcccggct cgttctacga gctcgacgcc    3060
gacggcaacc ggcagcgggc gcactacgac ggcctgccgg tcgagttcat cgccgcggcg    3120
atctcgacgc tgggttcgca gatcaccgac agcgacaccg gcttccagac ctaccacgtg    3180
atgaacccct acgatgacgg cgtcggtctg gacgagtacg tcgattggct ggtggacgcc    3240
ggctattcga tcgagcggat cgccgactac tccgaatggc tgcggcggtt cgagacctcg    3300
ctgcgggccc tgccggaccg gcagcgccag tactcgctgc tgccgctgct gcacaactac    3360
cgcacgccgg agaagccgat caacgggtcg atagctccca ccgacgtgtt ccgggcagcg    3420
gtgcaggagg cgaaaatcgg ccccgacaaa gacattccgc acgtgtcgcc gccggtcatc    3480
gtcaagtaca tcaccgacct gcagctgctc gggctgctct aa                      3522

<210> SEQ ID NO 8
<211> LENGTH: 1173
<212> TYPE: PRT
<213> ORGANISM: Mycobacterium avium
```

<400> SEQUENCE: 8

```
Met Ser Thr Ala Thr His Asp Glu Arg Leu Asp Arg Arg Val His Glu
1               5                   10                  15

Leu Ile Ala Thr Asp Pro Gln Phe Ala Ala Gln Pro Asp Pro Ala
            20                  25                  30

Ile Thr Ala Ala Leu Glu Gln Pro Gly Leu Arg Leu Pro Gln Ile Ile
            35                  40                  45

Arg Thr Val Leu Asp Gly Tyr Ala Asp Arg Pro Ala Leu Gly Gln Arg
50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
            85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
            115                 120                 125

Asp Met Ala Leu Gly Ala Ile Gly Ala Val Ser Val Pro Leu Gln Thr
130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
            165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
            195                 200                 205

Arg Leu Ser Ser Thr Gly Val Ala Val Gln Thr Leu Ala Glu Leu Leu
210                 215                 220

Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
            245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
            275                 280                 285

Phe Met Pro Met Ser His Val Met Gly Arg Ser Ile Leu Tyr Gly Thr
290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
            325                 330                 335

Val Pro Arg Ile Trp Glu Thr Leu Tyr Gly Glu Phe Gln Arg Gln Val
            340                 345                 350

Glu Arg Arg Leu Ser Glu Ala Gly Asp Ala Gly Glu Arg Arg Ala Val
            355                 360                 365

Glu Ala Glu Val Leu Ala Glu Gln Arg Gln Tyr Leu Leu Gly Gly Arg
            370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
```

```
            405                 410                 415
Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
            435                 440                 445

Ser Thr Asp Arg Pro His Pro Arg Gly Glu Leu Leu Leu Arg Thr Glu
            450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
            515                 520                 525

Gly Asn Ser Pro Leu Ile Arg Gln Ile Tyr Val Tyr Gly Asn Ser Ala
            530                 535                 540

Gln Pro Tyr Leu Leu Ala Val Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
            595                 600                 605

Gly Ile Arg Lys Leu Ala Trp Pro Lys Leu Lys Gln His Tyr Gly Glu
            610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
            675                 680                 685

Leu Thr Phe Gly Asn Leu Leu Arg Glu Ile Phe Asp Val Asp Val Pro
            690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Pro Asn Leu Pro
            755                 760                 765

Lys Pro Ala Thr Glu Val Arg Thr Val Leu Leu Thr Gly Ala Thr Gly
            770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
            820                 825                 830
```

Leu Ala His Tyr Gln Gln Leu Ala Ala Asp His Leu Glu Val Ile Ala
        835                 840                 845

Gly Asp Lys Gly Glu Ala Asn Leu Gly Leu Gly Gln Asp Val Trp Gln
    850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
                885                 890                 895

Thr Ala Glu Leu Ile Arg Leu Ala Leu Thr Ser Lys Gln Lys Pro Tyr
            900                 905                 910

Thr Tyr Val Ser Thr Ile Gly Val Gly Asp Gln Ile Glu Pro Gly Lys
            915                 920                 925

Phe Val Glu Asn Ala Asp Ile Arg Gln Met Ser Ala Thr Arg Ala Ile
        930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
                965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
        995                 1000                1005

Gly Ile Ala Pro Gly Ser Phe Tyr Glu Leu Asp Ala Asp Gly Asn
        1010                1015                1020

Arg Gln Arg Ala His Tyr Asp Gly Leu Pro Val Glu Phe Ile Ala
        1025                1030                1035

Ala Ala Ile Ser Thr Leu Gly Ser Gln Ile Thr Asp Ser Asp Thr
        1040                1045                1050

Gly Phe Gln Thr Tyr His Val Met Asn Pro Tyr Asp Asp Gly Val
        1055                1060                1065

Gly Leu Asp Glu Tyr Val Asp Trp Leu Val Asp Ala Gly Tyr Ser
        1070                1075                1080

Ile Glu Arg Ile Ala Asp Tyr Ser Glu Trp Leu Arg Arg Phe Glu
        1085                1090                1095

Thr Ser Leu Arg Ala Leu Pro Asp Arg Gln Arg Gln Tyr Ser Leu
        1100                1105                1110

Leu Pro Leu Leu His Asn Tyr Arg Thr Pro Glu Lys Pro Ile Asn
        1115                1120                1125

Gly Ser Ile Ala Pro Thr Asp Val Phe Arg Ala Ala Val Gln Glu
        1130                1135                1140

Ala Lys Ile Gly Pro Asp Lys Asp Ile Pro His Val Ser Pro Pro
        1145                1150                1155

Val Ile Val Lys Tyr Ile Thr Asp Leu Gln Leu Leu Gly Leu Leu
        1160                1165                1170

<210> SEQ ID NO 9
<211> LENGTH: 3525
<212> TYPE: DNA
<213> ORGANISM: Mycobacterium marinum

<400> SEQUENCE: 9

```
atgtcgccaa tcacgcgtga agagcggctc gagcgccgca tccaggacct ctacgccaac      60
gacccgcagt tcgccgccgc caaacccgcc acggcgatca ccgcagcaat cgagcggccg     120
```

-continued

```
ggtctaccgc taccccagat catcgagacc gtcatgaccg gatacgccga tcggccggct      180
ctcgctcagc gctcggtcga attcgtgacc gacgccggca ccggccacac cacgctgcga      240
ctgctccccc acttcgaaac catcagctac ggcgagcttt gggaccgcat cagcgcactg      300
gccgacgtgc tcagcaccga acagacggtg aaaccgggcg accgggtctg cttgttgggc      360
ttcaacagcg tcgactacgc cacgatcgac atgactttgg cgcggctggg cgcggtggcc      420
gtaccactgc agaccagcgc ggcgataacc cagctgcagc cgatcgtcgc cgagacccag      480
cccaccatga tcgcggccag cgtcgacgca ctcgctgacg ccaccgaatt ggctctgtcc      540
ggtcagaccg ctacccgagt cctggtgttc gaccaccacc ggcaggttga cgcacaccgc      600
gcagcggtcg aatccgcccg ggagcgcctg gccggctcgg cggtcgtcga aaccctggcc      660
gaggccatcg cgcgcggcga cgtgccccgc ggtgcgtccg ccggctcggc gcccggcacc      720
gatgtgtccg acgactcgct cgcgctactg atctacacct cgggcagcac gggtgcgccc      780
aagggcgcga tgtaccccg acgcaacgtt gcgaccttct ggcgcaagcg cacctggttc      840
gaaggcggct acgagccgtc gatcacgctg aacttcatgc caatgagcca cgtcatgggc      900
cgccaaatcc tgtacggcac gctgtgcaat ggcggcaccg cctacttcgt ggcgaaaagc      960
gatctctcca ccttgttcga agacctggcg ctggtgcggc ccaccgagct gaccttcgtg     1020
ccgcgcgtgt gggacatggt gttcgacgag tttcagagtg aggtcgaccg ccgcctggtc     1080
gacggcgccg accgggtcgc gctcgaagcc caggtcaagg ccgagatacg caacgacgtg     1140
ctcggtggac ggtataccag cgcactgacc ggctccgccc ctatctccga cgagatgaag     1200
gcgtgggtcg aggagctgct cgacatgcat ctggtcgagg gctacggctc caccgaggcc     1260
gggatgatcc tgatcgacgg agccattcgg cgcccggcgg tactcgacta caagctggtc     1320
gatgttcccg acctgggtta cttcctgacc gaccggccac atccgcgggg cgagttgctg     1380
gtcaagaccg atagtttgtt cccgggctac taccagcgag ccgaagtcac cgccgacgtg     1440
ttcgatgctg acgcttcta ccggaccggc gacatcatgg ccgaggtcgg ccccgaacag     1500
ttcgtgtacc tcgaccgccg caacaacgtg ttgaagctgt cgcagggcga gttcgtcacc     1560
gtctccaaac tcgaagcggt gtttggcgac agcccactgg tacggcagat ctacatctac     1620
ggcaacagcg cccgtgccta cctgttggcg gtgatcgtcc ccacccagga ggcgctggac     1680
gccgtgcctg tcgaggagct caaggcgcgg ctgggcgact cgctgcaaga ggtcgcaaag     1740
gccgccggcc tgcagtccta cgagatcccg cgcgacttca tcatcgaaac aacaccatgg     1800
acgctggaga acgcctgct caccggcatc cgcaagttgg ccaggccgca gctgaaaaag     1860
cattacggcg agcttctcga gcagatctac acggacctgg cacacggcca ggccgacgaa     1920
ctgcgctcgc tgcgccaaag cggtgccgat gcgccggtgc tggtgacggt gtgccgtgcg     1980
gcggccgcgc tgttgggcgg cagcgcctct gacgtccagc ccgatgcgca cttcaccgat     2040
ttgggcggcg actcgctgtc ggcgctgtcg ttcaccaacc tgctgcacga gatcttcgac     2100
atcgaagtgc cggtgggcgt catcgtcagc cccgccaacg acttgcaggc cctggccgac     2160
tacgtcgagg cggctcgcaa acccggctcg tcacggccga ccttcgcctc ggtccacggc     2220
gcctcgaatg gcaggtcac cgaggtgcat gccggtgacc tgtccctgga caaattcatc     2280
gatgccgcaa ccctggccga agctccccgg ctgccgccg caaacaccca gtgcgcacc     2340
gtgctgctga ccggcgccac cggcttcctc gggcgctacc tggccctgga atggctggag     2400
cggatggacc tggtcgacgg caaactgatc tgcctggtcc gggccaagtc cgacaccgaa     2460
gcacgggcgc ggctggacaa gacgttcgac agcggcgacc ccgaactgct ggcccactac     2520
```

-continued

```
cgcgcactgg ccggcgacca cctcgaggtg ctcgccggtg acaagggcga agccgacctc    2580
ggactggacc ggcagacctg gcaacgcctg gccgacacgg tcgacctgat cgtcgacccc    2640
gcggccctgg tcaaccacgt actgccatac agccagctgt cgggcccaa cgcgctgggc     2700 accgccgagc tgctgcggct ggcgctcacc tccaagatca agccctacag ctacacctcg    2760
acaatcggtg tcgccgacca gatcccgccg tcggcgttca ccgaggacgc cgacatccgg    2820
gtcatcagcg ccaccgcgc ggtcgacgac agctacgcca atggctactc gaacagcaag    2880
tgggccggcg aggtgctgtt gcgcgaggcg catgacctgt gtggcctgcc ggttgcggtg    2940
ttccgctgcg acatgatcct ggccgacacc acatgggcgg acagctcaa tgtgccggac    3000 atgttcaccc ggatgatcct gagcctggcg gccaccggta tcgcgccggg ttcgttctat    3060
gagcttgcgg ccgacggcgc ccggcaacgc gcccactatg acggtctgcc cgtcgagttc    3120
atcgccgagg cgatttcgac tttgggtgcg cagagccagg atggtttcca cacgtatcac    3180
gtgatgaacc cctacgacga cggcatcgga ctcgacgagt cgtcgactg gctcaacgag    3240 tccggttgcc ccatccagcg catcgctgac tatggcgact ggctgcagcg cttcgaaacc    3300
gcactgcgcg cactgcccga tcggcagcgg cacagctcac tgctgccgct gttgcacaac    3360
tatcggcagc cggagcggcc cgtccgcggg tcgatcgccc ctaccgatcg cttccgggca    3420
gcggtgcaag aggccaagat cggccccgac aaagacattc gcacgtcgg cgcgccgatc    3480 atcgtgaagt acgtcagcga cctgcgccta ctcggcctgc tctaa                    3525
```

<210> SEQ ID NO 10
<211> LENGTH: 1174
<212> TYPE: PRT
<213> ORGANISM: Mycobacterium marinum

<400> SEQUENCE: 10

```
Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190
```

```
His Arg Gln Val Asp Ala His Arg Ala Ala Val Glu Ser Ala Arg Glu
            195                 200                 205
Arg Leu Ala Gly Ser Ala Val Val Glu Thr Leu Ala Glu Ala Ile Ala
        210                 215                 220
Arg Gly Asp Val Pro Arg Gly Ala Ser Ala Gly Ser Ala Pro Gly Thr
225                 230                 235                 240
Asp Val Ser Asp Ser Leu Ala Leu Leu Ile Tyr Thr Ser Gly Ser
                245                 250                 255
Thr Gly Ala Pro Lys Gly Ala Met Tyr Pro Arg Asn Val Ala Thr
            260                 265                 270
Phe Trp Arg Lys Arg Thr Trp Phe Glu Gly Gly Tyr Glu Pro Ser Ile
        275                 280                 285
Thr Leu Asn Phe Met Pro Met Ser His Val Met Gly Arg Gln Ile Leu
    290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                325                 330                 335
Leu Thr Phe Val Pro Arg Val Trp Asp Met Val Phe Asp Glu Phe Gln
            340                 345                 350
Ser Glu Val Asp Arg Arg Leu Val Asp Gly Ala Asp Arg Val Ala Leu
        355                 360                 365
Glu Ala Gln Val Lys Ala Glu Ile Arg Asn Asp Val Leu Gly Gly Arg
    370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
            420                 425                 430
Ala Val Leu Asp Tyr Lys Leu Val Asp Val Pro Asp Leu Gly Tyr Phe
        435                 440                 445
Leu Thr Asp Arg Pro His Pro Arg Gly Glu Leu Leu Val Lys Thr Asp
    450                 455                 460
Ser Leu Phe Pro Gly Tyr Tyr Gln Arg Ala Glu Val Thr Ala Asp Val
465                 470                 475                 480
Phe Asp Ala Asp Gly Phe Tyr Arg Thr Gly Asp Ile Met Ala Glu Val
                485                 490                 495
Gly Pro Glu Gln Phe Val Tyr Leu Asp Arg Arg Asn Asn Val Leu Lys
            500                 505                 510
Leu Ser Gln Gly Glu Phe Val Thr Val Ser Lys Leu Glu Ala Val Phe
        515                 520                 525
Gly Asp Ser Pro Leu Val Arg Gln Ile Tyr Ile Tyr Gly Asn Ser Ala
    530                 535                 540
Arg Ala Tyr Leu Leu Ala Val Ile Val Pro Thr Gln Glu Ala Leu Asp
545                 550                 555                 560
Ala Val Pro Val Glu Glu Leu Lys Ala Arg Leu Gly Asp Ser Leu Gln
                565                 570                 575
Glu Val Ala Lys Ala Ala Gly Leu Gln Ser Tyr Glu Ile Pro Arg Asp
            580                 585                 590
Phe Ile Ile Glu Thr Thr Pro Trp Thr Leu Glu Asn Gly Leu Leu Thr
        595                 600                 605
Gly Ile Arg Lys Leu Ala Arg Pro Gln Leu Lys Lys His Tyr Gly Glu
```

```
                610              615              620
Leu Leu Glu Gln Ile Tyr Thr Asp Leu Ala His Gly Gln Ala Asp Glu
625              630              635              640

Leu Arg Ser Leu Arg Gln Ser Gly Ala Asp Ala Pro Val Leu Val Thr
                645              650              655

Val Cys Arg Ala Ala Ala Ala Leu Leu Gly Gly Ser Ala Ser Asp Val
            660              665              670

Gln Pro Asp Ala His Phe Thr Asp Leu Gly Gly Asp Ser Leu Ser Ala
            675              680              685

Leu Ser Phe Thr Asn Leu Leu His Glu Ile Phe Asp Ile Glu Val Pro
690              695              700

Val Gly Val Ile Val Ser Pro Ala Asn Asp Leu Gln Ala Leu Ala Asp
705              710              715              720

Tyr Val Glu Ala Ala Arg Lys Pro Gly Ser Ser Arg Pro Thr Phe Ala
                725              730              735

Ser Val His Gly Ala Ser Asn Gly Gln Val Thr Glu Val His Ala Gly
            740              745              750

Asp Leu Ser Leu Asp Lys Phe Ile Asp Ala Ala Thr Leu Ala Glu Ala
            755              760              765

Pro Arg Leu Pro Ala Ala Asn Thr Gln Val Arg Thr Val Leu Leu Thr
770              775              780

Gly Ala Thr Gly Phe Leu Gly Arg Tyr Leu Ala Leu Glu Trp Leu Glu
785              790              795              800

Arg Met Asp Leu Val Asp Gly Lys Leu Ile Cys Leu Val Arg Ala Lys
                805              810              815

Ser Asp Thr Glu Ala Arg Ala Arg Leu Asp Lys Thr Phe Asp Ser Gly
            820              825              830

Asp Pro Glu Leu Leu Ala His Tyr Arg Ala Leu Ala Gly Asp His Leu
            835              840              845

Glu Val Leu Ala Gly Asp Lys Gly Glu Ala Asp Leu Gly Leu Asp Arg
850              855              860

Gln Thr Trp Gln Arg Leu Ala Asp Thr Val Asp Leu Ile Val Asp Pro
865              870              875              880

Ala Ala Leu Val Asn His Val Leu Pro Tyr Ser Gln Leu Phe Gly Pro
                885              890              895

Asn Ala Leu Gly Thr Ala Glu Leu Leu Arg Leu Ala Leu Thr Ser Lys
            900              905              910

Ile Lys Pro Tyr Ser Tyr Thr Ser Thr Ile Gly Val Ala Asp Gln Ile
            915              920              925

Pro Pro Ser Ala Phe Thr Glu Asp Ala Asp Ile Arg Val Ile Ser Ala
930              935              940

Thr Arg Ala Val Asp Asp Ser Tyr Ala Asn Gly Tyr Ser Asn Ser Lys
945              950              955              960

Trp Ala Gly Glu Val Leu Leu Arg Glu Ala His Asp Leu Cys Gly Leu
                965              970              975

Pro Val Ala Val Phe Arg Cys Asp Met Ile Leu Ala Asp Thr Thr Trp
            980              985              990

Ala Gly Gln Leu Asn Val Pro Asp Met Phe Thr Arg Met Ile Leu Ser
            995              1000             1005

Leu Ala Ala Thr Gly Ile Ala Pro Gly Ser Phe Tyr Glu Leu Ala
    1010             1015             1020

Ala Asp Gly Ala Arg Gln Arg Ala His Tyr Asp Gly Leu Pro Val
    1025             1030             1035
```

| Glu | Phe | Ile | Ala | Glu | Ala | Ile | Ser | Thr | Leu | Gly | Ala | Gln | Ser | Gln |
| | 1040 | | | | 1045 | | | | | 1050 | | | | |

| Asp | Gly | Phe | His | Thr | Tyr | His | Val | Met | Asn | Pro | Tyr | Asp | Asp | Gly |
| 1055 | | | | | 1060 | | | | | 1065 | | | | |

| Ile | Gly | Leu | Asp | Glu | Phe | Val | Asp | Trp | Leu | Asn | Glu | Ser | Gly | Cys |
| 1070 | | | | | 1075 | | | | | 1080 | | | | |

| Pro | Ile | Gln | Arg | Ile | Ala | Asp | Tyr | Gly | Asp | Trp | Leu | Gln | Arg | Phe |
| 1085 | | | | | 1090 | | | | | 1095 | | | | |

| Glu | Thr | Ala | Leu | Arg | Ala | Leu | Pro | Asp | Arg | Gln | Arg | His | Ser | Ser |
| 1100 | | | | | 1105 | | | | | 1110 | | | | |

| Leu | Leu | Pro | Leu | Leu | His | Asn | Tyr | Arg | Gln | Pro | Glu | Arg | Pro | Val |
| 1115 | | | | | 1120 | | | | | 1125 | | | | |

| Arg | Gly | Ser | Ile | Ala | Pro | Thr | Asp | Arg | Phe | Arg | Ala | Ala | Val | Gln |
| 1130 | | | | | 1135 | | | | | 1140 | | | | |

| Glu | Ala | Lys | Ile | Gly | Pro | Asp | Lys | Asp | Ile | Pro | His | Val | Gly | Ala |
| 1145 | | | | | 1150 | | | | | 1155 | | | | |

| Pro | Ile | Ile | Val | Lys | Tyr | Val | Ser | Asp | Leu | Arg | Leu | Leu | Gly | Leu |
| 1160 | | | | | 1165 | | | | | 1170 | | | | |

Leu

<210> SEQ ID NO 11
<211> LENGTH: 3522
<212> TYPE: DNA
<213> ORGANISM: Artificial Sequence
<220> FEATURE:
<223> OTHER INFORMATION: Description of Artificial Sequence: Synthetic
      carboxylic acid reductase polynucleotide
      designated 891GA

<400> SEQUENCE: 11

```
atgagcaccg caacccatga tgaacgtctg gatcgtcgtg ttcatgaact gattgcaacc    60
gatccgcagt tgcagcagc acagccggat cctgcaatta ccgcagcact ggaacagcct   120
ggtctgcgtc tgccgcagat tattcgtacc gttctggatg ttatgcaga tcgtccggca   180
ctgggtcagc gtgttgttga atttgttacc gatgcaaaaa ccggtcgtac cagcgcacag   240
ctgctgcctc gttttgaaac cattacctat agcgaagttg cacagcgtgt tagcgcactg   300
ggtcgtgcac tgagtgatga tgcagttcat ccgggtgatc gtgtttgtgt tctgggtttt   360
aatagcgttg attatgccac cattgatatg gcactgggtg caattggtgc agttagcgtt   420
ccgctgcaga ccagcgcagc aattagcagc ctgcagccga ttgttgcaga aaccgaaccg   480
accctgattg caagcagcgt taatcagctg tcagatgcag ttcagctgat taccggtgca   540
gaacaggcac cgaccgtct ggttgttttt gattatcatc gcaggttga tgatcagcgt   600
gaagcagttc aggatgcagc agcacgtctg agcagcaccg tgttgcagt tcagaccctg   660
gcagaactgc tggaacgtgg taaagatctg cctgcagttg cagaaccgcc tgcagatgaa   720
gatagcctgg cactgctgat ttataccagc ggtagcacag tgcaccgaa aggtgcaatg   780
tatccgcaga gcaatgttgg taaaatgtgg cgtcgtggta gcaaaaattg gtttggtgaa   840
agcgcagcaa gcattaccct gaatttcatg ccgatgagcc atgttatggg tcgtagcatt   900
ctgtatggca ccctgggtaa tggtggcacc gcatattttg cagcacgtag cgatctgagc   960
accctgctgg aagatctgga actggttcgt ccgaccgaac tgaattttgt tccgcgtatt  1020
tgggaaaccc tgtatggtga atttcagcgt caggttgaac gtcgtctgag cgaagctggc  1080
gatgccggtg aacgtcgtgc agttgaagca gaagttctgg cagaacagcg tcagtatctg  1140
```

```
ctgggtggtc gttttacctt tgcaatgacc ggtagcgcac cgattagtcc ggaactgcgt    1200
aattgggttg aaagcctgct ggaaatgcat ctgatggatg gctatggtag caccgaagca    1260
ggtatggttc tgtttgatgg cgaaattcag cgtccgcctg tgattgatta taaactggtt    1320
gatgttccgg atctgggtta ttttagcacc gatcgtccgc atccgcgtgg tgaactgctg    1380
ctgcgtaccg aaaatatgtt tccgggttat tataaacgtg cagaaaccac cgcaggcgtt    1440
tttgatgaag atggttatta tcgtaccggt gatgtgtttg cagaaattgc accggatcgt    1500
ctggtttatg ttgatcgtcg taataatgtt ctgaaactgg cacagggtga atttgtgacc    1560
ctggccaaac tggaagcagt ttttggtaat agtccgctga ttcgtcagat ttatgtgtat    1620
ggtaatagcg cacagccgta tctgctggca gttgttgttc cgaccgaaga ggcactggca    1680
agcggtgatc cggaaaccct gaaaccgaaa attgcagata gcctgcagca ggttgcaaaa    1740
gaagcaggtc tgcagagcta tgaagttccg cgtgatttta ttattgaaac caccccgttt    1800
agcctggaaa atggtctgct gaccggtatt cgtaaactgg catggccgaa actgaaacag    1860
cattatggtg aacgcctgga acaaatgtat gcagatctgg cagcaggtca ggcaaatgaa    1920
ctggccgaac tgcgtcgtaa tggtgcacag gcaccggttc tgcagaccgt tagccgtgca    1980
gccggtgcaa tgctgggtag cgcagccagc gatctgagtc cggatgcaca ttttaccgat    2040
ctgggtggtg atagcctgag cgcactgacc tttggtaatc tgctgcgtga aattttgat     2100 gttgatgtgc cggttggtgt tattgttagt ccggctaatg atctggcagc cattgcaagc    2160
tatattgaag cagaacgtca gggtagcaaa cgtccgacct tgcaagcgt tcatggtcgt     2220 gatgcaaccg ttgttcgtgc agcagatctg accctggata aatttctgga tgcagaaacc    2280
ctggcagcag caccgaatct gccgaaaccg gcaaccgaag ttcgtaccgt gctgctgaca    2340
ggtgcaaccg gttttctggg tcgttatctg gcactggaat ggctggaacg tatggatatg    2400
gttgatggta agttattgc actggttcgt gcccgtagtg atgaagaagc acgcgcacgt    2460
ctggataaaa cctttgatag tggtgatccg aaactgctgg cacattatca gcagctggct    2520
gcagatcatc tggaagttat tgccggtgat aaaggtgaag caaatctggg tctgggtcag    2580
gatgtttggc agcgtctggc agataccgtt gatgttattg tggatccggc agcactggtt    2640
aatcatgttc tgccgtatag cgaactgttt ggtccgaatg cactgggcac cgcagaactg    2700
attcgtctgg cactgaccag caaacagaaa ccgtatacct atgttagcac cattggtgtt    2760
ggcgatcaga ttgaaccggg taaatttgtt gaaaatgccg atattcgtca gatgagcgca    2820
acccgtgcaa ttaatgatag ctatgcaaat ggctacggca atagcaaatg gcaggcgaa    2880 gttctgctgc gcgaagcaca tgatctgtgt ggtctgccgg ttgcagtttt tcgttgtgat    2940
atgattctgg ccgataccac ctatgcaggt cagctgaatc tgccggatat gtttacccgt    3000
ctgatgctga gcctggttgc aaccggtatt gcaccgggta gctttttatga actggatgca    3060 gatggtaatc gtcagcgtgc acattatgat ggcctgccgg ttgaatttat tgcagcagcc    3120
attagcaccc tgggttcaca gattaccgat agcgataccg ttttcagac ctatcatgtt     3180 atgaacccgt atgatgatgg tgttggtctg gatgaatatg ttgattggct ggttgatgcc    3240
ggttatagca ttgaacgtat tgcagattat agcgaatggc tgcgtcgctt tgaaacctca    3300
ctgcgtgcac tgccggatcg tcagcgccag tatagcctgc tgccgctgct gcacaattat    3360
cgtacaccgg aaaaaccgat taatggtagc attgcaccga ccgatgtttt tcgtgcagcc    3420
gttcaagaag ccaaaattgg tccggataaa gatattccgc atgttagccc tccggtgatt    3480
```
gttaaatata ttaccgatct gcagctgctg ggtctgctgt aa 3522

<210> SEQ ID NO 12
<211> LENGTH: 1173
<212> TYPE: PRT
<213> ORGANISM: Artificial Sequence
<220> FEATURE:
<223> OTHER INFORMATION: Description of Artificial Sequence: Synthetic carboxylic acid reductase polypeptide designated 891GA

<400> SEQUENCE: 12

```
Met Ser Thr Ala Thr His Asp Glu Arg Leu Asp Arg Arg Val His Glu
1               5                   10                  15

Leu Ile Ala Thr Asp Pro Gln Phe Ala Ala Gln Pro Asp Pro Ala
            20                  25                  30

Ile Thr Ala Ala Leu Glu Gln Pro Gly Leu Arg Leu Pro Gln Ile Ile
            35                  40                  45

Arg Thr Val Leu Asp Gly Tyr Ala Asp Arg Pro Ala Leu Gly Gln Arg
50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
            115                 120                 125

Asp Met Ala Leu Gly Ala Ile Gly Ala Val Ser Val Pro Leu Gln Thr
        130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
            195                 200                 205

Arg Leu Ser Ser Thr Gly Val Ala Val Gln Thr Leu Ala Glu Leu Leu
        210                 215                 220

Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
        275                 280                 285

Phe Met Pro Met Ser His Val Met Gly Arg Ser Ile Leu Tyr Gly Thr
    290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
            340                 345                 350
```

```
Glu Arg Arg Leu Ser Glu Ala Gly Asp Ala Gly Arg Arg Ala Val
        355                 360                 365

Glu Ala Glu Val Leu Ala Glu Gln Arg Gln Tyr Leu Leu Gly Gly Arg
    370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                405                 410                 415

Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
        435                 440                 445

Ser Thr Asp Arg Pro His Pro Arg Gly Glu Leu Leu Leu Arg Thr Glu
    450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
        515                 520                 525

Gly Asn Ser Pro Leu Ile Arg Gln Ile Tyr Val Tyr Gly Asn Ser Ala
    530                 535                 540

Gln Pro Tyr Leu Leu Ala Val Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
        595                 600                 605

Gly Ile Arg Lys Leu Ala Trp Pro Lys Leu Lys Gln His Tyr Gly Glu
    610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
        675                 680                 685

Leu Thr Phe Gly Asn Leu Leu Arg Glu Ile Phe Asp Val Asp Val Pro
    690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Ala Pro Asn Leu Pro
        755                 760                 765
```

```
Lys Pro Ala Thr Glu Val Arg Thr Val Leu Leu Thr Gly Ala Thr Gly
770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
                820                 825                 830

Leu Ala His Tyr Gln Gln Leu Ala Asp His Leu Glu Val Ile Ala
            835                 840                 845

Gly Asp Lys Gly Glu Ala Asn Leu Gly Leu Gly Gln Asp Val Trp Gln
850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
                885                 890                 895

Thr Ala Glu Leu Ile Arg Leu Ala Leu Thr Ser Lys Gln Lys Pro Tyr
                900                 905                 910

Thr Tyr Val Ser Thr Ile Gly Val Gly Asp Gln Ile Glu Pro Gly Lys
            915                 920                 925

Phe Val Glu Asn Ala Asp Ile Arg Gln Met Ser Ala Thr Arg Ala Ile
930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
                965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
            995                 1000                1005

Gly Ile Ala Pro Gly Ser Phe Tyr Glu Leu Asp Ala Asp Gly Asn
    1010                1015                1020

Arg Gln Arg Ala His Tyr Asp Gly Leu Pro Val Glu Phe Ile Ala
    1025                1030                1035

Ala Ala Ile Ser Thr Leu Gly Ser Gln Ile Thr Asp Ser Asp Thr
    1040                1045                1050

Gly Phe Gln Thr Tyr His Val Met Asn Pro Tyr Asp Asp Gly Val
    1055                1060                1065

Gly Leu Asp Glu Tyr Val Asp Trp Leu Val Asp Ala Gly Tyr Ser
    1070                1075                1080

Ile Glu Arg Ile Ala Asp Tyr Ser Glu Trp Leu Arg Arg Phe Glu
    1085                1090                1095

Thr Ser Leu Arg Ala Leu Pro Asp Arg Gln Arg Gln Tyr Ser Leu
    1100                1105                1110

Leu Pro Leu Leu His Asn Tyr Arg Thr Pro Glu Lys Pro Ile Asn
    1115                1120                1125

Gly Ser Ile Ala Pro Thr Asp Val Phe Arg Ala Ala Val Gln Glu
    1130                1135                1140

Ala Lys Ile Gly Pro Asp Lys Asp Ile Pro His Val Ser Pro Pro
    1145                1150                1155

Val Ile Val Lys Tyr Ile Thr Asp Leu Gln Leu Leu Gly Leu Leu
    1160                1165                1170
```

MICROORGANISMS FOR PRODUCING BUTADIENE AND METHODS RELATED THERETO

This application claims the benefit of priority of U.S. Provisional application Ser. No. 61/500,130, filed Jun. 22, 2011, U.S. Provisional application Ser. No. 61/502,264, filed Jun. 28, 2011, the entire contents of which are incorporated herein by reference.

The instant application contains a Sequence Listing which has been submitted via EFS-Web and is hereby incorporated by reference in its entirety. Said ASCII copy, created on Jun. 17, 2012, is named 871943-999148_US_Sequence_Listing.txt and is 77,797 bytes in size.

BACKGROUND OF THE INVENTION

The present invention relates generally to biosynthetic processes, and more specifically to organisms having butadiene or crotyl alcohol biosynthetic capability.

Over 25 billion pounds of butadiene (1,3-butadiene, BD) are produced annually and is applied in the manufacture of polymers such as synthetic rubbers and ABS resins, and chemicals such as hexamethylenediamine and 1,4-butanediol. Butadiene is typically produced as a by-product of the steam cracking process for conversion of petroleum feedstocks such as naphtha, liquefied petroleum gas, ethane or natural gas to ethylene and other olefins. The ability to manufacture butadiene from alternative and/or renewable feedstocks would represent a major advance in the quest for more sustainable chemical production processes One possible way to produce butadiene renewably involves fermentation of sugars or other feedstocks to produce diols, such as 1,4-butanediol or 1,3-butanediol, which are separated, purified, and then dehydrated to butadiene in a second step involving metal-based catalysis. Direct fermentative production of butadiene from renewable feedstocks would obviate the need for dehydration steps and butadiene gas (bp −4.4° C.) would be continuously emitted from the fermenter and readily condensed and collected. Developing a fermentative production process would eliminate the need for fossil-based butadiene and would allow substantial savings in cost, energy, and harmful waste and emissions relative to petrochemically-derived butadiene.

Microbial organisms and methods for effectively producing butadiene or crotyl alcohol from cheap renewable feedstocks such as molasses, sugar cane juice, and sugars derived from biomass sources, including agricultural and wood waste, as well as C1 feedstocks such as syngas and carbon dioxide, are described herein and include related advantages.

SUMMARY OF THE INVENTION

The invention provides non-naturally occurring microbial organisms containing butadiene or crotyl alcohol pathways comprising at least one exogenous nucleic acid encoding a butadiene or crotyl alcohol pathway enzyme expressed in a sufficient amount to produce butadiene or crotyl alcohol. The invention additionally provides methods of using such microbial organisms to produce butadiene or crotyl alcohol, by culturing a non-naturally occurring microbial organism containing butadiene or crotyl alcohol pathways as described herein under conditions and for a sufficient period of time to produce butadiene or crotyl alcohol.

BRIEF DESCRIPTION OF THE DRAWINGS

FIG. 10A shows the pathways for fixation of $CO_2$ to acetyl-CoA using the reductive TCA cycle.

FIG. 11A shows the pathways for fixation of $CO_2$ to acetyl-CoA using the reductive TCA cycle. FIG. 11B shows exemplary pathways for the biosynthesis of butadiene from acetyl-CoA; the enzymatic transformations shown are carried out by the following enzymes: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotonyl-CoA reductase (alcohol forming), G. crotonyl-CoA hydrolase, synthetase, transferase, H. crotonate reductase, I. crotyl alcohol kinase, J. 2-butenyl-4-phosphate kinase, K. butadiene synthase, L. crotyl alcohol diphosphokinase.

FIG. 12A shows the nucleotide sequence (SEQ ID NO: 1) of carboxylic acid reductase from *Nocardia iowensis* (GNM_720), and FIG. 12B shows the encoded amino acid sequence (SEQ ID NO: 2).

FIG. 13A shows the nucleotide sequence (SEQ ID NO: 3) of phosphpantetheine transferase, which was codon optimized, and FIG. 13B shows the encoded amino acid sequence (SEQ ID NO: 4).

FIG. 14A shows the nucleotide sequence (SEQ ID NO: 5) of carboxylic acid reductase from *Mycobacterium smegmatis* mc(2)155 (designated 890), and FIG. 14B shows the encoded amino acid sequence (SEQ ID NO: 6).

FIG. 15A shows the nucleotide sequence (SEQ ID NO: 7) of carboxylic acid reductase from *Mycobacterium avium* subspecies paratuberculosis K-10 (designated 891), and FIG. 15B shows the encoded amino acid sequence (SEQ ID NO: 8).

FIG. 16A shows the nucleotide sequence (SEQ ID NO: 9) of carboxylic acid reductase from *Mycobacterium marinum* M (designated 892), and FIG. 16B shows the encoded amino acid sequence (SEQ ID NO: 10).

FIG. 17A shows the nucleotide sequence (SEQ ID NO: 11) of carboxylic acid reductase designated 891GA, and FIG. 17B shows the encoded amino acid sequence (SEQ ID NO: 12).

DETAILED DESCRIPTION OF THE INVENTION

The present invention is directed to the design and production of cells and organisms having biosynthetic production capabilities for butadiene or crotyl alcohol. The invention, in particular, relates to the design of microbial organism capable of producing butadiene or crotyl alcohol by introducing one or more nucleic acids encoding a butadiene or a crotyl alcohol pathway enzyme.

In one embodiment, the invention utilizes in silico stoichiometric models of *Escherichia coli* metabolism that identify metabolic designs for biosynthetic production of butadiene or crotyl alcohol. The results described herein indicate that metabolic pathways can be designed and recombinantly engineered to achieve the biosynthesis of butadiene or crotyl alcohol in *Escherichia coli* and other cells or organisms. Biosynthetic production of butadiene or crotyl alcohol, for example, for the in silico designs can be confirmed by construction of strains having the designed metabolic genotype. These metabolically engineered cells or organisms also can be subjected to adaptive evolution to further augment butadiene or crotyl alcohol biosynthesis, including under conditions approaching theoretical maximum growth.

In certain embodiments, the butadiene biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to butadiene producing metabolic pathways from acetyl-CoA, glutaconyl-CoA, glutaryl-CoA, 3-aminobutyryl-CoA, 4-hydroxybutyryl-CoA, erythrose-4-phosphate or malonyl-CoA plus acetyl-CoA. In silico metabolic designs were identified that resulted in the biosynthesis of butadiene in microorganisms from each of these substrates or metabolic intermediates.

Strains identified via the computational component of the platform can be put into actual production by genetically engineering any of the predicted metabolic alterations, which lead to the biosynthetic production of butadiene or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

The maximum theoretical butadiene yield from glucose is 1.09 mol/mol (0.33 g/g).

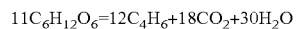

$$11C_6H_{12}O_6 = 12C_4H_6 + 18CO_2 + 30H_2O$$

Figure 2:
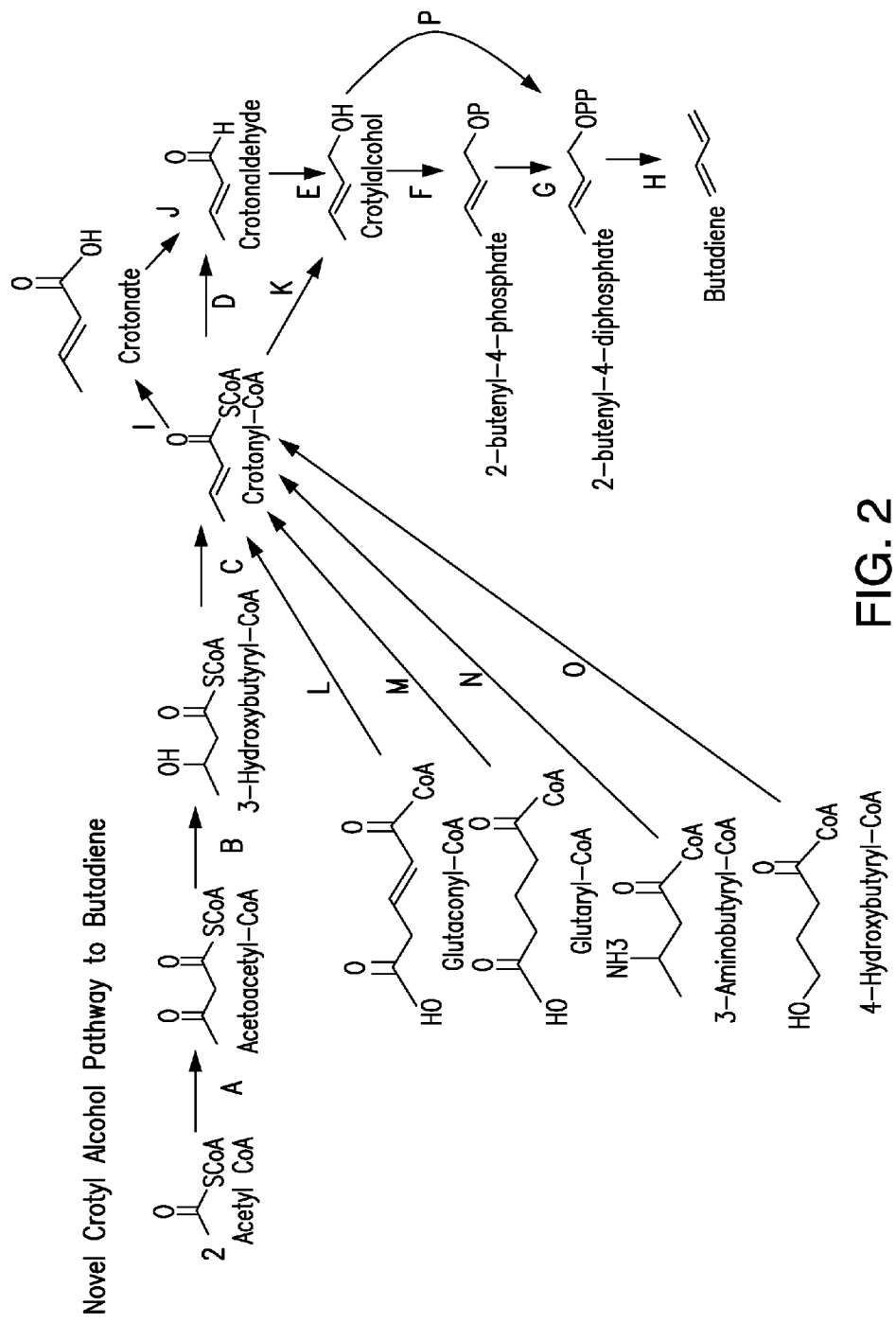
FIG. 2 shows exemplary pathways for production of butadiene from acetyl-CoA, glutaconyl-CoA, glutaryl-CoA, 3-aminobutyryl-CoA or 4-hydroxybutyryl-CoA via crotyl alcohol. Enzymes for transformation of the identified substrates to products include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotyl alcohol kinase, G. 2-butenyl-4-phosphate kinase, H. butadiene synthase, I. crotonyl-CoA hydrolase, synthetase, transferase, J. crotonate reductase, K. crotonyl-CoA reductase (alcohol forming), L. glutaconyl-CoA decarboxylase, M., glutaryl-CoA dehydrogenase, N. 3-aminobutyryl-CoA deaminase, O. 4-hydroxybutyryl-CoA dehydratase, P. crotyl alcohol diphosphokinase.
Figure 3:
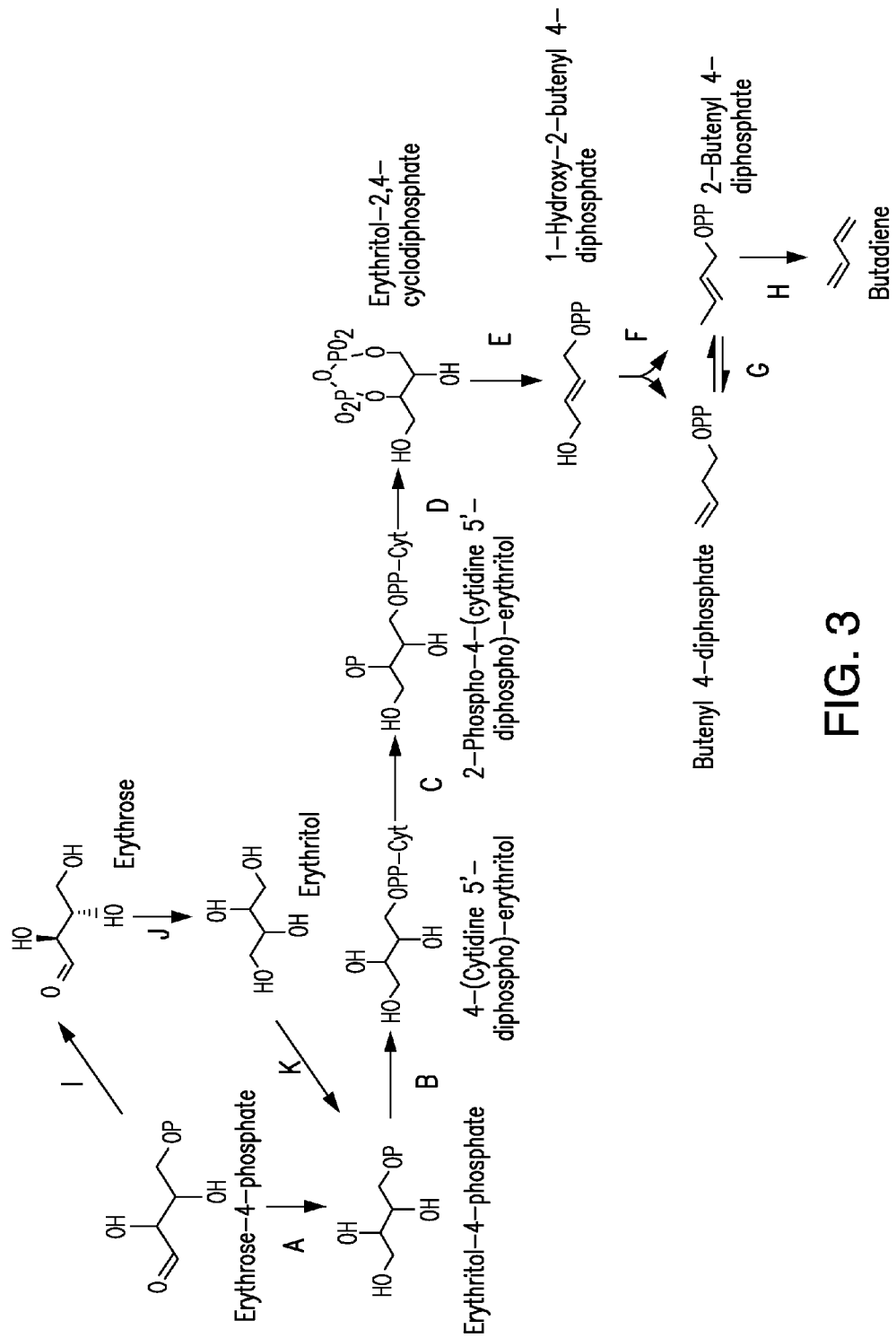
FIG. 3 shows exemplary pathways for production of butadiene from erythrose-4-phosphate. Enzymes for transformation of the identified substrates to products include: A. Erythrose-4-phosphate reductase, B. Erythritol-4-phospate cytidylyltransferase, C. 4-(cytidine 5'-diphospho)-erythritol kinase, D. Erythritol 2,4-cyclodiphosphate synthase, E. 1-Hydroxy-2-butenyl 4-diphosphate synthase, F. 1-Hydroxy-2-butenyl 4-diphosphate reductase, G. Butenyl 4-diphosphate isomerase, H. Butadiene synthase I. Erythrose-4-phosphate kinase, J. Erythrose reductase, K. Erythritol kinase.
Figure 4:
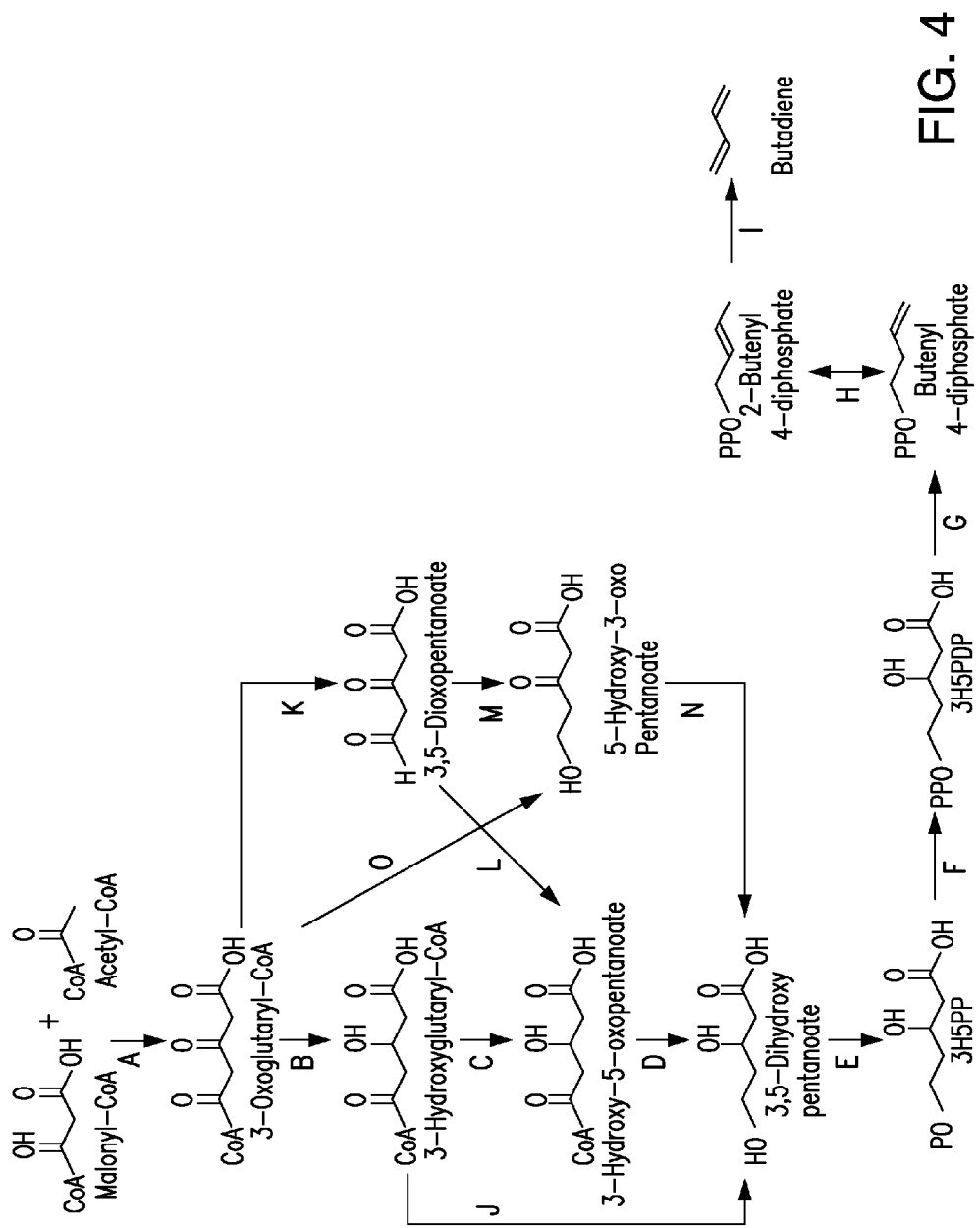
FIG. 4 shows an exemplary pathway for production of butadiene from malonyl-CoA plus acetyl-CoA. Enzymes for transformation of the identified substrates to products include: A. malonyl-CoA:acetyl-CoA acyltransferase, B. 3-oxoglutaryl-CoA reductase (ketone-reducing), C. 3-hydroxyglutaryl-CoA reductase (aldehyde forming), D. 3-hydroxy-5-oxopentanoate reductase, E. 3,5-dihydroxypentanoate kinase, F. 3H5PP kinase, G. 3H5PDP decarboxylase, H. butenyl 4-diphosphate isomerase, I. butadiene synthase, J. 3-hydroxyglutaryl-CoA reductase (alcohol forming), K. 3-oxoglutaryl-CoA reductase (aldehyde forming), L. 3,5-dioxopentanoate reductase (ketone reducing), M. 3,5-dioxopentanoate reductase (aldehyde reducing), N. 5-hydroxy-3-oxopentanoate reductase, O. 3-oxo-glutaryl-CoA reductase (CoA reducing and alcohol forming). Compound abbreviations include: 3H5PP=3-Hydroxy-5-phosphonatooxypentanoate and 3H5PDP=3-Hydroxy-5-[hydroxy(phosphonooxy)phosphoryl]oxy pentanoate.
Figure 5:
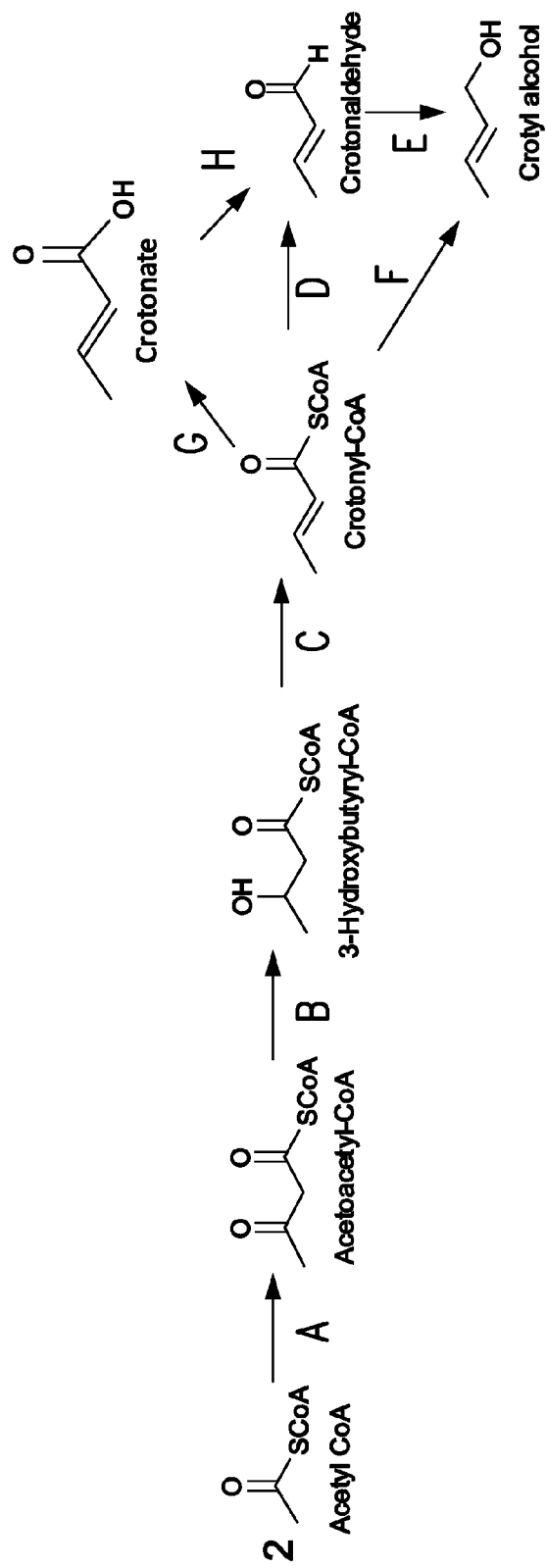
FIG. 5 shows an exemplary pathway for production of crotyl alcohol from acetyl-CoA. Enzymes for transformation of the identified substrates to products include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotonyl-CoA reductase (alcohol forming), G. crotonyl-CoA hydrolase, synthetase, transferase, and H. crotonate reductase.

The pathways presented in FIGS. 2 and 4 achieve a yield of 1.0 moles butadiene per mole of glucose utilized. Increasing product yields to theoretical maximum value is possible if cells are capable of fixing $CO_2$ through pathways such as the reductive (or reverse) TCA cycle or the Wood-Ljungdahl pathway. Organisms engineered to possess the pathway depicted in FIG. 3 are also capable of reaching near theoretical maximum yields of butadiene.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a butadiene or crotyl alcohol biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "butadiene," having the molecular formula $C_4H_6$ and a molecular mass of 54.09 g/mol (see FIGS. 2-4) (IUPAC name Buta-1,3-diene) is used interchangeably throughout with 1,3-butadiene, biethylene, erythrene, divinyl, vinylethylene. Butadiene is a colorless, non corrosive liquefied gas with a mild aromatic or gasoline-like odor. Butadiene is both explosive and flammable because of its low flash point.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having butadiene or crotyl alcohol biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; word-size: 11; filter: off Those skilled in the art will know what modifications can be made to the above parameters to either increase or decrease the stringency of the comparison, for example, and determine the relatedness of two or more sequences.

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase, a butadiene synthase, a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, an 3-aminobutyryl-CoA deaminase, a 4-hydroxybutyryl-CoA dehydratase or a crotyl alcohol diphosphokinase (FIG. 2). In one aspect, the non-naturally occurring microbial includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps A-C, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase (FIG. 2, steps A-C, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase, (FIG. 2, steps A-C, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps A-C, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase (FIG. 2, steps A-E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps L, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotyl alcohol kinase, a 2-butenyl-4-phosphate kinase, a butadiene synthase and crotonyl-CoA reductase (alcohol forming) (FIG. 2, steps L, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a butadiene synthase, a crotonyl-CoA reductase (alcohol forming) and a crotyl alcohol diphosphokinase (FIG. 2, steps L, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps L, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps L, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase (FIG. 2, steps L, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps M, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotyl alcohol kinase, a 2-butenyl-4-phosphate kinase, a butadiene synthase and crotonyl-CoA reductase (alcohol forming) (FIG. 2, steps M, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a butadiene synthase, a crotonyl-CoA reductase (alcohol forming) and a crotyl alcohol diphosphokinase (FIG. 2, steps M, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps M, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps M, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase (FIG. 2, steps M, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps N, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an 3-aminobutyryl-CoA deaminase, a crotyl alcohol kinase, a 2-butenyl-4-phosphate kinase, a butadiene synthase and crotonyl-CoA reductase (alcohol forming) (FIG. 2, steps N, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an 3-aminobutyryl-CoA deaminase, a butadiene synthase, a crotonyl-CoA reductase (alcohol forming) and a crotyl alcohol diphosphokinase (FIG. 2, steps N, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps N, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps N, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase (FIG. 2, steps N, C, D, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps O, D-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps O, K, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a butadiene synthase, a crotonyl-CoA reductase (alcohol forming) and a crotyl alcohol diphosphokinase (FIG. 2, steps O, K, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps O, I, J, E, F, G, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps O, I, J, E, P, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase (FIG. 2, steps L, C, D, E, P, H).

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase or an erythritol kinase (FIG. 3). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase (FIG. 3, steps A-F, and H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and butadiene synthase (FIG. 3, steps A-H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase (FIG. 3, steps I, J, K, B-F, H). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase (FIG. 3, steps I, J, K, B-H).

In some embodiments, the invention provides a non-naturally occurring microbial organism, including a microbial organism having a butadiene pathway having at least one exogenous nucleic acid encoding a butadiene pathway enzyme expressed in a sufficient amount to produce butadiene, the butadiene pathway including a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-hydroxyglutaryl-CoA reductase (alcohol forming), an 3-oxoglutaryl-CoA reductase (aldehyde forming), a 3,5-dioxopentanoate reductase (ketone reducing), a 3,5-dioxopentanoate reductase (aldehyde reducing), a 5-hydroxy-3-oxopentanoate reductase or an 3-oxo-glutaryl-CoA reductase (CoA reducing and alcohol forming) (FIG. 4). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase (FIG. 4, steps A-I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase. (FIG. 4, steps A, K, M, N, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing). (FIG. 4, steps A, K, L, D, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming). (FIG. 4, steps A, O, N, E, F, G, H, I). In one aspect, the non-naturally occurring microbial organism includes a microbial organism having a butadiene pathway having at least one exogenous nucleic acid encoding butadiene pathway enzymes expressed in a sufficient amount to produce butadiene, the butadiene pathway including a malonyl-CoA:acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy) phosphoryl]oxy pentanoate decarboxylase, a butenyl 4-diphosphate isomerase, a butadiene synthase and a 3-hydroxyglutaryl-CoA reductase (alcohol forming). (FIG. 4, steps A, B, J, E, F, G, H, I).

In an additional embodiment, the invention provides a non-naturally occurring microbial organism having a butadiene or a crotyl alcohol pathway, wherein the non-naturally occurring microbial organism comprises at least one exogenous nucleic acid encoding an enzyme or protein that converts a substrate to a product selected from the group consisting of acetyl-CoA to acetoacetyl-CoA, acetoacetyl-CoA to 3-hydroxybutyryl-CoA, 3-hydroxybutyryl-CoA to crotonyl-CoA, crotonyl-CoA to crotonaldehyde, crotonaldehyde to crotyl alcohol, crotyl alcohol to 2-betenyl-phosphate, 2-betenyl-phosphate to 2-butenyl-4-diphosphate, 2-butenyl-4-diphosphate to butadiene, erythrose-4-phosphate to erythritol-4-phosphate, erythritol-4-phosphate to 4-(cytidine 5'-diphospho)-erythritol, 4-(cytidine 5'-diphospho)-erythritol to 2-phospho-4-(cytidine 5'-diphospho)-erythritol, 2-phospho-4-(cytidine 5'-diphospho)-erythritol to erythritol-2,4-cyclodiphosphate, erythritol-2,4-cyclodiphosphate to 1-hydroxy-2-butenyl 4-diphosphate, 1-hydroxy-2-butenyl 4-diphosphate to butenyl 4-diphosphate, butenyl 4-diphosphate to 2-butenyl 4-diphosphate, 1-hydroxy-2-butenyl 4-diphosphate to 2-butenyl 4-diphosphate, 2-butenyl 4-diphosphate to butadiene, malonyl-CoA and acetyl-CoA to 3-oxoglutaryl-CoA, 3-oxoglutaryl-CoA to 3-hydroxyglutaryl-CoA to 3-hydroxy-5-oxopentanoate, 3-hydroxy-5-oxopentanoate to 3,5-dihydroxy pentanoate, 3,5-dihydroxy pentanoate to 3-hydroxy-5-phosphonatooxypentanoate, 3-hydroxy-5-phosphonatooxypentanoate to 3-hydroxy-5-[hydroxy(phosphonooxy)phosphoryl]oxy pentanoate, 3-hydroxy-5-[hydroxy(phosphonooxy)phosphoryl]oxy pentanoate to butenyl 4-biphosphate, glutaconyl-CoA to crotonyl-CoA, glutaryl-CoA to crotonyl-CoA, 3-aminobutyryl-CoA to crotonyl-CoA, 4-hydroxybutyryl-CoA to crotonyl-CoA, crotonyl-CoA to crotonate, crotonate to crotonaldehyde, crotonyl-CoA to crotyl alcohol, crotyl alcohol to 2-butenyl-4-diphosphate, erythrose-4-phosphate to erythrose, erythrose to erythritol, erythritol to erythritol-4-phosphate, 3-oxoglutaryl-CoA to 3,5-dioxopentanoate, 3,5-dioxopentanoate to 5-hydroxy-3-oxopentanoate, 5-hydroxy-3-oxopentanoate to 3,5-dihydroxypentanoate, 3-oxoglutaryl-CoA to 5-hydroxy-3-oxopentanoate, 3,5-dioxopentanoate to 3-hydroxy-5-oxopentanoate, 3-hydroxyglutaryl-CoA to 3,5-dihydroxypentanoate and oxaloacetate to malate, malate to fumarate, fumarate to succiniate, succinate to succinyl-CoA, succinyl-CoA to α-ketoglutarate, α-ketoglutarate to D-isocitrate, D-isocitrate to succinate, D-isocitrate to glyoxylate, glyoxylate and acetyl-CoA to malate, D-isocitrate to citrate, citrate to acetate, citrate to oxaloacetate, citrate to acetyl-CoA, acetyl-CoA to pyruvate, pyruvate to phosphoenolpyruvate, pyruvate to oxaloacetate, pyruvate to malate, phhosphoenolpyruvate to oxaloacetate. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a butadiene or a crotyl alcohol pathway, such as that shown in FIGS. 2-7 and 10-11.

While generally described herein as a microbial organism that contains a butadiene or a crotyl alcohol pathway, it is understood that the invention additionally provides a non-naturally occurring microbial organism comprising at least one exogenous nucleic acid encoding a butadiene or a crotyl alcohol pathway enzyme expressed in a sufficient amount to produce an intermediate of a butadiene or a crotyl alcohol pathway. For example, as disclosed herein, a butadiene pathway is exemplified in FIGS. 2-4. Therefore, in addition to a microbial organism containing a butadiene pathway that produces butadiene, the invention additionally provides a non-naturally occurring microbial organism comprising at least one exogenous nucleic acid encoding a butadiene pathway enzyme, where the microbial organism produces a butadiene pathway intermediate, for example, acetoacetyl-CoA, 3-hydroxybutyryl-CoA, crotonyl-CoA, crotonaldehyde, crotyl alcohol, 2-betenyl-phosphate, 2-butenyl-4-diphosphate, erythritol-4-phosphate, 4-(cytidine 5'-diphospho)-erythritol, 2-phospho-4-(cytidine 5'-diphospho)-erythritol, erythritol-2,4-cyclodiphosphate, 1-hydroxy-2-butenyl 4-diphosphate, butenyl 4-diphosphate, 2-butenyl 4-diphosphate, 3-oxoglutaryl-CoA, 3-hydroxyglutaryl-CoA, 3-hydroxy-5-oxopentanoate, 3,5-dihydroxy pentanoate, 3-hydroxy-5-phosphonatooxypentanoate, 3-hydroxy-5-[hydroxy(phosphonooxy) phosphoryl]oxy pentanoate, crotonate, erythrose, erythritol, 3,5-dioxopentanoate or 5-hydroxy-3-oxopentanoate.

It is understood that any of the pathways disclosed herein, as described in the Examples and exemplified in the Figures, including the pathways of FIGS. 2-7 and 10-11, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a butadiene or crotyl alcohol pathway intermediate can be utilized to produce the intermediate as a desired product.

This invention is also directed, in part to engineered biosynthetic pathways to improve carbon flux through a central metabolism intermediate en route to butadiene or crotyl alcohol. The present invention provides non-naturally occurring microbial organisms having one or more exogenous genes encoding enzymes that can catalyze various enzymatic transformations en route to butadiene or crotyl alcohol. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of butadiene or crotyl alcohol by (a) enhancing carbon fixation via the reductive TCA cycle, and/or (b) accessing additional reducing equivalents from gaseous carbon sources and/or syngas components such as CO, $CO_2$, and/or $H_2$. In addition to syngas, other sources of such gases include, but are not limted to, the atmosphere, either as found in nature or generated.

Figure 6:
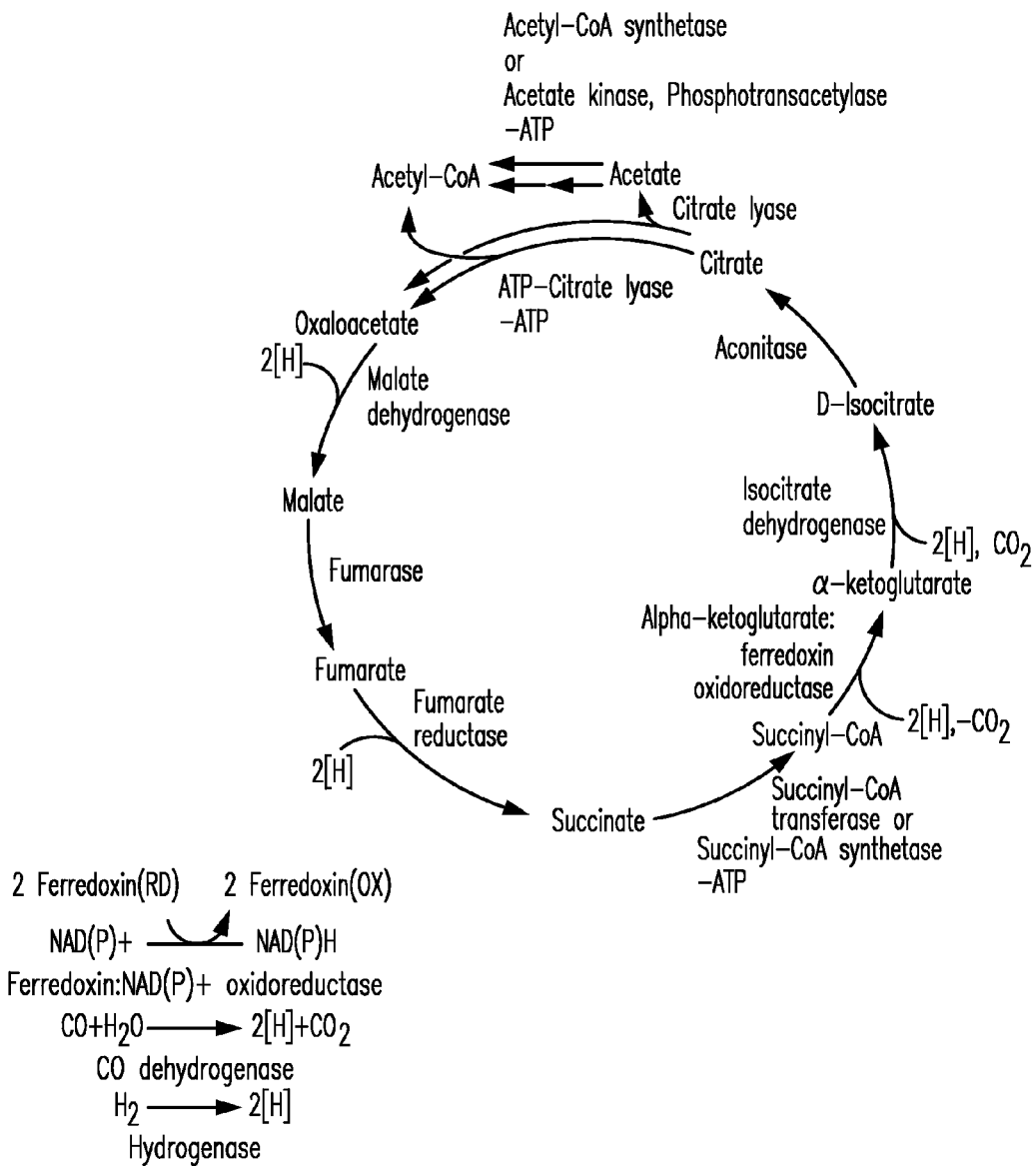
FIG. 6 shows the reverse TCA cycle for fixation of $CO_2$ on carbohydrates as substrates. The enzymatic transformations are carried out by the enzymes as shown.
Figure 7:
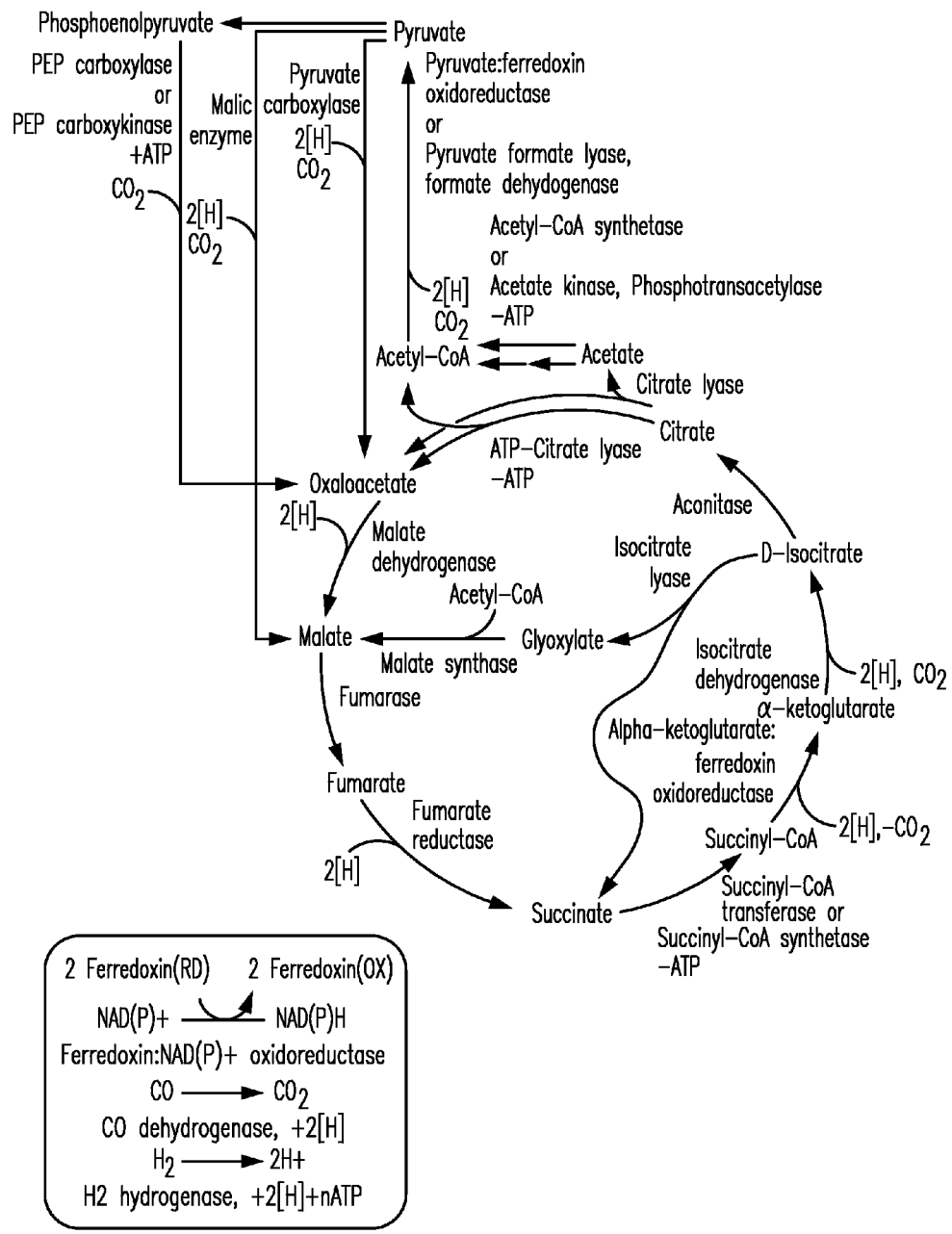
FIG. 7 shows the pathway for the reverse TCA cycle coupled with carbon monoxide dehydrogenase and hydrogenase for the conversion of syngas to acetyl-CoA.
Figure 8:
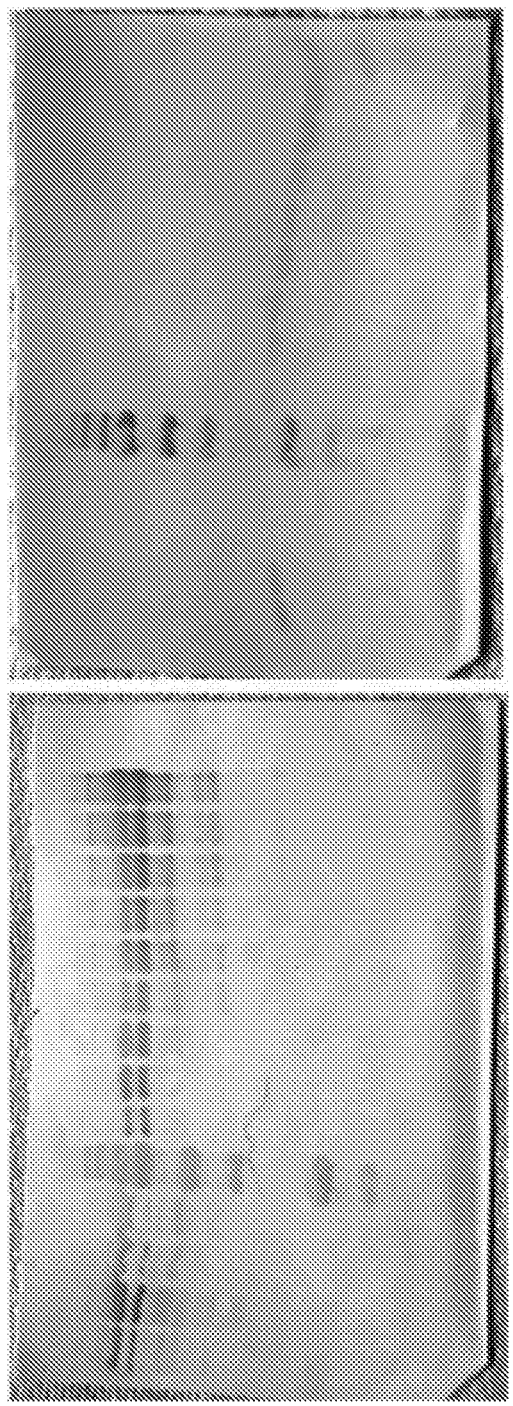
FIG. 8 shows Western blots of 10 micrograms ACS90 (lane 1), ACS91 (lane 2), Mta98/99 (lanes 3 and 4) cell extracts with size standards (lane 5) and controls of M. thermoacetica CODH (Moth_1202/1203) or Mtr (Moth_1197) proteins (50, 150, 250, 350, 450, 500, 750, 900, and 1000 ng).

The $CO_2$-fixing reductive tricarboxylic acid (RTCA) cycle is an endergenic anabolic pathway of $CO_2$ assimilation which uses reducing equivalents and ATP (FIG. 6). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes, can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, thioredoxins and reduced flavodoxins. The reducing equivalents, particularly NADH, NADPH, and reduced ferredoxin, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186: 2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate:ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase or by conversion of pyruvate to malate by malic enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the $NAD(P)^+$ dependent decarboxylation of alpha-ketoglutarate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H:ferredoxin oxidoreductase, carbon monoxide dehydrogenase, hydrogenase, and ferredoxin (see FIG. 7). Enzymes and the corresponding genes required for these activities are described herein.

Carbon from syngas or other gaseous carbon sources can be fixed via the reverse TCA cycle and components thereof. Specifically, the combination of certain carbon gas-utilization pathway components with the pathways for formation of butadiene or crotyl alcohol from acetyl-CoA results in high yields of these products by providing an efficient mechanism for fixing the carbon present in carbon dioxide, fed exogenously or produced endogenously from CO, into acetyl-CoA.

In some embodiments, a butadiene or crotyl alcohol pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having a butadiene or crotyl alcohol pathway includes at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a butadiene or crotyl alcohol pathway also comprising at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having a butadiene or crotyl alcohol pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, a pyruvate:ferredoxin oxidoreductase, isocitrate dehydrogenase, aconitase, and an alpha-ketoglutarate:ferredoxin oxidoreductase.

In some embodiments a non-naturally occurring microbial organism having a butadiene or crotyl alcohol pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce butadiene or crotyl alcohol.

In some embodiments, the non-naturally occurring microbial organism having a butadiene or crotyl alcohol pathway includes two exogenous nucleic acids, each encoding a reductive TCA pathway enzyme. In some embodiments, the non-naturally occurring microbial organism having a butadiene or crotyl alcohol pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, the non-naturally occurring microbial organism includes three exogenous nucleic acids encoding a citrate lyase, a fumarate reductase, and an alpha-ketoglutarate:ferredoxin oxidoreductase. In some embodiments, the non-naturally occurring microbial organism includes four exogenous nucleic acids encoding a pyruvate:ferredoxin oxidoreductase; a phosphoenolpyruvate carboxylase or a phosphoenolpyruvate carboxykinase, a CO dehydrogenase; and an H2 hydrogenase. In some embodiments, the non-naturally occurring microbial organism includes two exogenous nucleic acids encoding a CO dehydrogenase and an H2 hydrogenase.

In some embodiments, the non-naturally occurring microbial organisms having a butadiene or crotyl alcohol pathway further include an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism having a butadiene or crotyl alcohol pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having a butadiene or crotyl alcohol pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having a butadiene or crotyl alcohol pathway utilizes hydrogen for reducing equivalents. In some embodiments, the non-naturally occurring microbial organism having a butadiene or crotyl alcohol pathway utilizes CO for reducing equivalents. In some embodiments, the non-naturally occurring microbial organism having a butadiene or crotyl alcohol pathway utilizes combinations of CO and hydrogen for reducing equivalents.

In some embodiments, the non-naturally occurring microbial organism having a butadiene or crotyl alcohol pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having a butadiene or crotyl alcohol pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having a butadiene or crotyl alcohol pathway further includes at least one exogenous nucleic acid encoding a citrate lyase, an ATP-citrate lyase, a citryl-CoA synthetase, a citryl-CoA lyase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

It is understood by those skilled in the art that the above-described pathways for increasing product yield can be combined with any of the pathways disclosed herein, including those pathways depicted in the figures. One skilled in the art will understand that, depending on the pathway to a desired product and the precursors and intermediates of that pathway, a particular pathway for improving product yield, as discussed herein above and in the examples, or combination of such pathways, can be used in combination with a pathway to a desired product to increase the yield of that product or a pathway intermediate.

In one embodiment, the invention provides a non-naturally occurring microbial organism, comprising a microbial organism having a butadiene pathway comprising at least one exogenous nucleic acid encoding a butadiene pathway enzyme expressed in a sufficient amount to produce butadiene. Such a microbial organism can further comprise (a) a reductive TCA pathway comprising at least one exogenous nucleic acid encoding a reductive TCA pathway enzyme, wherein the at least one exogenous nucleic acid is selected from an ATP-citrate lyase, a citrate lyase, a citryl-CoA synthetase, a citryl-CoA lyase, a fumarate reductase, and an alpha-ketoglutarate:ferredoxin oxidoreductase; (b) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (c) at least one exogenous nucleic acid encodes an enzyme selected from a CO dehydrogenase, an $H_2$ hydrogenase, and combinations thereof. In such a microbial organism, a butadiene pathway can comprise a butadiene pathway disclosed herein. For example, the butadien pathway can be selected from: (i) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (ii) an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming); (iii) an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase; (iv) an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (v) an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (vi) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase. (vii) a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase. (viii) a glutaconyl-CoA decarboxylase, a crotyl alcohol kinase, a 2-butenyl-4-phosphate kinase, a butadiene synthase and crotonyl-CoA reductase (alcohol forming); (ix) a glutaconyl-CoA decarboxylase, a butadiene synthase, a crotonyl-CoA reductase (alcohol forming) and a crotyl alcohol diphosphokinase; (x) a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xi) a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase; (xii) a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase; (xiii) a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase; (xiv) a glutaryl-CoA dehydrogenase, a crotyl alcohol kinase, a 2-butenyl-4-phosphate kinase, a butadiene synthase and crotonyl-CoA reductase (alcohol forming); (xv) a glutaryl-CoA dehydrogenase, a butadiene synthase, a crotonyl-CoA reductase (alcohol forming) and a crotyl alcohol diphosphokinase; (xvi) a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xvii) a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase; (xviii) a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase; (xix) an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase; (xx) an 3-aminobutyryl-CoA deaminase, a crotyl alcohol kinase, a 2-butenyl-4-phosphate kinase, a butadiene synthase and crotonyl-CoA reductase (alcohol forming); (xxi) an 3-aminobutyryl-CoA deaminase, a butadiene synthase, a crotonyl-CoA reductase (alcohol forming) and a crotyl alcohol diphosphokinase; (xxii) an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxiii) an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase; (xxiv) a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase; (xxv) a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (xxvi) a 4-hydroxybutyryl-CoA dehydratase, a crotyl alcohol kinase, a 2-butenyl-4-phosphate kinase, a butadiene synthase and crotonyl-CoA reductase (alcohol forming); (xxvii) a 4-hydroxybutyryl-CoA dehydratase, a butadiene synthase, a crotonyl-CoA reductase (alcohol forming) and a crotyl alcohol diphosphokinase; (xxviii) a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxix) a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (xxx) a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase; (xxxi) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase; (xxxii) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and a butadiene synthase; (xxxiii) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase; (xxxiv) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase; (xxxv) a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase; (xxxvi) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase; (xxxvii) a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing); (xxxviii) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming); and (xxxix) a butadiene pathway comprising a malonyl-CoA:acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase and a 3-hydroxyglutaryl-CoA reductase (alcohol forming).

In such microbial organisms of the invention, a microbial organism comprising (a) can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In addition, a microbial organism comprising (b) can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In a particular embodiment, such a microbial organism can comprise two, three, four, five, six or seven exogenous nucleic acids each encoding a butadiene pathway enzyme. For example, such a microbial organism can comprise exogenous nucleic acids encoding each of the enzymes selected from: (i) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (ii) an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming); (iii) an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase; (iv) an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (v) an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (vi) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase; (vii) a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase; (viii) a glutaconyl-CoA decarboxylase, a crotyl alcohol kinase, a 2-butenyl-4-phosphate kinase, a butadiene synthase and crotonyl-CoA reductase (alcohol forming); (ix) a glutaconyl-CoA decarboxylase, a butadiene synthase, a crotonyl-CoA reductase (alcohol forming) and a crotyl alcohol diphosphokinase; (x) a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xi) a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase; (xii) a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase; (xiii) a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase; (xiv) a glutaryl-CoA dehydrogenase, a crotyl alcohol kinase, a 2-butenyl-4-phosphate kinase, a butadiene synthase and crotonyl-CoA reductase (alcohol forming); (xv) a glutaryl-CoA dehydrogenase, a butadiene synthase, a crotonyl-CoA reductase (alcohol forming) and a crotyl alcohol diphosphokinase; (xvi) a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xvii) a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase; (xviii) a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase; (xix) an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase; (xx) an 3-aminobutyryl-CoA deaminase, a crotyl alcohol kinase, a 2-butenyl-4-phosphate kinase, a butadiene synthase and crotonyl-CoA reductase (alcohol forming); (xxi) an 3-aminobutyryl-CoA deaminase, a butadiene synthase, a crotonyl-CoA reductase (alcohol forming) and a crotyl alcohol diphosphokinase; (xxii) an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxiii) an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase; (xxiv) a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase; (xxv) a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (xxvi) a 4-hydroxybutyryl-CoA dehydratase, a crotyl alcohol kinase, a 2-butenyl-4-phosphate kinase, a butadiene synthase and crotonyl-CoA reductase (alcohol forming); (xxvii) a 4-hydroxybutyryl-CoA dehydratase, a butadiene synthase, a crotonyl-CoA reductase (alcohol forming) and a crotyl alcohol diphosphokinase; (xxviii) a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxix) a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (xxx) a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase; (xxxi) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase; (xxxii) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and a butadiene synthase; (xxxiii) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase; (xxxiv) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase; (xxxv) a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase; (xxxvi) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase; (xxxvii) a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing); (xxxviii) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming); and (xxxix) a butadiene pathway comprising a malonyl-CoA:

acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase and a 3-hydroxyglutaryl-CoA reductase (alcohol forming).

Such microbial organisms of the invention can comprise two, three, four or five exogenous nucleic acids each encoding enzymes of (a), (b) or (c). For example, a microbial organism comprising (a) can comprise three exogenous nucleic acids encoding ATP-citrate lyase or citrate lyase, a fumarate reductase, and an alpha-ketoglutarate:ferredoxin oxidoreductase; a microbial organism comprising (b) can comprise four exogenous nucleic acids encoding pyruvate:ferredoxin oxidoreductase, a phosphoenolpyruvate carboxylase or a phosphoenolpyruvate carboxykinase, a CO dehydrogenase, and an H2 hydrogenase; or a microbial organism comprising (c) can comprise two exogenous nucleic acids encoding CO dehydrogenase and H2 hydrogenase. The invention further provides methods for producing butadiene by culturing such non-naturally occurring microbial organisms under conditions and for a sufficient period of time to produce butadiene.

The invention additionally provides a non-naturally occurring microbial organism, comprising a microbial organism having a crotyl alcohol pathway comprising at least one exogenous nucleic acid encoding a crotyl alcohol pathway enzyme expressed in a sufficient amount to produce crotyl alcohol. Such a microbial organism can further comprise (a) a reductive TCA pathway comprising at least one exogenous nucleic acid encoding a reductive TCA pathway enzyme, wherein the at least one exogenous nucleic acid is selected from an ATP-citrate lyase, a citrate lyase, a citryl-CoA synthetase, a citryl-CoA lyase, a fumarate reductase, and an alpha-ketoglutarate:ferredoxin oxidoreductase; (b) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (c) at least one exogenous nucleic acid encodes an enzyme selected from a CO dehydrogenase, an $H_2$ hydrogenase, and combinations thereof.

In such a microbial organism, the crotyl alcohol pathway can be selected from any of those disclosed herein and in the figures. For example, the crtoyl alcohol pathway can be selected from (i) an acetyl-CoA:acetyl-CoA acyltransferase; an acetoacetyl-CoA reductase; a 3-hydroxybutyryl-CoA dehydratase; a crotonyl-CoA hydrolase, synthase, or transferase; a crotonate reductase; and a crotonaldehyde reductase (alcohol forming); (ii) an acetyl-CoA:acetyl-CoA acyltransferase; an acetoacetyl-CoA reductase; a 3-hydroxybutyryl-CoA dehydratase; a crotonyl-CoA reductase (aldehyde forming); and a crotonaldehyde reductase (alcohol forming); (iii) an acetyl-CoA:acetyl-CoA acyltransferase; an acetoacetyl-CoA reductase; a 3-hydroxybutyryl-CoA dehydratase; and a crotonyl-CoA reductase (alcohol forming); (iv) a glutaconyl-CoA decarboxylase; a crotonyl-CoA hydrolase, synthase, or transferase; a crotonate reductase; and a crotonaldehyde reductase (alcohol forming); (v) a glutaconyl-CoA decarboxylase; a crotonyl-CoA reductase (aldehyde forming); and a crotonaldehyde reductase (alcohol forming); and (vi) a glutaconyl-CoA decarboxylase; and a crotonyl-CoA reductase (alcohol forming). (vii) a glutaryl-CoA dehydrogenase; a crotonyl-CoA hydrolase, synthase, or transferase; a crotonate reductase; and a crotonaldehyde reductase (alcohol forming); (viii) a glutaryl-CoA dehydrogenase; a crotonyl-CoA reductase (aldehyde forming); and a crotonaldehyde reductase (alcohol forming); (ix) a glutaryl-CoA dehydrogenase; and a crotonyl-CoA reductase (alcohol forming); (x) a 3-aminobutyryl-CoA deaminase; a crotonyl-CoA hydrolase, synthase, or transferase; a crotonate reductase; and a crotonaldehyde reductase (alcohol forming); (xi) a 3-aminobutyryl-CoA deaminase; a crotonyl-CoA reductase (aldehyde forming); and a crotonaldehyde reductase (alcohol forming); (xii) a 3-aminobutyryl-CoA deaminase; and a crotonyl-CoA reductase (alcohol forming); (xiii) a 4-hydroxybutyryl-CoA dehydratase; a crotonyl-CoA hydrolase, synthase, or transferase; a crotonate reductase; and a crotonaldehyde reductase (alcohol forming); (xiv) a 4-hydroxybutyryl-CoA dehydratase; a crotonyl-CoA reductase (aldehyde forming); and a crotonaldehyde reductase (alcohol forming); and (xv) a 4-hydroxybutyryl-CoA dehydratase; and a crotonyl-CoA reductase (alcohol forming).

Such a microbial organism of the invention comprising (a) can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. Such a microbial organism comprising (b) can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. Such a microbial organism can comprise two, three, four, five, six or seven exogenous nucleic acids each encoding a crotyl alcohol pathway enzyme.

For example, the microbial organism can comprise exogenous nucleic acids encoding each of the enzymes selected from (i) an acetyl-CoA:acetyl-CoA acyltransferase; an acetoacetyl-CoA reductase; a 3-hydroxybutyryl-CoA dehydratase; a crotonyl-CoA hydrolase, synthase, or transferase; a crotonate reductase; and a crotonaldehyde reductase (alcohol forming); (ii) an acetyl-CoA:acetyl-CoA acyltransferase; an acetoacetyl-CoA reductase; a 3-hydroxybutyryl-CoA dehydratase; a crotonyl-CoA reductase (aldehyde forming); and a crotonaldehyde reductase (alcohol forming); (iii) an acetyl-CoA:acetyl-CoA acyltransferase; an acetoacetyl-CoA reductase; a 3-hydroxybutyryl-CoA dehydratase; and a crotonyl-CoA reductase (alcohol forming); (iv) a glutaconyl-CoA decarboxylase; a crotonyl-CoA hydrolase, synthase, or transferase; a crotonate reductase; and a crotonaldehyde reductase (alcohol forming); (v) a glutaconyl-CoA decarboxylase; a crotonyl-CoA reductase (aldehyde forming); and a crotonaldehyde reductase (alcohol forming); (vi) a glutaconyl-CoA decarboxylase; and a crotonyl-CoA reductase (alcohol forming); (vii) a glutaryl-CoA dehydrogenase; a crotonyl-CoA hydrolase, synthase, or transferase; a crotonate reductase; and a crotonaldehyde reductase (alcohol forming); (viii) a glutaryl-CoA dehydrogenase; a crotonyl-CoA reductase (aldehyde forming); and a crotonaldehyde reductase (alcohol forming); (ix) a glutaryl-CoA dehydrogenase; and a crotonyl-CoA reductase (alcohol forming); (x) a 3-aminobutyryl-CoA deaminase; a crotonyl-CoA hydrolase, synthase, or transferase; a crotonate reductase; and a crotonaldehyde reductase (alcohol forming); (xi) a 3-aminobutyryl-CoA deaminase; a crotonyl-CoA reductase (aldehyde forming); and a crotonaldehyde reductase (alcohol forming); (xii) a 3-aminobutyryl-CoA deaminase; and a crotonyl-CoA reductase (alcohol forming). (xiii) a 4-hydroxybutyryl-CoA dehydratase; a crotonyl-CoA hydrolase, synthase, or transferase; a crotonate reductase; and a crotonaldehyde reductase (alcohol forming); (xiv) a 4-hydroxybutyryl-CoA dehydratase; a crotonyl-CoA reductase (aldehyde forming); and a crotonaldehyde reductase (alcohol forming); and (xv) a 4-hydroxybutyryl-CoA dehydratase; and a crotonyl-CoA reductase (alcohol forming).

Such microbial organisms of the invention can comprise two, three, four or five exogenous nucleic acids each encoding enzymes of (a), (b) or (c). For example, a microbial organism comprising (a) can comprise three exogenous nucleic acids encoding ATP-citrate lyase or citrate lyase, a fumarate reductase, and an alpha-ketoglutarate:ferredoxin oxidoreductase; a microbial organism comprising (b) can comprise four exogenous nucleic acids encoding pyruvate:ferredoxin oxidoreductase, a phosphoenolpyruvate carboxylase or a phosphoenolpyruvate carboxykinase, a CO dehydrogenase, and an $H_2$ hydrogenase; or a microbial organism comprising (c) can comprise two exogenous nucleic acids encoding CO dehydrogenase and H2 hydrogenase. The invention additionally provides methods for producing crotyl acohol, comprising culturing the non-naturally occurring microbial organism under conditions and for a sufficient period of time to produce crotyl alcohol.

In some embodiments, the carbon feedstock and other cellular uptake sources such as phosphate, ammonia, sulfate, chloride and other halogens can be chosen to alter the isotopic distribution of the atoms present in butadiene or crotyl alcohol or any butadiene or crotyl alcohol pathway intermediate. The various carbon feedstock and other uptake sources enumerated above will be referred to herein, collectively, as "uptake sources." Uptake sources can provide isotopic enrichment for any atom present in the product butadiene or crotyl alcohol or butadiene or crotyl alcohol pathway intermediate, or for side products generated in reactions diverging away from a butadiene or crotyl alcohol pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, a target isotopic ratio of an uptake source can be obtained via synthetic chemical enrichment of the uptake source. Such isotopically enriched uptake sources can be purchased commercially or prepared in the laboratory. In some embodiments, a target isotopic ratio of an uptake source can be obtained by choice of origin of the uptake source in nature. In some such embodiments, a source of carbon, for example, can be selected from a fossil fuel-derived carbon source, which can be relatively depleted of carbon-14, or an environmental carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

In some embodiments, the present invention provides butadiene or crotyl alcohol or a butadiene or crotyl alcohol intermediate that has a carbon-12, carbon-13, and carbon-14 ratio that reflects an atmospheric carbon uptake source. In some such embodiments, the uptake source is $CO_2$. In some embodiments, the present invention provides butadiene or crotyl alcohol or a butadiene or crotyl alcohol intermediate that has a carbon-12, carbon-13, and carbon-14 ratio that reflects petroleum-based carbon uptake source. In some embodiments, the present invention provides butadiene or crotyl alcohol or a butadiene or crotyl alcohol intermediate that has a carbon-12, carbon-13, and carbon-14 ratio that is obtained by a combination of an atmospheric carbon uptake source with a petroleum-based uptake source. Such combination of uptake sources is one means by which the carbon-12, carbon-13, and carbon-14 ratio can be varied.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the intermediates crotonate, 3,5-dioxopentanoate, 5-hydroxy-3-oxopentanoate, 3-hydroxy-5-oxopentanoate, 3-oxoglutaryl-CoA and 3-hydroxyglutaryl-CoA, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation: methyl crotanate; methyl-3,5-dioxopentanoate; methyl-5-hydroxy-3-oxopentanoate; methyl-3-hydroxy-5-oxopentanoate; 3-oxoglutaryl-CoA, methyl ester; 3-hydroxyglutaryl-CoA, methyl ester;

ethyl crotanate; ethyl-3,5-dioxopentanoate; ethyl-5-hydroxy-3-xopentanoate; ethyl-3-hydroxy-5-oxopentanoate; 3-oxoglutaryl-CoA, ethyl ester; 3-hydroxyglutaryl-CoA, ethyl ester; n-propyl crotanate; n-propyl-3,5-dioxopentanoate; n-propyl-5-hydroxy-3-oxopentanoate; n-propyl-3-hydroxy-5-oxopentanoate; 3-oxoglutaryl-CoA, n-propyl ester; and 3-hydroxyglutaryl-CoA, n-propyl ester. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more butadiene or crotyl alcohol biosynthetic pathways. Depending on the host microbial organism chosen for biosynthesis, nucleic acids for some or all of a particular butadiene or crotyl alcohol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve butadiene biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as butadiene.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the butadiene or crotyl alcohol biosynthetic pathway constituents of a selected host microbial organism, the non-naturally occurring microbial organisms of the invention will include at least one exogenously expressed butadiene or crotyl alcohol pathway-encoding nucleic acid and up to all encoding nucleic acids for one or more butadiene or crotyl alcohol biosynthetic pathways. For example, butadiene biosynthesis can be established in a host deficient in a pathway enzyme or protein through exogenous expression of the corresponding encoding nucleic acid. In a host deficient in all enzymes or proteins of a butadiene pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of butadiene can be included, such as an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H).

Given the teachings and guidance provided herein, those skilled in the art will understand that the number of encoding nucleic acids to introduce in an expressible form will, at least, parallel the butadiene or crotyl alcohol pathway deficiencies of the selected host microbial organism. Therefore, a non-naturally occurring microbial organism of the invention can have one, two, three, four, five, six, seven, eight, nine or ten, up to all nucleic acids encoding the enzymes or proteins constituting a butadiene or crotyl alcohol biosynthetic pathway disclosed herein. In some embodiments, the non-naturally occurring microbial organisms also can include other genetic modifications that facilitate or optimize butadiene or crotyl alcohol biosynthesis or that confer other useful functions onto the host microbial organism. One such other functionality can include, for example, augmentation of the synthesis of one or more of the butadiene or crotyl alcohol pathway precursors such as acetyl-CoA, glutaconyl-CoA, glutaryl-CoA, 3-aminobutyryl-CoA, 4-hydroxybutyryl-CoA, erythrose-4-phosphate or malonyl-CoA.

Generally, a host microbial organism is selected such that it produces the precursor of a butadiene or crotyl alcohol pathway, either as a naturally produced molecule or as an engineered product that either provides de novo production of a desired precursor or increased production of a precursor naturally produced by the host microbial organism. For example, acetyl-CoA, glutaconyl-CoA, glutaryl-CoA, 3-aminobutyryl-CoA, 4-hydroxybutyryl-CoA, erythrose-4-phosphate or malonyl-CoA are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a butadiene or crotyl alcohol pathway.

In some embodiments, a non-naturally occurring microbial organism of the invention is generated from a host that contains the enzymatic capability to synthesize butadiene or crotyl alcohol. In this specific embodiment it can be useful to increase the synthesis or accumulation of a butadiene or a crotyl alcohol pathway product to, for example, drive butadiene or crotyl alcohol pathway reactions toward butadiene or crotyl alcohol production. Increased synthesis or accumulation can be accomplished by, for example, overexpression of nucleic acids encoding one or more of the above-described butadiene or crotyl alcohol pathway enzymes or proteins. Overexpression the enzyme or enzymes and/or protein or proteins of the butadiene or crotyl alcohol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing butadiene or crotyl alcohol, through overexpression of one, two, three, four, five, six, seven, eight, nine, or ten, that is, up to all nucleic acids encoding butadiene or crotyl alcohol biosynthetic pathway enzymes or proteins. In addition, a non-naturally occurring organism can be generated by mutagenesis of an endogenous gene that results in an increase in activity of an enzyme in the butadiene or crotyl alcohol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a butadiene or crotyl alcohol biosynthetic pathway onto the microbial organism. Alternatively, encoding nucleic acids can be introduced to produce an intermediate microbial organism having the biosynthetic capability to catalyze some of the required reactions to confer butadiene or crotyl alcohol biosynthetic capability. For example, a non-naturally occurring microbial organism having a butadiene biosynthetic pathway can comprise at least two exogenous nucleic acids encoding desired enzymes or proteins, such as the combination of a crotyl alcohol kinase and a butadiene synthase, or alternatively a 4-(cytidine 5'-diphospho)-erythritol kinase and a butadiene synthase, or alternatively a 1-hydroxy-2-butenyl 4-diphosphate synthase and a butadiene synthase, or alternatively a 3-hydroxy-5-phosphonatooxypentanoate kinase and a butadiene synthase, or alternatively a crotonyl-CoA hydrolase and a crotyl alcohol diphosphokinase, or alternatively an erythrose reductase and butadiene synthase, or alternatively an 3-oxo-glutaryl-CoA reductase (CoA reducing and alcohol forming) and 3-Hydroxy-5-[hydroxy(phosphonooxy)phosphoryl]oxy pentanoate decarboxylase, or alternative an ATP-citrate lyase and butadiene synthase, or alternatively a pyruvate:ferredoxin oxidoreductase and a crotyl alcohol diphosphokinase, or alternatively a CO dehydrogenase and a butadiene synthase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a crotyl alcohol kinase, a 2-butenyl-4-phosphate kinase and a butadiene synthase, or alternatively a 1-hydroxy-2-butenyl 4-diphosphate synthase, a 1-hydroxy-2-butenyl 4-diphosphate reductase, and a butadiene synthase, or alternatively an 3-oxoglutaryl-CoA reductase, a 3-hydroxy-5-oxopentanoate reductase, and a butadiene synthase, or alternatively an acetyl-CoA:acetyl-CoA acyltransferase, a crotyl alcohol kinase and a butadiene synthase, or alternatively a glutaconyl-CoA decarboxylase, a crotonyl-CoA reductase (alcohol forming), and a crotyl alcohol diphosphokinase, or alternatively a an erythrose-4-phosphate kinase, a 4-(cytidine 5'-diphospho)-erythritol kinase and a 1-hydroxy-2-butenyl 4-diphosphate synthase, or alternatively a 3,5-dioxopentanoate reductase (aldehyde reducing), a butenyl 4-diphosphate isomerase, and a butadiene synthase, or alternatively a citrate lyase, a fumarate reductase, and a butadiene synthase, or alternatively a phosphoenolpyruvate carboxylase, a CO dehydrogenase, and a butadiene synthase, or alternatively an alpha-ketoglutarate:ferredoxin oxidoreductase, an H2 hydrogenase, and a crotyl alcohol diphosphokinase, and so forth, as desired, so long as the combination of enzymes and/or proteins of the desired biosynthetic pathway results in production of the corresponding desired product. Similarly, any combination of four, such as a crotonaldehyde reductase (alcohol forming), a crotyl alcohol kinase, a 2-butenyl-4-phosphate kinase and a butadiene synthase, or alternatively a 1-hydroxy-2-butenyl 4-diphosphate synthase, a 1-hydroxy-2-butenyl 4-diphosphate reductase, a butenyl 4-diphosphate isomerase and butadiene synthase, or alternatively a 3-hydroxy-5-phosphonatooxypentanoate kinase, a 3-hydroxy-5-[hydroxy(phosphonooxy)phosphoryl]oxy pentanoate kinase, a butenyl 4-diphosphate isomerase and a butadiene synthase, or alternatively an erythrose-4-phosphate reductase, an erythritol-4-phospate cytidylyltransferase, a 4-(cytidine 5'-diphospho)-erythritol kinase and a butadiene synthase, or alternatively an 3-aminobutyryl-CoA deaminase, a crotonyl-CoA reductase (alcohol forming), a crotyl alcohol diphosphokinase and a butadiene synthase, or alternatively an erythrose reductase, a 4-(cytidine 5'-diphospho)-erythritol kinase, an erythritol 2,4-cyclodiphosphate synthase and a 1-hydroxy-2-butenyl 4-diphosphate reductase, or alternatively a malonyl-CoA:acetyl-CoA acyltransferase, a 3-hydroxyglutaryl-CoA reductase (alcohol forming), a butenyl 4-diphosphate isomerase and a butadiene synthase, or alternatively citrate lyase, a fumarate reductase, an alpha-ketoglutarate:ferredoxin oxidoreductase, and a butadiene synthase, or alternatively a phosphoenolpyruvate carboxykinase, a CO dehydrogenase, an H2 hydrogenase and a crotyl alcohol diphosphokinase, or alternatively a pyruvate:ferredoxin oxidoreductase, a phosphoenolpyruvate carboxylase, a phosphoenolpyruvate carboxykinase, and a glutaconyl-CoA decarboxylase, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of butadiene or crotyl alcohol as described herein, the non-naturally occurring microbial organisms and methods of the invention also can be utilized in various combinations with each other and with other microbial organisms and methods well known in the art to achieve product biosynthesis by other routes. For example, one alternative to produce butadiene other than use of the butadiene producers is through addition of another microbial organism capable of converting a butadiene pathway intermediate to butadiene. One such procedure includes, for example, the fermentation of a microbial organism that produces a butadiene pathway intermediate. The butadiene pathway intermediate can then be used as a substrate for a second microbial organism that converts the butadiene pathway intermediate to butadiene. The butadiene pathway intermediate can be added directly to another culture of the second organism or the original culture of the butadiene pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, butadiene or crotyl alcohol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of butadiene can be accomplished by constructing a microbial organism that contains biosynthetic pathways for conversion of one pathway intermediate to another pathway intermediate or the product. Alternatively, butadiene also can be biosynthetically produced from microbial organisms through co-culture or co-fermentation using two organisms in the same vessel, where the first microbial organism produces a butadiene intermediate and the second microbial organism converts the intermediate to butadiene.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce butadiene or crotyl alcohol.

Sources of encoding nucleic acids for a butadiene or crotyl alcohol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acetobacter aceti, Acidaminococcus fermentans, Acinetobacter baylyi, Acinetobacter calcoaceticus, Acinetobacter* sp. ADP1, *Acinetobacter* sp. Strain M-1, *Actinobacillus succinogenes, Aeropyrum pernix, Allochromatium vinosum* DSM 180, *Anaerobiospirillum succiniciproducens, Aquifex aeolicus, Aquifex aeolicus, Arabidopsis thaliana, Arabidopsis thaliana col, Archaeoglobus fulgidus, Archaeoglobus fulgidus* DSM 4304, *Aromatoleum aromaticum EbN1, Ascaris suum, Aspergillus nidulans, Azoarcus* sp. CIB, *Azoarcus* sp. *T, Azotobacter vinelandii* DJ, *Bacillus cereus, Bacillus megaterium, Bacillus subtilis, Balnearium lithotrophicum, Bos Taurus*, BRC 13350, *Brucella melitensis, Burkholderia ambifaria* AMMD, *Burkholderia phymatum*, butyrate-producing bacterium L2-50, *Campylobacter curvus* 525.92, *Campylobacter jejuni, Candida albicans, Candida magnolia, Carboxydothermus hydrogenoformans, Chlorobium phaeobacteroides* DSM 266, *Chlorobium limicola, Chlorobium tepidum, Chloroflexus aurantiacus, Citrobacter youngae* ATCC 29220, *Clostridium acetobutylicum, Clostridium aminobutyricum, Clostridium beijerinckii, Clostridium beijerinckii* NCIMB 8052, *Clostridium beijerinckii* NRRL B593, *Clostridium botulinum* C str. Eklund, *Clostridium carboxidivorans* P7, *Clostridium cellulolyticum* H10, *Clostridium kluyveri, Clostridium kluyveri* DSM 555, *Clostridium novyi* NT, *Clostridium pasteurianum, Clostridium saccharoperbutylacetonicum, Corynebacterium glutamicum, Corynebacterium glutamicum* ATCC 13032, *Cupriavidus taiwanensis, Cyanobium* PCC7001, *Desulfovibrio africanus, DesulfoVibrio desulfuricans* G20, *Desulfovibrio desulfuricans* subsp. *desulfuricans* str. ATCC 27774, *Desulfovibrio fructosovorans* JJ, *Desulfovibrio vulgaris* str. Hildenborough, *Dictyostelium discoideum* AX4 DSM 266, *Enterococcus faecalis, Erythrobacter* sp. NAP1, *Escherichia coli* K12, *Escherichia coli* str. K-12 substr. MG1655, *Eubacterium rectale* ATCC 33656, *Fusobacterium nucleatum, Fusobacterium nucleatum* subsp. *nucleatum* ATCC 25586, *Geobacillus thermoglucosidasius, Geobacter metallireducens* GS-15, *Geobacter sulfurreducens, Haematococcus pluvialis, Haemophilus influenza, Haloarcula marismortui, Haloarcula marismortui* ATCC 43049, *Helicobacter pylori, Helicobacter pylori* 26695, *Homo sapiens, Hydrogenobacter thermophilus, Klebsiella pneumonia, Klebsiella pneumonia, Lactobacillus plantarum, Leuconostoc mesenteroides, Leuconostoc mesenteroides, Mannheimia succiniciproducens*, marine gamma proteobacterium HTCC2080, *Metallosphaera sedula, Methanocaldococcus jannaschii, Methanosarcina thermophila, Methanothermobacter thermautotrophicus, Methylobacterium extorquens, Moorella thermoacetica, Mus musculus, Mycobacterium avium* subsp. *paratuberculosis* K-10, *Mycobacterium bovis* BCG, *Mycobacterium marinum* M, *Mycobacterium smegmatis, Mycobacterium smegmatis* MC2 155, *Mycobacterium tuberculosis, Mycoplasma pneumoniae* M129, *Nocardia farcinica* IFM 10152, *Nocardia iowensis* (sp. NRRL 5646), *Nostoc* sp. PCC 7120, *Oryctolagus cuniculus, Paracoccus denitrificans, Pelobacter carbinolicus* DSM 2380, *Pelotomaculum thermopropionicum, Penicillium chrysogenum, Populus alba, Populus tremula×Populus alba, Porphyromonas ingivalis, Porphyromonas gingivalis* W83, *Pseudomonas aeruginosa, Pseudomonas aeruginosa* PA01, *Pseudomonas fluorescens, Pseudomonas fluorescens* Pf-5, *Pseudomonas knackmussii* (B13), *Pseudomonas putida, Pseudomonas putida* E23, *Pseudomonas putida* KT2440, *Pseudomonas* sp, *Pueraria Montana, Pyrobaculum aerophilum* str. IM2, *Pyrococcus furiosus, Ralstonia eutropha, Ralstonia eutropha* H16, *Ralstonia metallidurans, Rattus norvegicus, Rhodobacter capsulatus, Rhodobacter spaeroides, Rhodococcus rubber, Rhodopseudomonas palustris, Rhodopseudomonas palustris, Rhodopseudomonas palustris* CGA009, *Rhodospirillum rubrum, Roseburia intestinalis* L1-82, *Roseburia inulinivorans* DSM 16841, *Roseburia* sp. A2-183, *Roseiflexus castenholzii, Saccharomyces cerevisiae, Saccharomyces cerevisiae, Saccharopolyspora rythraea* NRRL 2338, *Salmonella enteric, Salmonella enterica* subsp., rizonae serovar, *Salmonella typhimurium, Schizosaccharomyces pombe, Simmondsia chinensis, Sinorhizobium meliloti, Sordaria macrospora, Staphylococcus ureus, Streptococcus pneumonia, Streptomyces coelicolor, Streptomyces griseus* subsp. *griseus, Streptomyces griseus* subsp. *griseus* NBRC 13350, *Streptomyces* sp. ACT-1, *Sulfolobus acidocalarius, Sulfolobus shibatae, Sulfobus solfataricus, Sulfolobus* sp. strain 7, *Sulfolobus tokodaii, Sulfurihydrogenibium subterraneum, Sulfurimonas denitrificans, Synechocystis* sp. strain PCC6803, *Syntrophus, ciditrophicus, Thauera aromatica, Thermoanaerobacter brockii* HTD4, *Thermoanaero-*

*bacter tengcongensis* MB4, *Thermocrinis albus, Thermosynechococcus elongates, Thermotoga maritime, Thermotoga maritime* MSB8, *Thermus hermophilus* HB8, *Thermus thermophilus, Thermus thermophilus, Thiobacillus denitrificans, Thiocapsa roseopersicina, Trichomonas vaginalis* G3, *Trichosporonoides megachiliensis, Trypanosoma brucei, Tsukamurella paurometabola* DSM 20162, *Yarrowia lipolytica, Yersinia intermedia* ATCC 29909, *Zea mays, Zoogloea ramigera, Zygosaccharomyces rouxii, Zymomonas mobilis*, as well as other exemplary species disclosed herein are available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite butadiene or crotyl alcohol biosynthetic activity for one or more genes in related or distant species, including for example, homologues, orthologs, paralogs and non-orthologous gene displacements of known genes, and the interchange of genetic alterations between organisms is routine and well known in the art. Accordingly, the metabolic alterations allowing biosynthesis of butadiene or crotyl alcohol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative butadiene or crotyl alcohol biosynthetic pathway exists in an unrelated species, butadiene or crotyl alcohol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize butadiene or crotyl alcohol.

Methods for constructing and testing the expression levels of a non-naturally occurring butadiene or crotyl alcohol-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of butadiene or crotyl alcohol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more butadiene or crotyl alcohol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase, a butadiene synthase, a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, an 3-aminobutyryl-CoA deaminase, a 4-hydroxybutyryl-CoA dehydratase or a crotyl alcohol diphosphokinase (FIG. 2). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps A-H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps A-C, K, F, G, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase (FIG. 2, steps A-C, K, P, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase, (FIG. 2, steps A-C, I, J, E, F, G, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps A-C, I, J, E, P, H). In one aspect, the method includes a microbial organism having a butadiene pathway including an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase (FIG. 2, steps A-E, P, H). In one aspect, the method includes a microbial organism having a butadiene pathway including a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps L, D-H). In one aspect, the method includes a microbial organism having a butadiene pathway including a glutaconyl-CoA decarboxylase, a crotyl alcohol kinase, a 2-butenyl-4-phosphate kinase, a butadiene synthase and crotonyl-CoA reductase (alcohol forming) (FIG. 2, steps L, K, F, G, H). In one aspect, the method includes a microbial organism having a butadiene pathway including a glutaconyl-CoA decarboxylase, a butadiene synthase, a crotonyl-CoA reductase (alcohol forming) and a crotyl alcohol diphosphokinase (FIG. 2, steps L, K, P, H). In one aspect, the method includes a microbial organism having a butadiene pathway including a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps L, I, J, E, F, G, H). In one aspect, the method includes a microbial organism having a butadiene pathway including a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps L, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase (FIG. 2, steps L, C, D, E, P, H). In one aspect, the method includes a microbial organism having a butadiene pathway including a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps M, D-H). In one aspect, the method includes a microbial organism having a butadiene pathway including a glutaryl-CoA dehydrogenase, a crotyl alcohol kinase, a 2-butenyl-4-phosphate kinase, a butadiene synthase and crotonyl-CoA reductase (alcohol forming) (FIG. 2, steps M, K, F, G, H). In one aspect, the method includes a microbial organism having a butadiene pathway including a glutaryl-CoA dehydrogenase, a butadiene synthase, a crotonyl-CoA reductase (alcohol forming) and a crotyl alcohol diphosphokinase (FIG. 2, steps M, K, P, H). In one aspect, the method includes a microbial organism having a butadiene pathway including a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps M, I, J, E, F, G, H). In one aspect, the method includes a microbial organism having a butadiene pathway including a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps M, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase (FIG. 2, steps M, C, D, E, P, H). In one aspect, the method includes a microbial organism having a butadiene pathway including an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps N, D-H). In one aspect, the method includes a microbial organism having a butadiene pathway including an 3-aminobutyryl-CoA deaminase, a crotyl alcohol kinase, a 2-butenyl-4-phosphate kinase, a butadiene synthase and crotonyl-CoA reductase (alcohol forming) (FIG. 2, steps N, K, F, G, H). In one aspect, the method includes a microbial organism having a butadiene pathway including an 3-aminobutyryl-CoA deaminase, a butadiene synthase, a crotonyl-CoA reductase (alcohol forming) and a crotyl alcohol diphosphokinase (FIG. 2, steps N, K, P, H). In one aspect, the method includes a microbial organism having a butadiene pathway including an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps N, I, J, E, F, G, H). In one aspect, the method includes a microbial organism having a butadiene pathway including an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps N, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase (FIG. 2, steps N, C, D, E, P, H). In one aspect, the method includes a microbial organism having a butadiene pathway including a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase (FIG. 2, steps O, D-H). In one aspect, the method includes a microbial organism having a butadiene pathway including a 4-hydroxybutyryl-CoA dehydratase, a crotyl alcohol kinase, a 2-butenyl-4-phosphate kinase, a butadiene synthase and crotonyl-CoA reductase (alcohol forming) (FIG. 2, steps O, K, F, G, H). In one aspect, the method includes a microbial organism having a butadiene pathway including a 4-hydroxybutyryl-CoA dehydratase, a butadiene synthase, a crotonyl-CoA reductase (alcohol forming) and a crotyl alcohol diphosphokinase (FIG. 2, steps O, K, P, H). In one aspect, the method includes a microbial organism having a butadiene pathway including a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase (FIG. 2, steps O, I, J, E, F, G, H). In one aspect, the method includes a microbial organism having a butadiene pathway including a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase (FIG. 2, steps O, I, J, E, P, H). In one aspect, the method includes a microbial organism having a butadiene pathway including a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase (FIG. 2, steps O, C, D, E, P, H).

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase or an erythritol kinase (FIG. 3). In one aspect, the method includes a microbial organism having a butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase (FIG. 3, steps A-F, and H). In one aspect, the method includes a microbial organism having a butadiene pathway including an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and butadiene synthase (FIG. 3, steps A-H). In one aspect, the method includes a microbial organism having a butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase (FIG. 3, steps I, J, K, B-F, H). In one aspect, the method includes a microbial organism having a butadiene pathway including an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase (FIG. 3, steps I, J, K, B-H).

In some embodiments, the invention provides a method for producing butadiene that includes culturing a non-naturally occurring microbial organism, including a microbial organism having a butadiene pathway, the butadiene pathway including at least one exogenous nucleic acid encoding a butadiene pathway enzyme expressed in a sufficient amount to produce butadiene, the butadiene pathway including a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 3-hydroxyglutaryl-CoA reductase (alcohol forming), an 3-oxoglutaryl-CoA reductase (aldehyde forming), a 3,5-dioxopentanoate reductase (ketone reducing), a 3,5-dioxopentanoate reductase (aldehyde reducing), a 5-hydroxy-3-oxopentanoate reductase or an 3-oxo-glutaryl-CoA reductase (CoA reducing and alcohol forming) (FIG. 4). In one aspect, the method includes a microbial organism having a butadiene pathway including a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase (FIG. 4, steps A-I). In one aspect, the method includes a microbial organism having a butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase. (FIG. 4, steps A, K, M, N, E, F, G, H, I). In one aspect, the method includes a microbial organism having a butadiene pathway including a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing). (FIG. 4, steps A, K, L, D, E, F, G, H, I). In one aspect, the method includes a microbial organism having a butadiene pathway including a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming). (FIG. 4, steps A, O, N, E, F, G, H, I). In one aspect, the method includes a microbial organism having a butadiene pathway including a malonyl-CoA:acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy (phosphonooxy)phosphoryl]oxy pentanoate decarboxylase, a butenyl 4-diphosphate isomerase, a butadiene synthase and a 3-hydroxyglutaryl-CoA reductase (alcohol forming). (FIG. 4, steps A, B, J, E, F, G, H, I).

In some embodiments, the invention provides a method for producing butadiene that includes culturing a non-naturally occurring microbial organism as described herein, including a microbial organism having a butadiene pathway comprising at least one exogenous nucleic acid encoding a butadiene pathway enzyme expressed in a sufficient amount to produce butadiene. Such a microbial organism can further comprise (a) a reductive TCA pathway comprising at least one exogenous nucleic acid encoding a reductive TCA pathway enzyme, wherein the at least one exogenous nucleic acid is selected from an ATP-citrate lyase, a citrate lyase, a citryl-CoA synthetase, a citryl-CoA lyase, a fumarate reductase, and an alpha-ketoglutarate:ferredoxin oxidoreductase; (b) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (c) at least one exogenous nucleic acid encodes an enzyme selected from a CO dehydrogenase, an $H_2$ hydrogenase, and combinations thereof. In such a microbial organism, a butadiene pathway can comprise a butadiene pathway disclosed herein. For example, the butadien pathway can be selected from: (i) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (ii) an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming); (iii) an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase; (iv) an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (v) an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (vi) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase. (vii) a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase. (viii) a glutaconyl-CoA decarboxylase, a crotyl alcohol kinase, a 2-butenyl-4-phosphate kinase, a butadiene synthase and crotonyl-CoA reductase (alcohol forming); (ix) a glutaconyl-CoA decarboxylase, a butadiene synthase, a crotonyl-CoA reductase (alcohol forming) and a crotyl alcohol diphosphokinase; (x) a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xi) a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase; (xii) a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase; (xiii) a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase; (xiv) a glutaryl-CoA dehydrogenase, a crotyl alcohol kinase, a 2-butenyl-4-phosphate kinase, a butadiene synthase and crotonyl-CoA reductase (alcohol forming); (xv) a glutaryl-CoA dehydrogenase, a butadiene synthase, a crotonyl-CoA reductase (alcohol forming) and a crotyl alcohol diphosphokinase; (xvi) a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xvii) a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase; (xviii) a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase; (xix) an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase; (xx) an 3-aminobutyryl-CoA deaminase, a crotyl alcohol kinase, a 2-butenyl-4-phosphate kinase, a butadiene synthase and crotonyl-CoA reductase (alcohol forming); (xxi) an 3-aminobutyryl-CoA deaminase, a butadiene synthase, a crotonyl-CoA reductase (alcohol forming) and a crotyl alcohol diphosphokinase; (xxii) an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxiii) an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase; (xxiv) a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase; (xxv) a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (xxvi) a 4-hydroxybutyryl-CoA dehydratase, a crotyl alcohol kinase, a 2-butenyl-4-phosphate kinase, a butadiene synthase and crotonyl-CoA reductase (alcohol forming); (xxvii) a 4-hydroxybutyryl-CoA dehydratase, a butadiene synthase, a crotonyl-CoA reductase (alcohol forming) and a crotyl alcohol diphosphokinase; (xxviii) a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxix) a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (xxx) a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase; (xxxi) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase; (xxxii) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and a butadiene synthase; (xxxiii) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase; (xxxiv) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase; (xxxv) a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase and a butadiene synthase; (xxxvi) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase; (xxxvii) a malonyl-CoA:acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing); (xxxviii) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming); and (xxxix) a butadiene pathway comprising a malonyl-CoA:acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase and a 3-hydroxyglutaryl-CoA reductase (alcohol forming).

In some embodiments, the invention provides a method for producing butadiene that includes culturing a non-naturally occurring microbial organism as described herein, including a microbial organism comprising (a) as described above, which can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In addition, a microbial organism comprising (b) as described above can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In a particular embodiment, such a microbial organism used in a method for producing butadiene can comprise two, three, four, five, six or seven exogenous nucleic acids each encoding a butadiene pathway enzyme. For example, such a microbial organism can comprise exogenous nucleic acids encoding each of the enzymes selected from: (i) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (ii) an acetyl-CoA:acetyl-CoA acyltransferase, an acetoacetyl-CoA reductase, a 3-hydroxybutyryl-CoA dehydratase, a crotyl alcohol kinase, a 2-butenyl-4-phosphate kinase, a butadiene synthase and crotonyl-CoA reductase (alcohol forming); (iii) an acetyl-CoA:acetyl-CoA acyltransferase, an acetoacetyl-CoA reductase, a 3-hydroxybutyryl-CoA dehydratase, a butadiene synthase, a crotonyl-CoA reductase (alcohol forming) and a crotyl alcohol diphosphokinase; (iv) an acetyl-CoA:acetyl-CoA acyltransferase, an acetoacetyl-CoA reductase, a 3-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (v) an acetyl-CoA:acetyl-CoA acyltransferase, an acetoacetyl-CoA reductase, a 3-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (vi) an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a butadiene synthase and a crotyl alcohol diphosphokinase; (vii) a glutaconyl-CoA decarboxylase, a crotonyl-CoA reductase (aldehyde forming), a crotonaldehyde reductase (alcohol forming), a crotyl alcohol kinase, a 2-butenyl-4-phosphate kinase and a butadiene synthase; (viii) a glutaconyl-CoA decarboxylase, a crotyl alcohol kinase, a 2-butenyl-4-phosphate kinase, a butadiene synthase and crotonyl-CoA reductase (alcohol forming); (ix) a glutaconyl-CoA decarboxylase, a butadiene synthase, a crotonyl-CoA reductase (alcohol forming) and a crotyl alcohol diphosphokinase; (x) a glutaconyl-CoA decarboxylase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xi) a glutaconyl-CoA decarboxylase, a crotonaldehyde reductase (alcohol forming), a butadiene synthase, a crotonyl-CoA hydrolase, synthetase or transferase, a crotonate reductase and a crotyl alcohol diphosphokinase; (xii) a 3-hydroxybutyryl-CoA dehydratase, a crotonyl-CoA reductase (aldehyde forming), a crotonaldehyde reductase (alcohol forming), a butadiene a glutaconyl-CoA decarboxylase and a crotyl alcohol diphosphokinase; (xiii) a glutaryl-CoA dehydrogenase, a crotonyl-CoA reductase (aldehyde forming), a crotonaldehyde reductase (alcohol forming), a crotyl alcohol kinase, a 2-butenyl-4-phosphate kinase and a butadiene synthase; (xiv) a glutaryl-CoA dehydrogenase, a crotyl alcohol kinase, a 2-butenyl-4-phosphate kinase, a butadiene synthase and crotonyl-CoA reductase (alcohol forming); (xv) a glutaryl-CoA dehydrogenase, a butadiene synthase, a crotonyl-CoA reductase (alcohol forming) and a crotyl alcohol diphosphokinase; (xvi) a glutaryl-CoA dehydrogenase, a crotonaldehyde reductase (alcohol forming), a crotyl alcohol kinase, a 2-butenyl-4-phosphate kinase, a butadiene synthase, a crotonyl-CoA hydrolase, synthetase, or transferase and a crotonate reductase; (xvii) a glutaryl-CoA dehydrogenase, a crotonaldehyde reductase (alcohol forming), a butadiene synthase, a crotonyl-CoA hydrolase, synthetase or transferase, a crotonate reductase and a crotyl alcohol diphosphokinase; (xviii) a 3-hydroxybutyryl-CoA dehydratase, a crotonyl-CoA reductase (aldehyde forming), a crotonaldehyde reductase (alcohol forming), a butadiene synthase, a glutaryl-CoA dehydrogenase and a crotyl alcohol diphosphokinase; (xix) an 3-aminobutyryl-CoA deaminase, a crotonyl-CoA reductase (aldehyde forming), a crotonaldehyde reductase (alcohol forming), a crotyl alcohol kinase, a 2-butenyl-4-phosphate kinase and a butadiene synthase; (xx) an 3-aminobutyryl-CoA deaminase, a crotyl alcohol kinase, a 2-butenyl-4-phosphate kinase, a butadiene synthase and crotonyl-CoA reductase (alcohol forming); (xxi) an 3-aminobutyryl-CoA deaminase, a butadiene synthase, a crotonyl-CoA reductase (alcohol forming) and a crotyl alcohol diphosphokinase; (xxii) an 3-aminobutyryl-CoA deaminase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxiii) an 3-aminobutyryl-CoA deaminase, a crotonaldehyde reductase (alcohol forming), a butadiene synthase, a crotonyl-CoA hydrolase, synthetase or transferase, a crotonate reductase and a crotyl alcohol diphosphokinase; (xxiv) a 3-hydroxybutyryl-CoA dehydratase, a crotonyl-CoA reductase (aldehyde forming), a crotonaldehyde reductase (alcohol forming), a butadiene synthase, a 3-aminobutyryl-CoA deaminase and a crotyl alcohol diphosphokinase; (xxv) a 4-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; (xxvi) a 4-hydroxybutyryl-CoA dehydratase, a crotyl alcohol kinase, a 2-butenyl-4-phosphate kinase, a butadiene synthase and crotonyl-CoA reductase (alcohol forming); (xxvii) a 4-hydroxybutyryl-CoA dehydratase, a butadiene synthase, a crotonyl-CoA reductase (alcohol forming) and a crotyl alcohol diphosphokinase; (xxviii) a 4-hydroxybutyryl-CoA dehydratase, a crotonaldehyde reductase (alcohol forming), a crotyl alcohol kinase, a 2-butenyl-4-phosphate kinase, a butadiene synthase, a crotonyl-CoA hydrolase, synthetase or transferase and a crotonate reductase; (xxix) a 4-hydroxybutyryl-CoA dehydratase, a crotonaldehyde reductase (alcohol forming), a butadiene synthase, a crotonyl-CoA hydrolase, synthetase or transferase, a crotonate reductase and a crotyl alcohol diphosphokinase; (xxx) a 3-hydroxybutyryl-CoA dehydratase, a crotonyl-CoA reductase (aldehyde forming), a crotonaldehyde reductase (alcohol forming), a butadiene synthase, a 4-hydroxybutyryl-CoA dehydratase and a crotyl alcohol diphosphokinase; (xxxi) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase and a butadiene synthase; (xxxii) an erythrose-4-phosphate reductase, an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase and a butadiene synthase; (xxxiii) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butadiene synthase, an erythrose-4-phosphate kinase, an erythrose reductase and a erythritol kinase; (xxxiv) an erythritol-4-phospate cytidylyltransferase, a 4-(cytidine 5'-diphospho)-erythritol kinase, an erythritol 2,4-cyclodiphosphate synthase, a 1-hydroxy-2-butenyl 4-diphosphate synthase, a 1-hydroxy-2-butenyl 4-diphosphate reductase, a butenyl 4-diphosphate isomerase, a butadiene synthase, an erythrose-4-phosphate kinase, an erythrose reductase and an erythritol kinase; (xxxv) a malonyl-CoA:acetyl-CoA acyltransferase, an 3-oxoglutaryl-CoA reductase (ketone-reducing), a 3-hydroxyglutaryl-CoA reductase (aldehyde forming), a 3-hydroxy-5-oxopentanoate reductase, a 3,5-dihydroxypentanoate kinase, a 3-hydroxy-5-phosphonatooxypentanoate kinase, a 3-hydroxy-5-[hydroxy (phosphonooxy)phosphoryl]oxy pentanoate decarboxylase, a butenyl 4-diphosphate isomerase and a butadiene synthase; (xxxvi) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy (phosphonooxy)phosphoryl]oxy pentanoate decarboxylase, a butenyl 4-diphosphate isomerase, a butadiene synthase, an 3-oxoglutaryl-CoA reductase (aldehyde forming), a 3,5-dioxopentanoate reductase (aldehyde reducing) and a 5-hydroxy-3-oxopentanoate reductase; (xxxvii) a malonyl-CoA: acetyl-CoA acyltransferase, a 3-hydroxy-5-oxopentanoate reductase, a 3,5-dihydroxypentanoate kinase, a 3-Hydroxy-5-phosphonatooxypentanoate kinase, a 3-Hydroxy-5-[hydroxy(phosphonooxy)phosphoryl]oxy pentanoate decarboxylase, a butenyl 4-diphosphate isomerase, a butadiene synthase, an 3-oxoglutaryl-CoA reductase (aldehyde forming) and a 3,5-dioxopentanoate reductase (ketone reducing); (xxxviii) a malonyl-CoA:acetyl-CoA acyltransferase, a 3,5-dihydroxypentanoate kinase, a 3-hydroxy-5-phosphonatooxypentanoate kinase, a 3-hydroxy-5-[hydroxy (phosphonooxy)phosphoryl]oxy pentanoate decarboxylase, a butenyl 4-diphosphate isomerase, a butadiene synthase, a 5-hydroxy-3-oxopentanoate reductase and a 3-oxo-glutaryl-CoA reductase (CoA reducing and alcohol forming); and (xxxix) a butadiene pathway comprising a malonyl-CoA:

acetyl-CoA acyltransferase, an 3-oxoglutaryl-CoA reductase (ketone-reducing), a 3,5-dihydroxypentanoate kinase, a 3-hydroxy-5-phosphonatooxypentanoate kinase, a 3-hydroxy-5-[hydroxy(phosphonooxy)phosphoryl]oxy pentanoate decarboxylase, a butenyl 4-diphosphate isomerase, a butadiene synthase and a 3-hydroxyglutaryl-CoA reductase (alcohol forming).

In some aspects, the invention provides a method for producing butatiene, wherein the microbial organisms of the invention comprise two, three, four or five exogenous nucleic acids each encoding enzymes of (a), (b) or (c) as described above. For example, a microbial organism comprising (a) can comprise thee exogenous nucleic acids encoding ATP-citrate lyase or citrate lyase, a fumarate reductase, and an alpha-ketoglutarate:ferredoxin oxidoreductase; a microbial organism comprising (b) can comprise four exogenous nucleic acids encoding pyruvate:ferredoxin oxidoreductase, a phosphoenolpyruvate carboxylase or a phosphoenolpyruvate carboxykinase, a CO dehydrogenase, and an H2 hydrogenase; or a microbial organism comprising (c) can comprise two exogenous nucleic acids encoding CO dehydrogenase and H2 hydrogenase. The invention further provides methods for producing butadiene by culturing such non-naturally occurring microbial organisms under conditions and for a sufficient period of time to produce butadiene.

In some embodiments, the invention provides a method for producing crotyl alcohol that includes culturing a non-naturally occurring microbial organism as described herein, including a microbial organism having a crotyl alcohol pathway comprising at least one exogenous nucleic acid encoding a crotyl alcohol pathway enzyme expressed in a sufficient amount to produce crotyl alcohol. Such a microbial organism can further comprise (a) a reductive TCA pathway comprising at least one exogenous nucleic acid encoding a reductive TCA pathway enzyme, wherein the at least one exogenous nucleic acid is selected from an ATP-citrate lyase, a citrate lyase, a citryl-CoA synthetase, a citryl-CoA lyase, a fumarate reductase, and an alpha-ketoglutarate:ferredoxin oxidoreductase; (b) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (c) at least one exogenous nucleic acid encodes an enzyme selected from a CO dehydrogenase, an $H_2$ hydrogenase, and combinations thereof.

In such a microbial organism used in a method for producing crotyl alcohol, the crotyl alcohol pathway can be selected from any of those disclosed herein and in the figures. For example, the crtoyl alcohol pathway can be selected from (i) an acetyl-CoA:acetyl-CoA acyltransferase; an acetoacetyl-CoA reductase; a 3-hydroxybutyryl-CoA dehydratase; a crotonyl-CoA hydrolase, synthase, or transferase; a crotonate reductase; and a crotonaldehyde reductase (alcohol forming); (ii) an acetyl-CoA:acetyl-CoA acyltransferase; an acetoacetyl-CoA reductase; a 3-hydroxybutyryl-CoA dehydratase; a crotonyl-CoA reductase (aldehyde forming); and a crotonaldehyde reductase (alcohol forming); (iii) an acetyl-CoA:acetyl-CoA acyltransferase; an acetoacetyl-CoA reductase; a 3-hydroxybutyryl-CoA dehydratase; and a crotonyl-CoA reductase (alcohol forming); (iv) a glutaconyl-CoA decarboxylase; a crotonyl-CoA hydrolase, synthase, or transferase; a crotonate reductase; and a crotonaldehyde reductase (alcohol forming); (v) a glutaconyl-CoA decarboxylase; a crotonyl-CoA reductase (aldehyde forming); and a crotonaldehyde reductase (alcohol forming); and (vi) a glutaconyl-CoA decarboxylase; and a crotonyl-CoA reductase (alcohol forming). (vii) a glutaryl-CoA dehydrogenase; a crotonyl-CoA hydrolase, synthase, or transferase; a crotonate reductase; and a crotonaldehyde reductase (alcohol forming); (viii) a glutaryl-CoA dehydrogenase; a crotonyl-CoA reductase (aldehyde forming); and a crotonaldehyde reductase (alcohol forming); (ix) a glutaryl-CoA dehydrogenase; and a crotonyl-CoA reductase (alcohol forming); (x) a 3-aminobutyryl-CoA deaminase; a crotonyl-CoA hydrolase, synthase, or transferase; a crotonate reductase; and a crotonaldehyde reductase (alcohol forming); (xi) a 3-aminobutyryl-CoA deaminase; a crotonyl-CoA reductase (aldehyde forming); and a crotonaldehyde reductase (alcohol forming); (xii) a 3-aminobutyryl-CoA deaminase; and a crotonyl-CoA reductase (alcohol forming); (xiii) a 4-hydroxybutyryl-CoA dehydratase; a crotonyl-CoA hydrolase, synthase, or transferase; a crotonate reductase; and a crotonaldehyde reductase (alcohol forming); (xiv) a 4-hydroxybutyryl-CoA dehydratase; a crotonyl-CoA reductase (aldehyde forming); and a crotonaldehyde reductase (alcohol forming); and (xv) a 4-hydroxybutyryl-CoA dehydratase; and a crotonyl-CoA reductase (alcohol forming).

In some aspects, the invention provides a method for producing crotyl alcohol, where a microbial organism comprising (a) can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In some aspects, such a microbial organism used in a method for producing crotyl alcohol include a microbial organimism comprising (b), which can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. Such a microbial organism can comprise two, three, four, five, six or seven exogenous nucleic acids each encoding a crotyl alcohol pathway enzyme.

For example, the microbial organism used in the methods for producing croytal alcohol as disclosed herein can comprise exogenous nucleic acids encoding each of the enzymes selected from (i) an acetyl-CoA:acetyl-CoA acyltransferase; an acetoacetyl-CoA reductase; a 3-hydroxybutyryl-CoA dehydratase; a crotonyl-CoA hydrolase, synthase, or transferase; a crotonate reductase; and a crotonaldehyde reductase (alcohol forming); (ii) an acetyl-CoA:acetyl-CoA acyltransferase; an acetoacetyl-CoA reductase; a 3-hydroxybutyryl-CoA dehydratase; a crotonyl-CoA reductase (aldehyde forming); and a crotonaldehyde reductase (alcohol forming); (iii) an acetyl-CoA:acetyl-CoA acyltransferase; an acetoacetyl-CoA reductase; a 3-hydroxybutyryl-CoA dehydratase; and a crotonyl-CoA reductase (alcohol forming); (iv) a glutaconyl-CoA decarboxylase; a crotonyl-CoA hydrolase, synthase, or transferase; a crotonate reductase; and a crotonaldehyde reductase (alcohol forming); (v) a glutaconyl-CoA decarboxylase; a crotonyl-CoA reductase (aldehyde forming); and a crotonaldehyde reductase (alcohol forming); (vi) a glutaconyl-CoA decarboxylase; and a crotonyl-CoA reductase (alcohol forming); (vii) a glutaryl-CoA dehydrogenase; a crotonyl-CoA hydrolase, synthase, or transferase; a crotonate reductase; and a crotonaldehyde reductase (alcohol forming); (viii) a glutaryl-CoA dehydrogenase; a crotonyl-CoA reductase (aldehyde forming); and a crotonaldehyde reductase (alcohol forming); (ix) a glutaryl-CoA dehydrogenase; and a crotonyl-CoA reductase (alcohol forming); (x) a 3-aminobutyryl-CoA deaminase; a crotonyl-CoA hydrolase, synthase, or transferase; a crotonate reductase; and a crotonaldehyde reductase (alcohol forming); (xi) a 3-aminobutyryl-CoA deaminase; a crotonyl-CoA reductase (aldehyde forming); and a crotonaldehyde reductase (alcohol forming); (xii) a 3-aminobutyryl-CoA deaminase; and a crotonyl-CoA reductase (alcohol forming). (xiii) a 4-hydroxybutyryl-CoA dehydratase; a crotonyl-CoA hydrolase, synthase, or transferase; a crotonate reductase; and a crotonaldehyde reductase (alcohol forming); (xiv) a 4-hydroxybutyryl-CoA dehydratase; a crotonyl-CoA reductase (aldehyde forming); and a crotonaldehyde reductase (alcohol forming); and (xv) a 4-hydroxybutyryl-CoA dehydratase; and a crotonyl-CoA reductase (alcohol forming).

Such microbial organisms used in a method for producing crotyl alcohol as disclosed herein can comprise two, three, four or five exogenous nucleic acids each encoding enzymes of (a), (b) or (c). For example, a microbial organism comprising (a) can comprise three exogenous nucleic acids encoding ATP-citrate lyase or citrate lyase, a fumarate reductase, and an alpha-ketoglutarate:ferredoxin oxidoreductase; a microbial organism comprising (b) can comprise four exogenous nucleic acids encoding a pyruvate:ferredoxin oxidoreductase, a phosphoenolpyruvate carboxylase or a phosphoenolpyruvate carboxykinase, a CO dehydrogenase, and an $H_2$ hydrogenase; or a microbial organism comprising (c) can comprise two exogenous nucleic acids encoding a CO dehydrogenase and an H2 hydrogenase.

Suitable purification and/or assays to test for the production of butadiene can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art. For typical Assay Methods, see Manual on Hydrocarbon Analysis (ASTM Manula Series, A. W. Drews, ed., 6th edition, 1998, American Society for Testing and Materials, Baltimore, Md.

The butadiene can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the butadiene producers can be cultured for the biosynthetic production of butadiene.

For the production of butadiene or crotyl alcohol, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of butadiene or crotyl alcohol.

In addition to renewable feedstocks such as those exemplified above, the butadiene or crotyl alcohol microbial organisms of the invention also can be modified for growth on syngas as its source of carbon. In this specific embodiment, one or more proteins or enzymes are expressed in the butadiene or crotyl alcohol producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate.

Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO_2 + 4H_2 + n\text{ADP} + n\text{Pi} \rightarrow CH_3COOH + 2H_2O + n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a butadiene or crotyl alcohol pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the butadiene or crotyl alcohol precursors, glyceraldehyde-3-phosphate, phosphoenolpyruvate, and pyruvate, by pyruvate: ferredoxin oxidoreductase and the enzymes of gluconeogenesis. Following the teachings and guidance provided herein for introducing a sufficient number of encoding nucleic acids to generate a butadiene or a crotyl alcohol pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, butadiene and any of the intermediate metabolites in the butadiene pathway. All that is required is to engineer in one or more of the required enzyme or protein activities to achieve biosynthesis of the desired compound or intermediate including, for example, inclusion of some or all of the butadiene biosynthetic pathways. Accordingly, the invention provides a non-naturally occurring microbial organism that produces and/or secretes butadiene when grown on a carbohydrate or other carbon source and produces and/or secretes any of the intermediate metabolites shown in the butadiene pathway when grown on a carbohydrate or other carbon source. The butadiene producing microbial organisms of the invention can initiate synthesis from an intermediate, for example, acetoacetyl-CoA, 3-hydroxybutyryl-CoA, crotonyl-CoA, crotonaldehyde, crotyl alcohol, 2-betenyl-phosphate, 2-butenyl-4-diphosphate, erythritol-4-phosphate, 4-(cytidine 5'-diphospho)-erythritol, 2-phospho-4-(cytidine 5'-diphospho)-erythritol, erythritol-2, 4-cyclodiphosphate, 1-hydroxy-2-butenyl 4-diphosphate, butenyl 4-diphosphate, 2-butenyl 4-diphosphate, 3-oxoglutaryl-CoA, 3-hydroxyglutaryl-CoA, 3-hydroxy-5-oxopentanoate, 3,5-dihydroxy pentanoate, 3-hydroxy-5-phosphonatooxypentanoate, 3-hydroxy-5-[hydroxy(phosphonooxy) phosphoryl]oxy pentanoate, crotonate, erythrose, erythritol, 3,5-dioxopentanoate or 5-hydroxy-3-oxopentanoate.

The non-naturally occurring microbial organisms of the invention are constructed using methods well known in the art as exemplified herein to exogenously express at least one nucleic acid encoding a butadiene or a crotyl alcohol pathway enzyme or protein in sufficient amounts to produce butadiene or crotyl alcohol. It is understood that the microbial organisms of the invention are cultured under conditions sufficient to produce butadiene or crotyl alcohol. Following the teachings and guidance provided herein, the non-naturally occurring microbial organisms of the invention can achieve biosynthesis of butadiene or crotyl alcohol resulting in intracellular concentrations between about 0.001-2000 mM or more. Generally, the intracellular concentration of butadiene or crotyl alcohol is between about 3-1500 mM, particularly between about 5-1250 mM and more particularly between about 8-1000 mM, including about 10 mM, 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the butadiene or crotyl alcohol producers can synthesize butadiene or crotyl alcohol at intracellular concentrations of 5-10 mM or more as well as all other concentrations exemplified herein. It is understood that, even though the above description refers to intracellular concentrations, butadiene or crotyl alcohol producing microbial organisms can produce butadiene or crotyl alcohol intracellularly and/or secrete the product into the culture medium.

In addition to the culturing and fermentation conditions disclosed herein, growth condition for achieving biosynthesis of butadiene or crotyl alcohol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in butadiene or crotyl alcohol or any butadiene or crotyl alcohol pathway intermediate. The various carbon feedstock and other uptake sources enumerated above will be referred to herein, collectively, as "uptake sources." Uptake sources can provide isotopic enrichment for any atom present in the product butadiene or crotyl alcohol or butadiene or crotyl alcohol pathway intermediate including any butadiene or crotyl alcohol impurities generated in diverging away from the pathway at any point. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}=-19$ per mil (Olsson, The use of Oxalic acid as a Standard. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}=-19$ per mil. This is equivalent to an absolute (AD 1950) $^{14}C/^{12}C$ ratio of $1.176\pm0.010\times10^{-12}$ (Karlen et al., Arkiv Geofysik, 4:465-471 (1968)). The standard calculations take into account the differential uptake of one istope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, Radiocarbon, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., Nuclear Instruments and Methods in Physics Research B, 172:281-287 (2000)). For example, carbon-14 dating has been used to quantify bio-based content in terephthalate-containing materials (Colonna et al., Green Chemistry, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides butadiene or crotyl alcohol or a butadiene or crotyl alcohol intermediate that has a carbon-12, carbon-13, and carbon-14 ratio that reflects an atmospheric carbon, also referred to as enviromental carbon, uptake source. For example, in some aspects the butadiene or crotyl alcohol or a butadiene or crotyl alcohol intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides butadiene or crotyl alcohol or a butadiene or crotyl alcohol intermediate that has a carbon-12, carbon-13, and carbon-14 ratio that reflects petroleum-based carbon uptake source. In this aspect, the butadiene or crotyl alcohol or a butadiene or crotyl alcohol intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides butadiene or crotyl alcohol or a butadiene or crotyl alcohol intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced butadiene or crotyl alcohol or butadiene or crotyl alcohol intermediate as disclosed herein, and to the products derived therefrom, wherein the butadiene or crotyl alcohol or a butadiene or crotyl alcohol intermediate has a carbon-12, carbon-13, and carbon-14 isotope ratio of about the same value as the $CO_2$ that occurs in the environment. For example, in some aspects the invention provides bioderived butadiene or crotyl alcohol or a bioderived butadiene or crotyl alcohol intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived butadiene or crotyl alcohol or a bioderived butadiene or crotyl alcohol intermediate as disclosed herein, wherein the bioderived product is chemically modified to generate a final product. Methods of chemically modifying a bioderived product of butadiene or crotyl alcohol, or an intermediate thereof, to generate a desired product are well known to those skilled in the art, as described herein. The invention further provides a polymer, synthetic rubber, resin, chemical, monomer, fine chemical, agricultural chemical, or pharmaceutical having a carbon-12 versus carbon-13 versus carbon-14 isotope ratio of about the same value as the $CO_2$ that occurs in the environment, wherein the polymer, synthetic rubber, resin, chemical, monomer, fine chemical, agricultural chemical, or pharmaceutical is generated directly from or in combination with bioderived butadiene or crotyl alcohol or a bioderived butadiene or crotyl alcohol intermediate as disclosed herein.

Butadiene is a chemical commonly used in many commercial and industrial applications. Non-limiting examples of such applications include production of polymers, such as synthetic rubbers and ABS resins, and chemicals, such as hexamethylenediamine and 1,4-butanediol. Accordingly, in some embodiments, the invention provides a biobased polymer, synthetic rubber, resin, or chemical comprising one or more bioderived butadiene or bioderived butadiene intermediate produced by a non-naturally occurring microorganism of the invention or produced using a method disclosed herein.

Crotyl alcohol is a chemical commonly used in many commercial and industrial applications. Non-limiting examples of such applications include production of crotyl halides, esters, and ethers, which in turn are chemical are chemical intermediates in the production of monomers, fine chemicals, such as sorbic acid, trimethylhydroquinone, crotonic acid and 3-methoxybutanol, agricultural chemicals, and pharmaceuticals. Crotyl alcohol can also be used as a precursor in the production of 1,3-butadiene. Accordingly, in some embodiments, the invention provides a biobased monomer, fine chemical, agricultural chemical, or pharmaceutical comprising one or more bioderived crotyl alcohol or bioderived crotyl alcohol intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides a biobased polymer, synthetic rubber, resin, or chemical comprising bioderived butadiene or bioderived butadiene intermediate, wherein the bioderived butadiene or bioderived butadiene intermediate includes all or part of the butadiene or butadiene intermediate used in the production of polymer, synthetic rubber, resin, or chemical. Thus, in some aspects, the invention provides a biobased polymer, synthetic rubber, resin, or chemical comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived butadiene or bioderived butadiene intermediate as disclosed herein. Additionally, in some aspects, the invention provides a biobased polymer, synthetic rubber, resin, or chemical wherein the butadiene or butadiene intermediate used in its production is a combination of bioderived and petroleum derived butadiene or butadiene intermediate. For example, a biobased polymer, synthetic rubber, resin, or chemical can be produced using 50% bioderived butadiene and 50% petroleum derived butadiene or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polymer, synthetic rubber, resin, or chemical using the bioderived butadiene or bioderived butadiene intermediate of the invention are well known in the art.

In some embodiments, the invention provides a biobased monomer, fine chemical, agricultural chemical, or pharmaceutical comprising bioderived crotyl alcohol or bioderived crotyl alcohol intermediate, wherein the bioderived crotyl alcohol or bioderived crotyl alcohol intermediate includes all or part of the crotyl alcohol or crotyl alcohol intermediate used in the production of monomer, fine chemical, agricultural chemical, or pharmaceutical. Thus, in some aspects, the invention provides a biobased monomer, fine chemical, agricultural chemical, or pharmaceutical comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived crotyl alcohol or bioderived crotyl alcohol intermediate as disclosed herein. Additionally, in some aspects, the invention provides a biobased monomer, fine chemical, agricultural chemical, or pharmaceutical wherein the crotyl alcohol or crotyl alcohol intermediate used in its production is a combination of bioderived and petroleum derived crotyl alcohol or crotyl alcohol intermediate. For example, a biobased monomer, fine chemical, agricultural chemical, or pharmaceutical can be produced using 50% bioderived crotyl alcohol and 50% petroleum derived crotyl alcohol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing monomer, fine chemical, agricultural chemical, or pharmaceutical using the bioderived crotyl alcohol or bioderived crotyl alcohol intermediate of the invention are well known in the art.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of butadiene or crotyl alcohol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of butadiene or crotyl alcohol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of butadiene or crotyl alcohol. Generally, and as with non-continuous culture procedures, the continuous and/or near-continuous production of butadiene or crotyl alcohol will include culturing a non-naturally occurring butadiene or crotyl alcohol producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of butadiene or crotyl alcohol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the butadiene or crotyl alcohol producers of the invention for continuous production of substantial quantities of butadiene or crotyl alcohol, the butadiene or crotyl alcohol producers also can be, for example, simultaneously subjected to chemical synthesis procedures to convert the product to other compounds or the product can be separated from the fermentation culture and sequentially subjected to chemical or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of butadiene or crotyl alcohol.

One computational method for identifying and designing metabolic alterations favoring biosynthesis of a desired product is the OptKnock computational framework (Burgard et al., Biotechnol. Bioeng. 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., Biotechnol. Prog. 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., Biotechnol. Bioeng. 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a butadiene or crotyl alcohol pathway can be introduced into a host organism. In some cases, it can be desirable to modify an activity of a butadiene or crotyl alcohol pathway enzyme or protein to increase production of butadiene or crotyl alcohol. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >10$^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., Biomol. Eng 22:11-19 (2005); Huisman and Lalonde, In Biocatalysis in the pharmaceutical and biotechnology industries pgs. 717-742 (2007), Patel (ed.), CRC Press; Otten and Quax. Biomol. Eng 22:1-9 (2005).; and Sen et al., Appl Biochem. Biotechnol 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a butadiene or crotyl alcohol pathway enzyme or protein.

EpPCR (Pritchard et al., J Theor. Biol. 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., Nucleic Acids Res. 32:e145 (2004); and Fujii et al., Nat. Protoc. 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, Proc Natl Acad Sci USA 91:10747-10751 (1994)); and Stemmer, Nature 370: 389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., Nat. Biotechnol. 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., Nucleic Acids Res 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, Nucleic Acids Res. 27:e18 (1999); and Volkov et al., Methods Enzymol. 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., Nat. Biotechnol. 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., J. Molec. Catalysis 26:119-129 (2003)). No DNA endonucleases are used. Unidirectional ssDNA is made by DNA polymerase with random primers or serial deletion with exonuclease. Unidirectional ssDNA are only templates and not primers. Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, Methods Mol. Biol 352:191-204 (2007); Bergquist et al., Biomol. Eng 22:63-72 (2005); Gibbs et al., Gene 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., Proc. Natl. Acad. Sci. USA 96:3562-3567 (1999); and Ostermeier et al., Nat. Biotechnol. 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., Nucleic Acids Res 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., Proc. Natl. Acad. Sci. USA 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., Biomol. Eng. 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., Biotechnol. J. 3:74-82 (2008); Wong et al., Nucleic Acids Res. 32:e26 (2004); and Wong et al., Anal. Biochem. 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., Nat. Biotechnol. 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., Nucleic Acids Res. 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., Nat. Biotechnol. 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., Methods Enzymol. 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. Methods Enzymol. 208: 564-586 (1991); and Reidhaar-Olson et al. Science 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., Angew. Chem. Int. Ed Engl. 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional ts mutator plasmids allow increases of 20 to 4000-X in random and natural mutation frequency during selection and block accumulation of deleterious mutations when selection is not required (Selifonova et al., Appl. Environ. Microbiol. 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., J. Mol. Biol. 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., Proc. Natl. Acad. Sci. USA 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., Proc. Natl. Acad. Sci. USA 99:15926-15931 (2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants (1050). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San Diego Calif.); 3) screening/selecting for desired properties; and 4) using improved clone(s), start over at another site and continue repeating until a desired activity is achieved (Reetz et al., Nat. Protoc. 2:891-903 (2007); and Reetz et al., Angew. Chem. Int. Ed Engl. 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE I

Pathways for Producing Butadiene

Figure 1:
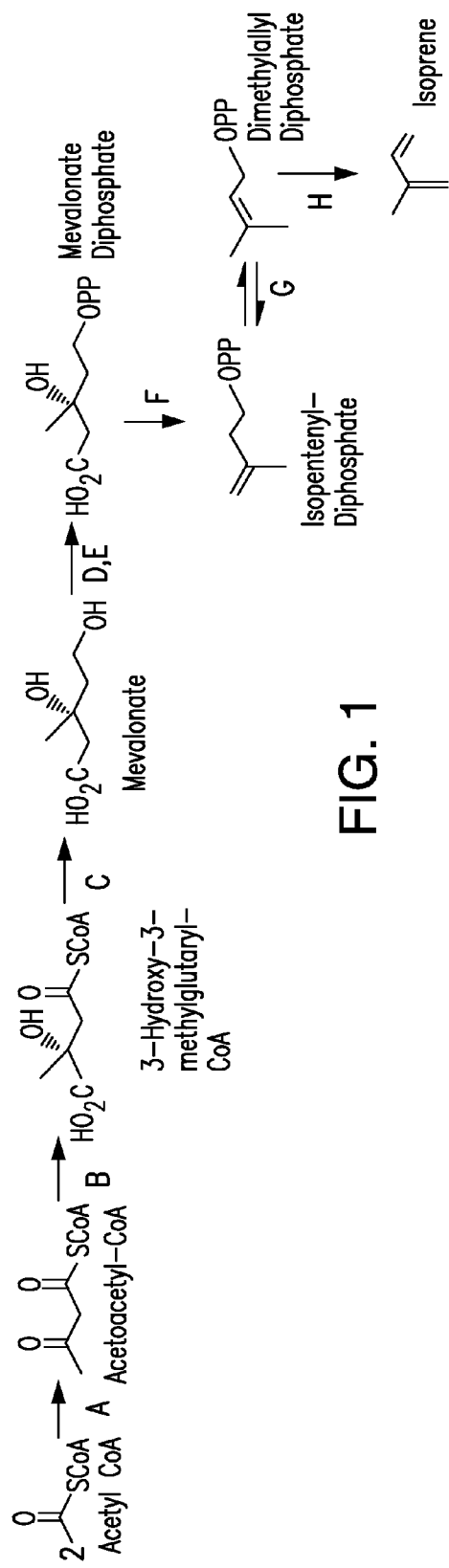
FIG. 1 shows a natural pathway to isoprenoids and terpenes. Enzymes for transformation of the identified substrates to products include: A. acetyl-CoA:acetyl-CoA acyltransferase, B. hydroxymethylglutaryl-CoA synthase, C. 3-hydroxy-3-methylglutaryl-CoA reductase (alcohol forming), D. mevalonate kinase, E. phosphomevalonate kinase, F. diphosphomevalonate decarboxylase, G. isopentenyl-diphosphate isomerase, H. isoprene synthase.

Disclosed herein are novel processes for the direct production of butadiene using engineered non-natural microorganisms that possess the enzymes necessary for conversion of common metabolites into the four carbon diene, 1,3-butadiene. One novel route to direct production of butadiene entails reduction of the known butanol pathway metabolite crotonyl-CoA to crotyl alcohol via reduction with aldehyde and alcohol dehydrogenases, followed by phosphorylation with kinases to afford crotyl pyrophosphate and subsequent conversion to butadiene using isoprene synthases or variants thereof (see FIG. 2). Another route (FIG. 3) is a variant of the well-characterized DXP pathway for isoprenoid biosynthesis. In this route, the substrate lacks a 2-methyl group and provides butadiene rather than isoprene via a butadiene synthase. Such a butadiene synthase can be derived from an isoprene synthase using methods, such as directed evolution, as described herein. Finally, FIG. 4 shows a pathway to butadiene involving the substrate 3-hydroxyglutaryl-CoA, which serves as a surrogate for the natural mevalonate pathway substrate 3-hydroxy-3-methyl-glutaryl-CoA (shown in FIG. 1). Enzyme candidates for steps A-P of FIG. 2, steps A-K of FIG. 3 and steps A-O of FIG. 4 are provided below.

Acetyl-CoA:acetyl-CoA acyltransferase (FIG. 2, Step A)

Acetoacetyl-CoA thiolase converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and 122 thlB from *C. acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem.* 269:31383-31389 (1994)).

| Protein | GenBank ID | GI number | Organism |
|---|---|---|---|
| AtoB | NP_416728 | 16130161 | *Escherichia coli* |
| ThlA | NP_349476.1 | 15896127 | *Clostridium acetobutylicum* |
| ThlB | NP_149242.1 | 15004782 | *Clostridium acetobutylicum* |
| ERG10 | NP_015297 | 6325229 | *Saccharomyces cerevisiae* |

Acetoacetyl-CoA reductase (FIG. 2, Step B)

Acetoacetyl-CoA reductase catalyzing the reduction of acetoacetyl-CoA to 3-hydroxybutyryl-CoA participates in the acetyl-CoA fermentation pathway to butyrate in several species of *Clostridia* and has been studied in detail (Jones et al., *Microbiol Rev.* 50:484-524 (1986)). The enzyme from *Clostridium acetobutylicum*, encoded by hbd, has been cloned and functionally expressed in *E. coli* (Youngleson et al., *J Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Yet other gene candidates demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene candidate is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., supra, (1988)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (WAKIL et al., *J Biol. Chem.* 207: 631-638 (1954)).

| Protein | Genbank ID | GI number | Organism |
|---|---|---|---|
| fadB | P21177.2 | 119811 | *Escherichia coli* |
| fadJ | P77399.1 | 3334437 | *Escherichia coli* |
| Hbd2 | EDK34807.1 | 146348271 | *Clostridium kluyveri* |
| Hbd1 | EDK32512.1 | 146345976 | *Clostridium kluyveri* |
| hbd | P52041.2 | 18266893 | *Clostridium acetobutylicum* |
| HSD17B10 | O02691.3 | 3183024 | *Bos Taurus* |
| phbB | P23238.1 | 130017 | *Zoogloea ramigera* |
| phaB | YP_353825.1 | 77464321 | *Rhodobacter sphaeroides* |

A number of similar enzymes have been found in other species of *Clostridia* and in *Metallosphaera sedula* (Berg et al., *Science*. 318:1782-1786 (2007)).

| Protein | GenBank ID | GI number | Organism |
|---|---|---|---|
| hbd | NP_349314.1 | NP_349314.1 | *Clostridium acetobutylicum* |
| hbd | AAM14586.1 | AAM14586.1 | *Clostridium beijerinckii* |
| Msed_1423 | YP_001191505 | YP_001191505 | *Metallosphaera sedula* |
| Msed_0399 | YP_001190500 | YP_001190500 | *Metallosphaera sedula* |
| Msed_0389 | YP_001190490 | YP_001190490 | *Metallosphaera sedula* |
| Msed_1993 | YP_001192057 | YP_001192057 | *Metallosphaera sedula* |

3-Hydroxybutyryl-CoA dehydratase (FIG. 2, Step C)

3-Hydroxybutyryl-CoA dehydratase (EC 4.2.1.55), also called crotonase, is an enoyl-CoA hydratase that reversibly dehydrates 3-hydroxybutyryl-CoA to form crotonyl-CoA. Crotonase enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab Eng.* 10:305-311 (2008); Boynton et al., *J Bacteriol.* 178:3015-3024 (1996)), *C. kluyveri* (Hillmer et al., *FEBS Lett.* 21:351-354 (1972)), and *Metallosphaera sedula* (Berg et al., *Science* 318:1782-1786 (2007a)) though the sequence of the latter gene is not known. The enoyl-CoA hydratase of *Pseudomonas putida*, encoded by ech, catalyzes the conversion of crotonyl-CoA to 3-hydroxybutyryl-CoA (Roberts et al., *Arch Microbiol.* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). Lastly, a number of *Escherichia coli* genes have been shown to demonstrate enoyl-CoA hydratase functionality including maoC (Park et al., *J Bacteriol.* 185: 5391-5397 (2003)), paaF (Ismail et al., *Eur. J Biochem.* 270: 3047-3054 (2003); Park et al., *Appl. Biochem. Biotechnol* 113-116:335-346 (2004); Park et al., *Biotechnol Bioeng* 86:681-686 (2004)) and paaG (Ismail et al., supra, (2003); Park and Lee, supra, (2004); Park and Yup, supra, (2004)). These proteins are identified below.

| Protein | GenBank ID | GI Number | Organism |
| --- | --- | --- | --- |
| crt | NP_349318.1 | 15895969 | *Clostridium acetobutylicum* |
| crt1 | YP_001393856.1 | 153953091 | *Clostridium kluyveri* |
| ech | NP_745498.1 | 26990073 | *Pseudomonas putida* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Crotonyl-CoA reductase (aldehyde forming) (FIG. 2, Step D)

Several acyl-CoA dehydrogenases are capable of reducing an acyl-CoA to its corresponding aldehyde. Thus they can naturally reduce crotonyl-CoA to crotonaldehyde or can be engineered to do so. Exemplary genes that encode such enzymes include the *Acinetobacter calcoaceticus* acyl encoding a fatty acyl-CoA reductase (Reiser et al., *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling et al., *J Bacteriol.* 178:871-880 (1996); Sohling et al., *J. Bacteriol.* 178:871-80 (1996))). SucD of *P. gingivalis* is another succinate semialdehyde dehydrogenase (Takahashi et al., *J. Bacteriol.* 182: 4704-4710 (2000)). These succinate semialdehyde dehydrogenases were specifically shown in ref. (Burk et al., WO/2008/115840: (2008)) to convert 4-hydroxybutyryl-CoA to 4-hydroxybutanal as part of a pathway to produce 1,4-butanediol. The enzyme acylating acetaldehyde dehydrogenase in *Pseudomonas* sp, encoded by bphG, is yet another capable enzyme as it has been demonstrated to oxidize and acylate acetaldehyde, propionaldehyde, butyraldehyde, isobutyraldehyde and formaldehyde (Powlowski et al., *J. Bacteriol.* 175:377-385 (1993)).

| Protein | GenBank ID | GI Number | Organism |
| --- | --- | --- | --- |
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science* 318:1782-1786 (2007b); Thauer, 318:1732-1733 (2007)). The enzyme utilizes NADPH as a cofactor and has been characterized in *Metallosphaera* and *Sulfolobus* spp (Alber et al., *J. Bacteriol.* 188: 8551-8559 (2006); Hugler et al., *J. Bacteriol.* 184:2404-2410 (2002)). The enzyme is encoded by Msed_0709 in *Metallosphaera sedula* (Alber et al., supra, (2006); Berg et al., supra, (2007b)). A gene encoding a malonyl-CoA reductase from *Sulfolobus tokodaii* was cloned and heterologously expressed in *E. coli* (Alber et al., supra, (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth, *Appl. Environ. Microbiol.* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999). These proteins are identified below.

| Protein | GenBank ID | GI Number | Organism |
| --- | --- | --- | --- |
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

Crotonaldehyde reductase (alcohol forming) (FIG. 2, Step E)

Enzymes exhibiting crotonaldehyde reductase (alcohol forming) activity are capable of forming crotyl alcohol from crotonaldehyde. The following enzymes can naturally possess this activity or can be engineered to exhibit this activity. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for $C_2$-$C_{14}$ (Tani et al., *Appl. Environ. Microbiol.* 66:5231-5235 (2000)), ADH2 from *Saccharomyces cerevisiae* (Atsumi et al., *Nature* 451: 86-89 (2008)), yqhD from *E. coli* which has preference for molecules longer than C(3) (Sulzenbacher et al., *J. Mol. Biol.* 342:489-502 (2004)), and bdh I and bdh II from *C. acetobutylicum* which converts butyraldehyde into butanol (Walter et al., *J. Bacteriol.* 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)). Cbei_2181 from *Clostridium beijerinckii* NCIMB 8052 encodes yet another useful alcohol dehydrogenase capable of converting crotonaldehyde to crotyl alcohol.

| Protein | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| Cbei_2181 | YP_001309304.1 | 150017050 | *Clostridium beijerinckii* NCIMB 8052 |

Enzymes exhibiting 4-hydroxybutyrate dehydrogenase activity (EC 1.1.1.61) also fall into this category. Such enzymes have been characterized in *Ralstonia eutropha* (Bravo et al., *J. Forensic Sci.* 49:379-387 (2004)), *Clostridium kluyveri* (Wolff et al., *Protein Expr. Pur* 6:206-212 (1995)) and *Arabidopsis thaliana* (Breitkreuz et al., *J. Biol. Chem.* 278:41552-41556 (2003)).

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Crotyl Alcohol Kinase (FIG. 2, Step F)

Crotyl alcohol kinase enzymes catalyze the transfer of a phosphate group to the hydroxyl group of crotyl alcohol. The enzymes described below naturally possess such activity or can be engineered to exhibit this activity. Kinases that catalyze transfer of a phosphate group to an alcohol group are members of the EC 2.7.1 enzyme class. The table below lists several useful kinase enzymes in the EC 2.7.1 enzyme class.

| Enzyme Commission Number | Enzyme Name |
|---|---|
| 2.7.1.1 | hexokinase |
| 2.7.1.2 | glucokinase |
| 2.7.1.3 | ketohexokinase |
| 2.7.1.4 | fructokinase |
| 2.7.1.5 | rhamnulokinase |
| 2.7.1.6 | galactokinase |
| 2.7.1.7 | mannokinase |
| 2.7.1.8 | glucosamine kinase |
| 2.7.1.10 | phosphoglucokinase |
| 2.7.1.11 | 6-phosphofructokinase |
| 2.7.1.12 | gluconokinase |
| 2.7.1.13 | dehydrogluconokinase |
| 2.7.1.14 | sedoheptulokinase |
| 2.7.1.15 | ribokinase |
| 2.7.1.16 | ribulokinase |
| 2.7.1.17 | xylulokinase |
| 2.7.1.18 | phosphoribokinase |
| 2.7.1.19 | phosphoribulokinase |
| 2.7.1.20 | adenosine kinase |
| 2.7.1.21 | thymidine kinase |
| 2.7.1.22 | ribosylnicotinamide kinase |
| 2.7.1.23 | NAD+ kinase |
| 2.7.1.24 | dephospho-CoA kinase |
| 2.7.1.25 | adenylyl-sulfate kinase |
| 2.7.1.26 | riboflavin kinase |
| 2.7.1.48 | uridine kinase |
| 2.7.1.49 | hydroxymethylpyrimidine kinase |
| 2.7.1.50 | hydroxyethylthiazole kinase |
| 2.7.1.51 | L-fuculokinase |
| 2.7.1.52 | fucokinase |
| 2.7.1.53 | L-xylulokinase |
| 2.7.1.54 | D-arabinokinase |
| 2.7.1.55 | allose kinase |
| 2.7.1.56 | 1-phosphofructokinase |
| 2.7.1.58 | 2-dehydro-3-deoxygalactonokinase |
| 2.7.1.59 | N-acetylglucosamine kinase |
| 2.7.1.60 | N-acylmannosamine kinase |
| 2.7.1.61 | acyl-phosphate-hexose phosphotransferase |
| 2.7.1.62 | phosphoramidate-hexose phosphotransferase |
| 2.7.1.63 | polyphosphate-glucose phosphotransferase |
| 2.7.1.64 | inositol 3-kinase |
| 2.7.1.65 | scyllo-inosamine 4-kinase |
| 2.7.1.66 | undecaprenol kinase |
| 2.7.1.67 | 1-phosphatidylinositol 4-kinase |
| 2.7.1.68 | 1-phosphatidylinositol-4-phosphate 5-kinase |
| 2.7.1.69 | protein-Np-phosphohistidine-sugar phosphotransferase |
| 2.7.1.70 | identical to EC 2.7.1.37. |
| 2.7.1.71 | shikimate kinase |
| 2.7.1.72 | streptomycin 6-kinase |
| 2.7.1.73 | inosine kinase |
| 2.7.1.94 | acylglycerol kinase |
| 2.7.1.95 | kanamycin kinase |
| 2.7.1.100 | S-methyl-5-thioribose kinase |
| 2.7.1.101 | tagatose kinase |
| 2.7.1.102 | hamamelose kinase |
| 2.7.1.103 | viomycin kinase |
| 2.7.1.105 | 6-phosphofructo-2-kinase |
| 2.7.1.106 | glucose-1,6-bisphosphate synthase |
| 2.7.1.107 | diacylglycerol kinase |
| 2.7.1.108 | dolichol kinase |
| 2.7.1.113 | deoxyguanosine kinase |
| 2.7.1.114 | AMP-thymidine kinase |
| 2.7.1.118 | ADP-thymidine kinase |
| 2.7.1.119 | hygromycin-B 7''-O-kinase |
| 2.7.1.121 | phosphoenolpyruvate-glycerone phosphotransferase |
| 2.7.1.122 | xylitol kinase |
| 2.7.1.127 | inositol-trisphosphate 3-kinase |
| 2.7.1.130 | tetraacyldisaccharide 4'-kinase |
| 2.7.1.134 | inositol-tetrakisphosphate 1-kinase |
| 2.7.1.136 | macrolide 2'-kinase |
| 2.7.1.137 | phosphatidylinositol 3-kinase |
| 2.7.1.138 | ceramide kinase |
| 2.7.1.140 | inositol-tetrakisphosphate 5-kinase |
| 2.7.1.142 | glycerol-3-phosphate-glucose phosphotransferase |
| 2.7.1.143 | diphosphate-purine nucleoside kinase |

| Enzyme Commission Number | Enzyme Name |
|---|---|
| 2.7.1.27 | erythritol kinase |
| 2.7.1.28 | triokinase |
| 2.7.1.29 | glycerone kinase |
| 2.7.1.30 | glycerol kinase |
| 2.7.1.31 | glycerate kinase |
| 2.7.1.32 | choline kinase |
| 2.7.1.33 | pantothenate kinase |
| 2.7.1.34 | pantetheine kinase |
| 2.7.1.35 | pyridoxal kinase |
| 2.7.1.36 | mevalonate kinase |
| 2.7.1.39 | homoserine kinase |
| 2.7.1.40 | pyruvate kinase |
| 2.7.1.41 | glucose-1-phosphate phosphodismutase |
| 2.7.1.42 | riboflavin phosphotransferase |
| 2.7.1.43 | glucuronokinase |
| 2.7.1.44 | galacturonokinase |
| 2.7.1.45 | 2-dehydro-3-deoxygluconokinase |
| 2.7.1.46 | L-arabinokinase |
| 2.7.1.47 | D-ribulokinase |
| 2.7.1.74 | deoxycytidine kinase |
| 2.7.1.76 | deoxyadenosine kinase |
| 2.7.1.77 | nucleoside phosphotransferase |

-continued

| Enzyme Commission Number | Enzyme Name |
|---|---|
| 2.7.1.78 | polynucleotide 5'-hydroxyl-kinase |
| 2.7.1.79 | diphosphate-glycerol phosphotransferase |
| 2.7.1.80 | diphosphate-serine phosphotransferase |
| 2.7.1.81 | hydroxylysine kinase |
| 2.7.1.82 | ethanolamine kinase |
| 2.7.1.83 | pseudouridine kinase |
| 2.7.1.84 | alkylglycerone kinase |
| 2.7.1.85 | β-glucoside kinase |
| 2.7.1.86 | NADH kinase |
| 2.7.1.87 | streptomycin 3"-kinase |
| 2.7.1.88 | dihydrostreptomycin-6-phosphate 3'a-kinase |
| 2.7.1.89 | thiamine kinase |
| 2.7.1.90 | diphosphate-fructose-6-phosphate 1-phosphotransferase |
| 2.7.1.91 | sphinganine kinase |
| 2.7.1.92 | 5-dehydro-2-deoxygluconokinase |
| 2.7.1.93 | alkylglycerol kinase |
| 2.7.1.144 | tagatose-6-phosphate kinase |
| 2.7.1.145 | deoxynucleoside kinase |
| 2.7.1.146 | ADP-dependent phosphofructokinase |
| 2.7.1.147 | ADP-dependent glucokinase |
| 2.7.1.148 | 4-(cytidine 5'-diphospho)-2-C-methyl-D-erythritol kinase |
| 2.7.1.149 | 1-phosphatidylinositol-5-phosphate 4-kinase |
| 2.7.1.150 | 1-phosphatidylinositol-3-phosphate 5-kinase |
| 2.7.1.151 | inositol-polyphosphate multikinase |
| 2.7.1.153 | phosphatidylinositol-4,5-bisphosphate 3-kinase |
| 2.7.1.154 | phosphatidylinositol-4-phosphate 3-kinase |
| 2.7.1.156 | adenosylcobinamide kinase |
| 2.7.1.157 | N-acetylgalactosamine kinase |
| 2.7.1.158 | inositol-pentakisphosphate 2-kinase |
| 2.7.1.159 | inositol-1,3,4-trisphosphate 5/6-kinase |
| 2.7.1.160 | 2'-phosphotransferase |
| 2.7.1.161 | CTP-dependent riboflavin kinase |
| 2.7.1.162 | N-acetylhexosamine 1-kinase |
| 2.7.1.163 | hygromycin B 4-O-kinase |
| 2.7.1.164 | O-phosphoseryl-tRNASec kinase |

A good candidate for this step is mevalonate kinase (EC 2.7.1.36) that phosphorylates the terminal hydroxyl group of the methyl analog, mevalonate, of 3,5-dihydroxypentanote. Some gene candidates for this step are erg12 from *S. cerevisiae*, mvk from *Methanocaldococcus jannaschi*, MVK from *Homo sapeins*, and mvk from *Arabidopsis thaliana* col.

| Protein | GenBank ID | GI Number | Organism |
|---|---|---|---|
| erg12 | CAA39359.1 | 3684 | Sachharomyces cerevisiae |
| mvk | Q58487.1 | 2497517 | Methanocaldococcus jannaschii |
| mvk | AAH16140.1 | 16359371 | Homo sapiens |
| M\mvk | NP_851084.1 | 30690651 | Arabidopsis thaliana |

Glycerol kinase also phosphorylates the terminal hydroxyl group in glycerol to form glycerol-3-phosphate. This reaction occurs in several species, including *Escherichia coli, Saccharomyces cerevisiae*, and *Thermotoga maritima*. The *E. coli* glycerol kinase has been shown to accept alternate substrates such as dihydroxyacetone and glyceraldehyde (Hayashi et al., *J Biol. Chem.* 242:1030-1035 (1967)). T, maritime has two glycerol kinases (Nelson et al., *Nature* 399:323-329 (1999)). Glycerol kinases have been shown to have a wide range of substrate specificity. Crans and Whiteside studied glycerol kinases from four different organisms (*Escherichia coli, S. cerevisiae, Bacillus stearothermophilus*, and *Candida mycoderma*) (Crans et al., *J. Am. Chem. Soc.* 107:7008-7018 (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic con stants of the enzyme from all four organisms were very similar. The gene candidates are:

| Protein | GenBank ID | GI Number | Organism |
|---|---|---|---|
| glpK | AP_003883.1 | 89110103 | Escherichia coli K12 |
| glpK1 | NP_228760.1 | 15642775 | Thermotoga maritime MSB8 |
| glpK2 | NP_229230.1 | 15642775 | Thermotoga maritime MSB8 |
| Gut1 | NP_011831.1 | 82795252 | Saccharomyces cerevisiae |

Homoserine kinase is another possible candidate that can lead to the phosphorylation of 3,5-dihydroxypentanoate. This enzyme is also present in a number of organisms including *E. coli, Streptomyces* sp, and *S. cerevisiae*. Homoserine kinase from *E. coli* has been shown to have activity on numerous substrates, including, L-2-amino,1,4-butanediol, aspartate semialdehyde, and 2-amino-5-hydroxyvalerate (Huo et al., *Biochemistry* 35:16180-16185 (1996); Huo et al., *Arch. Biochem. Biophys.* 330:373-379 (1996)). This enzyme can act on substrates where the carboxyl group at the alpha position has been replaced by an ester or by a hydroxymethyl group. The gene candidates are:

| Protein | GenBank ID | GI Number | Organism |
|---|---|---|---|
| thrB | BAB96580.2 | 85674277 | Escherichia coli K12 |
| SACT1DRAFT_4809 | ZP_06280784.1 | 282871792 | Streptomyces sp. ACT-1 |
| Thr1 | AAA35154.1 | 172978 | Saccharomyces serevisiae |

2-Butenyl-4-phosphate kinase (FIG. 2, Step G)

2-Butenyl-4-phosphate kinase enzymes catalyze the transfer of a phosphate group to the phosphate group of 2-butenyl-4-phosphate. The enzymes described below naturally possess such activity or can be engineered to exhibit this activity. Kinases that catalyze transfer of a phosphate group to another phosphate group are members of the EC 2.7.4 enzyme class. The table below lists several useful kinase enzymes in the EC 2.7.4 enzyme class.

| Enzyme Commission Number | Enzyme Name |
|---|---|
| 2.7.4.1 | polyphosphate kinase |
| 2.7.4.2 | phosphomevalonate kinase |
| 2.7.4.3 | adenylate kinase |
| 2.7.4.4 | nucleoside-phosphate kinase |
| 2.7.4.6 | nucleoside-diphosphate kinase |
| 2.7.4.7 | phosphomethylpyrimidine kinase |
| 2.7.4.8 | guanylate kinase |
| 2.7.4.9 | dTMP kinase |
| 2.7.4.10 | nucleoside-triphosphate-adenylate kinase |
| 2.7.4.11 | (deoxy)adenylate kinase |
| 2.7.4.12 | T2-induced deoxynucleotide kinase |
| 2.7.4.13 | (deoxy)nucleoside-phosphate kinase |
| 2.7.4.14 | cytidylate kinase |
| 2.7.4.15 | thiamine-diphosphate kinase |
| 2.7.4.16 | thiamine-phosphate kinase |
| 2.7.4.17 | 3-phosphoglyceroyl-phosphate-polyphosphate phosphotransferase |
| 2.7.4.18 | farnesyl-diphosphate kinase |
| 2.7.4.19 | 5-methyldeoxycytidine-5'-phosphate kinase |
| 2.7.4.20 | dolichyl-diphosphate-polyphosphate phosphotransferase |
| 2.7.4.21 | inositol-hexakisphosphate kinase |
| 2.7.4.22 | UMP kinase |
| 2.7.4.23 | ribose 1,5-bisphosphate phosphokinase |
| 2.7.4.24 | diphosphoinositol-pentakisphosphate kinase |

Phosphomevalonate kinase enzymes are of particular interest. Phosphomevalonate kinase (EC 2.7.4.2) catalyzes the analogous transformation to 2-butenyl-4-phosphate kinase. This enzyme is encoded by erg8 in *Saccharomyces cerevisiae* (Tsay et al., *Mol. Cell Biol.* 11:620-631 (1991)) and mvaK2 in *Streptococcus pneumoniae*, *Staphylococcus aureus* and *Enterococcus faecalis* (Doun et al., *Protein Sci.* 14:1134-1139 (2005); Wilding et al., *J Bacteriol.* 182:4319-4327 (2000)). The *Streptococcus pneumoniae* and *Enterococcus faecalis* enzymes were cloned and characterized in *E. coli* (Pilloff et al., *J Biol. Chem.* 278:4510-4515 (2003); Doun et al., *Protein Sci.* 14:1134-1139 (2005)).

| Protein | GenBank ID | GI Number | Organism |
| --- | --- | --- | --- |
| Erg8 | AAA34596.1 | 171479 | *Saccharomyces cerevisiae* |
| mvaK2 | AAG02426.1 | 9937366 | *Staphylococcus aureus* |
| mvaK2 | AAG02457.1 | 9937409 | *Streptococcus pneumoniae* |
| mvaK2 | AAG02442.1 | 9937388 | *Enterococcus faecalis* |

Butadiene synthase (FIG. 2, Step H)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., Metabolic Eng, 2010, 12 (1), 70-79; Sharkey et al., Plant Physiol., 2005, 137 (2), 700-712), and *Populus tremula*×*Populus alba* (Miller et al., Planta, 2001, 213 (3), 483-487). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
| --- | --- | --- | --- |
| ispS | BAD98243.1 | 63108310 | *Populus alba* |
| ispS | AAQ84170.1 | 35187004 | *Pueraria montana* |
| ispS | CAC35696.1 | 13539551 | *Populus tremula* × *Populus alba* |

Crotonyl-CoA hydrolase, synthetase, transferase (FIG. 2, Step I)

Crotonyl-CoA hydrolase catalyzes the conversion of crotonyl-CoA to crotonate. The enzymes described below naturally possess such activity or can be engineered to exhibit this activity. 3-Hydroxyisobutyryl-CoA hydrolase efficiently catalyzes the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., supra; Shimomura et al., *Methods Enzymol.* 324: 229-240 (2000)) and *Homo sapiens* (Shimomura et al., supra). The *H. sapiens* enzyme also accepts 3-hydroxybutyryl-CoA and 3-hydroxypropionyl-CoA as substrates (Shimomura et al., supra). Candidate genes by sequence homology include hibch of *Saccharomyces cerevisiae* and BC_2292 of *Bacillus cereus*. These proteins are identified below.

| Protein | GenBank ID | GI Number | Organism |
| --- | --- | --- | --- |
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

Several eukaryotic acetyl-CoA hydrolases (EC 3.1.2.1) have broad substrate specificity and thus represent suitable candidate enzymes. For example, the enzyme from *Rattus norvegicus* brain (Robinson et al., Res. Commun. 71:959-965 (1976)) can react with butyryl-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., Plant. Physiol. 94:20-27 (1990)). The acetyl-CoA hydrolase, ACH1, from *S. cerevisiae* represents another candidate hydrolase (Buu et al., J. Biol. Chem. 278:17203-17209 (2003)). These proteins are identified below.

| Protein | GenBank ID | GI Number | Organism |
| --- | --- | --- | --- |
| acot12 | NP_570103.1 | 18543355 | *Rattus norvegicus* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J Biol. Chem. 280:38125-38132 (2005)) and the closest *E. coli* homolog, tesB, which can also hydrolyze a broad range of CoA thioesters (Naggert et al., J Biol. Chem. 266:11044-11050 (1991)). A similar enzyme has also been characterized in the rat liver (Deana et al., Biochem. Int. 26:767-773 (1992)). Other potential *E. coli* thioester hydrolases include the gene products of tesA (Bonner et al., Chem. 247:3123-3133 (1972)), ybgC (Kuznetsova et al., FEMS Microbiol Rev 29:263-279 (2005); and (Zhuang et al., FEBS Lett. 516:161-163 (2002)), paaI (Song et al., J Biol. Chem. 281:11028-11038 (2006)), and ybdB (Leduc et al., J Bacteriol. 189:7112-7126 (2007)). These proteins are identified below.

| Protein | GenBank ID | GI Number | Organism |
| --- | --- | --- | --- |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., FEBS. Lett. 405:209-212 (1997)). This suggests that the enzymes encoding succinyl-CoA:3-ketoacid-CoA transferases and acetoacetyl-CoA: acetyl-CoA transferases can also serve as candidates for this reaction step but would require certain mutations to change their function. These proteins are identified below.

| Protein | GenBank ID | GI Number | Organism |
|---|---|---|---|
| gctA | CAA57199 | 559392 | Acidaminococcus fermentans |
| gctB | CAA57200 | 559393 | Acidaminococcus fermentans |

Crotonyl-CoA synthetase catalyzes the conversion of crotonyl-CoA to crotonate. The enzymes described below naturally possess such activity or can be engineered to exhibit this activity. One candidate enzyme, ADP-forming acetyl-CoA synthetase (ACD, EC 6.2.1.13), couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus*, *H. marismortui* and *P. aerophilum* have all been cloned, functionally expressed, and characterized in *E. coli* (Musfeldt et al., supra; Brasen et al., supra). These proteins are identified below.

| Protein | GenBank ID | GI Number | Organism |
|---|---|---|---|
| AF1211 | NP_070039.1 | 11498810 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |

Another candidate CoA synthetase is succinyl-CoA synthetase. The sucCD genes of *E. coli* form a succinyl-CoA synthetase complex which naturally catalyzes the formation of succinyl-CoA from succinate with the concaminant consumption of one ATP, a reaction which is reversible in vivo (Buck et al., *Biochem.* 24:6245-6252 (1985)). These proteins are identified below.

| Protein | GenBank ID | GI Number | Organism |
|---|---|---|---|
| sucC | NP_415256.1 | 16128703 | Escherichia coli |
| sucD | AAC73823.1 | 1786949 | Escherichia coli |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependant conversion of acetoacetate into acetoacetyl-CoA. These proteins are identified below.

| Protein | GenBank ID | GI Number | Organism |
|---|---|---|---|
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |

Crotonyl-CoA transferase catalyzes the conversion of crotonyl-CoA to crotonate. The enzymes described below naturally possess such activity or can be engineered to exhibit this activity. Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA:acetate:CoA transferase and propionyl-CoA:acetate:CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters*, 171(1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. These proteins are identified below.

| Protein | GenBank ID | GI Number | Organism |
|---|---|---|---|
| Ach1 | AAX19660.1 | 60396828 | Roseburia sp. A2-183 |
| ROSINTL182_07121 | ZP_04743841.2 | 257413684 | Roseburia intestinalis L1-82 |
| ROSEINA2194_03642 | ZP_03755203.1 | 225377982 | Roseburia inulinivorans DSM 16841 |

| Protein | GenBank ID | GI Number | Organism |
|---|---|---|---|
| EUBREC_3075 | YP_002938937.1 | 238925420 | Eubacterium rectale ATCC 33656 |
| pct | CAB77207.1 | 7242549 | Clostridium propionicum |
| NT01CX_2372 | YP_878445.1 | 118444712 | Clostridium novyi NT |
| Cbei_4543 | YP_001311608.1 | 150019354 | Clostridium beijerinckii NCIMB 8052 |
| CBC_A0889 | ZP_02621218.1 | 168186583 | Clostridium botulinum C str. Eklund |
| ygfH | NP_417395.1 | 16130821 | Escherichia coli str. K-12 substr. MG1655 |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

An additional candidate enzyme is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)). These proteins are identified below.

| Protein | GenBank ID | GI Number | Organism |
|---|---|---|---|
| pcaI | AAN69545.1 | 24985644 | Pseudomonas putida |
| pcaJ | NP_746082.1 | 26990657 | Pseudomonas putida |
| pcaI | YP_046368.1 | 50084858 | Acinetobacter sp. ADP1 |
| pcaJ | AAC37147.1 | 141776 | Acinetobacter sp. ADP1 |
| pcaI | NP_630776.1 | 21224997 | Streptomyces coelicolor |
| pcaJ | NP_630775.1 | 21224996 | Streptomyces coelicolor |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |

A CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)). These proteins are identified below.

| Protein | GenBank ID | GI Number | Organism |
|---|---|---|---|
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum ATCC 13032 |

| Protein | GenBank ID | GI Number | Organism |
|---|---|---|---|
| cg0592 | YP_224801.1 | 62389399 | Corynebacterium glutamicum ATCC 13032 |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium saccharoperbutylacetonicum |
| ctfB | AAP42565.1 | 31075385 | Clostridium saccharoperbutylacetonicum |

The above enzymes can also exhibit the desired activities on crotonyl-CoA. Additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279: 45337-45346 (2004)). These proteins are identified below.

| Protein | GenBank ID | GI Number | Organism |
|---|---|---|---|
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118: 315-321 (1981)). The enzyme has been cloned and expressed in *E. coli* (Mack et al., *Eur. J. Biochem.* 226:41-51 (1994)). These proteins are identified below.

| Protein | GenBank ID | GI Number | Organism |
| --- | --- | --- | --- |
| gctA | CAA57199.1 | 559392 | *Acidaminococcus fermentans* |
| gctB | CAA57200.1 | 559393 | *Acidaminococcus fermentans* |

Crotonate reductase (FIG. 2, Step J)

Crotonate reductase enzymes are capable of catalyzing the conversion of crotonate to crotonaldehyde. The enzymes described below naturally possess such activity or can be engineered to exhibit this activity. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Protein | GenBank ID | GI Number | Organism |
| --- | --- | --- | --- |
| Car | AAR91681.1 | 40796035 | *Nocardia iowensis* (sp. NRRL 5646) |
| Npt | ABI83656.1 | 114848891 | *Nocardia iowensis* (sp. NRRL 5646) |

Additional car and npt genes can be identified based on sequence homology.

| Protein | GenBank ID | GI Number | Organism |
| --- | --- | --- | --- |
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Protein | GenBank ID | GI Number | Organism |
| --- | --- | --- | --- |
| griC | YP_001825755.1 | 182438036 | *Streptomyces griseus* subsp. *griseus* NBRC 13350 |
| Grid | YP_001825756.1 | 182438037 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Protein | GenBank ID | GI Number | Organism |
| --- | --- | --- | --- |
| LYS2 | AAA34747.1 | 171867 | *Saccharomyces cerevisiae* |
| LYS5 | P50113.1 | 1708896 | *Saccharomyces cerevisiae* |

| Protein | GenBank ID | GI Number | Organism |
|---|---|---|---|
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Crotonyl-CoA reductase (alcohol forming) (FIG. 2, Step K)

Crotonaldehyde reductase (alcohol forming) enzymes catalyze the 2 reduction steps required to form crotyl alcohol from crotonyl-CoA. Exemplary 2-step oxidoreductases that convert an acyl-CoA to an alcohol are provided below. Such enzymes can naturally convert crotonyl-CoA to crotyl alcohol or can be engineered to do so. These enzymes include those that transform substrates such as acetyl-CoA to ethanol (e.g., adhE from *E. coli* (Kessler et al., *FEBS. Lett.* 281:59-63 (1991))) and butyryl-CoA to butanol (e.g. adhE2 from *C. acetobutylicum* (Fontaine et al., *J. Bacteriol.* 184:821-830 (2002))). The adhE2 enzyme from *C. acetobutylicum* was specifically shown in ref. (Burk et al., supra, (2008)) to produce BDO from 4-hydroxybutyryl-CoA. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)).

| Protein | GenBank ID | GI Number | Organism |
|---|---|---|---|
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |

Another exemplary enzyme can convert malonyl-CoA to 3-HP. An NADPH-dependent enzyme with this activity has been characterized in *Chloroflexus aurantiacus* where it participates in the 3-hydroxypropionate cycle (Hugler et al., supra, (2002); Strauss et al., 215:633-643 (1993)). This enzyme, with a mass of 300 kDa, is highly substrate-specific and shows little sequence similarity to other known oxidoreductases (Hugler et al., supra, (2002)). No enzymes in other organisms have been shown to catalyze this specific reaction; however there is bioinformatic evidence that other organisms can have similar pathways (Klatt et al., *Environ Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
|---|---|---|---|
| mcr | AAS20429.1 | 42561982 | Chloroflexus aurantiacus |
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

Glutaconyl-CoA decarboxylase (FIG. 2, Step L)

Glutaconyl-CoA decarboxylase enzymes, characterized in glutamate-fermenting anaerobic bacteria, are sodium-ion translocating decarboxylases that utilize biotin as a cofactor and are composed of four subunits (alpha, beta, gamma, and delta) (Boiangiu et al., *J Mol. Microbiol Biotechnol* 10:105-119 (2005); Buckel, *Biochim Biophys Acta.* 1505:15-27 (2001)). Such enzymes have been characterized in *Fusobacterium nucleatum* (Beatrix et al., *Arch Microbiol.* 154:362-369 (1990)) and *Acidaminococcus fermentans* (Braune et al., *Mol. Microbiol* 31:473-487 (1999)). Analogs to the *F. nucleatum* glutaconyl-CoA decarboxylase alpha, beta and delta subunits are found in *S. aciditrophicus*. A gene annotated as an enoyl-CoA dehydrogenase, syn_00480, another GCD, is located in a predicted operon between a biotin-carboxyl carrier (syn_00479) and a glutaconyl-CoA decarboxylase alpha subunit (syn_00481). The protein sequences for exemplary gene products can be found using the following GenBank accession numbers shown below.

| Protein | GenBank ID | GI Number | Organism |
|---|---|---|---|
| gcdA | CAA49210 | 49182 | Acidaminococcus fermentans |
| gcdC | AAC69172 | 3777506 | Acidaminococcus fermentans |
| gcdD | AAC69171 | 3777505 | Acidaminococcus fermentans |
| gcdB | AAC69173 | 3777507 | Acidaminococcus fermentans |
| FN0200 | AAL94406 | 19713641 | Fusobacterium nucleatum |
| FN0201 | AAL94407 | 19713642 | Fusobacterium nucleatum |
| FN0204 | AAL94410 | 19713645 | Fusobacterium nucleatum |
| syn_00479 | YP_462066 | 85859864 | Syntrophus aciditrophicus |
| syn_00481 | YP_462068 | 85859866 | Syntrophus aciditrophicus |
| syn_01431 | YP_460282 | 85858080 | Syntrophus aciditrophicus |
| syn_00480 | ABC77899 | 85722956 | Syntrophus aciditrophicus |

Glutaryl-CoA dehydrogenase (FIG. 2 Step M)

Glutaryl-CoA dehydrogenase (GCD, EC 1.3.99.7 and EC 4.1.1.70) is a bifunctional enzyme that catalyzes the oxidative decarboxylation of glutaryl-CoA to crotonyl-CoA (FIG. 3, step 3). Bifunctional GCD enzymes are homotetramers that utilize electron transfer flavoprotein as an electron acceptor (Hartel et al., *Arch Microbiol.* 159:174-181 (1993)). Such enzymes were first characterized in cell extracts of *Pseudomonas* strains KB740 and K172 during growth on aromatic compounds (Hartel et al., supra, (1993)), but the associated genes in these organisms is unknown. Genes encoding glutaryl-CoA dehydrogenase (gcdH) and its cognate transcriptional regulator (gcdR) were identified in *Azoarcus* sp. CIB (Blazquez et al., *Environ Microbiol.* 10:474-482 (2008)). An *Azoarcus* strain deficient in gcdH activity was used to identify the a heterologous gene gcdH from *Pseudomonas putida* (Blazquez et al., supra, (2008)). The cognate transcriptional regulator in *Pseudomonas putida* has not been identified but the locus PP_0157 has a high sequence homology (>69% identity) to the *Azoarcus* enzyme. Additional GCD enzymes are found in *Pseudomonas fluorescens* and *Paracoccus denitrificans* (Husain et al., *J Bacteriol.* 163:709-715 (1985)). The human GCD has been extensively studied, overexpressed in *E. coli* (Dwyer et al., *Biochemistry* 39:11488-11499 (2000)), crystallized, and the catalytic mechanism involving a conserved glutamate residue in the active site has been described (Fu et al., *Biochemistry* 43:9674-9684 (2004)). A GCD in *Syntrophus aciditrophicus* operates in the $CO_2$-assimilating direction during growth on crotonate (Mouttaki et al., *Appl Environ Microbiol.* 73:930-938 (2007))). Two GCD genes in *S. aciditrophicus* were identified by protein sequence homology to the *Azoarcus* GcdH: syn_00480 (31%) and syn_01146 (31%). No significant homology was found to the *Azoarcus* GcdR regulatory protein. The protein sequences for exemplary gene products can be found using the following GenBank accession numbers shown below.

| Protein | GenBank ID | GI Number | Organism |
|---|---|---|---|
| gcdH | ABM69268.1 | 123187384 | *Azoarcus* sp. CIB |
| gcdR | ABM69269.1 | 123187385 | *Azoarcus* sp. CIB |
| gcdH | AAN65791.1 | 24981507 | *Pseudomonas putida* KT2440 |
| PP_0157 (gcdR) | AAN65790.1 | 24981506 | *Pseudomonas putida* KT2440 |
| gcdH | YP_257269.1 | 70733629 | *Pseudomonas fluorescens* Pf-5 |
| gcvA (gcdR) | YP_257268.1 | 70733628 | *Pseudomonas fluorescens* Pf-5 |
| gcd | YP_918172.1 | 119387117 | *Paracoccus denitrificans* |
| gcdR | YP_918173.1 | 119387118 | *Paracoccus denitrificans* |
| gcd | AAH02579.1 | 12803505 | *Homo sapiens* |
| syn_00480 | ABC77899 | 85722956 | *Syntrophus aciditrophicus* |
| syn_01146 | ABC76260 | 85721317 | *Syntrophus aciditrophicus* |

3-Aminobutyryl-CoA deaminase (FIG. 2, Step N)

3-aminobutyryl-CoA is an intermediate in lysine fermentation. It also can be formed from acetoacetyl-CoA via a transaminase or an aminating dehydrogenase. 3-aminobutyryl-CoA deaminase (or 3-aminobutyryl-CoA ammonia lyase) catalyzes the deamination of 3-aminobutyryl-CoA to form crotonyl-CoA. This reversible enzyme is present in *Fusobacterium nucleatum*, *Porphyromonas gingivalis*, *Thermoanaerobacter tengcongensis*, and several other organisms and is co-localized with several genes involved in lysine fermentation (Kreimeyer et al., *J Biol Chem*, 2007, 282(10) 7191-7197).

| Protein | GenBank ID | GI Number | Organism |
|---|---|---|---|
| kal | NP_602669.1 | 19705174 | *Fusobacterium nucleatum* subsp. *nucleatum* ATCC 25586 |
| kal | NP_905282.1 | 34540803 | *Porphyromonas gingivalis* W83 |
| kal | NP_622376.1 | 20807205 | *Thermoanaerobacter tengcongensis* MB4 |

4-Hydroxybutyryl-CoA dehydratase (FIG. 2, Step O)

Several enzymes naturally catalyze the dehydration of 4-hydroxybutyryl-CoA to crotonoyl-CoA. This transformation is required for 4-aminobutyrate fermentation by *Clostridium aminobutyricum* (Scherf et al., *Eur. J Biochem.* 215:421-429 (1993)) and succinate-ethanol fermentation by *Clostridium kluyveri* (Scherf et al., *Arch. Microbiol* 161:239-245 (1994)). The transformation is also a key step in Archaea, for example, *Metallosphaera sedula*, as part of the 3-hydroxypropionate/4-hydroxybutyrate autotrophic carbon dioxide assimilation pathway (Berg et al., supra, (2007)). The reversibility of 4-hydroxybutyryl-CoA dehydratase is well-documented (Muh et al., Biochemistry. 35:11710-11718 (1996); Friedrich et al., *Angew. Chem. Int. Ed. Engl.* 47:3254-3257 (2008); Muh et al., *Eur. J. Biochem.* 248:380-384 (1997)) and the equilibrium constant has been reported to be about 4 on the side of crotonoyl-CoA (Scherf and Buckel, supra, (1993)).

| Protein | GenBank ID | GI Number | Organism |
|---|---|---|---|
| AbfD | CAB60035 | 70910046 | *Clostridium aminobutyricum* |
| AbfD | YP_001396399 | 153955634 | *Clostridium kluyveri* |
| Msed_1321 | YP_001191403 | 146304087 | *Metallosphaera sedula* |
| Msed_1220 | YP_001191305 | 146303989 | *Metallosphaera sedula* |

Crotyl alcohol diphosphokinase (FIG. 2, Step P)

Crotyl alcohol diphosphokinase enzymes catalyze the transfer of a diphosphate group to the hydroxyl group of crotyl alcohol. The enzymes described below naturally possess such activity or can be engineered to exhibit this activity. Kinases that catalyze transfer of a diphosphate group are members of the EC 2.7.6 enzyme class. The table below lists several useful kinase enzymes in the EC 2.7.6 enzyme class.

| Enzyme Commission Number | Enzyme Name |
|---|---|
| 2.7.6.1 | ribose-phosphate diphosphokinase |
| 2.7.6.2 | thiamine diphosphokinase |
| 2.7.6.3 | 2-amino-4-hydroxy-6-hydroxymethyldihydropteridine diphosphokinase |
| 2.7.6.4 | nucleotide diphosphokinase |
| 2.7.6.5 | GTP diphosphokinase |

Of particular interest are ribose-phosphate diphosphokinase enzymes which have been identified in *Escherichia coli* (Hove-Jenson et al., J Biol Chem, 1986, 261(15); 6765-71) and *Mycoplasma pneumoniae* M129 (McElwain et al, International Journal of Systematic Bacteriology, 1988, 38:417-423) as well as thiamine diphosphokinase enzymes. Exemplary thiamine diphosphokinase enzymes are found in *Arabidopsis thaliana* (Ajjawi, Plant Mol Biol, 2007, 65(1-2); 151-62).

| Protein | GenBank ID | GI Number | Organism |
|---|---|---|---|
| prs | NP_415725.1 | 16129170 | *Escherichia coli* |
| prsA | NP_109761.1 | 13507812 | *Mycoplasma pneumoniae* M129 |
| TPK1 | BAH19964.1 | 222424006 | *Arabidopsis thaliana* col |
| TPK2 | BAH57065.1 | 227204427 | *Arabidopsis thaliana* col |

Erythrose-4-phosphate reductase (FIG. 3, Step A)

In Step A of the pathway, erythrose-4-phosphate is converted to erythritol-4-phosphate by the erythrose-4-phosphate reductase or erythritol-4-phosphate dehydrogenase. The reduction of erythrose-4-phosphate was observed in *Leuconostoc oenos* during the production of erythritol (Veiga-da-Cunha et al., *J Bacteriol.* 175:3941-3948 (1993)). NADPH was identified as the cofactor (Veiga-da-Cunha et al., supra, (1993)). However, gene for erythrose-4-phosphate was not identified. Thus, it is possible to identify the erythrose-4-phosphate reductase gene from *Leuconostoc oenos* and apply to this step. Additionally, enzymes catalyzing similar reactions can be utilized for this step. An example of these enzymes is 1-deoxy-D-xylulose-5-phosphate reductoisomerase (EC 1.1.1.267) catalyzing the conversion of 1-deoxy-D-xylulose 5-phosphate to 2-C-methyl-D-erythritol-4-phosphate, which has one additional methyl group comparing to Step A. The dxr or ispC genes encode the 1-deoxy-D-xylulose-5-phosphate reductoisomerase have been well studied: the Dxr proteins from *Escherichia coli* and *Mycobacterium tuberculosis* were purified and their crystal structures were determined (Yajima et al., *Acta Crystallogr. Sect. F. Struct. Biol. Cryst. Commun.* 63:466-470 (2007); Mac et al., *J Mol. Biol.* 345:115-127 (2005); Henriksson et al., *Acta Crystallogr. D. Biol. Crystallogr.* 62:807-813 (2006); Henriksson et al., *J. Biol. Chem.* 282:19905-19916 (2007)); the Dxr protein from *Synechocystis* sp was studied by site-directed mutagenesis with modified activity and altered kinetics (Fernandes et al., *Biochim. Biophys. Acta* 1764:223-229

(2006); Fernandes et al., *Arch. Biochem. Biophys.* 444:159-164 (2005)). Furthermore, glyceraldehyde 3-phosphate reductase YghZ from *Escherichia coli* catalyzes the conversion between glyceraldehyde 3-phosphate and glycerol-3-phosphate (Desai et al., *Biochemistry* 47:7983-7985 (2008)) can also be applied to this step. The following genes can be used for Step A conversion:

| Protein | GenBank ID | GI Number | Organism |
| --- | --- | --- | --- |
| dxr | P45568.2 | 2506592 | *Escherichia coli* strain K12 |
| dxr | A5U6M4.1 | 166218269 | *Mycobacterium tuberculosis* |
| dxr | Q55663.1 | 2496789 | *Synechocystis* sp. strain PCC6803 |
| yghZ | NP_417474.1 | 16130899 | *Escherichia coli* strain K12 |

Erythritol-4-phospate cytidylyltransferase (FIG. 3, Step B)

In Step B of the pathway, erythritol-4-phosphate is converted to 4-(cytidine 5'-diphospho)-erythritol by the erythritol-4-phospate cytidylyltransferase or 4-(cytidine 5'-diphospho)-erythritol synthase. The exact enzyme for this step has not been identified. However, enzymes catalyzing similar reactions can be applied to this step. An example is the 2-C-methyl-D-erythritol 4-phosphate cytidylyltransferase or 4-(cytidine 5'-diphospho)-2-C-methyl-D-erythritol synthase (EC 2.7.7.60). The 2-C-methyl-D-erythritol 4-phospate cytidylyltransferase is in the methylerythritol phosphate pathway for the isoprenoid biosynthesis and catalyzes the conversion between 2-C-methyl-D-erythritol 4-phospate and 4-(cytidine 5'-diphospho)-2-C-methyl-D-erythritol, with an extra methyl group comparing to Step B conversion. The 2-C-methyl-D-erythritol 4-phosphate cytidylyltransferase is encoded by ispD gene and the crystal structure of *Escherichia coli* IspD was determined (Kemp et al., *Acta Crystallogr. D. Biol. Crystallogr.* 57:1189-1191 (2001); Kemp et al., *Acta Crystallogr. D. Biol. Crystallogr.* 59:607-610 (2003); Richard et al., *Nat. Struct. Biol.* 8:641-648 (2001)). The ispD gene from *Mycobacterium tuberculosis* H37Rv was cloned and expressed in *Escherichia coli*, and the recombinant proteins were purified with N-terminal His-tag (Shi et al., *J Biochem. Mol. Biol.* 40:911-920 (2007)). Additionally, the *Streptomyces coelicolor* ispD gene was cloned and expressed in *E. coli*, and the recombinant proteins were characterized physically and kinetically (Cane et al., *Bioorg. Med. Chem.* 9:1467-1477 (2001)). The following genes can be used for Step B conversion:

| Protein | GenBank ID | GI Number | Organism |
| --- | --- | --- | --- |
| ispD | Q46893.3 | 2833415 | *Escherichia coli* strain K12 |
| ispD | A5U8Q7.1 | 166215456 | *Mycobacterium tuberculosis* |
| ispD | Q9L0Q8.1 | 12230289 | *Streptomyces coelicolor* |

4-(Cytidine 5'-diphospho)-erythritol kinase (FIG. 3, Step C)

In Step C of the pathway, 4-(cytidine 5'-diphospho)-erythritol is converted to 2-phospho-4-(cytidine 5'-diphospho)-erythritol by the 4-(cytidine 5'-diphospho)-erythritol kinase. The exact enzyme for this step has not been identified. However, enzymes catalyzing similar reactions can be applied to this step. An example is the 4-diphosphocytidyl-2-C-methylerythritol kinase (EC 2.7.1.148). The 4-diphosphocytidyl-2-C-methylerythritol kinase is also in the methylerythritol phosphate pathway for the isoprenoid biosynthesis and catalyzes the conversion between 4-(cytidine 5'-diphospho)-2-C-methyl-D-erythritol and 2-phospho-4-(cytidine 5'-diphospho)-2-C-methyl-D-erythritol, with an extra methyl group comparing to Step C conversion. The 4-diphosphocytidyl-2-C-methylerythritol kinase is encoded by ispE gene and the crystal structures of *Escherichia coli, Thermus thermophilus* HB8, and *Aquifex aeolicus* IspE were determined (Sgraja et al., *FEBS J* 275:2779-2794 (2008); Miallau et al., *Proc. Natl. Acad. Sci. U.S.A* 100:9173-9178 (2003); Wada et al., *J Biol. Chem.* 278:30022-30027 (2003)). The ispE genes from above organism were cloned and expressed, and the recombinant proteins were purified for crystallization. The following genes can be used for Step C conversion:

| Protein | GenBank ID | GI Number | Organism |
| --- | --- | --- | --- |
| ispE | P62615.1 | 50402174 | *Escherichia coli* strain K12 |
| ispE | P83700.1 | 51316201 | *Thermus thermophilus* HB8 |
| ispE | O67060.1 | 6919911 | *Aquifex aeolicus* |

Erythritol 2,4-cyclodiphosphate synthase (FIG. 3, Step D)

In Step D of the pathway, 2-phospho-4-(cytidine 5'-diphospho)-erythritol is converted to erythritol-2,4-cyclodiphosphate by the Erythritol 2,4-cyclodiphosphate synthase. The exact enzyme for this step has not been identified. However, enzymes catalyzing similar reactions can be applied to this step. An example is the 2-C-methyl-D-erythritol 2,4-cyclodiphosphate synthase (EC 4.6.1.12). The 2-C-methyl-D-erythritol 2,4-cyclodiphosphate synthase is also in the methylerythritol phosphate pathway for the isoprenoid biosynthesis and catalyzes the conversion between 2-phospho-4-(cytidine 5' diphospho)-2-C-methyl-D-erythritol and 2-C-methyl-D-erythritol-2,4-cyclodiphosphate, with an extra methyl group comparing to step D conversion. The 2-C-methyl-D-erythritol 2,4-cyclodiphosphate synthase is encoded by ispF gene and the crystal structures of *Escherichia coli, Thermus thermophilus, Haemophilus influenzae,* and *Campylobacter jejuni* IspF were determined (Richard et al., *J Biol. Chem.* 277:8667-8672 (2002); Steinbacher et al., *J Mol. Biol.* 316:79-88 (2002); Lehmann et al., *Proteins* 49:135-138 (2002); Kishida et al., *Acta Crystallogr. D. Biol. Crystallogr.* 59:23-31 (2003); Gabrielsen et al., *J Biol. Chem.* 279:52753-52761 (2004)). The ispF genes from above organism were cloned and expressed, and the recombinant proteins were purified for crystallization. The following genes can be used for Step D conversion:

| Protein | GenBank ID | GI Number | Organism |
| --- | --- | --- | --- |
| ispF | P62617.1 | 51317402 | *Escherichia coli* strain K12 |
| ispF | Q8RQP5.1 | 51701599 | *Thermus thermophilus* HB8 |
| ispF | P44815.1 | 1176081 | *Haemophilus influenzae* |
| ispF | Q9PM68.1 | 12230305 | *Campylobacter jejuni* |

1-Hydroxy-2-butenyl 4-diphosphate synthase (FIG. 3, Step E)

Step E of FIG. 3 entails conversion of erythritol-2,4-cyclodiphosphate to 1-hydroxy-2-butenyl 4-diphosphate by 1-hydroxy-2-butenyl 4-diphosphate synthase. An enzyme with this activity has not been characterized to date. This transformation is analogous to the reduction of 2-C-methyl-D-erythritol-2,4-cyclodiphosphate to 1-hydroxy-2-methyl-2-(E)-butenyl 4-diphosphate by (E)-4-hydroxy-3-methylbut-2-enyl-diphosphate synthase (EC 1.17.7.1). This enzyme is an iron-sulfur protein that participates in the non-mevalonate pathway for isoprenoid biosynthesis found in bacteria and plants. Most bacterial enzymes including the *E. coli* enzyme, encoded by ispG, utilize reduced ferredoxin or flavodoxin as an electron donor (Zepeck et al., *J Org. Chem.* 70:9168-9174

(2005)). An analogous enzyme from the thermophilic cyanobacterium *Thermosynechococcus elongatus* BP-1, encoded by gcpE, was heterologously expressed and characterized in *E. coli* (Okada et al., *J Biol. Chem.* 280:20672-20679 (2005)). Additional enzyme candidates from *Thermus thermophilus* and *Arabidopsis thaliana* have been characterized and expressed in *E. coli* (Seemann et al., *J Biol. Inorg. Chem.* 10:131-137 (2005); Kollas et al., *FEBS Lett.* 532:432-436 (2002)).

| Protein | GenBank ID | GI Number | Organism |
| --- | --- | --- | --- |
| ispG | NP_417010.1 | 16130440 | *Escherichia coli* |
| gcpE | NP_681786.1 | 22298539 | *Thermosynechococcus elongatus* |
| gcpE | AAO21364.1 | 27802077 | *Thermus thermophilus* |
| gcpE | AAO15446.1 | 27462472 | *Arabidopsis thaliana* |

1-Hydroxy-2-butenyl 4-diphosphate reductase (FIG. 3, Step F)

The concurrent dehydration and reduction of 1-hydroxy-2-butenyl 4-diphosphate is catalyzed by an enzyme with 1-hydroxy-2-butenyl 4-diphosphate reductase activity (FIG. 3, Step F). Such an enzyme will form a mixture of products, butenyl 4-diphosphate or 2-butenyl 4-diphosphate. An analogous reaction is catalyzed by 4-hydroxy-3-methylbut-2-enyl diphosphate reductase (EC 1.17.1.2) in the non-mevalonate pathway for isoprenoid biosynthesis. This enzyme is an iron-sulfur protein that utilizes reduced ferredoxin or flavodoxin as an electron donor. Maximal activity of 4-hydroxy-3-methylbut-2-enyl diphosphate reductase *E. coli*, encoded by ispH, requires both flavodoxin and flavodoxin reductase (Wolff et al., *FEBS Lett.* 541:115-120 (2003); Grawert et al., *J Am. Chem. Soc.* 126:12847-12855 (2004)). In the characterized catalytic system, reduced flavodoxin is regenerated by the NAD(P)+-dependent flavodoxin reductase. The enzyme from *Aquifex aeolicus*, encoded by lytB, was expressed as a His-tagged enzyme in *E. coli* and characterized (Altincicek et al., *FEBS Lett.* 532:437-440 (2002)). An analogous enzyme in plants is encoded by hdr of *Arabidopsis thaliana* (Botella-Pavia et al., *Plant J* 40:188-199 (2004)).

| Protein | GenBank ID | GI Number | Organism |
| --- | --- | --- | --- |
| ispH | AAL38655.1 | 18652795 | *Escherichia coli* |
| lytB | O67625.1 | 8928180 | *Aquifex aeolicus* |
| hdr | NP_567965.1 | 18418433 | *Arabidopsis thaliana* |

Altering the expression level of genes involved in iron-sulfur cluster formation can have an advantageous effect on the activities of iron-sulfur proteins in the proposed pathways (for example, enzymes required in Steps E and F of FIG. 3). In *E. coli*, it was demonstrated that overexpression of the iron-sulfur containing protein IspH (analogous to Step F of FIG. 3) is enhanced by coexpression of genes from the isc region involved in assembly of iron-sulfur clusters (Grawert et al., *J Am. Chem. Soc.* 126:12847-12855 (2004)). The gene cluster is composed of the genes icsS, icsU, icsA, hscB, hscA and fdx. Overexpression of these genes was shown to improve the synthetic capability of the iron-sulfur assembly pipeline, required for functional expression of iron-sulfur proteins. A similar approach can be applicable in the current application.

| Protein | GenBank ID | GI Number | Organism |
| --- | --- | --- | --- |
| iscS | AAT48142.1 | 48994898 | *Escherichia coli* |
| iscU | AAC75582.1 | 1788878 | *Escherichia coli* |
| iscA | AAC75581.1 | 1788877 | *Escherichia coli* |
| hscB | AAC75580.1 | 1788876 | *Escherichia coli* |
| hscA | AAC75579.1 | 1788875 | *Escherichia coli* |
| fdx | AAC75578.1 | 1788874 | *Escherichia coli* |

Butenyl 4-diphosphate isomerase (FIG. 3, Step G)

Butenyl 4-diphosphate isomerase catalyzes the reversible interconversion of 2-butenyl-4-diphosphate and butenyl-4-diphosphate. The following enzymes can naturally possess this activity or can be engineered to exhibit this activity. Useful genes include those that encode enzymes that interconvert isopenenyl diphosphate and dimethylallyl diphosphate. These include isopentenyl diphosphate isomerase enzymes from *Escherichia coli* (Rodríguez-Concepción et al., FEBS Lett, 473(3):328-332), *Saccharomyces cerevisiae* (Anderson et al., J Biol Chem, 1989, 264(32); 19169-75), and *Sulfolobus shibatae* (Yamashita et al, Eur J Biochem, 2004, 271(6); 1087-93). The reaction mechanism of isomerization, catalyzed by the Idi protein of *E. coli*, has been characterized in mechanistic detail (de Ruyck et al., *J Biol. Chem.* 281: 17864-17869 (2006)). Isopentenyl diphosphate isomerase enzymes from *Saccharomyces cerevisiae, Bacillus subtilis* and *Haematococcus pluvialis* have been heterologously expressed in *E. coli* (Laupitz et al., *Eur. J Biochem.* 271:2658-2669 (2004); Kajiwara et al., *Biochem. J* 324 (Pt 2):421-426 (1997)).

| Protein | GenBank ID | GI Number | Organism |
| --- | --- | --- | --- |
| Idi | NP_417365.1 | 16130791 | *Escherichia coli* |
| IDI1 | NP_015208.1 | 6325140 | *Saccharomyces cerevisiae* |
| Idi | BAC82424.1 | 34327946 | *Sulfolobus shibatae* |
| Idi | AAC32209.1 | 3421423 | *Haematococcus pluvialis* |
| Idi | BAB32625.1 | 12862826 | *Bacillus subtilis* |

Butadiene synthase (FIG. 3, Step H)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 579 (11), 2514-2518 (2005)), *Pueraria montana* (Lindberg et al., *Metabolic Eng*, 12(1):70-79 (2010); Sharkey et al., *Plant Physiol.*, 137(2):700-712 (2005)), and *Populus tremula×Populus alba* (Miller et al., *Planta*, 213(3):483-487 (2001)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
| --- | --- | --- | --- |
| ispS | BAD98243.1 | 63108310 | *Populus alba* |
| ispS | AAQ84170.1 | 35187004 | *Pueraria montana* |
| ispS | CAC35696.1 | 13539551 | *Populus tremula × Populus alba* |

Erythrose-4-phosphate kinase (FIG. 3, Step I)

In Step I of the pathway, erythrose-4-phosphate is converted to erythrose by the erythrose-4-phosphate kinase. In industrial fermentative production of erythritol by yeasts, glucose was converted to erythrose-4-phosphate through the pentose phosphate pathway and erythrose-4-phosphate was dephosphorylated and reduced to produce erythritol (Moon et al., *Appl. Microbiol Biotechnol.* 86:1017-1025 (2010)). Thus, erythrose-4-phosphate kinase is present in many of these erythritol-producing yeasts, including *Trichosporonoides megachiliensis* SN-G42 (Sawada et al., *J Biosci. Bioeng.* 108: 385-390 (2009)), *Candida magnolia* (Kohl et al., *Biotechnol. Lett.* 25:2103-2105 (2003)), and *Torula* sp. (HAJNY et al., *Appl. Microbiol* 12:240-246 (1964); Oh et al. *J Ind. Microbiol Biotechnol.* 26:248-252 (2001)). However, the erythrose-4-phosphate kinase genes were not identified get. There are many polyol phosphotransferases with wide substrate range that can be applied to this step. An example is the triose kinase (EC 2.7.1.28) catalyzing the reversible conversion between glyceraldehydes and glyceraldehydes-3-phosphate, which are one carbon shorter comparing to Step I. Other examples include the xylulokinase (EC 2.7.1.17) or arabinokinase (EC 2.7.1.54) that catalyzes phosphorylation of 5C polyol aldehyde. The following genes can be used for Step I conversion:

| Protein | GenBank ID | GI Number | Organism |
|---|---|---|---|
| xylB | P09099.1 | 139849 | *Escherichia coli* strain K12 |
| xks1 | P42826.2 | 1723736 | *Saccharomyces cerevisiae* |
| xylB | P29444.1 | 267426 | *Klebsiella pneumoniae* |
| dak1 | Q9HFC5 | 74624685 | *Zygosaccharomyces rouxii* |

Erythrose reductase (FIG. 3, Step J)

In Step J of the pathway, erythrose is converted to erythritol by the erythrose reductase. In industrial fermentative production of erythritol by yeasts, glucose was converted to erythrose-4-phosphate through the pentose phosphate pathway and erythrose-4-phosphate was dephosphorylated and reduced to produce erythritol (Moon et al., supra, (2010)). Thus, erythrose reductase is present in many of these erythritol-producing yeasts, including *Trichosporonoides megachiliensis* SN-G42 (Sawada et al., supra, (2009)), *Candida magnolia* (Kohl et al., supra, (2003)), and *Torula* sp. (HAJNY et al., supra, (1964); Oh et al., supra, (2001)). Erythrose reductase was characterized and purified from *Torula corallina* (Lee et al., *Biotechnol. Prog.* 19:495-500 (2003); Lee et al., *Appl. Environ. Microbiol* 68:4534-4538 (2002)), *Candida magnolia* (Lee et al., *Appl. Environ. Microbiol* 69:3710-3718 (2003)) and *Trichosporonoides megachiliensis* SN-G42 (Sawada et al., supra, (2009)). Several erythrose reductase genes were cloned and can be applied to Step J. The following genes can be used for Step J conversion:

| Protein | GenBank ID | GI Number | Organism |
|---|---|---|---|
| alr | ACT78580.1 | 254679867 | *Candida magnoliae* |
| er1 | BAD90687.1 | 60458781 | *Trichosporonoides megachiliensis* |
| er2 | BAD90688.1 | 60458783 | *Trichosporonoides megachiliensis* |
| er3 | BAD90689.1 | 60458785 | *Trichosporonoides megachiliensis* |

Erythritol kinase (FIG. 3, Step K)

In Step K of the pathway, erythritol is converted to erythritol-4-phosphate by the erythritol kinase. Erythritol kinase (EC 2.7.1.27) catalyzes the phosphorylation of erythritol. Erythritol kinase was characterized in erythritol utilizing bacteria such as *Brucella abortus* (Sperry et al., *J Bacteriol.* 121:619-630 (1975)). The eryA gene of *Brucella abortus* has been functionally expressed in *Escherichia coli* and the resultant EryA was shown to catalyze the ATP-dependent conversion of erythritol to erythritol-4-phosphate (Lillo et al., *Bioorg. Med. Chem. Lett.* 13:737-739 (2003)). The following genes can be used for Step K conversion:

| Protein | GenBank ID | GI Number | Organism |
|---|---|---|---|
| eryA | Q8YCU8 | 81850596 | *Brucella melitensis* |
| eriA | Q92NH0 | 81774560 | *Sinorhizobium meliloti* |
| eryA | YP_001108625.1 | 134102964 | *Saccharopolyspora erythraea* NRRL 2338 |

Malonyl-CoA:acetyl-CoA acyltransferase (FIG. 4, Step A)

In Step A of the pathway described in FIG. 4, malonyl-CoA and acetyl-CoA are condensed to form 3-oxoglutaryl-CoA by malonyl-CoA:acetyl-CoA acyl transferase, a beta-keothiolase. Although no enzyme with activity on malonyl-CoA has been reported to date, a good candidate for this transformation is beta-ketoadipyl-CoA thiolase (EC 2.3.1.174), also called 3-oxoadipyl-CoA thiolase that converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *J Bacteriol.* 176:6479-6488 (1994)) and *Acinetobacter calcoaceticus* (Doten et al., *J Bacteriol.* 169:3168-3174 (1987)). The gene products encoded by pcaF in *Pseudomonas* strain B13 (Kaschabek et al., *J Bacteriol.* 184:207-215 (2002)), phaD in *Pseudomonas putida* U (Olivera et al., supra, (1998)), paaE in *Pseudomonas fluorescens* ST (Di Gennaro et al., *Arch Microbiol.* 88:117-125 (2007)), and paaJ from *E. coli* (Nogales et al., *Microbiology*, 153:357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*. These enzymes can also be employed for the synthesis of 3-oxoglutaryl-CoA, a compound structurally similar to 3-oxoadipyl-CoA.

| Protein | GenBank ID | GI Number | Organism |
|---|---|---|---|
| paaJ | NP_415915.1 | 16129358 | *Escherichia coli* |
| pcaF | AAL02407 | 17736947 | *Pseudomonas knackmussii* (B13) |
| phaD | AAC24332.1 | 3253200 | *Pseudomonas putida* |
| pcaF | AAA85138.1 | 506695 | *Pseudomonas putida* |
| pcaF | AAC37148.1 | 141777 | *Acinetobacter calcoaceticus* |
| paaE | ABF82237.1 | 106636097 | *Pseudomonas fluorescens* |
| bkt | YP_777652.1 | 115360515 | *Burkholderia ambifaria* AMMD |
| bkt | AAG06977.1 | 9949744 | *Pseudomonas aeruginosa* PAO1 |
| pcaF | AAG03617.1 | 9946065 | *Pseudomonas aeruginosa* PAO1 |

Another relevant beta-ketothiolase is oxopimeloyl-CoA: glutaryl-CoA acyltransferase (EC 2.3.1.16) that combines glutaryl-CoA and acetyl-CoA to form 3-oxopimeloyl-CoA. An enzyme catalyzing this transformation is found in *Ralstonia eutropha* (formerly known as *Alcaligenes eutrophus*), encoded by genes bktB and bktC (Slater et al., *J. Bacteriol.* 180:1979-1987 (1998); Haywood et al., *FEMS Microbiology Letters* 52:91-96 (1988)). The sequence of the BktB protein is known; however, the sequence of the BktC protein has not been reported. The pim operon of *Rhodopseudomonas palustris* also encodes a beta-ketothiolase, encoded by pimB, predicted to catalyze this transformation in the degradative direction during benzoyl-CoA degradation (Harrison et al., *Microbiology* 151:727-736 (2005)). A beta-ketothiolase enzyme candidate in *S. aciditrophicus* was identified by sequence homology to bktB (43% identity, evalue=1e-93).

| Protein | GenBank ID | GI Number | Organism |
| --- | --- | --- | --- |
| bktB | YP_725948 | 11386745 | Ralstonia eutropha |
| pimB | CAE29156 | 39650633 | Rhodopseudomonas palustris |
| syn_02642 | YP_462685.1 | 85860483 | Syntrophus aciditrophicus |

Beta-ketothiolase enzymes catalyzing the formation of beta-ketovaleryl-CoA from acetyl-CoA and propionyl-CoA can also be able to catalyze the formation of 3-oxoglutaryl-CoA. Zoogloea ramigera possesses two ketothiolases that can form β-ketovaleryl-CoA from propionyl-CoA and acetyl-CoA and R. eutropha has a β-oxidation ketothiolase that is also capable of catalyzing this transformation (Slater et al., J. Bacteriol, 180:1979-1987 (1998)). The sequences of these genes or their translated proteins have not been reported, but several candidates in R. eutropha, Z. ramigera, or other organisms can be identified based on sequence homology to bktB from R. eutropha. These include:

| Protein | GenBank ID | GI Number | Organism |
| --- | --- | --- | --- |
| phaA | YP_725941.1 | 113867452 | Ralstonia eutropha |
| h16_A1713 | YP_726205.1 | 113867716 | Ralstonia eutropha |
| pcaF | YP_728366.1 | 116694155 | Ralstonia eutropha |
| h16_B1369 | YP_840888.1 | 116695312 | Ralstonia eutropha |
| h16_A0170 | YP_724690.1 | 113866201 | Ralstonia eutropha |
| h16_A0462 | YP_724980.1 | 113866491 | Ralstonia eutropha |
| h16_A1528 | YP_726028.1 | 113867539 | Ralstonia eutropha |
| h16_B0381 | YP_728545.1 | 116694334 | Ralstonia eutropha |
| h16_B0662 | YP_728824.1 | 116694613 | Ralstonia eutropha |
| h16_B0759 | YP_728921.1 | 116694710 | Ralstonia eutropha |
| h16_B0668 | YP_728830.1 | 116694619 | Ralstonia eutropha |
| h16_A1720 | YP_726212.1 | 113867723 | Ralstonia eutropha |
| h16_A1887 | YP_726356.1 | 113867867 | Ralstonia eutropha |
| phbA | P07097.4 | 135759 | Zoogloea ramigera |
| bktB | YP_002005382.1 | 194289475 | Cupriavidus taiwanensis |
| Rmet_1362 | YP_583514.1 | 94310304 | Ralstonia metallidurans |
| Bphy_0975 | YP_001857210.1 | 186475740 | Burkholderia phymatum |

Additional candidates include beta-ketothiolases that are known to convert two molecules of acetyl-CoA into acetoacetyl-CoA (EC 2.1.3.9). Exemplary acetoacetyl-CoA thiolase enzymes include the gene products of atoB from E. coli (Martin et al., supra, (2003)), thlA and thlB from C. acetobutylicum (Hanai et al., supra, (2007); Winzer et al., supra, (2000)), and ERG10 from S. cerevisiae (Hiser et al., supra, (1994)).

| Protein | GenBank ID | GI Number | Organism |
| --- | --- | --- | --- |
| toB | NP_416728 | 16130161 | Escherichia coli |
| thlA | NP_349476.1 | 15896127 | Clostridium acetobutylicum |
| thlB | NP_149242.1 | 15004782 | Clostridium acetobutylicum |
| ERG10 | NP_015297 | 6325229 | Saccharomyces cerevisiae |

3-oxoglutaryl-CoA reductase (ketone-reducing) (FIG. 4, Step B)

This enzyme catalyzes the reduction of the 3-oxo group in 3-oxoglutaryl-CoA to the 3-hydroxy group in Step B of the pathway shown in FIG. 4.

3-Oxoacyl-CoA dehydrogenase enzymes convert 3-oxoacyl-CoA molecules into 3-hydroxyacyl-CoA molecules and are often involved in fatty acid beta-oxidation or phenylacetate catabolism. For example, subunits of two fatty acid oxidation complexes in E. coli, encoded by fadB and fadJ, function as 3-hydroxyacyl-CoA dehydrogenases (Binstock et al., Methods Enzymol. 71 Pt C:403-411 (1981)). Furthermore, the gene products encoded by phaC in Pseudomonas putida U (Olivera et al., supra, (1998)) and paaC in Pseudomonas fluorescens ST (Di et al., supra, (2007)) catalyze the reversible oxidation of 3-hydroxyadipyl-CoA to form 3-oxoadipyl-CoA, during the catabolism of phenylacetate or styrene. In addition, given the proximity in E. coli of paaH to other genes in the phenylacetate degradation operon (Nogales et al., supra, (2007)) and the fact that paaH mutants cannot grow on phenylacetate (Ismail et al., supra, (2003)), it is expected that the E. coli paaH gene encodes a 3-hydroxyacyl-CoA dehydrogenase.

| Protein | GenBank ID | GI Number | Organism |
| --- | --- | --- | --- |
| fadB | P21177.2 | 119811 | Escherichia coli |
| fadJ | P77399.1 | 3334437 | Escherichia coli |
| paaH | NP_415913.1 | 16129356 | Escherichia coli |
| phaC | NP_745425.1 | 26990000 | Pseudomonas putida |
| paaC | ABF82235.1 | 106636095 | Pseudomonas fluorescens |

3-Hydroxybutyryl-CoA dehydrogenase, also called acetoacetyl-CoA reductase, catalyzes the reversible NAD(P)H-dependent conversion of acetoacetyl-CoA to 3-hydroxybutyryl-CoA. This enzyme participates in the acetyl-CoA fermentation pathway to butyrate in several species of Clostridia and has been studied in detail (Jones and Woods, supra, (1986)). Enzyme candidates include hbd from C. acetobutylicum (Boynton et al., J. Bacteriol. 178:3015-3024 (1996)), hbd from C. beijerinckii (Colby et al., Appl Environ. Microbiol 58:3297-3302 (1992)), and a number of similar enzymes from Metallosphaera sedula (Berg et al., supra, (2007)). The enzyme from Clostridium acetobutylicum, encoded by hbd, has been cloned and functionally expressed in E. coli (Youngleson et al., supra, (1989)). Yet other genes demonstrated to reduce acetoacetyl-CoA to 3-hydroxybutyryl-CoA are phbB from Zoogloea ramigera (Ploux et al., supra, (1988)) and phaB from Rhodobacter sphaeroides (Alber et al., supra, (2006)). The former gene is NADPH-dependent, its nucleotide sequence has been determined (Peoples and Sinskey, supra, (1989)) and the gene has been expressed in E. coli. Additional genes include hbd1 (C-terminal domain) and hbd2 (N-terminal domain) in Clostridium kluyveri (Hillmer and Gottschalk, Biochim. Biophys. Acta 3334:12-23 (1974)) and HSD17B10 in Bos taurus (WAKIL et al., supra, (1954)).

| Protein | GenBank ID | GI Number | Organism |
| --- | --- | --- | --- |
| hbd | NP_349314.1 | 15895965 | Clostridium acetobutylicum |
| hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| hbd2 | EDK34807.1 | 146348271 | Clostridium kluyveri |
| hbd1 | EDK32512.1 | 146345976 | Clostridium kluyveri |
| HSD17B10 | O02691.3 | 3183024 | Bos taurus |
| phaB | YP_353825.1 | 77464321 | Rhodobacter sphaeroides |
| phbB | P23238.1 | 130017 | Zoogloea ramigera |

3-hydroxy glutaryl-CoA reductase (aldehyde forming) (FIG. 4, Step C)

3-hydroxyglutaryl-CoA reductase reduces 3-hydroxyglutaryl-CoA to 3-hydroxy-5-oxopentanoate. Several acyl-CoA dehydrogenases reduce an acyl-CoA to its corresponding aldehyde (EC 1.2.1). Exemplary genes that encode such enzymes include the Acinetobacter calcoaceticus acr 1 encoding a fatty acyl-CoA reductase (Reiser and Somerville, supra, (1997)), the *Acinetobacter* sp. M-1 fatty acyl-CoA reductase (Ishige et al., supra, (2002)), and a CoA- and NADP-dependent succinate semialdehyde dehydrogenase encoded by the sucD gene in *Clostridium kluyveri* (Sohling and Gottschalk, supra, (1996); Sohling and Gottschalk, supra, (1996)). SucD of *P. gingivalis* is another succinate semialdehyde dehydrogenase (Takahashi et al., supra, (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al., supra, (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol Biochem.* 71:58-68 (2007)).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |

| Protein | GenBank ID | GI Number | Organism |
|---|---|---|---|
| bld | AAP42563.1 | 31075383 | *Clostridium saccharoperbutylacetonicum* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., supra, (2007b); Thauer, supra, (2007)). The enzyme utilizes NADPH as a cofactor and has been characterized in *Metallosphaera* and *Sulfolobus* spp (Alber et al., supra, (2006); Hugler et al., supra, (2002)). The enzyme is encoded by Msed_0709 in *Metallosphaera sedula* (Alber et al., supra, (2006); Berg et al., supra, (2007b)). A gene encoding a malonyl-CoA reductase from *Sulfolobus tokodaii* was cloned and heterologously expressed in *E. coli* (Alber et al., supra, (2006)). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another acyl-CoA reductase (aldehyde forming) candidate is the ald gene from *Clostridium beijerinckii* (Toth et al., *Appl Environ. Microbiol* 65:4973-4980 (1999)). This enzyme has been reported to reduce acetyl-CoA and butyryl-CoA to their corresponding aldehydes. This gene is very similar to cutE that encodes acetaldehyde dehydrogenase of *Salmonella typhimurium* and *E. coli* (Toth et al., supra, (1999)).

| Protein | GenBank ID | GI Number | Organism |
|---|---|---|---|
| MSED_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 9473535 | *Clostridium beijerinckii* |
| eutE | AAA80209 | 687645 | *Salmonella typhimurium* |
| eutE | P77445 | 2498347 | *Escherichia coli* |

3-hydroxy-5-oxopentanoate reductase (FIG. 4, Step D)

This enzyme reduces the terminal aldehyde group in 3-hydroxy-5-oxopentanote to the alcohol group. Exemplary genes encoding enzymes that catalyze the conversion of an aldehyde to alcohol (i.e., alcohol dehydrogenase or equivalently aldehyde reductase, 1.1.1.a) include alrA encoding a medium-chain alcohol dehydrogenase for C2-C14 (Tani et al., supra, (2000)), ADH2 from *Saccharomyces cerevisiae* (Atsumi et al., supra, (2008)), yqhD from *E. coli* which has preference for molecules longer than C(3) (Sulzenbacher et al., supra, (2004)), and bdh I and bdh II from *C. acetobutylicum* which converts butyryaldehyde into butanol (Walter et al., supra, (1992)). The gene product of yqhD catalyzes the reduction of acetaldehyde, malondialdehyde, propionaldehyde, butyraldehyde, and acrolein using NADPH as the cofactor (Perez et al., 283:7346-7353 (2008); Perez et al., *J Biol. Chem.* 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)).

| Protein | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Enzymes exhibiting 4-hydroxybutyrate dehydrogenase activity (EC 1.1.1.61) also fall into this category. Such enzymes have been characterized in *Ralstonia eutropha* (Bravo et al., supra, (2004)), *Clostridium kluyveri* (Wolff and Kenealy, supra, (1995)) and *Arabidopsis thaliana* (Breitkreuz et al., supra, (2003)). The *A. thaliana* enzyme was cloned and characterized in yeast [12882961]. Yet another gene is the alcohol dehydrogenase adhI from *Geobacillus thermoglucosidasius* (Jeon et al., *J Biotechnol* 135:127-133 (2008)).

| Protein | GenBank ID | GI Number | Organism |
|---|---|---|---|
| 4hbd | YP_726053.1 | 113867564 | *Ralstonia eutropha* H16 |
| 4hbd | EDK35022.1 | 146348486 | *Clostridium kluyveri* |

| Protein | GenBank ID | GI Number | Organism |
|---|---|---|---|
| 4hbd | Q94B07 | 75249805 | Arabidopsis thaliana |
| adhI | AAR91477.1 | 40795502 | Geobacillus thermoglucosidasius |

Another exemplary enzyme is 3-hydroxyisobutyrate dehydrogenase (EC 1.1.1.31) which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J Mol Biol* 352:905-17 (2005)). The reversibility of the human 3-hydroxyisobutyrate dehydrogenase was demonstrated using isotopically-labeled substrate (Manning et al., *Biochem J* 231:481-4 (1985)). Additional genes encoding this enzyme include 3hidh in *Homo sapiens* (Hawes et al., *Methods Enzymol* 324:218-228 (2000)) and *Oryctolagus cuniculus* (Hawes et al., supra, (2000); Chowdhury et al., *Biosci. Biotechnol Biochem.* 60:2043-2047 (1996)), mmsb in *Pseudomonas aeruginosa*, and dhat in *Pseudomonas putida* (Aberhart et al., *J Chem. Soc. [Perkin 1]* 6:1404-1406 (1979); Chowdhury et al., supra, (1996); Chowdhury et al., *Biosci. Biotechnol Biochem.* 67:438-441 (2003)).

| Protein | GenBank ID | GI Number | Organism |
|---|---|---|---|
| P84067 | P84067 | 75345323 | Thermus thermophilus |
| mmsb | P28811.1 | 127211 | Pseudomonas aeruginosa |
| dhat | Q59477.1 | 2842618 | Pseudomonas putida |
| 3hidh | P31937.2 | 12643395 | Homo sapiens |
| 3hidh | P32185.1 | 416872 | Oryctolagus cuniculus |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi B., *Journal of Plant Pathology* 159:671-674 (2002); Stadtman, *J. Am. Chem. Soc.* 77:5765-5766 (1955)). This enzyme has not been associated with a gene in any organism to date. NADPH-dependent malonate semialdehyde reductase catalyzes the reverse reaction in autotrophic CO2-fixing bacteria. Although the enzyme activity has been detected in *Metallosphaera sedula*, the identity of the gene is not known (Alber et al., supra, (2006)).

3,5-dihydroxypentanoate kinase (FIG. 4, Step E)

This enzyme phosphorylates 3,5-dihydroxypentanotae in FIG. 4 (Step E) to form 3-hydroxy-5-phosphonatooxypentanoate (3H5PP). This transformation can be catalyzed by enzymes in the EC class 2.7.1 that enable the ATP-dependent transfer of a phosphate group to an alcohol.

A good candidate for this step is mevalonate kinase (EC 2.7.1.36) that phosphorylates the terminal hydroxyl group of the methyl analog, mevalonate, of 3,5-dihydroxypentanote. Some gene candidates for this step are erg12 from *S. cerevisiae*, mvk from *Methanocaldococcus jannaschi*, MVK from *Homo sapeins*, and mvk from *Arabidopsis thaliana* col.

| Protein | GenBank ID | GI Number | Organism |
|---|---|---|---|
| erg12 | CAA39359.1 | 3684 | Sachharomyces cerevisiae |
| mvk | Q58487.1 | 2497517 | Methanocaldococcus jannaschii |
| mvk | AAH16140.1 | 16359371 | Homo sapiens |
| M\mvk | NP_851084.1 | 30690651 | Arabidopsis thaliana |

Glycerol kinase also phosphorylates the terminal hydroxyl group in glycerol to form glycerol-3-phosphate. This reaction occurs in several species, including *Escherichia coli*, *Saccharomyces cerevisiae*, and *Thermotoga maritima*. The *E. coli* glycerol kinase has been shown to accept alternate substrates such as dihydroxyacetone and glyceraldehyde (Hayashi and Lin, supra, (1967)). T, maritime has two glycerol kinases (Nelson et al., supra, (1999)). Glycerol kinases have been shown to have a wide range of substrate specificity. Crans and Whiteside studied glycerol kinases from four different organisms (*Escherichia coli, S. cerevisiae, Bacillus stearothermophilus*, and *Candida mycoderma*) (Crans and Whitesides, supra, (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar. The gene candidates are:

| Protein | GenBank ID | GI Number | Organism |
|---|---|---|---|
| glpK | AP_003883.1 | 89110103 | Escherichia coli K12 |
| glpK1 | NP_228760.1 | 15642775 | Thermotoga maritime MSB8 |
| glpK2 | NP_229230.1 | 15642775 | Thermotoga maritime MSB8 |
| Gut1 | NP_011831.1 | 82795252 | Saccharomyces cerevisiae |

Homoserine kinase is another possible candidate that can lead to the phosphorylation of 3,5-dihydroxypentanoate. This enzyme is also present in a number of organisms including *E. coli*, *Streptomyces* sp, and *S. cerevisiae*. Homoserine kinase from *E. coli* has been shown to have activity on numerous substrates, including, L-2-amino,1,4-butanediol, aspartate semialdehyde, and 2-amino-5-hydroxyvalerate (Huo and Viola, supra, (1996); Huo and Viola, supra, (1996)). This enzyme can act on substrates where the carboxyl group at the alpha position has been replaced by an ester or by a hydroxymethyl group. The gene candidates are:

| Protein | GenBank ID | GI Number | Organism |
|---|---|---|---|
| thrB | BAB96580.2 | 85674277 | Escherichia coli K12 |
| SACT1DRAFT_4809 | ZP_06280784.1 | 282871792 | Streptomyces sp. ACT-1 |
| Thr1 | AAA35154.1 | 172978 | Saccharomyces serevisiae |

3H5PP kinase (FIG. 4, Step F)

Phosphorylation of 3H5PP to 3H5PDP is catalyzed by 3H5PP kinase (FIG. 4, Step F). Phosphomevalonate kinase (EC 2.7.4.2) catalyzes the analogous transformation in the mevalonate pathway. This enzyme is encoded by erg8 in *Saccharomyces cerevisiae* (Tsay et al., *Mol. Cell Biol.* 11:620-631 (1991)) and mvaK2 in *Streptococcus pneumoniae, Staphylococcus aureus* and *Enterococcus faecalis* (Doun et al., *Protein Sci.* 14:1134-1139 (2005); Wilding et al., *J. Bacteriol.* 182:4319-4327 (2000)). The *Streptococcus pneumoniae* and *Enterococcus faecalis* enzymes were cloned and characterized in *E. coli* (Pilloff et al., *J Biol. Chem.* 278:4510-4515 (2003); Doun et al., *Protein Sci.* 14:1134-1139 (2005)).

| Protein | GenBank ID | GI Number | Organism |
|---|---|---|---|
| Erg8 | AAA34596.1 | 171479 | *Saccharomyces cerevisiae* |
| mvaK2 | AAG02426.1 | 9937366 | *Staphylococcus aureus* |
| mvaK2 | AAG02457.1 | 9937409 | *Streptococcus pneumoniae* |
| mvaK2 | AAG02442.1 | 9937388 | *Enterococcus faecalis* |

3H5PDP decarboxylase (FIG. 4, Step G)

Butenyl 4-diphosphate is formed from the ATP-dependent decarboxylation of 3H5PDP by 3H5PDP decarboxylase (FIG. 4, Step G). Although an enzyme with this activity has not been characterized to date a similar reaction is catalyzed by mevalonate diphosphate decarboxylase (EC 4.1.1.33), an enzyme participating in the mevalonate pathway for isoprenoid biosynthesis. This reaction is catalyzed by MVD1 in *Saccharomyces cerevisiae*, MVD in *Homo sapiens* and MDD in *Staphylococcus aureus* and *Trypsonoma brucei* (Toth et al., *J Biol. Chem.* 271:7895-7898 (1996); Byres et al., *J Mol. Biol.* 371:540-553 (2007)).

| Protein | GenBank ID | GI Number | Organism |
|---|---|---|---|
| MVD1 | P32377.2 | 1706682 | *Saccharomyces cerevisiae* |
| MVD | NP_002452.1 | 4505289 | *Homo sapiens* |
| MDD | ABQ48418.1 | 147740120 | *Staphylococcus aureus* |
| MDD | EAN78728.1 | 70833224 | *Trypsonoma brucei* |

Butenyl 4-diphosphate isomerase (FIG. 4, Step H)

Butenyl 4-diphosphate isomerase catalyzes the reversible interconversion of 2-butenyl-4-diphosphate and butenyl-4-diphosphate. The following enzymes can naturally possess this activity or can be engineered to exhibit this activity. Useful genes include those that encode enzymes that interconvert isopenenyl diphosphate and dimethylallyl diphosphate. These include isopentenyl diphosphate isomerase enzymes from *Escherichia coli* (Rodríguez-Concepción et al., *FEBS Lett*, 473(3):328-332), *Saccharomyces cerevisiae* (Anderson et al., *J Biol Chem*, 1989, 264(32); 19169-75), and *Sulfolobus shibatae* (Yamashita et al., *Eur J Biochem*, 2004, 271(6); 1087-93). The reaction mechanism of isomerization, catalyzed by the Idi protein of *E. coli*, has been characterized in mechanistic detail (de Ruyck et al., *J Biol. Chem.* 281:17864-17869 (2006)). Isopentenyl diphosphate isomerase enzymes from *Saccharomyces cerevisiae, Bacillus subtilis* and *Haematococcus pluvialis* have been heterologously expressed in *E. coli* (Laupitz et al., *Eur. J Biochem.* 271:2658-2669 (2004); Kajiwara et al., *Biochem. J* 324 (Pt 2):421-426 (1997)).

| Protein | GenBank ID | GI Number | Organism |
|---|---|---|---|
| Idi | NP_417365.1 | 16130791 | *Escherichia coli* |
| IDI1 | NP_015208.1 | 6325140 | *Saccharomyces cerevisiae* |
| Idi | BAC82424.1 | 34327946 | *Sulfolobus shibatae* |
| Idi | AAC32209.1 | 3421423 | *Haematococcus pluvialis* |
| Idi | BAB32625.1 | 12862826 | *Bacillus subtilis* |

Butadiene synthase (FIG. 4, Step I)

Butadiene synthase catalyzes the conversion of 2-butenyl-4-diphosphate to 1,3-butadiene. The enzymes described below naturally possess such activity or can be engineered to exhibit this activity. Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., *Metabolic Eng,* 12(1):70-79 (2010); Sharkey et al., *Plant Physiol.,* 137(2):700-712 (2005)), and *Populus tremula×Populus alba* (Miller et al., Planta, 213(3):483-487 (2001)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | *Populus alba* |
| ispS | AAQ84170.1 | 35187004 | *Pueraria montana* |
| ispS | CAC35696.1 | 13539551 | *Populus tremula × Populus alba* |

3-Hydroxy glutaryl-CoA reductase (alcohol forming) (FIG. 4, Step J)

This step catalyzes the reduction of the acyl-CoA group in 3-hydroxyglutaryl-CoA to the alcohol group. Exemplary bifunctional oxidoreductases that convert an acyl-CoA to alcohol include those that transform substrates such as acetyl-CoA to ethanol (e.g., adhE from *E. coli* (Kessler et al., supra, (1991)) and butyryl-CoA to butanol (e.g. adhE2 from *C. acetobutylicum* (Fontaine et al., supra, (2002)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., supra, (1972); Koo et al., supra, (2005)).

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., supra, (2002); Strauss and Fuchs, supra, (1993)). This enzyme, with a mass of 300 kDa, is highly substrate-specific and shows little sequence similarity to other known oxidoreductases (Hugler et al., supra, (2002)). No enzymes in other organisms have been shown to catalyze this specific reaction; however there is bioinformatic evidence that other organisms can have similar pathways (Klatt et al., supra, (2007)). Enzyme candidates in other organisms including *Roseiflexus castenholzii, Erythrobacter* sp. NAP1 and marine gamma proteobacterium HTCC2080 can be inferred by sequence similarity.

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced to their corresponding alcohols by enzymes such as the jojoba (*Sim-* mondsia chinensis) FAR which encodes an alcohol-forming fatty acyl-CoA reductase. Its overexpression in *E. coli* resulted in FAR activity and the accumulation of fatty alcohol (Metz et al., *Plant Physiology* 122:635-644 (2000)).

| Protein | GenBank ID | GI Number | Organism |
|---------|------------|-----------|----------|
| FAR | AAD38039.1 | 5020215 | *Simmondsia chinensis* |

Another candidate for catalyzing this step is 3-hydroxy-3-methylglutaryl-CoA reductase (or HMG-CoA reductase). This enzyme reduces the CoA group in 3-hydroxy-3-methylglutaryl-CoA to an alcohol forming mevalonate. Gene candidates for this step include:

| Protein | GenBank ID | GI Number | Organism |
|---------|------------|-----------|----------|
| HMG1 | CAA86503.1 | 587536 | *Saccharomyces cerevisiae* |
| HMG2 | NP_013555 | 6323483 | *Saccharomyces cerevisiae* |
| HMG1 | CAA70691.1 | 1694976 | *Arabidopsis thaliana* |
| hmgA | AAC45370.1 | 2130564 | *Sulfolobus solfataricus* |

The hmgA gene of *Sulfolobus solfataricus*, encoding 3-hydroxy-3-methylglutaryl-CoA reductase, has been cloned, sequenced, and expressed in *E. coli* (Bochar et al., *J Bacteriol.* 179:3632-3638 (1997)). *S. cerevisiae* also has two HMG-CoA reductases in it (Basson et al., *Proc. Natl. Acad. Sci. U.S.A* 83:5563-5567 (1986)). The gene has also been isolated from *Arabidopsis thaliana* and has been shown to complement the HMG-COA reductase activity in *S. cerevisiae* (Learned et al., *Proc. Natl. Acad. Sci. U.S.A* 86:2779-2783 (1989)).

3-oxoglutaryl-CoA reductase (aldehyde forming) (FIG. 4, Step K)

Several acyl-CoA dehydrogenases are capable of reducing an acyl-CoA to its corresponding aldehyde. Thus they can naturally reduce 3-oxoglutaryl-CoA to 3,5-dioxopentanoate or can be engineered to do so. Exemplary genes that encode such enzymes were discussed in FIG. 4, Step C.

3,5-dioxopentanoate reductase (ketone reducing) (FIG. 4, Step L)

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130: 329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional candidate for this step is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismaiel et al., *J. Bacteriol.* 175:5097-5105 (1993)) and *T. brockii* (Lamed et al., *Biochem. J* 195:183-190 (1981); Peretz et al., *Biochemistry.* 28:6549-6555 (1989)). Methyl ethyl ketone reductase, or alternatively, 2-butanol dehydrogenase, catalyzes the reduction of MEK to form 2-butanol. Exemplary enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)).

| Protein | GenBank ID | GI Number | Organism |
|---------|------------|-----------|----------|
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |

| Protein | GenBank ID | GI Number | Organism |
|---------|------------|-----------|----------|
| adh | AAA23199.2 | 60592974 | *Clostridium beijerinckii* NRRL B593 |
| adh | P14941.1 | 113443 | *Thermoanaerobacter brockii* HTD4 |
| adhA | AAC25556 | 3288810 | *Pyrococcus furiosus* |
| adh-A | CAD36475 | 21615553 | *Rhodococcus ruber* |

A number of organisms can catalyze the reduction of 4-hydroxy-2-butanone to 1,3-butanediol, including those belonging to the genus *Bacillus, Brevibacterium, Candida*, and *Klebsiella* among others, as described by Matsuyama et al. U.S. Pat. No. 5,413,922. A mutated *Rhodococcus* phenylacetaldehyde reductase (Sar268) and a *Leifonia* alcohol dehydrogenase have also been shown to catalyze this transformation at high yields (Itoh et al., *Appl. Microbiol. Biotechnol.* 75(6):1249-1256).

Homoserine dehydrogenase (EC 1.1.1.13) catalyzes the NAD(P)H-dependent reduction of aspartate semialdehyde to homoserine. In many organisms, including *E. coli*, homoserine dehydrogenase is a bifunctional enzyme that also catalyzes the ATP-dependent conversion of aspartate to aspartyl-4-phosphate (Starnes et al., *Biochemistry* 11:677-687 (1972)). The functional domains are catalytically independent and connected by a linker region (Sibilli et al., *J Biol Chem* 256:10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., *Biochemistry* 41:3720-3725 (2002)). This can be applied to other bifunctional threonine kinases including, for example, hom1 of *Lactobacillus plantarum* (Cahyanto et al., *Microbiology* 152: 105-112 (2006)) and *Arabidopsis thaliana*. The monofunctional homoserine dehydrogenases encoded by hom6 in *S. cerevisiae* (Jacques et al., *Biochim Biophys Acta* 1544:28-41 (2001)) and hom2 in *Lactobacillus plantarum* (Cahyanto et al., supra, (2006)) have been functionally expressed and characterized in *E. coli*.

| Protein | GenBank ID | GI number | Organism |
|---------|------------|-----------|----------|
| thrA | AAC73113.1 | 1786183 | *Escherichia coli* K12 |
| akthr2 | O81852 | 75100442 | *Arabidopsis thaliana* |
| hom6 | CAA89671 | 1015880 | *Saccharomyces cerevisiae* |

| Protein | GenBank ID | GI number | Organism |
|---------|------------|-----------|----------|
| hom1 | CAD64819 | 28271914 | *Lactobacillus plantarum* |
| hom2 | CAD63186 | 28270285 | *Lactobacillus plantarum* |

3,5-dioxopentanoate reductase (aldehyde reducing) (FIG. 4, Step M)

Several aldehyde reducing reductases are capable of reducing an aldehyde to its corresponding alcohol. Thus they can naturally reduce 3,5-dioxopentanoate to 5-hydroxy-3-oxopentanoate or can be engineered to do so. Exemplary genes that encode such enzymes were discussed in FIG. 4, Step D.

5-hydroxy-3-oxopentanoate reductase (FIG. 4, Step N)

Several ketone reducing reductases are capable of reducing a ketone to its corresponding hydroxyl group. Thus they can naturally reduce 5-hydroxy-3-oxopentanoate to 3,5-dihydroxypentanoate or can be engineered to do so. Exemplary genes that encode such enzymes were discussed in FIG. 4, Step L.

3-oxo-glutaryl-CoA reductase (CoA reducing and alcohol forming) (FIG. 4, Step O)

3-oxo-glutaryl-CoA reductase (CoA reducing and alcohol forming) enzymes catalyze the 2 reduction steps required to form 5-hydroxy-3-oxopentanoate from 3-oxo-glutaryl-CoA. Exemplary 2-step oxidoreductases that convert an acyl-CoA to an alcohol were provided for FIG. 4, Step J. Such enzymes can naturally convert 3-oxo-glutaryl-CoA to 5-hydroxy-3-oxopentanoate or can be engineered to do so.

EXAMPLE II

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three $CO_2$-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each step of the reductive TCA cycle are shown below.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha(4)beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum, Sulfurihydrogenibium subterraneum* and other members of the bacterial phylum *Aquificae* (Hugler et al., *Environ. Microbiol.* 9:81-92 (2007)). This acitivy has been reported in some fungi as well. Exemplary organisms include *Sordaria macrospora* (Nowrousian et al., *Curr. Genet.* 37:189-93 (2000), *Aspergillus nidulans, Yarrowia lipolytica* (Hynes and Murray, *Eukaryotic Cell*, July: 1039-1048, (2010) and *Aspergillus niger* (Meijer et al. *J. Ind. Microbiol. Biotechnol.* 36:1275-1280 (2009). Other candidates can be found based on sequence homology. Information related to hese enzymes is tabulated below:

| Protein | GenBank ID | GI Number | Organism |
|---|---|---|---|
| aclA | BAB21376.1 | 12407237 | *Chlorobium limicola* |
| aclB | BAB21375.1 | 12407235 | *Chlorobium limicola* |
| aclA | AAM72321.1 | 21647054 | *Chlorobium tepidum* |
| aclB | AAM72322.1 | 21647055 | *Chlorobium tepidum* |
| aclA | ABI50076.1 | 114054981 | *Balnearium lithotrophicum* |
| aclB | ABI50075.1 | 114054980 | *Balnearium lithotrophicum* |
| aclA | ABI50085.1 | 114055040 | *Sulfurihydrogenibium subterraneum* |
| aclB | ABI50084.1 | 114055039 | *Sulfurihydrogenibium subterraneum* |
| aclA | AAX76834.1 | 62199504 | *Sulfurimonas denitrificans* |
| aclB | AAX76835.1 | 62199506 | *Sulfurimonas denitrificans* |
| acl1 | XP_504787.1 | 50554757 | *Yarrowia lipolytica* |

| Protein | GenBank ID | GI Number | Organism |
|---|---|---|---|
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| aclB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., *PNAS* 99(14): 9509-14 (2002).

| Protein | GenBank ID | GI Number | Organism |
|---|---|---|---|
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |

| Protein | GenBank ID | GI Number | Organism |
|---|---|---|---|
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278: 25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278: 45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology includefuml from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352: 175-181 (1998)), which localize to the cytosol and promitochondrion, respectively, and are used during anaerobic growth on glucose (Arikawa et al., *FEMS Microbiol. Lett.* 165:111-116 (1998)).

| Protein | GenBank ID | GI Number | Organism |
|---|---|---|---|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., *Biochemistry* 24:6245-6252 (1985)). These proteins are identified below:

| Protein | GenBank ID | GI Number | Organism |
|---|---|---|---|
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from CO2 and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., *Archaea. Adv. Protein Chem.* 48:101-180 (1996)). Enzymes in this class are reversible and function in the carboxylation direction in organisms that fix carbon by the RTCA cycle such as *Hydrogenobacter thermophilus, Desulfobacter hydrogenophilus* and *Chlorobium* species (Shiba et al. 1985; Evans et al., *Proc. Natl. Acad. ScI. U.S.A.* 55:92934 (1966); Buchanan, 1971). The two-subunit enzyme from *H. thermophilus*, encoded by korAB, has been cloned and expressed in *E. coli* (Yun et al., *Biochem. Biophys. Res. Commun.* 282:589-594 (2001)). A five subunit OFOR from the same organism with strict substrate specificity for succinyl-CoA, encoded byforDABGE, was recently identified and expressed in *E. coli* (Yun et al. 2002). The kinetics of CO2 fixation of both *H. thermophilus* OFOR enzymes have been characterized (Yamamoto et al., *Extremophiles* 14:79-85 (2010)). A CO2-fixing OFOR from *Chlorobium thiosulfatophilum* has been purified and characterized but the genes encoding this enzyme have not been identified to date. Enzyme candidates in *Chlorobium* species can be inferred by sequence similarity to the *H. thermophilus* genes. For example, the *Chlorobium limicola* genome encodes two similar proteins. Acetogenic bacteria such as *Moorella thermoacetica* are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon Sulfolobus sp. strain 7, encoded by ST2300, has been extensively studied (Zhang et al. 1996. A plasmid-based expression system has been developed for efficiently expressing this protein in E. coli (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from Aeropyrum pernix str. K1 was recently cloned into E. coli, characterized, and found to react with 2-oxoglutarate and a broad range of 2-oxoacids (Nishizawa et al., FEBS Lett. 579:2319-2322 (2005)). Another exemplary OFOR is encoded by oorDABC in Helicobacter pylori (Hughes et al. 1998). An enzyme specific to alpha-ketoglutarate has been reported in Thauera aromatics (Dorner and Boll, J, Bacteriol. 184 (14), 3975-83 (2002). A similar enzyme can be found in Rhodospirillum rubrum by sequence homology. A two subunit enzyme has also been identified in Chlorobium tepidum (Eisen et al., PNAS 99(14): 9509-14 (2002)).

| Protein | GenBank ID | GI Number | Organism |
|---|---|---|---|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |
| Ape1473 | BAA80471.2 | 116062794 | Aeropyrum pernix |
| oorD | NP_207383.1 | 15645213 | Helicobacter pylori |
| oorA | NP_207384.1 | 15645214 | Helicobacter pylori |
| oorB | NP_207385.1 | 15645215 | Helicobacter pylori |
| oorC | NP_207386.1 | 15645216 | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatica |
| korB | CAD27440.1 | 19571178 | Thauera aromatica |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of NAD(P)$^+$. IDH enzymes in Saccharomyces cerevisiae and Escherichia coli are encoded by IDP1 and icd, respectively (Haselbeck and McAlister-Henn, J. Biol. Chem. 266:2339-2345 (1991); Nimmo, H. G., Biochem. J. 234:317-2332 (1986)). The reverse reaction in the reductive TCA cycle, the reductive carboxylation of 2-oxoglutarate to isocitrate, is favored by the NADPH-dependent $CO_2$-fixing IDH from Chlorobium limicola and was functionally expressed in E. coli (Kanao et al., Eur. J. Biochem. 269:1926-1931 (2002)). A similar enzyme with 95% sequence identity is found in the C. tepidum genome in additiaton to some other candidates listed below.

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |

| Protein | GenBank ID | GI Number | Organism |
|---|---|---|---|
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In H. thermophilus the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, Mol. Microbiol. 62:748-759 (2006)). This enzyme is a large complex composed of two subunits. Biotinylation of the large (A) subunit is required for enzyme function (Aoshima et al., Mol. Microbiol. 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in H. thermophilus. The kinetic parameters of this enzyme indicate that the enzyme only operates in the reductive carboxylation direction in vivo, in contrast to isocitrate dehydrogenase enzymes in other organisms (Aoshima and Igarashi, J. Bacteriol. 190:2050-2055 (2008)). Based on sequence homology, gene candidates have also been found in Thiobacillus denitrificans and Thermocrinis albus.

| Protein | GenBank ID | GI Number | Organism |
|---|---|---|---|
| cfiA | BAF34932.1 | 116234991 | Hydrogenobacter thermophilus |
| cifB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and isocitrate via the intermediate cis-aconitate. Two aconitase enzymes are encoded in the E. coli genome by acnA and acnB. AcnB is the main catabolic enzyme, while AcnA is more stable and appears to be active under conditions of oxidative or acid stress (Cunningham et al., Microbiology 143 (Pt 12):3795-3805 (1997)). Two isozymes of aconitase in Salmonella typhimurium are encoded by acnA and acnB (Horswill and Escalante-Semerena, Biochemistry 40:4703-4713 (2001)). The S. cerevisiae aconitase, encoded by ACO1, is localized to the mitochondria where it participates in the TCA cycle (Gangloff et al., Mol. Cell. Biol. 10:3551-3561 (1990)) and the cytosol where it participates in the glyoxylate shunt (Regev-Rudzki et al., Mol. Biol. Cell. 16:4163-4171 (2005)).

| Protein | GenBank ID | GI Number | Organism |
| --- | --- | --- | --- |
| acnA | AAC7438.1 | 1787531 | Escherichia coli |
| acnB | AAC73229.1 | 2367097 | Escherichia coli |
| HP0779 | NP_207572.1 | 15645398 | Helicobacter pylori 26695 |
| H16_B0568 | CAJ95365.1 | 113529018 | Ralstonia eutropha |
| DesfrDRAFT_3783 | ZP_07335307.1 | 303249064 | Desulfovibrio fructosovorans JJ |
| Suden_1040 (acnB) | ABB44318.1 | 78497778 | Sulfurimonas denitrificans |
| Hydth_0755 | ADO45152.1 | 308751669 | Hydrogenobacter thermophilus |
| CT0543 (acn) | AAM71785.1 | 21646475 | Chlorobium tepidum |
| Clim_2436 | YP_001944436.1 | 189347907 | Chlorobium limicola |
| Clim_0515 | ACD89607.1 | 189340204 | Chlorobium limicola |
| acnA | NP_460671.1 | 16765056 | Salmonella typhimurium |
| acnB | NP_459163.1 | 16763548 | Salmonella typhimurium |
| ACO1 | AAA34389.1 | 170982 | Saccharomyces cerevisiae |

Pyruvate:ferredoxin oxidoreductase (PFOR) catalyzes the reversible oxidation of pyruvate to form acetyl-CoA. The PFOR from *Desulfovibrio africanus* has been cloned and expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that prtotects it against inactivation in the form of oxygen. This disulfide bond and the stability in the presence of oxygen has been found in other *Desulfovibrio* species also (Vita et al., Biochemistry, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatas* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

| Protein | GenBank ID | GI Number | Organism |
| --- | --- | --- | --- |
| DesfrDRAFT_0121 | ZP_07331646.1 | 303245362 | Desulfovibrio fructosovorans JJ |
| Por | CAA70873.1 | 1770208 | Desulfovibrio africanus |
| por | YP_012236.1 | 46581428 | Desulfovibrio vulgaris str. Hildenborough |
| Dde_3237 | ABB40031.1 | 78220682 | DesulfoVibrio desulfuricans G20 |
| Ddes_0298 | YP_002478891.1 | 220903579 | Desulfovibrio desulfuricans subsp. desulfuricans str. ATCC 27774 |
| Por | YP_428946.1 | 83588937 | Moorella thermoacetica |
| YdbK | NP_415896.1 | 16129339 | Escherichia coli |
| nifJ (CT1628) | NP_662511.1 | 21674446 | Chlorobium tepidum |
| CJE1649 | YP_179630.1 | 57238499 | Campylobacter jejuni |
| nifJ | ADE85473.1 | 294476085 | Rhodobacter capsulatus |
| porE | BAA95603.1 | 7768912 | Hydrogenobacter thermophilus |
| porD | BAA95604.1 | 7768913 | Hydrogenobacter thermophilus |
| porA | BAA95605.1 | 7768914 | Hydrogenobacter thermophilus |
| porB | BAA95606.1 | 776891 | Hydrogenobacter thermophilus |
| porG | BAA95607.1 | 7768916 | Hydrogenobacter thermophilus |
| FqrB | YP_001482096.1 | 157414840 | Campylobacter jejuni |
| HP1164 | NP_207955.1 | 15645778 | Helicobacter pylori |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., J. Biol. Chem. 256:815-82 (1981); Bremer, J., Eur. J. Biochem. 8:535-540 (1969); Gong et al., J. Biol. Chem. 275:13645-13653 (2000)). Enzyme engineering efforts have improved the *E. coli* PDH enzyme activity under anaerobic conditions (Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the *E. coli* PDH, the *B. subtilis* complex is active and required for growth under anaerobic conditions (Nakano et al., J. Bacteriol. 179:6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter* vinelandii are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol 27:477-492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that pflA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., J Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., J. Bacteriol. 177: 2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several *Clostridia* and *Methanosarcina thermophile*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:$NADP^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:$NADP^+$ oxidoreductase enzyme is encoded in the *E. coli* genome by fpr (Bianchi et al. 1993). Ferredoxin:$NAD^+$ oxidoreductase utilizes reduced ferredoxin to generate NADH from $NAD^+$. In several organisms, including *E. coli*, this enzyme is a component of multifunctional dioxygenase enzyme complexes. The ferredoxin:$NAD^+$ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., J. Bacteriol. 190:784-791 (2008)) provide a means to generate NADH or NADPH from reduced ferredoxin. Additional ferredoxin:NAD(P)+ oxidoreductases have been annotated in *Clostridium carboxydivorans* P7.

| Protein | GenBank ID | GI Number | Organism |
| --- | --- | --- | --- |
| HP1164 | NP_207955.1 | 15645778 | *Helicobacter pylori* |
| RPA3954 | CAE29395.1 | 39650872 | *Rhodopseudomonas palustris* |
| fpr | BAH29712.1 | 225320633 | *Hydrogenobacter thermophilus* |
| yumC | NP_391091.2 | 255767736 | *Bacillus subtilis* |
| CJE0663 | AAW35824.1 | 57167045 | *Campylobacter jejuni* |
| fpr | P28861.4 | 399486 | *Escherichia coli* |

| Protein | GenBank ID | GI Number | Organism |
|---|---|---|---|
| hcaD | AAC75595.1 | 1788892 | Escherichia coli |
| LOC100282643 | NP_001149023.1 | 226497434 | Zea mays |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |

Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica*, *Clostridium carboxidivorans* P7 and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| fdx | CAA12251.1 | 3724172 | Thauera aromatica |
| CHY_2405 | YP_361202.1 | 78044690 | Carboxydothermus hydrogenoformans |
| fer | YP_359966.1 | 78045103 | Carboxydothermus hydrogenoformans |
| fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA: acetyl-CoA transferase activity (Sohling and Gottschalk, J. Bacteriol. 178:871-880 (1996)). In addition, the activity is present in *Trichomonas vaginalis* (van Grinsven et al. 2008) and *Trypanosoma brucei* (Riviere et al. 2004). The succinyl-CoA: acetate CoA-transferase from *Acetobacter aceti*, encoded by aarC, replaces succinyl-CoA synthetase in a variant TCA cycle (Mullins et al. 2008). Similar succinyl-CoA transferase activities are also present in *Trichomonas vaginalis* (van Grinsven et al. 2008), *Trypanosoma brucei* (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

| Protein | GenBank ID | GI Number | Organism |
| --- | --- | --- | --- |
| cat1 | P38946.1 | 729048 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| pcaI | AAN69545.1 | 24985644 | Pseudomonas putida |
| pcaJ | NP_746082.1 | 26990657 | Pseudomonas putida |
| aarC | ACD85596.1 | 189233555 | Acetobacter aceti |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanaka et al. 2002). The aforementioned proteins are identified below.

| Protein | GenBank ID | GI Number | Organism |
| --- | --- | --- | --- |
| HPAG1_0676 | YP_627417 | 108563101 | Helicobacter pylori |

| Protein | GenBank ID | GI Number | Organism |
| --- | --- | --- | --- |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Converting succinate to succinyl-CoA by succinyl-CoA:3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA: acetate: CoA transferase. Acetoacetyl-CoA: acetate: CoA transferase converts acetoacetyl-CoA and acetate to acetoacetate and acetyl-CoA, or vice versa. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., Biosci. Biotechnol Biochem. 71:58-68 (2007)) are shown below.

| Protein | GenBank ID | GI Number | Organism |
| --- | --- | --- | --- |
| AtoA | NP_416726.1 | 2492994 | Escherichia coli |
| AtoD | NP_416725.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatics* (Leutwein and Heider, J. Bact. 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
| --- | --- | --- | --- |
| bbsE | AAF89840 | 9622535 | Thauera aromatica |

| Protein | GenBank ID | GI Number | Organism |
| --- | --- | --- | --- |
| Bbsf | AAF89841 | 9622536 | Thauera aromatica |
| bbsE | AAU45405.1 | 52421824 | Azoarcus sp. T |
| bbsF | AAU45406.1 | 52421825 | Azoarcus sp. T |
| bbsE | YP_158075.1 | 56476486 | Aromatoleum aromaticum EbN1 |
| bbsF | YP_158074.1 | 56476485 | Aromatoleum aromaticum EbN1 |
| Gmet_1521 | YP_384480.1 | 78222733 | Geobacter metallireducens GS-15 |
| Gmet_1522 | YP_384481.1 | 78222734 | Geobacter metallireducens GS-15 |

Additionally, ygfH encodes a propionyl CoA:succinate CoA transferase in *E. coli* (Haller et al., Biochemistry, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

| Protein | GenBank ID | GI Number | Organism |
| --- | --- | --- | --- |
| ygfH | NP_417395.1 | 16130821 | Escherichia coli str. K-12 substr. MG1655 |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |

| Protein | GenBank ID | GI Number | Organism |
| --- | --- | --- | --- |
| yinte0001_14430 | ZP_04635364.1 | 238791727 | Yersinia intermedia ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88 (1997); Bott and Dimroth, *Mol. Microbiol.* 14:347-356 (1994)). The aforementioned proteins are tabulated below.

| Protein | GenBank ID | GI Number | Organism |
| --- | --- | --- | --- |
| citF | AAC73716.1 | 1786832 | Escherichia coli |
| citE | AAC73717.2 | 87081764 | Escherichia coli |
| citD | AAC73718.1 | 1786834 | Escherichia coli |
| citC | AAC73719.2 | 87081765 | Escherichia coli |
| citG | AAC73714.1 | 1786830 | Escherichia coli |
| citX | AAC73715.1 | 1786831 | Escherichia coli |
| citF | CAA71633.1 | 2842397 | Leuconostoc mesenteroides |
| citE | CAA71632.1 | 2842396 | Leuconostoc mesenteroides |
| citD | CAA71635.1 | 2842395 | Leuconostoc mesenteroides |
| citC | CAA71636.1 | 3413797 | Leuconostoc mesenteroides |
| citG | CAA71634.1 | 2842398 | Leuconostoc mesenteroides |
| citX | CAA71634.1 | 2842398 | Leuconostoc mesenteroides |
| citF | NP_459613.1 | 16763998 | Salmonella typhimurium |
| cite | AAL19573.1 | 16419133 | Salmonella typhimurium |
| citD | NP_459064.1 | 16763449 | Salmonella typhimurium |
| citC | NP_459616.1 | 16764001 | Salmonella typhimurium |
| citG | NP_459611.1 | 16763996 | Salmonella typhimurium |
| citX | NP_459612.1 | 16763997 | Salmonella typhimurium |
| citF | CAA56217.1 | 565619 | Klebsiella pneumoniae |
| cite | CAA56216.1 | 565618 | Klebsiella pneumoniae |
| citD | CAA56215.1 | 565617 | Klebsiella pneumoniae |
| citC | BAH66541.1 | 238774045 | Klebsiella pneumoniae |
| citG | CAA56218.1 | 565620 | Klebsiella pneumoniae |
| citX | AAL60463.1 | 18140907 | Klebsiella pneumoniae |

Acetate kinase (EC 2.7.2.1) catalyzes the reversible ATP-dependent phosphorylation of acetate to acetylphosphate. Exemplary acetate kinase enzymes have been characterized in many organisms including *E. coli*, *Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
| --- | --- | --- | --- |
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
| --- | --- | --- | --- |
| Pta | NP_416800.1 | 71152910 | Escherichia coli |

| Protein | GenBank ID | GI Number | Organism |
| --- | --- | --- | --- |
| Pta | P39646 | 730415 | Bacillus subtilis |
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174: 6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, J. Bacteriol. 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

| Protein | GenBank ID | GI Number | Organism |
|---|---|---|---|
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

The product yields per C-mol of substrate of microbial cells synthesizing reduced fermentation products such as butadiene or crotyl alcohol, are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, $NAD(P)^+$, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

Here, we show specific examples of how additional redox availability from CO and/or $H_2$ can improve the yields of reduced products such as butadiene or crotyl alcohol.

The maximum theoretical yield to produce butadiene from glucose is 1 mole/mole (0.3 g/g) based on the pathway described in FIG. 2. For the pathway described in FIG. 4, the maximum theoretical yield under aerobic conditions is 0.28 g/g. The maximum theoretical yield based on stoichiometry is 1.09 mole/mole (0.33 g/g). Using rTCA and hydrogen, this yield can be improved to 2 mole/mole glucose (0.6 g/g). Similar yield improvements can be attained for crotyl alcohol via the proposed routes.

When both feedstocks of sugar and syngas are available, the syngas components CO and $H_2$ can be utilized to generate reducing equivalents by employing the hydrogenase and CO dehydrogenase. The reducing equivalents generated from syngas components will be utilized to power the glucose to butadiene or crotyl alcohol production pathways.

As shown in above example, a combined feedstock strategy where syngas is combined with a sugar-based feedstock or other carbon substrate can greatly improve the theoretical yields. In this co-feeding appoach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of butadiene or crotyl alcohol production from glucose or sugar, the theoretical yields improve from 1.09 mol butadiene or crotyl alcohol per mol of glucose to 2 mol butadiene or crotyl alcohol per mol of glucose. Such improvements provide environmental and economic benefits and greatly enhance sustainable chemical production.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
|---|---|---|---|
| CODH (putative) | YP_430813 | 83590804 | *Moorella thermoacetica* |
| CODH-II (CooS-II) | YP_358957 | 78044574 | *Carboxydothermus hydrogenoformans* |

| Protein | GenBank ID | GI Number | Organism |
|---|---|---|---|
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to *E. coli* and other enteric bacteria are multiple genes encoding up to four hydrogenases (Sawers, G., *Antonie Van Leeuwenhoek* 66:57-88 (1994); Sawers et al., *J Bacteriol.* 164:1324-1331 (1985); Sawers and Boxer, *Eur. J Biochem.* 156:265-275 (1986); Sawers et al., *J Bacteriol.* 168:398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., How *E. coli* is equipped to oxidize hydrogen under different redox conditions, *J Biol Chem* published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
|---|---|---|---|
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |
| HyaF | AAC74062.1 | 1787211 | Escherichia coli |

| Protein | GenBank ID | GI Number | Organism |
| --- | --- | --- | --- |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., Appl Microbiol Biotechnol 76(5):1035-42 (2007)). Hydrogenase activity in E. coli is also dependent upon the expression of the hyp genes whose corresponding proteins are involved in the assembly of the hydrogenase complexes (Jacobi et al., Arch. Microbiol 158:444-451 (1992); Rangarajan et al., J. Bacteriol, 190: 1447-1458 (2008)).

| Protein | GenBank ID | GI Number | Organism |
| --- | --- | --- | --- |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |

| Protein | GenBank ID | GI Number | Organism |
| --- | --- | --- | --- |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

| Protein | GenBank ID | GI Number | Organism |
| --- | --- | --- | --- |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The M. thermoacetica hydrogenases are suitable for a host that lacks sufficient endogenous hydrogenase activity. M. thermoacetica can grow with $CO_2$ as the exclusive carbon source indicating that reducing equivalents are extracted from $H_2$ to enable acetyl-CoA synthesis via the Wood-Ljungdahl pathway (Drake, H. L., J. Bacteriol. 150:702-709 (1982); Drake and Daniel, Res. Microbiol. 155:869-883 (2004); Kellum and Drake, J. Bacteriol. 160:466-469 (1984)) (see FIG. 2A). M. thermoacetica has homologs to several hyp, hyc, and hyf genes from E. coli. The protein sequences encoded for by these genes are identified by the following GenBank accession numbers.

Proteins in M. thermoacetica whose genes are homologous to the E. coli hyp genes are shown below.

| Protein | GenBank ID | GI Number | Organism |
| --- | --- | --- | --- |
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |

Proteins in M. thermoacetica that are homologous to the E. coli Hydrogenase 3 and/or 4 proteins are listed in the following table.

| Protein | GenBank ID | GI Number | Organism |
| --- | --- | --- | --- |
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |

In addition, several gene clusters encoding hydrogenase functionality are present in M. thermoacetica and their corresponding protein sequences are provided below.

| Protein | GenBank ID | GI Number | Organism |
| --- | --- | --- | --- |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Ralstonia eutropha H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-

20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
|---|---|---|---|
| HoxF | NP_942727.1 | 38637753 | Ralstonia eutropha H16 |
| HoxU | NP_942728.1 | 38637754 | Ralstonia eutropha H16 |
| HoxY | NP_942729.1 | 38637755 | Ralstonia eutropha H16 |
| HoxH | NP_942730.1 | 38637756 | Ralstonia eutropha H16 |
| HoxW | NP_942731.1 | 38637757 | Ralstonia eutropha H16 |
| HoxI | NP_942732.1 | 38637758 | Ralstonia eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCKJ, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

| Protein | GenBank ID | GI Number | Organism |
| --- | --- | --- | --- |
| maeA | NP_415996 | 90111281 | *Escherichia coli* |
| maeB | NP_416958 | 16130388 | *Escherichia coli* |
| NAD-ME | P27443 | 126732 | *Ascaris suum* |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein.

Enzymes, genes and methods for engineering pathways from succinyl-CoA to various products into a microorganism are now known in the art. The additional reducing equivalents obtained from CO and/or $H_2$, as disclosed herein, improve the yields of butadiene or crotyl alcohol when utilizing carbohydrate-based feedstock.

Enzymes, genes and methods for engineering pathways from glycolysis intermediates to various products into a microorganism are known in the art. The additional reducing equivalents obtained from CO and $H_2$, as described herein, improve the yields of all these products, including butadiene and crotyl alcohol, on carbohydrates.

EXAMPLE III

Methods for Handling CO and Anaerobic Cultures

This example describes methods used in handling CO and anaerobic cultures.

A. Handling of CO in Small Quantities for Assays and Small Cultures. CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Threfore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures. Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions. Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology. Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 µM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM-made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

EXAMPLE IV

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., *Biochemistry* 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mL of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude E. coli cell extracts of ACS90 and ACS91 (CODH-ACS operon of M. thermoacetica with and without, respectively, the first cooC). 10 microliters of extract were added at a time, mixed and assayed. Reduced $CH_3$ viologen turns purple. The results of an assay are shown in Table I.

TABLE I

Crude extract CO Oxidation Activities.

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

Averages
ACS90 0.057 U/mg
ACS91 0.045 U/mg
Mta99 0.0018 U/mg

Mta98/Mta99 are E. coli MG1655 strains that express methanol methyltransferase genes from M. thermoacetia and, therefore, are negative controls for the ACS90 ACS91 E. coli strains that contain M. thermoacetica CODH operons.

If ~1% of the cellular protein is CODH, then these figures would be approximately 100× less than the 500 U/mg activity of pure M. thermoacetica CODH. Actual estimates based on Western blots are 0.5% of the cellular protein, so the activity is about 50× less than for M. thermoacetica CODH. Nevertheless, this experiment demonstrates CO oxidation activity in recombinant E. coli with a much smaller amount in the negative controls. The small amount of CO oxidation ($CH_3$ viologen reduction) seen in the negative controls indicates that E. coli may have a limited ability to reduce $CH_3$ viologen.

Figure 9:
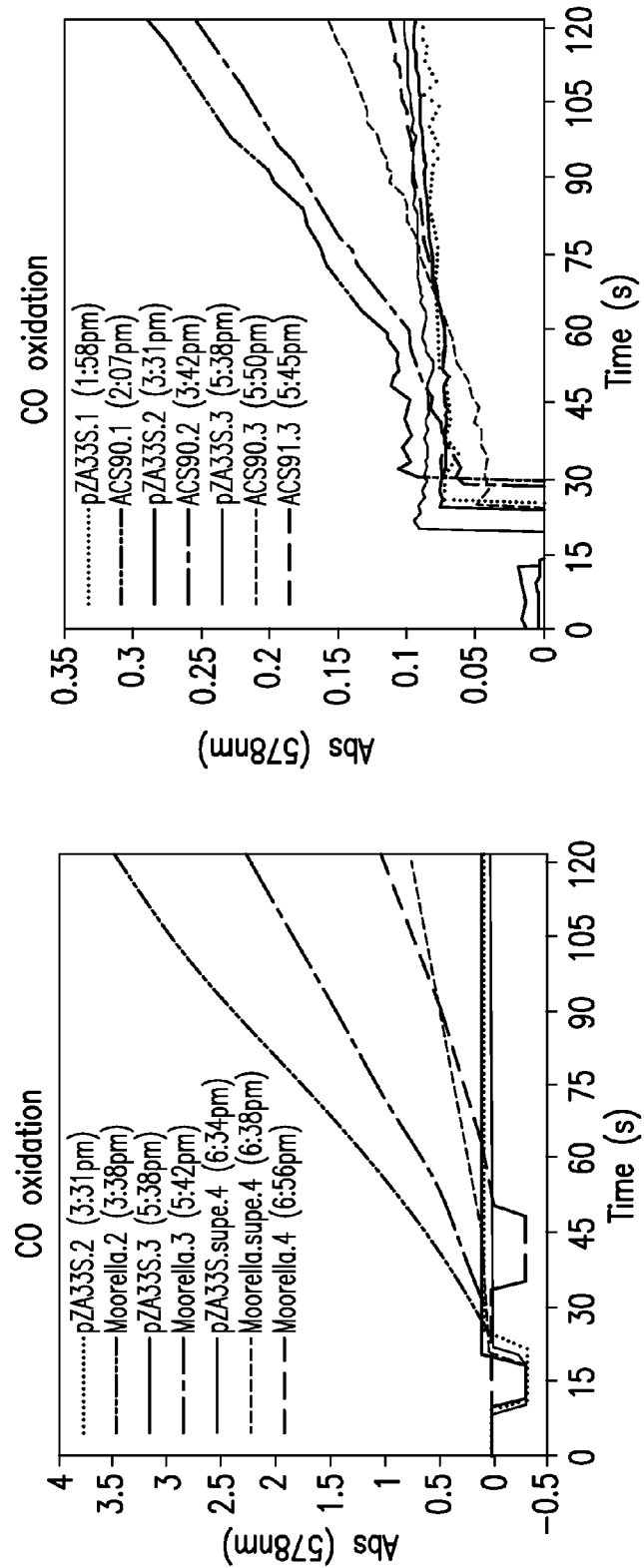
FIG. 9 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified M. thermoacetica CODH-ACS and Mtr proteins and were visualized using an alkaline phosphatase-linked goat-anti-rabbit secondary antibody. The Westerns were performed and results are shown in FIG. 9. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant E. coli cells express multiple components of a 7 gene operon. In addition, both the methyltransferase and corrinoid iron sulfur protein were active in the same recombinant E. coli cells. These proteins are part of the same operon cloned into the same cells.

Figure 10A:
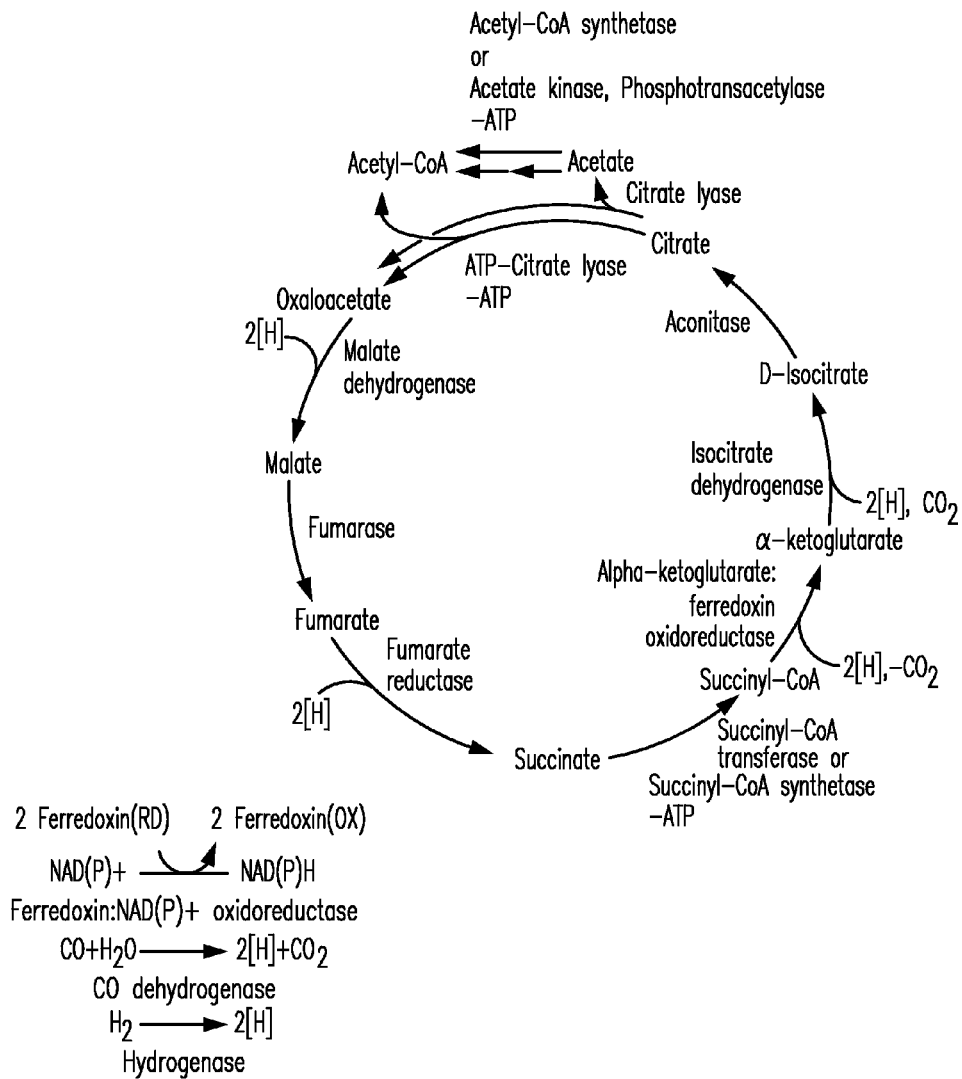
FIGS. 10A and B show exemplary pathways to crotyl alcohol.
Figure 10B:
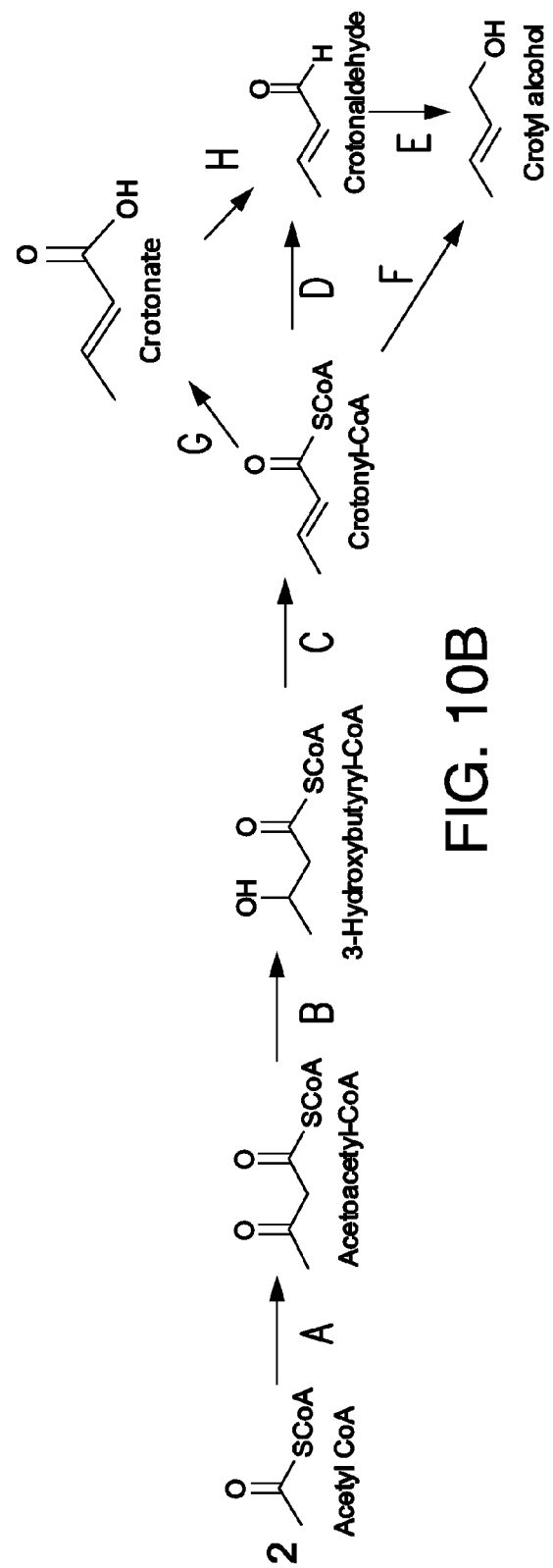
FIG. 10B shows exemplary pathways for the biosynthesis of crotyl alcohol from acetyl-CoA; the enzymatic transformations shown are carried out by the following enzymes: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotonyl-CoA reductase (alcohol forming), G. crotonyl-CoA hydrolase, synthetase, transferase, and H. crotonate reductase.
Figure 11A:
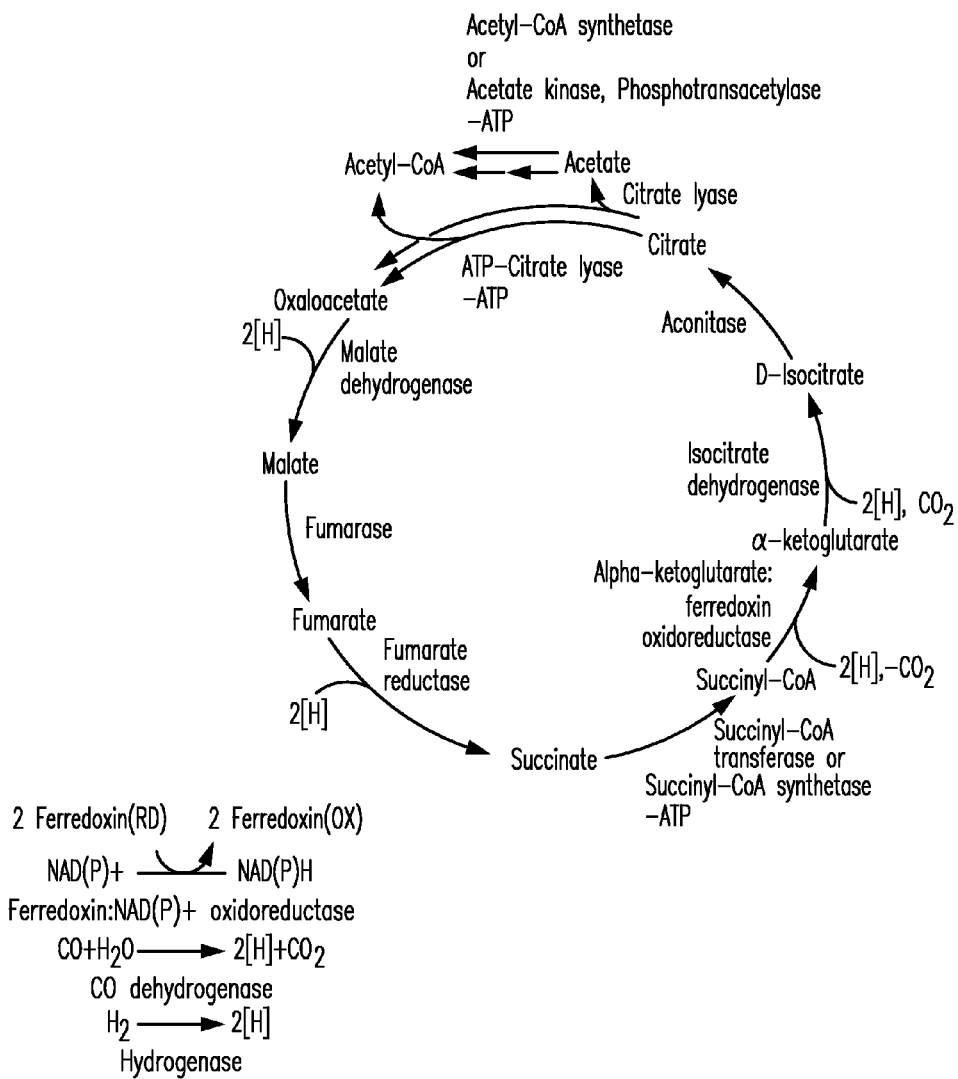
FIGS. 11A and 11B show exemplary pathways to butadiene.
Figure 11B:
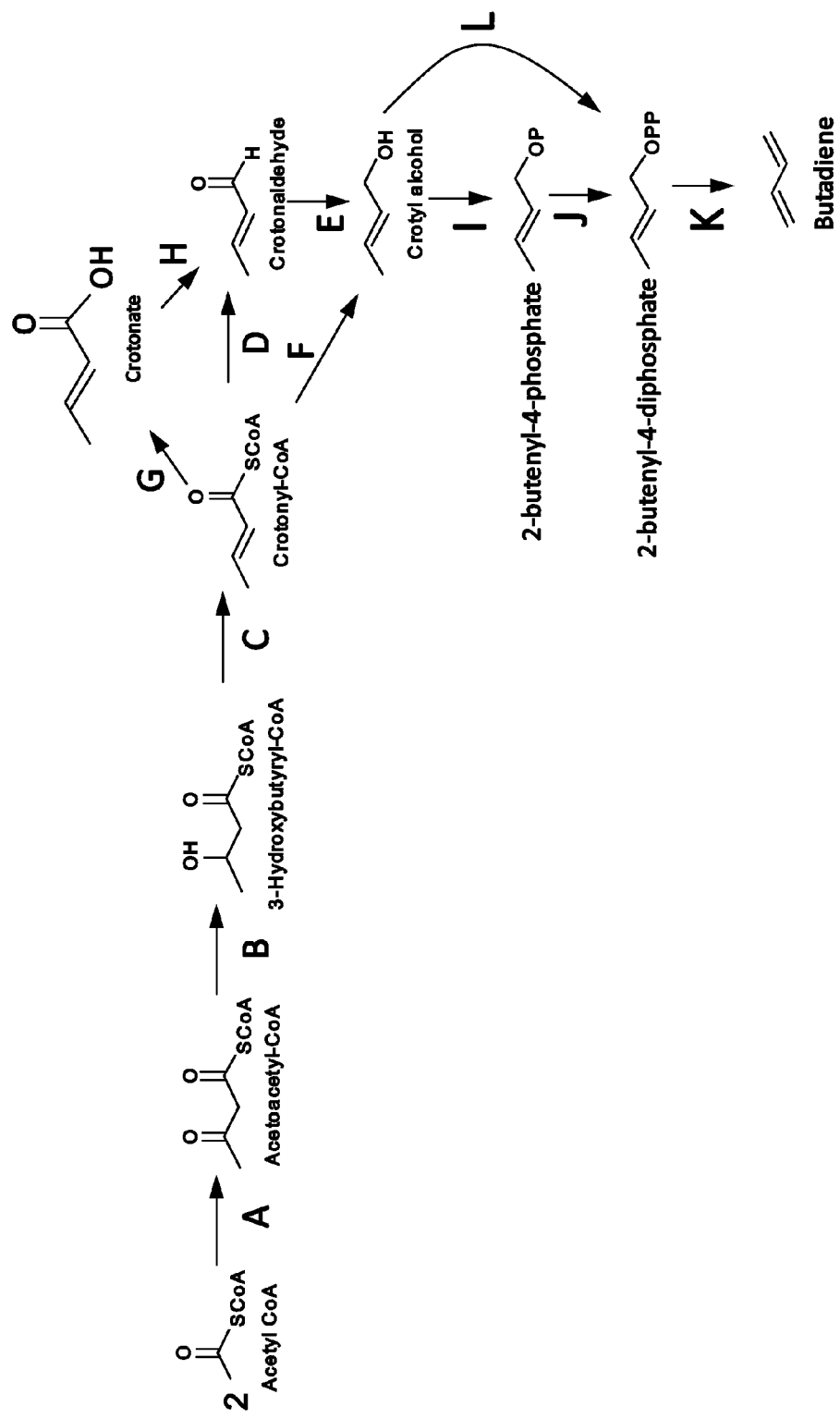

The CO oxidation assays were repeated using extracts of Moorella thermoacetica cells for the positive controls. Though CODH activity in E. coli ACS90 and ACS91 was measurable, it was at about 130-150× lower than the M. thermoacetica control. The results of the assay are shown in FIG. 10. Briefly, cells (M. thermoacetica or E. coli with the CODH/ACS operon; ACS90 or ACS91 or empty vector: pZA33S) were grown and extracts prepared as described herein. Assays were performed as described above at 55° C. at various times on the day the extracts were prepared. Reduction of methylviologen was followed at 578 nm over a 120 sec time course.

These results describe the CO oxidation (CODH) assay and results. Recombinant E. coli cells expressed CO oxidation activity as measured by the methyl viologen reduction assay.

EXAMPLE V

E. coli CO Tolerance Experiment and CO Concentration Assay (Myoglobin Assay)

This example describes the tolerance of E. coli for high concentrations of CO.

To test whether or not E. coli can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table II.

TABLE II

Carbon Monoxide Concentrations, 36 hrs.

| Strain and Growth Conditions | Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table II indicate that the cultures grew whether or not a strain was cultured in the presence of CO or not. These results indicate that E. coli can tolerate exposure to CO under anaerobic conditions and that E. coli cells expressing the CODH-ACS operon can metabolize some of the CO.

These results demonstrate that E. coli cells, whether expressing CODH/ACS or not, were able to grow in the presence of saturating amounts of CO. Furthermore, these grew equally well as the controls in nitrogen in place of CO. This experiment demonstrated that laboratory strains of E. coli are insensitive to CO at the levels achievable in a syngas project performed at normal atmospheric pressure. In addition, preliminary experiments indicated that the recombinant E. coli cells expressing CODH/ACS actually consumed some CO, probably by oxidation to carbon dioxide.

EXAMPLE VI

Exemplary Carboxylic Acid Reductases

This example describes the use of carboxylic acid reductases to carry out the conversion of a caroboxylic acid to an aldehyde.

1.2.1.e Acid Reductase. The conversion of unactivated acids to aldehydes can be carried out by an acid reductase. Examples of such conversions include, but are not limited, the conversion of 4-hydroxybutyrate, succinate, alpha-ketoglutarate, and 4-aminobutyrate to 4-hydroxybutanal, succinate semialdehyde, 2,5-dioxopentanoate, and 4-aminobutanal, respectively. One notable carboxylic acid reductase can be found in Nocardia iowensis which catalyzes the magnesium, ATP and NADPH-dependent reduction of carboxylic acids to their corresponding aldehydes (Venkitasubramanian et al., J.

Biol. Chem. 282:478-485 (2007)). This enzyme is encoded by the car gene and was cloned and functionally expressed in E. coli (Venkitasubramanian et al., J. Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industires, ed. R. N. Patel, Chapter 15, pp. 425-440, CRC Press LLC, Boca Raton, Fla. (2006)).

| Gene | Accession No. | GI No. | Organism |
|---|---|---|---|
| car | AAR91681.1 | 40796035 | Nocardia iowensis (sp. NRRL 5646) |
| npt | ABI83656.1 | 114848891 | Nocardia iowensis (sp. NRRL 5646) |

Additional car and npt genes can be identified based on sequence homology.

| Gene | Accession No. | GI No. | Organism |
|---|---|---|---|
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |

An additional enzyme candidate found in Streptomyces griseus is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., J. Antibiot. 60(6): 380-387 (2007)). Co-expression of griC and griD with SGR_665, an enzyme similar in sequence to the Nocardia iowensis npt, can be beneficial.

| Gene | Accession No. | GI No. | Organism |
|---|---|---|---|
| griC | 182438036 | YP_001825755.1 | Streptomyces griseus subsp. griseus NBRC 13350 |
| griD | 182438037 | YP_001825756.1 | Streptomyces griseus subsp. griseus NBRC 13350 |
| MSMEG_2956 | YP_887275.1 | YP_887275.1 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |

-continued

| Gene | Accession No. | GI No. | Organism |
|---|---|---|---|
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., Gene 98:141-145 (1991)), *Candida albicans* (Guo et al., Mol. Genet. Genomics 269:271-279 (2003)), and *Schizosaccharomyces pombe* (Ford et al., Curr. Genet. 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., J. Biol. Chem. 278:8250-8256 (2003)). The gene encoding the *P. chrysogenum* PPTase has not been identified to date.

| Gene | Accession No. | GI No. | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

Cloning and Expression of Carboxylic Acid Reductase. *Escherichia coli* is used as a target organism to engineer the pathway for butadiene or crotyl alcohol. *E. coli* provides a good host for generating a non-naturally occurring microorganism capable of producing butadiene or crotyl alcohol. *E. coli* is amenable to genetic manipulation and is known to be capable of producing various intermediates and products effectively under various oxygenation conditions.

To generate a microbial organism strain such as an *E. coli* strain engineered to produce butadiene or crotyl alcohol, nucleic acids encoding a carboxylic acid reductase and phosphopantetheine transferase are expressed in *E. coli* using well known molecular biology techniques (see, for example, Sambrook, supra, 2001; Ausubel supra, 1999). In particular, car genes from *Nocardia iowensis* (designated 720), *Mycobacterium smegmatis* mc(2)155 (designated 890), *Mycobacterium avium* subspecies *paratuberculosis* K-10 (designated 891) and *Mycobacterium marinum* M (designated 892) were cloned into pZS*13 vectors (Expressys, Ruelzheim, Germany) under control of PA1/lacO promoters. The npt (ABI83656.1) gene (i.e., 721) was cloned into the pKJL33S vector, a derivative of the original mini-F plasmid vector PML31 under control of promoters and ribosomal binding sites similar to those used in pZS*13.

The car gene (GNM_720) was cloned by PCR from *Nocardia* genomic DNA. Its nucleic acid and protein sequences are shown in FIGS. 12A and 12B, respectively. A codon-optimized version of the npt gene (GNM_721) was synthesized by GeneArt (Regensburg, Germany). Its nucleic acid and protein sequences are shown in FIGS. 13A and 13B, respectively. The nucleic acid and protein sequences for the *Mycobacterium smegmatis* mc(2)155 (designated 890), *Mycobacterium avium* subspecies *paratuberculosis* K-10 (designated 891) and *Mycobacterium marinum* M (designated 892) genes and enzymes can be found in FIGS. 14, 15, and 16, respectively. The plasmids are transformed into a host cell to express the proteins and enzymes required for butadiene or crotyl alcohol production or intermediates thereof.

Additional CAR variants were generated. A codon optimized version of CAR 891 was generated and designated 891 GA. The nucleic acid and amino acid sequences of CAR 891GA are shown in FIGS. 17A and 17B, respectively. Over 2000 CAR variants were generated. In particular, all 20 amino acid combinations were made at positions V295, M296, G297, G391, G421, D413, G414, Y415, G416, and S417, and additional variants were tested as well. Exemplary CAR variants include: E16K; Q95L; L100M; A1011T; K823E; T941S; H15Q; D198E; G446C; S392N; F699L; V883I; F467S; T987S; R12H; V295G; V295A; V295S; V295T; V295G; V295V; V295L; V295I; V295M; V295P; V295F; V295Y; V295W; V295D; V295E; V295N; V295Q; V295H; V295K; V295R; M296G; M296A; M296S; M296T; M296C; M296V; M296L; M296I; M296M; M296P; M296F; M296Y; M296W; M296D; M296E; M296N; M296Q; M296H; M296K; M296R; G297G; G297A; G297S; G297T; G297C; G297V; G297L; G297I; G297M; G297P; G297F; G297Y; G297W; G297D; G297E; G297N; G297Q; G297H; G297K; G297R; G391G; G391A; G391S; G391T; G391C; G391V; G391L; G391I; G391M; G391P; G391F; G391Y; G391W; G391D; G391E; G391N; G391Q; G391H; G391K; G391R; G421G; G421A; G421S; G421T; G421C; G421V; G421L; G421I G421M; G421P; G421F; G421Y; G421W; G421D; G421E; G421N; G421Q; G421H; G421K; G421R; D413G; D413A; D413S; D413T; D413C; D413V; D413L; D413I; D413M; D413P; D413F; D413Y; D413W; D413D; D413E; D413N; D413Q; D413H; D413K; D413R; G414G; G414A; G414S; G414T; G414C; G414V; G414L; G414I; G414M; G414P; G414F; G414Y; G414W; G414D; G414E; G414N; G414Q; G414H; G414K; G414R; Y415G; Y415A; Y415S; Y415T; Y415C; Y415V; Y415L; Y415I; Y415M; Y415P; Y415F; Y415Y; Y415W; Y415D; Y415E; Y415N; Y415Q; Y415H; Y415K; Y415R; G416G; G416A; G416S; G416T; G416C; G416V; G416L; G416I; G416M; G416P; G416F; G416Y; G416W; G416D; G416E; G416N; G416Q; G416H; G416K; G416R; S417G; S417A; S417S; S417T; S417C;

S417V S417L; S417I; S417M; S417P; S417F; S417Y; S417W; S417D; S417E; S417N; S417Q; S417H; S417K; and S417R.

The CAR variants were screened for activity, and numerous CAR variants were found to exhibit CAR activity.

This example describes the use of CAR for converting carboxylic acids to aldehydes.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, said microbial organism having a butadiene pathway and comprising at least two exogenous nucleic acids each encoding a butadiene pathway enzyme expressed in a sufficient amount to produce butadiene, wherein said butadiene pathway comprises the butadiene pathway enzymes of an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase; said microbial organism further comprising:
(a) a reductive TCA pathway comprising at least one exogenous nucleic acid encoding a citryl-CoA synthetase or a citryl-CoA lyase; or
(b) a reductive TCA pathway comprising at least one exogenous nucleic acid encoding a phosphoenolpyruvate carboxylase or a phosphoenolpyruvate carboxykinase.

2. The non-naturally occurring microbial organism of claim 1, wherein said microbial organism comprising (a) further comprises an exogenous nucleic acid encoding an enzyme selected from an ATP-citrate lyase, a citrate lyase, a fumarate reductase, an alpha-ketoglutarate:ferredoxin oxidoreductase, a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof.

3. The non-naturally occurring microbial organism of claim 1, wherein said microbial organism comprising (b) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

4. The non-naturally occurring microbial organism of claim 1, wherein said microbial organism comprises two, three, four, five, six or seven exogenous nucleic acids each encoding an enzyme of the butadiene pathway.

5. The non-naturally occurring microbial organism of claim 1, wherein said microbial organism comprises exogenous nucleic acids encoding each of the enzymes of an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, a 2-butenyl-4-phosphate kinase and a butadiene synthase.

6. The non-naturally occurring microbial organism of claim 1, wherein said microbial organism comprises two or three exogenous nucleic acids each encoding enzymes of (a) or (b).

7. The non-naturally occurring microbial organism of claim 6, wherein said microbial organism comprising (a) comprises four exogenous nucleic acids encoding a citryl-CoA synthetase, a citryl-CoA lyase, a fumarate reductase, and an alpha-ketoglutarate: ferredoxin oxidoreductase;
wherein said microbial organism comprising (b) comprises four exogenous nucleic acids encoding a pyruvate:ferredoxin oxidoreductase, a phosphoenolpyruvate carboxylase or a phosphoenolpyruvate carboxykinase, a CO dehydrogenase, and an $H_2$ hydrogenase; or
wherein said microbial organism comprising (a) or (b) comprises two exogenous nucleic acids encoding CO dehydrogenase and $H_2$ hydrogenase.

8. The non-naturally occurring microbial organism of claim 1, wherein said at least one exogenous nucleic acid is a heterologous nucleic acid.

9. The non-naturally occurring microbial organism of claim 1, wherein said non-naturally occurring microbial organism is in a substantially anaerobic culture medium.

10. The non-naturally occurring microbial organism of claim 1, wherein said microbial organism comprises two exogenous nucleic acids each encoding an enzyme of the butadiene pathway.

11. The non-naturally occurring microbial organism of claim 1, wherein said microbial organism comprises three exogenous nucleic acids each encoding an enzyme of the butadiene pathway.

12. The non-naturally occurring microbial organism of claim 1, wherein said microbial organism comprises four exogenous nucleic acids each encoding an enzyme of the butadiene pathway.

13. The non-naturally occurring microbial organism of claim 1, wherein said microbial organism comprises five exogenous nucleic acids each encoding an enzyme of the butadiene pathway.

14. The non-naturally occurring microbial organism of claim 1, wherein said microbial organism comprises six exogenous nucleic acids each encoding an enzyme of the butadiene pathway.

15. The non-naturally occurring microbial organism of claim 1, wherein said microbial organism comprises seven exogenous nucleic acids each encoding an enzyme of the butadiene pathway.

16. A method for producing butadiene, comprising culturing the non-naturally occurring microbial organism of claim 1 under conditions and for a sufficient period of time to produce butadiene.

* * * * *